US011279729B2

(12) United States Patent
Parrag et al.

(10) Patent No.: US 11,279,729 B2
(45) Date of Patent: Mar. 22, 2022

(54) HETERODIMER COMPOSITIONS AND METHODS FOR THE TREATMENT OF OCULAR DISORDERS

(71) Applicant: Ripple Therapeutics Corporation, Toronto (CA)

(72) Inventors: Ian Charles Parrag, Mississauga (CA); Wendy Alison Naimark, Toronto (CA); Matthew Alexander John Statham, Milton (CA); Georgios Rizis, Toronto (CA); Kyle Giovanni Battiston, Toronto (CA)

(73) Assignee: RIPPLE THERAPEUTICS CORPORATION, Toronto (CA)

( * ) Notice: Subject to any disclaimer, the term of this patent is extended or adjusted under 35 U.S.C. 154(b) by 0 days.

(21) Appl. No.: 17/350,888

(22) Filed: Jun. 17, 2021

(65) Prior Publication Data
US 2021/0347809 A1 Nov. 11, 2021

Related U.S. Application Data

(63) Continuation of application No. PCT/IB2021/000332, filed on Apr. 29, 2021.

(60) Provisional application No. 63/019,182, filed on May 1, 2020.

(51) Int. Cl.
C07J 7/00 (2006.01)
A61K 9/00 (2006.01)

(52) U.S. Cl.
CPC ............. *C07J 7/008* (2013.01); *A61K 9/0024* (2013.01)

(58) Field of Classification Search
CPC .............................. C07J 7/008; A61K 9/0024
See application file for complete search history.

(56) References Cited

U.S. PATENT DOCUMENTS

| | | | |
|---|---|---|---|
| 3,591,612 A | 7/1971 | Allais et al. |
| 3,663,579 A | 5/1972 | Stache et al. |
| 4,024,871 A | 5/1977 | Stephenson |
| 4,198,405 A | 4/1980 | Enomoto et al. |
| 4,318,908 A | 3/1982 | Enomoto et al. |
| 4,532,316 A | 7/1985 | Henn |
| 4,833,215 A | 5/1989 | Jedlinski et al. |
| 4,916,193 A | 4/1990 | Tang et al. |
| 5,013,841 A | 5/1991 | Matsumoto et al. |
| 5,217,493 A | 6/1993 | Raad et al. |
| 5,250,524 A | 10/1993 | Kramer et al. |
| 5,321,099 A | 6/1994 | Goldwasser et al. |
| 5,387,598 A | 2/1995 | Rossignol |
| 5,512,558 A | 4/1996 | Enhsen et al. |
| 5,578,621 A | 11/1996 | Rossignol |
| 5,798,115 A | 8/1998 | Santerre et al. |
| 5,856,348 A | 1/1999 | Rossignol |
| 5,859,038 A | 1/1999 | Rossignol |
| 5,886,013 A | 3/1999 | Rossignol |
| 5,965,590 A | 10/1999 | Rossignol |
| 5,968,961 A | 10/1999 | Rossignol |
| 6,020,353 A | 2/2000 | Rossignol |
| 6,051,576 A | 4/2000 | Ashton et al. |
| 6,096,525 A | 8/2000 | Patnaik |
| 6,117,894 A | 9/2000 | Rossignol |
| 6,127,507 A | 10/2000 | Santerre |
| 6,299,604 B1 | 10/2001 | Ragheb et al. |
| 6,344,035 B1 | 2/2002 | Chudzik et al. |
| 6,429,300 B1 | 8/2002 | Kurz et al. |
| 6,602,915 B2 | 8/2003 | Uhrich |
| 6,689,350 B2 | 2/2004 | Uhrich |
| 6,703,037 B1 | 3/2004 | Hubbell et al. |
| 6,770,725 B2 | 8/2004 | Santerre |
| 8,349,309 B2 | 1/2013 | Santerre et al. |
| 8,968,626 B2 | 3/2015 | Pham et al. |
| 9,056,048 B2 | 6/2015 | Diamond et al. |
| 9,604,949 B2 | 3/2017 | Ellis et al. |
| 10,588,862 B2 | 3/2020 | Parrag et al. |
| 10,632,075 B2 | 4/2020 | Parrag et al. |
| 10,945,958 B2 | 3/2021 | Parrag et al. |
| 10,959,954 B2 | 3/2021 | Parrag et al. |

(Continued)

FOREIGN PATENT DOCUMENTS

AU 2012258480 A1 12/2012
CA 1148166 A 6/1983

(Continued)

OTHER PUBLICATIONS

Bach et al., Retention of Antibacterial Activity and Bacterial Colonization of Antiseptic-Bonded Central Venous Catheters. J. Antimicrob. Chemother. 37:315-322 (1996).

(Continued)

*Primary Examiner* — Barbara P Badio
(74) *Attorney, Agent, or Firm* — Wilson Sonsini Goodrich & Rosati

(57) ABSTRACT

Described herein are processable compositions comprising at least one moiety that is processable in its free form. Also described herein are compositions and methods for the treatment of ocular diseases or disorders including glaucoma, blepharitis, ocular inflammation, diabetic macular edema, posterior inflammation, anterior inflammation, macular degeneration (e.g., wet macular degeneration (AMD) or dry AMD), post-cataract surgery, and retinal vein occlusion. Said compositions and methods comprise steroids and prostaglandins which demonstrate anti-inflammatory activity, intraocular pressure (IOP) lowering, and/or other desirable activities. Injection of said compositions in the eye provides therapeutic benefit to patients suffering from ocular disorders.

11 Claims, 37 Drawing Sheets

(56) References Cited

U.S. PATENT DOCUMENTS

| | | |
|---|---|---|
| 2003/0035787 A1 | 2/2003 | Uhrich |
| 2003/0039689 A1 | 2/2003 | Chen et al. |
| 2003/0118528 A1 | 6/2003 | Walters et al. |
| 2003/0158598 A1 | 8/2003 | Ashton et al. |
| 2003/0203030 A1 | 10/2003 | Ashton et al. |
| 2004/0087664 A1 | 5/2004 | Marcus et al. |
| 2004/0180036 A1 | 9/2004 | Ashton et al. |
| 2005/0008695 A1 | 1/2005 | Ashton et al. |
| 2005/0031577 A1 | 2/2005 | Uhrich |
| 2005/0070470 A1 | 3/2005 | Coy et al. |
| 2005/0159609 A1 | 7/2005 | King et al. |
| 2005/0164994 A1 | 7/2005 | Ashton et al. |
| 2005/0220839 A1 | 10/2005 | DeWitt et al. |
| 2005/0255079 A1 | 11/2005 | Santerre et al. |
| 2010/0062974 A1 | 3/2010 | LaRonde et al. |
| 2011/0243884 A1 | 10/2011 | O'Shea et al. |
| 2013/0289223 A1 | 10/2013 | Santerre et al. |
| 2014/0256696 A1 | 9/2014 | Sinha et al. |
| 2016/0038651 A1 | 2/2016 | Santerre et al. |
| 2017/0028078 A1 | 2/2017 | Mandell et al. |
| 2019/0247311 A1 | 8/2019 | Parrag et al. |
| 2020/0071275 A1 | 3/2020 | Delong et al. |
| 2020/0276179 A1 | 9/2020 | Kopczynski et al. |
| 2021/0030667 A1 | 2/2021 | Parrag et al. |
| 2021/0113457 A1 | 4/2021 | Parrag et al. |
| 2021/0205222 A1 | 7/2021 | Parrag et al. |

FOREIGN PATENT DOCUMENTS

| | | |
|---|---|---|
| CA | 2461099 A1 | 4/2003 |
| CA | 2467321 A1 | 11/2005 |
| CA | 2571320 A1 | 11/2005 |
| CA | 2906238 A1 | 9/2014 |
| CH | 592687 A5 | 11/1977 |
| CN | 101099867 A | 1/2008 |
| CN | 1968715 B | 12/2010 |
| CN | 110746593 A | 2/2020 |
| FR | 2007815 A1 | 1/1970 |
| JP | S50123654 A | 9/1975 |
| JP | H07501470 A | 2/1995 |
| JP | H0924093 A | 1/1997 |
| JP | 2000501318 A | 2/2000 |
| JP | 2007537168 A | 12/2007 |
| WO | WO-9511907 A1 | 5/1995 |
| WO | WO-9520567 A1 | 8/1995 |
| WO | WO-9528393 A1 | 10/1995 |
| WO | WO-9729778 A2 | 8/1997 |
| WO | WO-9807458 A1 | 2/1998 |
| WO | WO-9850035 A1 | 11/1998 |
| WO | WO-9906430 A1 | 2/1999 |
| WO | WO-9912990 A1 | 3/1999 |
| WO | WO-0209768 A2 | 2/2002 |
| WO | WO-03028527 A2 | 4/2003 |
| WO | WO-03040104 A1 | 5/2003 |
| WO | WO-03043657 A1 | 5/2003 |
| WO | WO-2004016214 A2 | 2/2004 |
| WO | WO-2005110485 A1 | 11/2005 |
| WO | WO-2007056457 A2 | 5/2007 |
| WO | WO-2010040187 A1 | 4/2010 |
| WO | WO-2010040188 A1 | 4/2010 |
| WO | WO-2011120044 A1 | 9/2011 |
| WO | WO-2012109445 A1 | 8/2012 |
| WO | WO-2012139164 A1 | 10/2012 |
| WO | WO-2013106528 A1 | 7/2013 |
| WO | WO-2014000033 A1 | 1/2014 |
| WO | WO-2014134689 A1 | 9/2014 |
| WO | WO-2014138190 A1 | 9/2014 |
| WO | WO-2014139033 A1 | 9/2014 |
| WO | WO-2015168014 A1 | 11/2015 |
| WO | WO-2017041142 A1 | 3/2017 |
| WO | WO-2017053638 A1 | 3/2017 |
| WO | WO-2017083794 A1 | 5/2017 |
| WO | WO-2018165710 A1 | 9/2018 |
| WO | WO-2018165711 A1 | 9/2018 |
| WO | WO-2019118924 A1 | 6/2019 |
| WO | WO-2019148291 A1 | 8/2019 |
| WO | WO-2019148293 A1 | 8/2019 |
| WO | WO-2019148294 A1 | 8/2019 |
| WO | WO-2019210215 A1 | 10/2019 |
| WO | WO-2020154815 A1 | 8/2020 |
| WO | WO-2021005417 A1 | 1/2021 |
| WO | WO-2021014217 A1 | 1/2021 |
| WO | WO-2021024039 A1 | 2/2021 |
| WO | WO-2021024041 A1 | 2/2021 |
| WO | WO-2021220061 A2 | 11/2021 |

OTHER PUBLICATIONS

Berge et al. Pharmaceutical Salts. Journal of Pharmaceutical Sciences 66(1):1-19 (Jan. 1977).

Blondeau. Fluoroquinolones: mechanism of action, classification, and development of resistance. Sury Ophthalmol. 49 Suppl 2:S73-8 (2004).

Budavari. The Merck Index—Fourteenth Edition Merck Research Laboratories. Whitehouse Station, NJ, pp. 1306-1307 (2006).

Burger. Isosterism and Bioisosterism in Drug Design, in Progress in Drug Research 287-328 (Ernst Jucker, ed., Birkhauser Verlag) (1991).

Chanphai et al. Conjugation of steroids with PAMAM nanoparticles. Colloids and Surfaces B: Biointerfaces 136:1035-1041 (2015).

Cheng et al., Intravitreal sustained-release dexamethasone device in the treatment of experimental uveitis. Invest Ophthalmol Vis Sci. 36(2):442-53 (1995).

Chirife et al., In vitro antibacterial activity of concentrated polyethylene glycol 400 solutions. Antimicrob Agents Chemother. 24(3):409-12 (1983).

Coessens et al., Synthesis and In Vitro Stability of Macromolecular Prodrugs of Norfloxacin. J. Cont. Release 47:283-291 (1997).

Ditizio et al., A Liposomal Hydrogel for the Prevention of Bacterial Adhesion to Catheters. Biomaterials 19:1877-1884 (1998).

Gaudana et al. Ocular drug delivery. AAPS J. 12(3):348-360 (2010).

Ghosh. Monomers and Polymers from Nalidixic Acid—Synthesis, Characterization, and Hydrolysis Study, in Progress in Biomedical Polymers, Ed. Gebekin et al., Plenum Press, New York, pp. 335-345 (1990).

Ghosh. Studies Directed Towards Polymeric Quinloone Antibiotics—Synthesis of Potential Monomers From Nalidixic Acid. Polymeric Mat. Sci. Engin. 59:790-793 (1988).

Gower et al. Drug discovery in ophthalmology: past success, present challenges, and future opportunities. BMC Ophthalmology 16:11 (Jan. 16, 2016).

Howard-Sparks et al. A Novel Chemical Delivery System Comprising an Ocular Sustained Re-lease Formulation of a 3a-17a-21-trihydroxy-5B-pregnan-20-one-BIS-5-Fluorouracil Coding. Drug Dev Ind Pharm 33:677-682 (2007).

Janout et al., Bioconjugate-Based Molecular Umbrellas. Bioconjugate Chemistry, 20(2):183-192 (E-Pub Nov. 20, 2008).

Janout et al. Molecular umbrella-amphotercin B conjugates. Bioconjugate Chemistry 25:1408-1411 (2014).

Kanra et al., The short-term efficacy and safety of dexamethasone implant in a difficult-to-treat patient population with persistent diabetic macular edema. Ret Vit. 26(3):221-7 (2017) (English Abstract).

Kerns et al., Piperazinyl-linked fluoroquinolone dimers possessing potent antibacterial activity against drug-resistant strains of Staphylococcus aureus. Bioorg Med Chem Lett. 13(10):1745-9 (2003).

Li et al., Dimeric and Oligomeric Steroids. Chem Rev. 97(1):283-304 (1997).

Manolakis et el. Novel L-DOPA-derived poly(ester amide)s: monomers, polymers, and the first L-DOPA-functionalized biobased adhesive tape. Macromol Rapid Commun 35(1):71-6 (2014).

Michael et al. Enhanced RNA binding of dimerized aminoglycosides. Bioorg Med Chem 7:1361-1371 (1999).

Modak et al., A New Method for the Direct Incorporation of Antibiotic in Prosthetic Vascular Grafts. Surg. Gynecol. Obstet. 164:143-147 (1987).

(56) References Cited

OTHER PUBLICATIONS

Morimoto et al. New dimeric morphine from opium poppy (*Papaver somuniferum*) and its physiological function. J Nat Prod 66(7):987-989 (2003).
Nahar et al. A review on steroid dimers: 2011-2019. Steroids 164:108736 (2020).
Nahar et al. A review on synthetic and natural steroid dimers: 1997-2006. Current Medicinal Chemistry 14:1349-1370 (2007).
Nathan et al., Copolymers of Lysine and Polyethylene Glycol: A New Family of Functionalized Drug Carriers, Bioconjug. Chem. 4:54-62 (1993).
Nishida et al., Studies on synthesis of antibacterial agent (NM441). I. Kinetics and mechanism of the reaction of 4-(bromomethyl)-5-methyl-1,3-dioxo1-2-one with 1-substituted piperazine (NM394). Bull Chem Soc Jpn. 67:1419-26 (1994).
Nosova et al., Synthesis of new fluorinated derivatives of quinolinecarboxylic acids. Chem Heterocycl Compd 38(8):922-8 (2002).
Odian (Principles of Polymerization, 4th ed.(2004).
Paris et al. Glycerides as prodrugs. 3. Synthesis and antiinflammatory activity of [1-(p-chlorobenzoyl)-5-methoxy-2-methylindole-3-acetyl]glycerides (indomethacin glycerides). J Med Chem 23(1):9-13 (1980).
Paryze et al., A new approach to steroid dimers and macrocycles by the reaction of 3-chlorocarbonyl derivatives of bile acids with 0,0-, N,N-, and S,S-dinucleophiles. Tetrahedron Lett. 53(46):6212-5 (2012).
Patani et al. Bioisosterism: A Rational Approach in Drug Design. Chem. Rev. 96:3147-3176 (1996).
PCT/CA2014/050284 International Search Report and Written Opinion dated Jun. 2, 2014.
PCT/CA2019/050133 International Search Report and Written Opinion dated Apr. 29, 2019.
PCT/CA2019/050135 International Search Report and Written Opinion dated Apr. 29, 2019.
PCT/CA2019/050136 International Search Report and Written Opinion dated Apr. 29, 2019.
PCT/CA2020/050117 International Search Report and Written Opinion dated Apr. 15, 2020.
PCT/IB2020/000620 International Search Report and Written Opinion dated Oct. 30, 2020.
PCT/IB2020/000656 International Search Report and Written Opinion dated Nov. 16, 2020.
PCT/IB/2020/000659 International Search Report and Written Opinion dated Dec. 14, 2020.
PCT/IB2020/000663 International Search Report and Written Opinion dated Dec. 1, 2020.
Peng et al. Pharmacological properties of bivalent ligands containing butorphan linked to nalbuphine, naltrexone, and naloxone at mu, delta, and kappa opioid receptors. J Med Chem 50(9):2254-2258 (2007).
Ren et al., Macromolecular prodrug of dexamethasone prevents particle-induced peri-implant osteolysis with reduced systemic side effects. J Control Release. 175:1-9 (2014) (24 pages).
Robin et al. Medication adherence in patients with ocular hypertension or glaucoma. Exp. Rev. Ophth. 14:4-5, 199-210 (2019).
Roseeuw et al., Polymeric Prodrugs of Antibiotics with Improved Efficiency. J. Mater. Sci. Mater. Med. 10:743-746 (1999).
Sarker et al. Chapter 6: Applications of Steroid Dimers, in Steroid Dimer: Chemistry and Applications in Drug Design and Delivery, John Wiley & Sons Ltd. pp. 379-407 (2012).
Step-growth Polymerization. http://en.wikipedia.org/wiki/Step-growth_polymerization, retrieved on Jan. 12, 2012 (11 pages).
Svobodova et al. Recent advances in steroidal supramolecular gels. RSC Advances 2:4985-5007 (2012).
U.S. Appl. No. 16/396,135 Office Action dated Jul. 3, 2019.
U.S. Appl. No. 16/396,400 Office Action dated Jun. 24, 2019.
U.S. Appl. No. 16/396,400 Office Action dated Oct. 15, 2019.
U.S. Appl. No. 16/396,400 Response to Non-Final Office Action dated Sep. 24, 2019.
U.S. Appl. No. 16/698,372 Office Action dated Jan. 21, 2020.
U.S. Appl. No. 16/698,372 Office Action dated May 26, 2020.
U.S. Appl. No. 16/699,305 Office Action dated Feb. 3, 2020.
U.S. Appl. No. 16/699,305 Office Action dated May 26, 2020.
Woo et al., Biological characterization of a novel biodegradable antimicrobial polymer synthesized with fluoroquinolones, J. Biomat. Res., 59(1):35-45 (2002).
Woo et al., Synthesis and characterization of a novel biodegradable antimicrobial polymer, Biomaterials, 21:1235-1246 (2000).
Xue et al., New dimeric cholesteryl-based A(LS)2 gelators with remarkable gelling abilities: organogel formation at room temperature. J Colloid Interface Sci. 361(2):556-64 (2011).
Yang et al. Utilization of quinolone drugs as monomers: characterization of the synthesis reaction products for poly(norfloxacin diisocyanatododecane polycaprolactone). Biomacromolecules 2(1):134-41 (2001).
Dao et al. Targeting the Estrogen Receptor using Steroid-Therapeutic Drug Conjugates (Hy-brids). Bioconjugate Chemistry 23(11):2139-2158 (2012).
Jurček et al. Succinobucol's New Coat—Conjugation with Steroids to Alter Its Drug Effect and Bioavailability. 16(11):9404-9420 (2011).
Navacchia et al. Bile Acid Conjugates with Anticancer Activity: Most Recent Research. Molecules 26(1):25 (2020).
PCT/IB2021/000332 International Search Report and Written Opinion dated Nov. 17, 2021.

HETERODIMER COMPOSITIONS AND METHODS FOR THE TREATMENT OF OCULAR DISORDERS

CROSS-REFERENCES

This application is a continuation of International Application No. PCT/IB2021/000332 filed on Apr. 29, 2021, which claims the benefit of U.S. Provisional Application No. 63/019,182, filed May 1, 2020, which are hereby incorporated by reference in their entirety herein.

BACKGROUND OF THE INVENTION

Prostaglandins (prostaglandin analogs) are a front-line medication in the treatment of glaucoma and can be used in the treatment of other ocular disorders. In some instances, prostaglandins are useful for lowering intraocular pressure (IOP), a major risk factor in glaucoma. Typically, prostaglandins are ophthalmically formulated and delivered in the form of eye drops. To provide efficacy, however, frequent ophthalmic administration of prostaglandins is often required. For example, latanoprost given once a day has been reported to have a mean IOP lowering of about 35%.

SUMMARY OF THE INVENTION

Provided in certain embodiments herein are compounds comprising a first radical (D1) and a second radical (D2) (e.g., having the formula: D1-L-D2). In certain instances, D1 is a processable group (also referred to herein as a processable radical), L is a linker, and D2 is a drug (also referred herein as a drug radical). In certain embodiments, L is a hydrolyzable linker or bond, such that when the compound of formula D1-L-D2 is (e.g., ophthalmically) administered (or when present in or otherwise exposed to an aqueous environment, such as a buffering solution, tears, serum, or the like), D1 and D2 are released (e.g., in their free, non-radical form). In certain instances, the (e.g., covalent) joining of a group D1 to an active agent D2 (e.g., non-processable active agent) through a linker L (e.g., D1-L-D2), provides a compound comprising an otherwise non-processable drug (e.g., D2-L-D2 (e.g., D2-D2)) in a processable form. In certain instances, a drug (such as a prostaglandin) is joined with a processable group (such as a steroid or other radical of a formula described herein, such as Formula (I)). In certain instances, the processable group D1 may or may not itself be processable when in free form, but when combined with D2 (e.g., through a linker L) provides a solid (e.g., at a physiological temperature) that is processable (e.g., at a temperature above a physiological temperature).

Provided in certain instances herein is a platform for providing compounds and implants (e.g., with high drug content, low excipient content (e.g., that would otherwise need to be removed), and other benefits, such as described herein) that provide long-lasting release of therapeutics (e.g., prostaglandins, steroids, beta-blockers, and/or the like) in biological and therapeutic applications, such as in ocular (e.g., implant) administration.

In some instances, compounds provided herein (e.g., joining a non-processable drug, such as a prostaglandin, radical to a processable, such as a steroid, radical, such as through a (e.g., hydrolyzable) linker) are processable into forms (e.g., implants, coatings, or other bodies), such as that are capable of being administered to (e.g., an eye of) an individual in need thereof. In some instances, such compounds are processable without the need for additional excipients or materials (e.g., controlled release polymers, matrices, or other components). In certain instances, the no or low amounts of additional excipients or materials facilitates high levels of drug delivery, while limiting impact of drug delivery (e.g., a small implant can have high quantities of drug).

In certain instances, such compounds (or implants comprising such compounds) are administered to (e.g., implanted into) an individual, such that sustained and/or otherwise controlled (e.g., local) delivery of the drug is achieved. In some instances, delivery of the compounds (e.g., in the form of an implant, coating, etc.) facilitate delivery of a drug component or radical thereof for an extended period of time, such as for weeks, months, or more. In certain instances, compounds, formulations, and implants provided herein facilitate the long term delivery of drugs to an individual in need thereof, such as without the need for frequent dosing. For example, as discussed herein, prostaglandins are often formulated and administered as eye drops, such as with daily administration. In some instances, without rigid compliance to frequent administration is required to maintain (e.g., optimal) therapeutic efficacy. With the compounds provided herein, however, long term delivery of such drugs can be achieved from weeks, months, or more, with infrequent administration (e.g., once a year, twice a year, or the like).

In some embodiments, the group D1 is also an active agent or drug (e.g., radical thereof). In certain embodiments, D1 and D2 are both effective in the treatment of a single indication, such that administration of a compound herein provides a combination therapeutic effect. For example, in some embodiments, D1 is a steroid and D2 is a prostaglandin. In certain embodiments, such as in therapies for the treatment of glaucoma, the anti-inflammatory effect of the steroid and the ocular pressure lowering effect of the prostaglandin both provide therapeutic effect. In some embodiments, such as wherein the compound is formulated as or with an implant, D1 is an anti-inflammatory (e.g., steroid) and reduces or minimizes an inflammatory response to the implant.

Provided in certain embodiments herein are compounds, such as described herein, (e.g., pharmaceutical) compositions comprising compounds described herein, and methods of making and using compounds provided herein. In some embodiments, methods of using the compounds provided herein include methods of treating disorders in individuals in need thereof, such as disorders treatable by a drug D2 (e.g., in its free form). In some embodiments, methods of treatment provided herein comprise methods of treating ocular disorders, such as glaucoma. It is to be understood that disclosures of methods provided herein explicitly include disclosures of pharmaceutical compositions comprising (e.g., an effective amount) of a compound provided herein for such uses.

Provided in certain embodiments herein is a compound comprising a first radical and a second radical, the first radical comprising the structure of Formula (I):

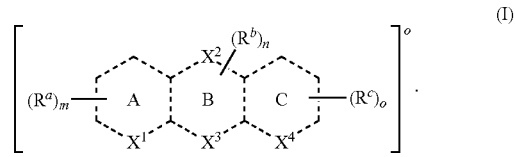

In certain embodiments, ⚊ is a single bond or a double bond. In some embodiments, each $R^a$, $R^b$, and $R^c$ is independently selected from the group consisting of oxo, halogen, —CN, —NO$_2$, alkyl, heteroalkyl, cycloalkyl, heterocycloalkyl, alkoxy, amino (e.g., dihydroamino, alkylamino, or arylamino), hydroxy, or thiol, wherein the alkyl, heteroalkyl, cycloalkyl, or heterocycloalkyl is optionally substituted. In certain embodiments, any one of $R^a$, $R^b$, or $R^c$ are taken together with another of $R^a$, $R^b$, or $R^c$ to form a substituted or an unsubstituted cycloalkyl or heterocycloalkyl. In some embodiments, $X^1$, $X^2$, $X^3$, and $X^4$ are each independently selected from the group consisting of a bond and $Q_y$, wherein each Q is independently selected from the group consisting of —O—, —NR—, —S(R)$_x$—, and —C(R)$_z$—. In some embodiments, y is 1-3. In certain embodiments, each x is independently 0-5. In some embodiments, each z is independently 1 or 2 (e.g., depending on degree of saturation). In certain embodiments, each of m, n, and o are independently 0-6. In certain embodiments, each R is independently selected from the group consisting of hydrogen, halogen, alkyl, heteroalkyl, cycloalkyl, heterocycloalkyl, alkoxy, amino (e.g., dihydroamino, alkylamino, or arylamino), hydroxy, and thiol (e.g., wherein the alkyl, heteroalkyl, cycloalkyl, or heterocycloalkyl is optionally substituted), or each R is taken together with another R to form an oxo. In some embodiments, the second radical is a therapeutically active agent (or drug). In certain embodiments, the first radical (e.g., steroid) is different than the second radical (e.g., prostaglandin). In some embodiments, either the first radical, the second radical, or both the first radical and the second radical is not a steroid. Also provided in certain embodiments herein are pharmaceutically-acceptable salts or solvates of a compound of Formula (I).

In some embodiments, the second radical is a drug. In some embodiments, the drug is a prostaglandin. In some embodiments, the prostaglandin is selected from the group consisting of latanoprost, latanoprost acid, travoprost, travoprost acid, tafluprost, tafluprost acid, bimatoprost, bimatoprost acid, sepetaprost, and sepetaprost acid, or a fragment or radical of any of the foregoing.

In some embodiments, $X^1$ is $Q_1$. In some embodiments, $X^2$ is a bond. In some embodiments, $X^3$ is $Q_2$. In some embodiments, $X^4$ is $Q_1$. In some embodiments, $X^1$ and $X^4$ are each $Q_1$. In some embodiments, $X^2$ is a bond and $X^3$ is $Q_2$. In some embodiments, Q is —C(R)$_1$— or —C(R)$_2$—. In some embodiments, $X^1$ and $X^4$ are each independently —C(R)$_1$— or —C(R)$_2$—. In some embodiments, $X^2$ is a bond and $X^3$ is —C(R)$_2$C(R)$_2$—, —C(R)C(R)$_2$—, or —C(R)C(R)—. In some embodiments, $X^1$ and $X^4$ are each —C(R)$_2$—, and $X^2$ is a bond and $X^3$ is —C(R)$_2$C(R)$_2$— or —C(R)C(R)$_2$—.

In some embodiments, each R is independently hydrogen, halogen, alkyl, heteroalkyl, hydroxy, amino (e.g., dihydroamino, alkylamino, or arylamino), or taken together with another R to form an oxo. In some embodiments, each R is independently hydrogen, halogen, alkyl, hydroxy, or taken together with another R to form an oxo. In some embodiments, each R is independently hydrogen or halogen. In some embodiments, each R is independently hydrogen or alkyl. In some embodiments, each R is independently hydrogen or hydroxy. In some embodiments, each R is independently hydrogen or taken together with another R to form an oxo.

In some embodiments, the alkyl, heteroalkyl, cycloalkyl, heterocycloalkyl, alkoxy, amino (e.g., dihydroamino, alkylamino, or arylamino), hydroxy, or thiol of R is optionally substituted. In some embodiments, R combines with one of $R^a$, $R^b$, or $R^c$ to form an optionally substituted cycloalkyl or an optionally substituted heterocycloalkyl. In some embodiments, R is amino and combines with one of $R^a$, $R^b$, or $R^c$ to form an optionally substituted heterocycloalkyl. In some embodiments, R is amino and combines with one of $R^a$ or $R^c$ to form a heterocycloalkyl substituted with optionally substituted alkyl.

In some embodiments, provided herein is a compound comprising a first radical and a second radical, the first radical comprising a structure of Formula (IA):

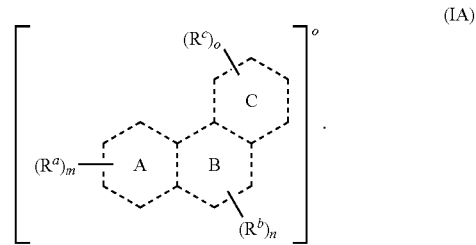

(IA)

In some embodiments, ⚊ is a single bond or a double bond). In some embodiments, each $R^a$, $R^b$, and $R^c$ are independently selected from the group consisting of oxo, halogen, —CN, —NO$_2$, alkyl, heteroalkyl, cycloalkyl, heterocycloalkyl, alkoxy, amino (e.g., dihydroamino, alkylamino, or arylamino), hydroxy, or thiol, wherein the alkyl, heteroalkyl, cycloalkyl, or heterocycloalkyl is optionally substituted. In some embodiments, each of m, n, and o are independently 0-6. In some embodiments, any one of $R^a$, $R^b$, or $R^c$ are taken together with another of $R^a$, $R^b$, or $R^c$ to form a substituted or an unsubstituted cycloalkyl or heterocycloalkyl. In some embodiments, the second radical is a therapeutically active agent (or drug) and the first radical (e.g., steroid) being different than the second radical (e.g., prostaglandin). In some embodiments, either the first radical, the second radical, or both the first radical and the second radical is not a steroid. Also provided in certain embodiments herein are pharmaceutical salts or solvates of a compound of Formula (IA).

In some embodiments, both the first radical and the second radical have a structure of Formula (I) or Formula (IA). In some embodiments, the first radical has a structure of Formula (I) or Formula (IA) and the second radical does not have a structure of Formula (I) or Formula (IA). In some embodiments, the structure of Formula (I) or Formula (IA) has a melt and/or glass transition temperature at a temperature of at least 20° C. (e.g., at least 25° C., at least 30° C., at least 37° C., at least 40° C., at least 50° C., at least 100° C., or more) in its free form.

In some embodiments, n is 4. In some embodiments, n is 3. In some embodiments, n is 2. In some embodiments, n is 1. In some embodiments, each $R^b$ is independently hydrogen, halogen, alkyl, heteroalkyl, hydroxy, amino (e.g., dihydroamino, alkylamino, or arylamino), or taken together with another $R^b$ to form an oxo. In some embodiments, each $R^b$ is independently hydrogen, halogen, alkyl, hydroxy, or taken together with another $R^b$ to form an oxo. In some embodiments, each $R^b$ is independently hydrogen or halogen. In some embodiments, each $R^b$ is independently hydrogen or alkyl. In some embodiments, each $R^b$ is independently hydrogen or hydroxy. In some embodiments, each $R^b$ is independently hydrogen or taken together with another $R^b$ to form an oxo.

In some embodiments, the alkyl, heteroalkyl, cycloalkyl, heterocycloalkyl, alkoxy, amino (e.g., dihydroamino, alkylamino, or arylamino), hydroxy, or thiol of $R^b$ is optionally substituted. In some embodiments, $R^b$ combines with one of $R^a$, $R^b$, or $R^c$ to form an optionally substituted cycloalkyl or an optionally substituted heterocycloalkyl. In some embodiments, $R^b$ is amino and combines with one of $R^a$ or $R^c$ to form an optionally substituted heterocycloalkyl. In some embodiments, $R^b$ is amino and combines with one of $R^a$ or $R^c$ to form a heterocycloalkyl substituted with optionally substituted alkyl.

In some embodiments, one of $R^c$ is taken together with another $R^c$ to form an optionally substituted cycloalkyl or an optionally substituted heterocycloalkyl. In some embodiments, one of $R^c$ is taken together with another $R^c$ to form an optionally substituted cycloalkyl. In some embodiments, one of $R^c$ is taken together with another $R^c$ to form a cycloalkyl substituted with one or more substituent, each substituent selected from the group consisting of oxo, halogen, alkyl, heteroalkyl, cycloalkyl, heterocycloalkyl, alkoxy, amino (e.g., dihydroamino, alkylamino, or arylamino), hydroxy, or thiol, wherein the alkyl, heteroalkyl, cycloalkyl, alkoxy, amino, thiol, or heterocycloalkyl is optionally substituted.

In some embodiments, $R^a$, $R^b$, and $R^c$ (e.g., of Formula (I) or Formula (IA)) are each optionally and independently substituted with one or more groups, each group independently selected from —OH, oxo, alkyl (e.g., alkenyl), heteroalkyl, cycloalkyl, or alkoxy, wherein the alkyl, heteroalkyl, cycloalkyl, or alkoxy, is further optionally substituted. In certain embodiments, the alkyl, heteroalkyl, cycloalkyl, or heterocycloalkyl of each $R^a$, $R^b$, or $R^c$ (e.g., of Formula (I) or Formula (IA)) is, independently, substituted or not substituted. In some embodiments, each group is independently not substituted or substituted with any one or more substituent described herein. In specific embodiments, each group is independently not substituted or substituted with one or more substituent, wherein each substituent is selected from the group consisting of —OH, oxo, alkyl, heteroalkyl, cycloalkyl, or alkoxy, wherein the alkyl, heteroalkyl, cycloalkyl, or alkoxy, is further optionally substituted.

In some embodiments, the substituted or unsubstituted cycloalkyl or heterocycloalkyl (e.g., of Formula (I) or Formula (IA)) are each optionally and independently substituted with one or more groups, each group independently selected from —OH, oxo, alkyl (e.g., alkenyl, alkynyl), —S-alkyl, —NH-alkyl, halogen, heteroalkyl, cycloalkyl, or alkoxy, wherein the alkyl (e.g., —S-alkyl, —NH— alkyl), heteroalkyl, cycloalkyl, or alkoxy, is further optionally substituted. In certain embodiments, substituted or unsubstituted cycloalkyl or heterocycloalkyl are, independently, substituted or not substituted. In some embodiments, each group is independently not substituted or substituted with any one or more substituent described herein. In specific embodiments, each group is independently not substituted or substituted with one or more substituent, wherein each substituent is selected from the group consisting of —OH, oxo, alkyl (e.g., alkenyl, alkynyl), —S-alkyl, —NH-alkyl, halogen, heteroalkyl, cycloalkyl, or alkoxy, wherein the alkyl (e.g., —S-alkyl, —NH-alkyl), heteroalkyl, cycloalkyl, or alkoxy, is further optionally substituted. In some embodiments, the cycloalkyl (e.g., of Formula (I) or Formula (IA)) is substituted with oxo, —OH, optionally substituted alkyl, or optionally substituted alkoxy. In some embodiments, the alkyl is substituted with one or more halogen, oxo, —OH, alkyl (e.g., alkenyl), —S-alkyl, —NH-alkyl, alkoxy, wherein the alkyl (e.g., —S— alkyl, —NH-alkyl) or alkoxy is further optionally substituted. In some embodiments, the alkyl is methyl.

In some embodiments, provided herein is a compound comprising a first radical and a second radical, the first radical comprising a structure of Formula (IB):

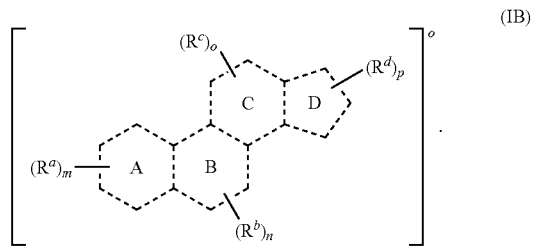

In some embodiments, ⟋ is a single bond or a double bond). In some embodiments, each $R^a$, $R^b$, $R^c$, and $R^d$ are independently selected from the group consisting of oxo, halogen, —CN, —NO$_2$, alkyl, heteroalkyl, cycloalkyl, heterocycloalkyl, alkoxy, amino (e.g., dihydroamino, alkylamino, or arylamino), hydroxy, or thiol, wherein the alkyl, heteroalkyl, cycloalkyl, or heterocycloalkyl is optionally substituted. In some embodiments, each of m, n, o, and p are independently 0-6. In some embodiments, any one of $R^a$, $R^b$, $R^c$, and $R^d$ are taken together with another of $R^a$, $R^b$, $R^c$, and $R^d$ to form a substituted or an unsubstituted cycloalkyl or heterocycloalkyl. In some embodiments, the second radical is a therapeutically active agent (or drug) and the first radical (e.g., steroid) being different than the second radical (e.g., prostaglandin). In some embodiments, either the first radical, the second radical, or both the first radical and the second radical is not a steroid. Also provided in certain embodiments herein are pharmaceutical salts or solvates of a compound of Formula (IB).

In some embodiments, Ring B of any one of Formula (I), Formula (IA), or Formula (IB) is an optionally substituted cycloalkyl. In some embodiments, Ring B of any one of Formula (I), Formula (IA), or Formula (IB) does not comprise a heteroatom within the ring (e.g., Ring B is optionally substituted cycloalkyl). In some embodiments, Ring B of any one of Formula (I), Formula (IA), or Formula (IB) comprises only single bonds. In some embodiments, Ring B of any one of Formula (I), Formula (IA), or Formula (IB) comprises at least one double bond. In some embodiments, Ring B of any one of Formula (I), Formula (IA), or Formula (IB) is attached to at least one ring (e.g., Ring A and/or Ring C) that comprises at least one double bond. In some embodiments, Ring A comprises at least one double bond. In some embodiments, Ring C comprises at least one double bond. In some embodiments, Ring A and Ring C each independently comprise at least one double bond. In some embodiments, Ring B of any one of Formula (I), Formula (IA), or Formula (IB) is attached to at least one ring (e.g., Ring A and or Ring C) that is aromatic. In some embodiments, Ring B of any one of Formula (I) or Formula (IA) is aromatic. In some embodiments, Ring A, Ring B, and Ring C of any one of Formula (I) or Formula (IA) are each aromatic.

In some embodiments, m is 4. In some embodiments, m is 3. In some embodiments, m is 2. In some embodiments, m is 1. In some embodiments, n is 3. In some embodiments, n is 2. In some embodiments, n is 1. In some embodiments, n is 0. In some embodiments, o is 5. In some embodiments, o is 4. In some embodiments, o is 3. In some embodiments, o is 2. In some embodiments, o is 1. In some embodiments, p is 3. In some embodiments, p is 2. In some embodiments, p is 1.

In some embodiments, each $R^a$, $R^b$, $R^c$, and $R^d$ are independently selected from the group consisting of oxo, halogen, alkyl, heteroalkyl, cycloalkyl, heterocycloalkyl, alkoxy, amino (e.g., dihydroamino, alkylamino, or arylamino), hydroxy, or thiol, wherein the alkyl, heteroalkyl, cycloalkyl, alkoxy, amino (e.g., dihydroamino, alkylamino, or arylamino), hydroxy, thiol, or heterocycloalkyl is optionally substituted. In some embodiments, each $R^a$ is independently selected from —OH, oxo, halogen, alkyl, or alkoxy, wherein the alkyl or alkoxy is optionally substituted. In some embodiments, each $R^b$ is independently selected from —OH, oxo, halogen, or optionally substituted alkyl. In some embodiments, each $R^c$ is independently selected from —OH, oxo, or optionally substituted alkyl. In some embodiments, each $R^d$ is independently selected from —OH, oxo, alkyl (e.g., alkenyl or alkynyl), heteroalkyl, or each $R^a$ is taken together to form an oxo, wherein the alkyl or heteroalkyl is optionally substituted. In some embodiments, the substituted alkyl of $R^d$ is —COOH, —(C=O)alkyl, —(C=O)Oalkyl, —O(C=O)Oalkyl, —(C=O)Salkyl, wherein the alkyl is optionally substituted with —OH or halogen. In some embodiments, one $R^d$ is taken together with another $R^d$ to form a substituted or unsubstituted cycloalkyl or heterocycloalkyl.

In some embodiments, the alkyl of any one of $R^a$, $R^b$, $R^c$, or $R^d$ is $C_1$-$C_3$ alkyl. In some embodiments, the alkyl of any one of $R^a$, $R^b$, $R^c$, or $R^d$ is substituted with oxo and further optionally substituted with alkyl, hydroxy, halogen, heteroalkyl, alkoxy, thioether, wherein the alkyl, alkoxy, thioether, or heteroalkyl is further optionally substituted. In some embodiments, the alkoxy of any one of $R^a$, $R^b$, $R^c$, or $R^d$ is $C_1$-$C_3$ alkoxy.

In some embodiments, Ring A is aromatic. In some embodiments, Ring A comprises at least one double bond. In some embodiments, Ring A comprises one double bond. In some embodiments, Ring A comprises two double bonds. In some embodiments, Ring B comprises at least one double bond. In some embodiments, Ring B comprises one double bond. In some embodiments, Ring C comprises one double bond. In some embodiments, Ring D comprises one double bond. In some embodiments, Ring A comprises at least one double bond and each of Ring B, Ring C, and Ring D consist of single bonds. In some embodiments, Ring A is aromatic and each of Ring B, Ring C, and Ring D consist of single bonds. In some embodiments, Ring A comprises at least one double bond and at least one of Ring B, Ring C, or Ring D comprises a double bond. In some embodiments, Ring A is aromatic and at least one of Ring B, Ring C, or Ring D comprises a double bond. In some embodiments, Ring A comprises at least one double bond and Ring B comprises a double bond. In some embodiments, Ring A comprises at least one double bond and Ring C comprises a double bond. In some embodiments, Ring A comprises at least one double bond and Ring D comprises a double bond.

In some embodiments, provided herein is a compound comprising a first radical and a second radical, the first radical comprising a structure of Formula (IC):

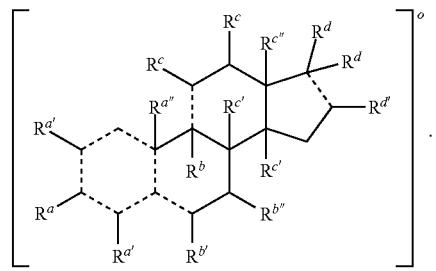

In some embodiments, ⌇ is a single bond or a double bond. In some embodiments, $R^a$ is hydrogen, —OH, or oxo. In some embodiments, each $R^{a'}$ is independently selected from hydrogen, —OH, halogen, $C_1$-$C_3$ alkyl, and alkoxy. In some embodiments, $R^{a''}$ is absent, hydrogen, or $C_1$-$C_3$ alkyl. In some embodiments, $R^b$ is absent, hydrogen, halogen, or $C_1$-$C_3$ alkyl. In some embodiments, $R^{b'}$ is hydrogen, halogen, —OH, oxo, or $C_1$-$C_3$ alkyl. In some embodiments, $R^{b''}$ is hydrogen or —OH. In some embodiments, each $R^c$ is independently hydrogen, —OH, oxo, or $C_1$-$C_3$ alkyl. In some embodiments, each $R^{c'}$ is independently hydrogen or $C_1$-$C_3$ alkyl. In some embodiments, $R^{c''}$ is hydrogen, —OH, $C_1$-$C_3$ alkyl, or —C(=O)H. In some embodiments, each $R^d$ is independently hydrogen, —OH, —COOH, alkyl (e.g., alkylene, alkenyl, or alkynyl), heteroalkyl, or each $R^d$ is taken together to form an oxo, wherein the alkyl or heteroalkyl is optionally substituted. In some embodiments, $R^{d'}$ is hydrogen, —OH, $C_1$-$C_3$ alkyl (e.g., alkylene or alkenyl), or heteroalkyl. In some embodiments, one $R^d$ is taken together with $R^{d'}$ to form a substituted or unsubstituted cycloalkyl or heterocycloalkyl. In some embodiments, either the first radical, the second radical, or both the first radical and the second radical is not a steroid. In some embodiments, the second radical is a therapeutically active agent (or drug) and the first radical (e.g., steroid) being different than the second radical (e.g., prostaglandin. Also provided in certain embodiments herein are pharmaceutical salts or solvates of a compound of Formula (IC).

In some embodiments, the structure of any one of Formula (I), Formula (IA), Formula (IB), or Formula (IC) consists of single bonds. In some embodiments, the structure of any one of Formula (I), Formula (IA), Formula (IB), or Formula (IC) comprises at least one double bond. In some embodiments, the structure of any one of Formula (I), Formula (IA), Formula (IB), or Formula (IC) comprises one double bond. In some embodiments, the structure of any one of Formula (I), Formula (IA), Formula (IB), or Formula (IC) comprises two double bonds. In some embodiments, the structure of any one of Formula (I), Formula (IA), Formula (IB), or Formula (IC) comprises three double bonds. In some embodiments, the structure of any one of Formula (I), Formula (IA), Formula (IB), or Formula (IC) comprises at least one aromatic ring. In some embodiments, the structure of any one of Formula (I), Formula (IA), Formula (IB), or Formula (IC) comprises one aromatic ring.

In some embodiments, $R^a$ is —OH. In some embodiments, $R^a$ is —OH and attached to a fully saturated cycloalkyl. In some embodiments, $R^a$ is —OH and attached to an aryl. In some embodiments, $R^a$ is oxo. In some embodiments, $R^a$ is oxo and is adjacent to at least one double bond. In some embodiments, $R^a$ is oxo and is adjacent to one double bond. In some embodiments, $R^a$ is oxo and is adjacent to two double bonds.

In some embodiments, each $R^{a'}$ is independently hydrogen or halogen (e.g., fluoro or chloro). In some embodiments, each $R^{a'}$ is independently hydrogen or $C_1$-$C_3$ alkyl. In some embodiments, each $R^{a'}$ is independently hydrogen or $C_1$-$C_3$ alkoxy. In some embodiments, each $R^{a'}$ is attached to a single bond. In some embodiments, each $R^{a'}$ is hydrogen. In some embodiments, at least one $R^{a'}$ is attached to a double bond. In some embodiments, one $R^{a'}$ is attached to a double bond. In some embodiments, each $R^{a'}$ is attached to a double bond. In some embodiments, each $R^{a'}$ is independently hydrogen or $C_1$-$C_3$ alkyl and attached to a single bond. In some embodiments, each $R^{a'}$ is independently hydrogen or halogen, and one $R^{a'}$ is attached to a double bond. In some embodiments, each $R^{a'}$ is hydrogen and attached to a single bond. In some embodiments, each $R^{a'}$ is hydrogen and attached to a double bond. In some embodiments, each $R^{a'}$ is attached to an aryl and independently hydrogen or $C_1$-$C_3$ alkoxy. In some embodiments, each $R^{a'}$ is hydrogen and attached to an aryl.

In some embodiments, $R^{a''}$ is absent. In some embodiments, $R^{a''}$ is hydrogen. In some embodiments, $R^{a''}$ is $C_1$-$C_3$ alkyl. In some embodiments, $R^a$ is —OH or oxo, each $R^{a'}$ is independently hydrogen or $C_1$-$C_3$ alkyl, and $R^{a''}$ is $C_1$-$C_3$ alkyl. In some embodiments, $R^a$ is —OH or oxo, each $R^{a'}$ is independently hydrogen or $C_1$-$C_3$ alkoxy, and $R^{a''}$ is $C_1$-$C_3$ alkyl. In some embodiments, $R^a$ is oxo, each $R^{a'}$ is independently hydrogen or halogen (e.g., fluoro or chloro), and $R^{a''}$ is $C_1$-$C_3$ alkyl (e.g., methyl). In some embodiments, $R^a$ is oxo, each $R^{a'}$ is independently hydrogen or $C_1$-$C_3$ alkyl (e.g., methyl), and $R^{a''}$ is $C_1$-$C_3$ alkyl (e.g., methyl). In some embodiments, $R^a$ is oxo, each $R^{a'}$ is hydrogen, and $R^{a''}$ is $C_1$-$C_3$ alkyl (e.g., methyl). In some embodiments, $R^a$ is —OH, each $R^{a'}$ is independently hydrogen or $C_1$-$C_3$ alkoxy (e.g., methoxy), and $R^{a''}$ is absent. In some embodiments, $R^a$ is —OH, each $R^{a'}$ is hydrogen, and $R^{a''}$ is $C_1$-$C_3$ alkyl (e.g., methyl). In some embodiments, $R^a$ is —OH, each $R^{a'}$ is hydrogen, and $R^{a''}$ is absent.

In some embodiments, $R^b$ is absent. In some embodiments, $R^b$ is hydrogen. In some embodiments, $R^b$ is halogen (e.g., fluoro or chloro). In some embodiments, $R^{b'}$ is hydrogen. In some embodiments, $R^{b'}$ is halogen (e.g., fluoro or chloro). In some embodiments, $R^{b'}$ is —OH. In some embodiments, $R^{b'}$ is -oxo. In some embodiments, $R^{b'}$ is $C_1$-$C_3$ alkyl (e.g., methyl). In some embodiments, $R^{b'}$ is hydrogen, halogen (e.g., fluoro or chloro), or $C_1$-$C_3$ alkyl (e.g., methyl) and attached to a single bond. In some embodiments, $R^{b'}$ is hydrogen or $C_1$-$C_3$ alkyl (e.g., methyl) and attached to a double bond. In some embodiments, $R^{b''}$ is hydrogen. In some embodiments, $R^{b''}$ is —OH.

In some embodiments, $R^b$ is hydrogen or halogen (e.g., fluoro or chloro), $R^{b'}$ is hydrogen, halogen (e.g., fluoro or chloro), or $C_1$-$C_3$ alkyl (e.g., methyl), and $R^{b''}$ is hydrogen. In some embodiments, $R^b$ is hydrogen or halogen (e.g., fluoro or chloro), $R^{b'}$ is hydrogen or halogen (e.g., fluoro or chloro), and $R^{b''}$ is hydrogen. In some embodiments, $R^b$ is halogen (e.g., fluoro or chloro), $R^{b'}$ is halogen (e.g., fluoro or chloro), and $R^{b''}$ is hydrogen. In some embodiments, $R^b$ is halogen (e.g., fluoro or chloro), $R^{b'}$ is hydrogen, and $R^{b''}$ is hydrogen. In some embodiments, $R^b$ is hydrogen, $R^{b'}$ is halogen (e.g., fluoro or chloro), and $R^{b''}$ is hydrogen. In some embodiments, $R^b$ is hydrogen, $R^{b'}$ is $C_1$-$C_3$ alkyl (e.g., methyl), and $R^{b''}$ is hydrogen. In some embodiments, $R^b$ is hydrogen, $R^{b'}$ is hydrogen, and $R^{b''}$ is —OH. In some embodiments, $R^b$ is hydrogen, $R^{b'}$ is oxo, and $R^{b''}$ is hydrogen. In some embodiments, $R^b$, $R^{b'}$, and $R^{b''}$ are each hydrogen.

In some embodiments, each $R^c$ is independently hydrogen or —OH. In some embodiments, each $R^c$ is independently hydrogen or oxo. In some embodiments, each $R^c$ is hydrogen. In some embodiments, each $R^{c'}$ is hydrogen. In some embodiments, each $R^{c'}$ is $C_1$-$C_3$ alkyl. In some embodiments, $R^{c''}$ is hydrogen. In some embodiments, $R^{c''}$ is $C_1$-$C_3$ alkyl. In some embodiments, $R^{c''}$ is —C(=O)H.

In some embodiments, each $R^c$ is hydrogen, each $R^{c'}$ is hydrogen, and $R^{c''}$ is $C_1$-$C_3$ alkyl. In some embodiments, each $R^c$ is independently hydrogen or —OH, each $R^{c'}$ is hydrogen, and $R^{c''}$ is $C_1$-$C_3$ alkyl. In some embodiments, each $R^c$ is independently hydrogen or oxo, each $R^{c'}$ is hydrogen, and $R^{c''}$ is $C_1$-$C_3$ alkyl. In some embodiments, each $R^c$ is independently hydrogen or —OH, each $R^{c'}$ is hydrogen, and $R^{c''}$ is —C(=O)H. In some embodiments, each $R^c$ is independently hydrogen or —OH, each $R^{c'}$ is $C_1$-$C_3$ alkyl, and $R^{c''}$ is hydrogen.

In some embodiments, one $R^d$ is absent and $R^{d'}$ and the other $R^d$ are attached to a double bond. In some embodiments, the $R^{d'}$ and the other $R^d$ attached to a double bond are each hydrogen.

In some embodiments, one $R^d$ is hydrogen and the other $R^d$ is —OH, —COOH, alkyl (e.g., alkylene, alkenyl, or alkynyl), heteroalkyl, wherein the alkyl or heteroalkyl is optionally substituted. In some embodiments, one $R^d$ is alkyl and the other $R^d$ is —OH, —COOH, alkyl (e.g., alkylene, alkenyl, or alkynyl), heteroalkyl, wherein the alkyl or heteroalkyl is optionally substituted. In some embodiments, one $R^d$ is optionally substituted alkoxy and the other $R^d$ is —OH, —COOH, alkyl (e.g., alkylene, alkenyl, or alkynyl), heteroalkyl, wherein the alkyl or heteroalkyl is optionally substituted. In some embodiments, one $R^d$ is —OH and the other $R^d$ is —COOH, alkyl (e.g., alkylene, alkenyl, or alkynyl), heteroalkyl, wherein the alkyl or heteroalkyl is optionally substituted. In some embodiments, each $R^d$ is independently hydrogen or —OH. In some embodiments, each $R^d$ is independently optionally substituted alkyl or —OH. In some embodiments, each $R^d$ is independently —COOH or —OH. In some embodiments, each $R^d$ is independently —COOH or optionally substituted alkoxy. In some embodiments, each $R^d$ is taken together to form an oxo. In some embodiments, each $R^d$ is taken together to form an optionally substituted alkenyl. In some embodiments, the alkenyl is substituted with —COOH and alkyl. In some embodiments, the alkyl comprises saturated and unsaturated carbon bonds. In some embodiments, each $R^d$ is independently optionally substituted alkyl or hydrogen. In some embodiments, the alkyl consists of saturated carbon bonds. In some embodiments, the alkyl is substituted with $C_1$-$C_3$ alkyl and alkyl further substituted with —COOH. In some embodiments, the alkyl is substituted with $C_1$-$C_3$ alkyl and alkyl further substituted with —OH.

In some embodiments, $R^{d'}$ is hydrogen. In some embodiments, $R^{d'}$ is —OH. In some embodiments, $R^{d'}$ is $C_1$-$C_3$ alkyl (e.g., alkylene or alkenyl). In some embodiments, the $C_1$-$C_3$ alkyl is methyl. In some embodiments, the $C_1$-$C_3$ alkyl is CHCH. In some embodiments, $R^{d'}$ is heteroalkyl. In some embodiments, the heteroalkyl is —O(C=O)$C_1$-$C_3$ alkyl.

In some embodiments, one $R^d$ is taken together with $R^{d'}$ to form an optionally substituted cycloalkyl or optionally substituted heterocycloalkyl. In some embodiments, one $R^d$ is taken together with $R^{d'}$ to form a heterocycloalkyl substituted with one or more alkyl groups. In some embodiments, one $R^d$ is optionally substituted alkyl and the other $R^d$ is taken together with $R^{d'}$ to form a heterocycloalkyl substituted with one or more alkyl groups. In some embodiments, the alkyl is substituted with oxo and —OH. In some embodiments, the alkyl is substituted with oxo and alkyl further substituted with halogen (e.g., fluoro or chloro). In some embodiments, the heterocycloalkyl is an optionally substituted dioxolane. In some embodiments, the optionally substituted dioxolane is 2,2-dimethyl-1,3-dioxolane. In some embodiments, the optionally substituted dioxolane is 1,4-dioxaspiro[4.4]nonane.

In some embodiments, each $R^d$ is independently hydrogen or optionally substituted alkyl and $R^{d'}$ is hydrogen. In some embodiments, each $R^d$ is independently hydrogen or optionally substituted alkyl and $R^{d'}$ is $C_1$-$C_3$ alkyl. In some embodiments, each $R^d$ is independently optionally substituted alkyl and $R^{d'}$ is hydrogen. In some embodiments, each $R^d$ is independently —OH or optionally substituted alkyl and $R^{d'}$ is hydrogen. In some embodiments, each $R^d$ is independently —COOH or optionally substituted alkoxy and $R^{d'}$ is hydrogen. In some embodiments, each $R^d$ is independently —OH or optionally substituted alkyl and $R^{d'}$ is $C_1$-$C_3$ alkyl. In some embodiments, each $R^d$ is independently —OH or optionally substituted alkyl and $R^{d'}$ is —OH. In some embodiments, each $R^d$ is independently —OH or optionally substituted alkyl and $R^{d'}$ is alkyl (e.g., alkenyl). In some embodiments, each $R^d$ is independently hydrogen or —OH and $R^{d'}$ is hydrogen. In some embodiments, each $R^d$ is independently —OH or —COOH and $R^{d'}$ is hydrogen. In some embodiments, each $R^d$ and $R^{d'}$ are hydrogen. In some embodiments, each $R^d$ is optionally substituted alkenyl and $R^{d'}$ is optionally substituted alkoxy. In some embodiments, each $R^d$ is taken together to form an oxo and $R^{d'}$ is hydrogen. In some embodiments, one $R^d$ is optionally substituted alkyl and the other $R^d$ is taken together with $R^{d'}$ is to form an optionally substituted heterocycloalkyl.

In some embodiments, the alkyl or heteroalkyl of $R^d$ or $R^{d'}$ is substituted with one or more of the group consisting of —SH, —OH, —COOH, oxo, halogen, amino (e.g., dihydroamino, alkylamino, or arylamino), alkyl (e.g., alkenyl, alkynyl), heteroalkyl, ester, amide, sulfonic acid, and sulfone. In some embodiments, one $R^d$ is taken together with $R^{d'}$ to form substituted heterocycloalkyl.

In some embodiments, the alkyl of $R^d$ is substituted with oxo and alkyl further substituted with hydroxyl. In some embodiments, the alkyl of $R^d$ is substituted with oxo and alkyl further substituted with halogen (e.g., fluorine or chlorine). In some embodiments, the alkyl of $R^d$ is substituted with oxo and $C_1$-$C_3$ alkyl. In some embodiments, the alkyl of $R^d$ is substituted with oxo and alkyl further substituted with alkoxy further substituted with oxo and $C_1$-$C_3$ alkyl. In some embodiments, the alkyl of $R^d$ is substituted with alkyl and alkyl further substituted with oxo and amino further substituted with alkyl further substituted with sulfonic acid. In some embodiments, the alkyl of $R^d$ is substituted with oxo and thiol (e.g., thioether) further substituted with $C_1$-$C_3$ alkyl further substituted with halogen (e.g., fluorine or chlorine). In some embodiments, the alkyl of $R^d$ is substituted with —OH. In some embodiments, the alkyl of $R^d$ is substituted with oxo and hydroxyl (e.g., ether) further substituted with $C_1$-$C_3$ alkyl further substituted with halogen (e.g., fluorine or chlorine). In some embodiments, the alkoxy of $R^d$ is substituted with oxo and alkoxy further substituted with alkyl.

In some embodiments, the $C_1$-$C_3$ alkyl is methyl, ethyl, propyl, isopropyl, butyl, or tert-butyl. In some embodiments, the $C_1$-$C_3$ alkyl is methyl. In some embodiments, the $C_1$-$C_3$ alkoxy is methoxy, ethyoxy, propyoxy, or isopropoxy. In some embodiments, the $C_1$-$C_3$ alkyl is methoxy.

In some embodiments, the first radical and the second radical are joined by a linker (e.g., a bond). In some embodiments, the first radical is joined to the second radical through any one of $R^a$, $R^b$, $R^c$, or $R^d$ of the first radical. In some embodiments, the first radical is joined to the second radical through any one of $R^a$, $R^b$, $R^c$, or $R^d$, and the $R^a$, $R^b$, $R^c$, or $R^d$ through which the first radical is joined to the second radical comprises a hydroxyl radical (e.g., when together with the linker or second radical (where the linker is a bond), forms an ether), a thiol radical (e.g., when together with the linker or second radical (where the linker is a bond), forms a thioether), or a carboxylate radical (e.g., when taken together with the linker or second radical (where the linker is a bond), forms an ester or carbonate). In some embodiments, the connection between the thiol radical forms a thioester, a disulfide, or a thiocarbonate. In some embodiments, the connection between the carboxylate radical forms an anhydride. In some embodiments, the first radical is joined to the second radical through any one of $R^a$, $R^b$, $R^c$, or $R^d$, and the $R^a$, $R^b$, $R^c$, or $R^d$ through which the first radical is joined to the second radical comprises an amino radical (e.g., when together with the linker or second radical (where the linker is a bond), forms an amide, carbamate, or thiocarbamate).

In some embodiments, the $R^a$, $R^b$, $R^c$, or $R^d$ through which the first radical is joined to the second radical comprises a hydroxyl radical which together with the linker or with the second radical forms an ether. In some embodiments, the $R^a$, $R^b$, $R^c$, or $R^d$ through which the first radical is joined to the second radical comprises a thiol radical which together with the linker or the second radical forms a thioether. In some embodiments, the $R^a$, $R^b$, $R^c$, or $R^d$ through which the first radical is joined to the second radical comprises a carboxylate radical which together with the linker or the second radical forms an ester or a carbonate.

In some embodiments, the first radical has a structure of Formula (I), Formula (IA), Formula (IB), or Formula (IC) and the second radical does not have a structure of Formula (I), Formula (IA), Formula (IB), or Formula (IC). In some embodiments, the structure of Formula (I), Formula (IA), Formula (IB), or Formula (IC) has a melt and/or glass transition temperature at a temperature of at least 20° C. (e.g., at least 25° C., at least 30° C., at least 37° C., at least 40° C., at least 50° C., at least 100° C., or more) in its free form.

In some embodiments, both the first radical and the second radical consist of the three-membered ring system of Formula (I), Formula (IA), Formula (IB), or Formula (IC). In some embodiments, the first radical is a central nervous system (CNS) agent. In some embodiments, the radical of Formula (I), Formula (IA), Formula (IB), or Formula (IC) is a steroid, an opioid agonist, an opioid antagonist, an adrenergic receptor antagonist (e.g., β-blocker, α-1 blocker), or a serotonergic antagonist (e.g., serotonin 5-HT3 receptor antagonist). In some embodiments, the first radical is an anti-inflammatory agent, an anti-psychotic agent (e.g., typical anti-psychotic, atypicalantipsychotic, schizophrenia, or the like), or the like. In some embodiments, the IOP lowering agent is a beta-blocker. In some embodiments, the beta-blocker is timolol.

In some embodiments, the second radical is an intraocular pressure (IOP) lowering agent. In some embodiments, the first radical is an anti-inflammatory agent and the second radical is an intraocular pressure (IOP) lowering agent. In some embodiments, the first radical is an IOP lowering steroid (e.g., anecortave) or benign steroid (e.g., cholesterol)

and the second radical is an IOP lowering agent. In some embodiments, the IOP lowering agent is a prostaglandin.

In some embodiments, the first radical is a solid (e.g., having a melting point of at least 30° C.) in its free form. In some embodiments, the second radical is a liquid (e.g., having a melting point of less than 30° C.) in its free form. In some embodiments, the first radical is a steroid (e.g., dexamethasone, anecortave, etc.). In some embodiments, the steroid is a corticosteroid (e.g., glucocorticoid or mineralcorticoid), a sex steroid, a neurosteroid, an aminosteroid, or a secosteroid. In some embodiments, the second radical is not a steroid (or does not have a structure of any one of Formula (I), Formula (IA), Formula (IB), or Formula (IC)). In some embodiments, the first radical is a steroid and the second radical is a prostaglandin.

In some embodiments, the second radical has a structure of Formula (II):

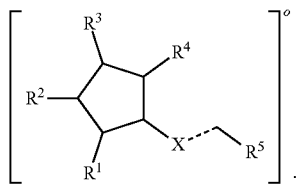

(II)

In some embodiments, $\diagup$ is a single bond or a double bond. In some embodiments, $R^1$, $R^2$, $R^3$, $R^4$, and $R^5$ are each independently selected from one or more of the group consisting of hydrogen, oxo, halo, alkyl, heteroalkyl, cycloalkyl, heterocycloalkyl, alkoxy, amino (e.g., dihydroamino, alkylamino, or arylamino), hydroxyl, and thiol, wherein the alkyl, heteroalkyl, cycloalkyl, and heterocycloalkyl is optionally substituted. In some embodiments, any one of $R^1$, $R^2$, $R^3$, $R^4$, or $R^5$ are taken together to form an optionally substituted cycloalkyl or heterocycloalkyl. In some embodiments, X is selected from the group consisting of —O—, —NR—, —S(R)$_a$—, and —C(R)$_b$—. In some embodiments, a is independently 0-2. In some embodiments, b is independently 1 or 2. Also provided in certain embodiments herein are pharmaceutical salts or solvates of a compound of Formula (II).

In some embodiments, X is S, —C(R)$_1$—, or —C(R)$_2$—. In some embodiments, X is S attached to a single bond. In some embodiments, X is —CH— or —CH$_2$—.

In some embodiments, $R^4$ is alkyl substituted with one or more groups, each group being independently selected from —C(═O)OC$_1$-C$_3$alkyl, —COOH, —CONH$_2$, —CONHC$_1$-C$_3$alkyl, and/or alkyl (e.g., alkylene or alkenyl). In some embodiments, $R^4$ is alkyl substituted with —COOH. In some embodiments, $R^4$ is alkyl substituted with —C(═O)OC$_1$-C$_3$alkyl. In some embodiments, $R^4$ is alkyl substituted with —CONH$_2$. In some embodiments, $R^4$ is alkyl substituted with —CONHC$_1$-C$_3$alkyl. In some embodiments, the alkyl of $R^4$ comprises at least one double bond. In some embodiments, the alkyl of $R^4$ comprises one double bond. In some embodiments, the alkyl of $R^4$ comprises two double bonds. In some embodiments, the two double bonds form an allene.

In some embodiments, $R^5$ is alkyl substituted with one or more groups, each group being independently selected from halogen, —OH, oxo, alkyl (e.g., alkynyl), alkoxy, aryl, and aryloxy, wherein alkyl (e.g., alkynyl), aryl, or aryloxy is optionally substituted. In some embodiments, the alkyl is substituted with one or more groups, each group being independently selected from halogen, —OH, oxo, alkyl (e.g., alkynyl), aryl, or aryloxy, wherein the alkyl (e.g., alkynyl), aryl, or aryloxy is optionally substituted. In some embodiments, the aryl or aryloxy is substituted with one or more halogen groups. In some embodiments, the aryl or aryloxy is unsubstituted.

In some embodiments, the second radical has a structure of Formula (IIA):

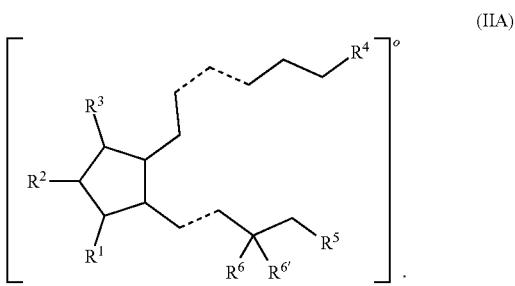

(IIA)

In some embodiments, each $\diagup$ is independently a single bond or a double bond. In some embodiments, $R^1$, $R^2$, $R^3$, $R^4$, and $R^5$ are each independently selected from one or more of the group consisting of hydrogen, oxo, halo, alkyl, heteroalkyl, cycloalkyl, heterocycloalkyl, alkoxy, amino (e.g., dihydroamino, alkylamino, or arylamino), hydroxyl, and thiol, wherein the alkyl, heteroalkyl, cycloalkyl, and heterocycloalkyl is optionally substituted.

In some embodiments, Formula (IIA) comprises three double bonds. In some embodiments, Formula (IIA) comprises two double bonds. In some embodiments, Formula (IIA) comprises one double bond.

In some embodiments, $R^1$ and $R^3$ are each independently —OH or oxo. In some embodiments, $R^1$ is oxo, $R^2$ is hydrogen, and $R^3$ is —OH. In some embodiments, $R^3$ is oxo, $R^2$ is hydrogen, and $R^1$ is —OH. In some embodiments, $R^1$ and $R^3$ are each —OH and $R^2$ is hydrogen.

In some embodiments, $R^4$ is —C(═O)OC$_1$-C$_3$alkyl, —COOH, —CONH$_2$, or —CONHC$_1$-C$_3$alkyl. In some embodiments, $R^4$ is —COOH. In some embodiments, $R^4$ is —CONH$_2$.

In some embodiments, $R^5$ is alkyl or aryloxy, wherein the alkyl and aryloxy are optionally substituted. In some embodiments, $R^5$ is alkyl. In some embodiments, the alkyl is butyl or hexyl. In some embodiments, $R^5$ is alkyl substituted with optionally substituted aryl or optionally substituted alkyl. In some embodiments, the alkyl is substituted with unsubstituted aryl. In some embodiments, the alkyl is substituted with alkyl (e.g., but-2-yne). In some embodiments, $R^5$ is unsubstituted aryloxy. In some embodiments, $R^5$ is aryloxy substituted with one or more alkyl (e.g., —CF$_3$) or halo (fluoro or chloro) groups. In some embodiments, the aryloxy is substituted with —CF$_3$.

In some embodiments, $R^6$ and $R^{6'}$ are each fluoro. In some embodiments, $R^6$ is H or methyl and $R^{6'}$ is —OH. In some embodiments, $R^6$ is H and $R^{6'}$ is —OH. In some embodiments, $R^6$ is methyl and $R^{6'}$ is —OH. In some embodiments, $R^6$ and $R^{6'}$ are taken together to form an oxo.

In some embodiments, $R^3$ and $R^4$ of Formula (II) are taken together to form an optionally substituted cycloalkyl or heterocycloalkyl. In some embodiments, $R^3$ and $R^4$ of Formula (II) are taken together to form heterocycloalkyl substituted with optionally substituted alkyl (e.g., alkenyl). In some embodiments, $R^3$ and $R^4$ of Formula (II) are taken together to form a heterocycloalkyl substituted with alkyl (e.g., alkenyl) substituted with —COOH or —C(═O)OC$_1$-C$_3$alky. In some embodiments, the heterocycloalkyl is substituted with alkyl further substituted with —COOH or —C(═O)OC$_1$-C$_3$alkyl. In some embodiments, the heterocycloalkyl is substituted with alkenyl further substituted with alkyl, which is further substituted with —COOH or —C(═O)OC$_1$-C$_3$alkyl. In some embodiments the alkyl or alkenyl is substituted with —COOH.

In some embodiments, the second radical has a structure of Formula (IIB):

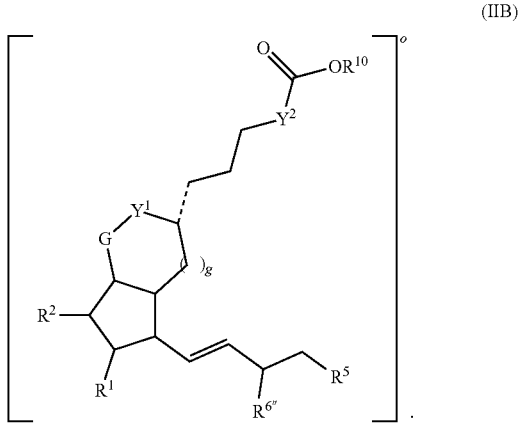

In some embodiments, ⌁ is a single bond or a double bond. In some embodiments, $R^2$, and $R^5$ are each independently selected from one or more of the group consisting of hydrogen, oxo, halo, alkyl, heteroalkyl, cycloalkyl, heterocycloalkyl, alkoxy, amino (e.g., dihydroamino, alkylamino, or arylamino), hydroxyl, and thiol, wherein the alkyl, heteroalkyl, cycloalkyl, and heterocycloalkyl is optionally substituted. In some embodiments, $R^{6''}$ is oxo or —OH. In some embodiments, $Y^1$ and $Y^2$ are each independently a bond or alkylene. In some embodiments, G is O or CH$_2$. In some embodiments, g is 1 or 2. In some embodiments, $R^{10}$ is alkyl or H. Also provided in certain embodiments herein are pharmaceutical salts or solvates of a compound of Formula (IIB).

In some embodiments, G is O and $Y^1$ is a bond. In some embodiments, $Y^2$ is methylene. In some embodiments, g is 1. In some embodiments, G is O and $Y^1$ is a alkylene. In some embodiments, $Y^2$ is a bond. In some embodiments, g is 2.

In some embodiments, $R^1$ is oxo or —OH. In some embodiments, $R^1$ is —OH. In some embodiments, $R^1$ is —OH and $R^2$ is hydrogen. In some embodiments, $R^{6''}$ is —OH. In some embodiments, $R^5$ is alkyl. In some embodiments, $R^5$ is substituted aryl.

In some embodiments, G is O, $Y^1$ is a bond, $Y^2$ is methylene, g is 1, $R^1$ is —OH, $R^2$ is hydrogen, $R^5$ is alkyl, $R^{6''}$ is —OH, and $R^{10}$ is H. In some embodiments, G is O, $Y^1$ is a methylene, $Y^2$ is a bond, g is 2, $R^1$ is —OH, $R^2$ is hydrogen, $R^5$ is substituted aryl, $R^{6''}$ is —OH, and $R^{10}$ is H or C$_1$-C$_3$alkyl.

In some embodiments, $R^5$ is selected from one or more of the group consisting of —O—, —OH, halogen, alkyl (e.g., alkynyl), aryl, wherein the alkyl (e.g., alkynyl) and aryl are optionally substituted with one or more of alkyl (e.g., fluoroalkyl), halogen, and —OH. In some embodiments, $R^5$ is optionally substituted aryl or optionally substituted —O-aryl. In some embodiments, $R^5$ is alkyl or aryloxy, wherein the alkyl and optionally substituted aryloxy. In some embodiments, $R^5$ is alkyl. In some embodiments, the alkyl is butyl or hexyl. In some embodiments, $R^5$ is unsubstituted aryloxy. In some embodiments, the aryloxy is substituted with one or two —F. In some embodiments, $R^5$ is an aryl or O-aryl, each of which is unsubstituted. In some embodiments, $R^5$ is an aryl or O-aryl, each of which is substituted with one or more of halogen or haloalkyl (e.g., trifluoroalkyl, e.g., trifluoromethyl).

In certain embodiments, provided herein is a compound comprising a first radical or a second radical, wherein the first radical has a structure of any one of Formula (I), Formula (IA), Formula (IB), or Formula (IC) and the second radical has a structure of any one of Formula (II), Formula (IIA), or Formula (IIB). In some embodiments, the first radical (e.g., having a structure of any one of Formula (I), Formula (IA), Formula (IB), or Formula (IC)) and the second radical (e.g., Formula (II), Formula (IIA), or Formula (IIB)) are joined by a linker (e.g., hydrolyzable linker). In some embodiments, the linker is a bond.

In certain embodiments, provided herein is a compound comprising a steroid. In some embodiments, provided herein is a compound comprising a prostaglandin. In some embodiments, provided herein is a compound comprising a linker (e.g., hydrolyzable linker). In some embodiments, the linker adjoins (e.g., covalently) the steroid and the prostaglandin. Also provided in certain embodiments herein are pharmaceutical salts or solvates of a compound.

In certain aspects, provided herein is a compound having the structure of Formula (III):

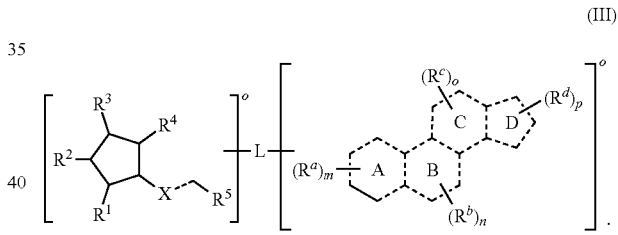

In some embodiments, ⌁ is a single bond or a double bond. In some embodiments, each $R^a$, $R^b$, $R^c$, and $R^d$ are independently selected from the group consisting of oxo, halogen, —CN, —NO$_2$, alkyl, heteroalkyl, cycloalkyl, heterocycloalkyl, alkoxy, amino (e.g., dihydroamino, alkylamino, or arylamino), hydroxy, or thiol, wherein the alkyl, alkynyl, heteroalkyl, cycloalkyl, or heterocycloalkyl is optionally substituted. In some embodiments, any one of $R^a$, $R^b$, $R^c$, and $R^d$ are taken together with another of $R^d$, $R^b$, $R^c$, and $R^d$ to form an substituted or unsubstituted cycloalkyl or heterocycloalkyl. In some embodiments, each of m, n, o, and p are independently 0-6. In some embodiments, $R^1$, $R^2$, $R^3$, $R^4$, and $R^5$ are each independently selected from one or more of the group consisting of hydrogen, oxo, halo, alkyl, heteroalkyl, cycloalkyl, heterocycloalkyl, alkoxy, amino (e.g., dihydroamino, alkylamino, or arylamino), hydroxyl, and thiol, wherein the alkyl, heteroalkyl, cycloalkyl, and heterocycloalkyl is optionally substituted. In some embodiments, L is a linker. Also provided in certain embodiments herein are pharmaceutical salts or solvates of a compound of Formula (III).

In some embodiments, the optional substitution of any one of the groups of Formula (III) are as provided elsewhere herein (e.g., as in for Formula (IB) or Formula (II)).

In certain aspects, provided herein is a compound having the structure of Formula (IV):

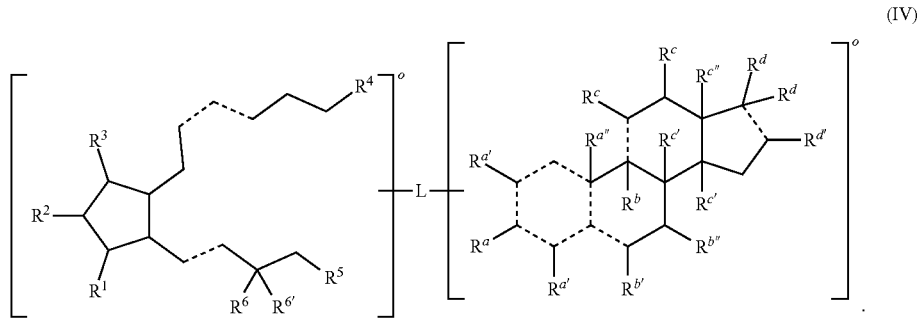

(IV)

In some embodiments, ⌢ is a single bond or a double bond. In some embodiments, $R^a$ is hydrogen, —OH, or oxo. In some embodiments, each $R^{a'}$ is independently selected from hydrogen, —OH, halogen, $C_1$-$C_3$ alkyl, and alkoxy. In some embodiments, $R^{a''}$ is absent, hydrogen, or $C_1$-$C_3$ alkyl. In some embodiments, $R^b$ is absent, hydrogen, halogen, or $C_1$-$C_3$ alkyl. In some embodiments, $R^{b'}$ is hydrogen, halogen, —OH, oxo, or $C_1$-$C_3$ alkyl. In some embodiments, $R^{b''}$ is hydrogen or —OH. In some embodiments, each $R^c$ is independently hydrogen, —OH, oxo, or $C_1$-$C_3$ alkyl. In some embodiments, each $R^{c'}$ is independently hydrogen or $C_1$-$C_3$ alkyl. In some embodiments, $R^{c''}$ is hydrogen, —OH, $C_1$-$C_3$ alkyl, or —C(=O)H. In some embodiments, each $R^d$ is independently hydrogen, —OH, —COOH, alkyl (e.g., alkylene, alkenyl, or alkynyl), heteroalkyl, or each $R^d$ is taken together to form an oxo, wherein the alkyl or heteroalkyl is optionally substituted. In some embodiments, $R^{d'}$ is hydrogen, —OH, $C_1$-$C_3$ alkyl (e.g., alkylene or alkenyl), or heteroalkyl. In some embodiments, one $R^d$ is taken together with $R^{d'}$ to form a substituted or unsubstituted cycloalkyl or heterocycloalkyl. In some embodiments, $R^1$, $R^2$, $R^3$, $R^4$, and $R^5$ are each independently selected from one or more of the group consisting of hydrogen, oxo, halo, alkyl, heteroalkyl, cycloalkyl, heterocycloalkyl, alkoxy, amino (e.g., dihydroamino, alkylamino, or arylamino), hydroxyl, and thiol, wherein the alkyl, heteroalkyl, cycloalkyl, and heterocycloalkyl is optionally substituted. In some embodiments, $R^6$ and $R^{6'}$ are each independently hydrogen, halogen, alkyl, or $R^6$ and $R^{6'}$ are taken together to form an oxo. Also provided in certain embodiments herein are pharmaceutical salts or solvates of a compound of Formula (IV).

In certain aspects, provided herein is a compound having the structure of Formula (V):

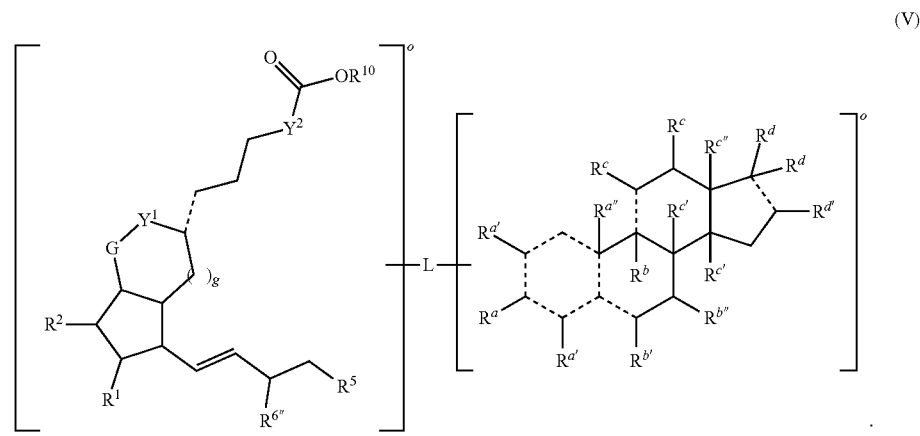

(V)

In some embodiments, ⟋⟋ is a single bond or a double bond. In some embodiments, $R^a$ is hydrogen, —OH, or oxo. In some embodiments, each $R^{a'}$ is independently selected from hydrogen, —OH, halogen, $C_1$-$C_3$ alkyl, and alkoxy. In some embodiments, $R^{a''}$ is absent, hydrogen, or $C_1$-$C_3$ alkyl. In some embodiments, $R^b$ is absent, hydrogen, halogen, or $C_1$-$C_3$ alkyl. In some embodiments, $R^{b'}$ is hydrogen, halogen, —OH, oxo, or $C_1$-$C_3$ alkyl. In some embodiments, $R^{b''}$ is hydrogen or —OH. In some embodiments, each $R^c$ is independently hydrogen, —OH, oxo, or $C_1$-$C_3$ alkyl. In some embodiments, each $R^{c'}$ is independently hydrogen or $C_1$-$C_3$ alkyl. In some embodiments, $R^{c''}$ is hydrogen, —OH, $C_1$-$C_3$ alkyl, or —C(=O)H. In some embodiments, each $R^d$ is independently hydrogen, —OH, —COOH, alkyl (e.g., alkylene, alkenyl, or alkynyl), heteroalkyl, or each $R^d$ is taken together to form an oxo, wherein the alkyl or heteroalkyl is optionally substituted. In some embodiments, $R^{d'}$ is hydrogen, —OH, $C_1$-$C_3$ alkyl (e.g., alkylene or alkenyl), or heteroalkyl. In some embodiments, one $R^d$ is taken together with $R^{d'}$ to form a substituted or unsubstituted cycloalkyl or heterocycloalkyl. In some embodiments, $R^1$, $R^2$, and $R^5$ are each independently selected from one or more of the group consisting of hydrogen, oxo, halo, alkyl, heteroalkyl, cycloalkyl, heterocycloalkyl, alkoxy, amino (e.g., dihydroamino, alkylamino, or arylamino), hydroxyl, and thiol, wherein the alkyl, heteroalkyl, cycloalkyl, and heterocycloalkyl is optionally substituted. In some embodiments, $R^{6''}$ is oxo or —OH. In some embodiments, $Y^1$ and $Y^2$ are each independently a bond or alkylene. In some embodiments, G is O or $CH_2$. In some embodiments, g is 1 or 2. In some embodiments, $R^{10}$ is alkyl or H. In some embodiments, L is a linker. Also provided in certain embodiments herein are pharmaceutical salts or solvates of a compound of Formula (V).

In some embodiments, a hydroxyl radical or a carboxylate radical of any one of Formula (I), Formula (IA), Formula (IB), or Formula (IC) is attached to a hydroxyl radical or a carboxylate radical of another of any one of Formula (I), Formula (IA), Formula (IB), or Formula (IC) through a linker. In some embodiments, a hydroxyl radical or a carboxylate radical of any one of Formula (I), Formula (IA), Formula (IB), or Formula (IC) is attached to a hydroxyl radical or a carboxylate radical of any one of Formula (II), Formula (IIA), or Formula (IIB) through a linker. In some embodiments, a hydroxyl radical of any one of Formula (I), Formula (IA), Formula (IB), or Formula (IC) is attached to a hydroxyl radical of any one of Formula (II), Formula (IIA), or Formula (IIB) through a linker. In some embodiments, a hydroxyl radical of any one of Formula (I), Formula (IA), Formula (IB), or Formula (IC) is attached to a carboxylate radical of any one of Formula (II), Formula (IIA), or Formula (IIB) through a linker. In some embodiments, a carboxylate radical of any one of Formula (I), Formula (IA), Formula (IB), or Formula (IC) is attached to a hydroxyl radical of any one of Formula (II), Formula (IIA), or Formula (IIB) through a linker. In some embodiments, a carboxylate radical of any one of Formula (I), Formula (IA), Formula (IB), or Formula (IC) is attached to a carboxylate radical of any one of Formula (II), Formula (IIA), or Formula (IIB) through a linker. In some embodiments, the linker is a bond. In some embodiments, the linker is oxo.

In some embodiments, any one of $R^a$, $R^{a'}$, $R^b$, $R^{b'}$, $R^c$, $R^{c'}$, $R^d$, or $R^{d'}$ is an ester radical, a hydroxyl radical, a carboxylate radical, and any one of $R^1$, $R^2$, $R^3$, $R^4$, $R^5$, $R^6$, $R^{6'}$, $R^{6''}$, or $R^{10}$ is an amide radical, a thiol radical, a hydroxyl radical, or a carboxylate radical. In some embodiments, any one of $R^a$, $R^{a'}$, $R^b$, $R^{b'}$, $R^{b''}$, $R^{c''}$, $R^d$, or $R^{d'}$ is an ester radical, a hydroxyl radical, or a carboxylate radical, and any one of $R^1$, $R^2$, $R^3$, $R^4$, $R^5$, $R^6$, $R^{6'}$, $R^{6''}$, or $R^{10}$ is a hydroxyl radical or a carboxylate radical. In some embodiments, any radical of $R^a$, $R^{a'}$, $R^b$, $R^{b'}$, $R^c$, $R^{c''}$, $R^d$, or $R^{d'}$ is adjoined to any radical of $R^1$, $R^2$, $R^3$, $R^4$, $R^5$, $R^6$, $R^{6'}$, $R^{6''}$, or $R^{10}$ by a linker. In some embodiments, any radical of $R^a$, $R^{a'}$, $R^b$, $R^{b''}$, $R^c$, $R^{c''}$, $R^d$, or $R^{d'}$ is adjoined to any radical of $R^4$, $R^5$, $R^6$, $R^{6'}$, $R^{6''}$, or $R^{10}$ by a linker. In some embodiments, any radical of $R^a$, $R^b$, $R^c$, or $R^d$ is adjoined to any radical of $R^4$, $R^5$, $R^6$, $R^{6'}$, $R^{6''}$, or $R^{10}$ by a linker. In some embodiments, any radical of $R^d$ or $R^{d'}$ is adjoined to any radical of $R^4$, $R^5$, $R^6$, $R^{6'}$, $R^{6''}$, or $R^{10}$ by a linker. In some embodiments, a radical of $R^d$ is adjoined to any radical of $R^4$, $R^6$, $R^{6'}$, $R^{6''}$, or $R^{10}$ by a linker. In some embodiments, a radical of $R^d$ is adjoined to a radical of $R^4$ or $R^{10}$ by a linker. In some embodiments, a radical of of $R^d$ is adjoined to any radical of $R^6$, $R^{6'}$, or $R^{6''}$ by a linker. In some embodiments, the linker is oxo. In some embodiments, the linker is a bond.

In some embodiments, the linker is a bond, alkyl, heteroalkyl, or alkoxy, wherein the alkyl, heteroalkyl, or alkoxy is optionally substituted. In some embodiments, the alkyl, heteroalkyl, or alkoxy are each independently substituted with one or more groups, each group being independently selected from the group consisting of —O—, —S—, silicone, amino, optionally substituted alkyl (e.g., alkenyl, alkynyl, branched (e.g., polypropylene), haloalkyl), optionally substituted heteroalkyl (e.g., polyTHF), and optionally substituted cycloalkyl. In some embodiments, the linker is alkyl (alkylene) and the alkyl (alkylene) is substituted with one or more groups selected from —OH, halo, oxo, alkyl, heteroalkyl, cycloalkyl, and heterocycloalkyl. In some embodiments, the linker is an unsubstituted alkyl (alkylene). In some embodiments, the linker is heteroalkyl (heteroalkylene) and the heteroalkyl (heteroalkylene) is substituted with one or more groups selected from halo or alkyl. In some embodiments, the linker is unsubstituted heteroalkyl (heteroalkylene). In some embodiments, the linker is a bond.

In some embodiments, the linker comprises one or more linker group, each linker group being independently selected from a bond, alkyl, cycloalkyl, heteroalkyl, or alkoxy, wherein the alkyl, cycloalkyl, heteroalkyl, or alkoxy is optionally substituted. In some embodiments, the linker is a bond, alkyl, cycloalkyl, heteroalkyl, or alkoxy, wherein the alkyl, cycloalkyl, heteroalkyl, or alkoxy is optionally substituted. In some embodiments, the alkyl, cycloalkyl, heteroalkyl, or alkoxy are each independently substituted with one or more substitutent, each substituent being independently selected from the group consisting of —O— (e.g., —OH), —S— (e.g., —SH), silicone, amino, optionally substituted alkyl (e.g., alkenyl, alkynyl, branched (e.g., polypropylene), haloalkyl), optionally substituted heteroalkyl (e.g., polyTHF), and optionally substituted cycloalkyl. In some embodiments, the linker comprises one or more linker group, each linker group being independently selected from alkyl (alkylene) and cycloalkyl (cycloalkylene). In some embodiments, the linker is alkyl (alkylene) or cycloalkyl (cycloalkylene). In some embodiments, the alkyl (alkylene) or cycloalkyl (cycloalkylene) is unsubstituted or substituted with one or more substituent, each substituent being independently selected from the group consisting of —OH, halo, oxo, alkyl, heteroalkyl, cycloalkyl, and heterocycloalkyl. In some embodiments, the linker comprises an unsubstituted or substituted alkylene-cycloalkylene-alkylene.

In some embodiments, the linker comprises at least one oxo. In some embodiments, the linker is oxo. In some embodiments, the linker comprises at least one carbamate. In some embodiments, the linker is a carbamate. In some embodiments, the linker comprises at least one ester. In some embodiments, the linker is an ester.

In some embodiments, the linker comprises one or more linker groups selected from oxo, —O—, —S—, unsubstituted alkylene, C=O(CH$_2$CH$_2$)$_n$C=O, C=O(CHCH)$_n$C=O, C=O(OCH$_2$CH$_2$O)$_n$C=O, O(CH$_2$CH$_2$O)$_n$, and C=O(CH$_2$CH$_2$O)$_n$, (CH(CH$_3$)C(=O)O)$_n$, wherein n is 1-20. In some embodiments, the linker is a bond, unsubstituted alkylene, C=O(CH$_2$CH$_2$)$_n$C=O, C=O(CHCH)$_n$C=O, C=O(OCH$_2$CH$_2$O)$_n$C=O, O(CH$_2$CH$_2$O)$_n$, C=O(CH$_2$CH$_2$O)$_n$, (CH(CH$_3$)C(=O)O)$_n$, and C=O(CH$_2$CH$_2$)$_n$C=O(CH(CH$_3$)C(=O)O)$_n$, wherein n is 1-20. In some embodiments, n is 1-10. In some embodiments, n is 6. In some embodiments, n is 5. In some embodiments, n is 4. In some embodiments, n is 3. In some embodiments, n is 2. In some embodiments, n is 1.

In some embodiments, the linker comprises one or more linker group, each linker group being independently selected from the group consisting of a bond, —O—, —O(C=O)—, —O(C=O)—O—, —S—, unsubstituted alkylene, unsubstituted cycloalkylene, C=O(CH$_2$CH$_2$)$_n$C=O, C=O(CHCH)$_n$C=O, C=O(OCH$_2$CH$_2$O)$_n$C=O, O(CH$_2$CH$_2$O)$_n$, and C=O(CH$_2$CH$_2$O)$_n$, and (CH(CH$_3$)C(=O)O)$_n$, wherein n is 1-20. In some embodiments, the linker is a bond, unsubstituted alkylene, unsubstituted alkylene-cycloalkylene-alkylene, C=O(CH$_2$CH$_2$)$_n$C=O, C=O(CHCH)$_n$C=O, C=O(OCH$_2$CH$_2$O)$_n$C=O, O(CH$_2$CH$_2$O)$_n$, and C=O(CH$_2$CH$_2$O)$_n$, (CH(CH$_3$)C(=O)O)$_n$, C=O(CH$_2$CH$_2$)$_n$C=O(CH(CH$_3$)C(=O)O)$_n$, wherein n is 1-20. In some embodiments, n is 1-10. In some embodiments, n is 6. In some embodiments, n is 5. In some embodiments, n is 4. In some embodiments, n is 3. In some embodiments, n is 2. In some embodiments, n is 1.

In some embodiments, the linker is hydrolyzed in a buffered solution. In some embodiments, the linker is hydrolytically labile. In some embodiments, the linker is hydrolyzed by water. In some embodiments, the linker is hydrolyzed by an enzyme. In some embodiments, the enzyme is a hydrolase (e.g., a protease or an esterase). In some embodiments, the enzyme is an esterase.

In some embodiments, the first radical is a (e.g., hydroxyl or carboxyl) radical of a compound selected from the group consisting of:

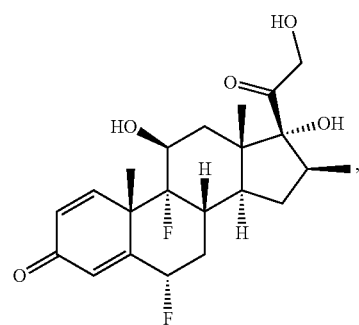

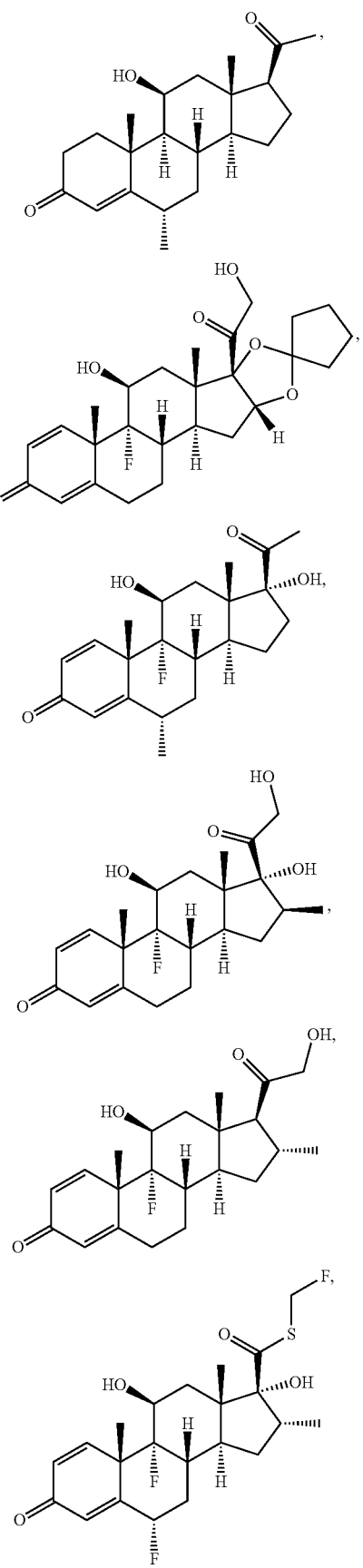

-continued
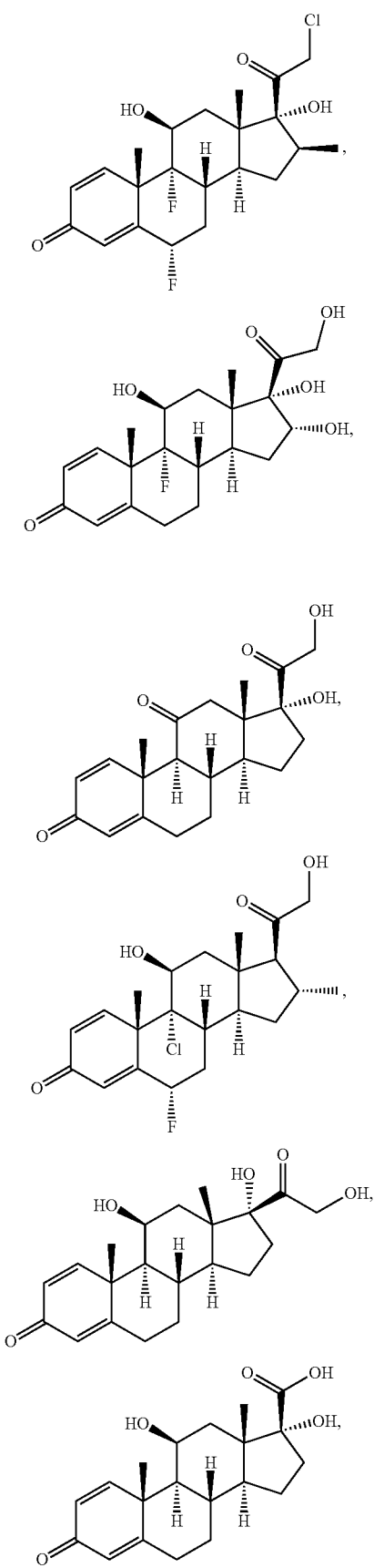
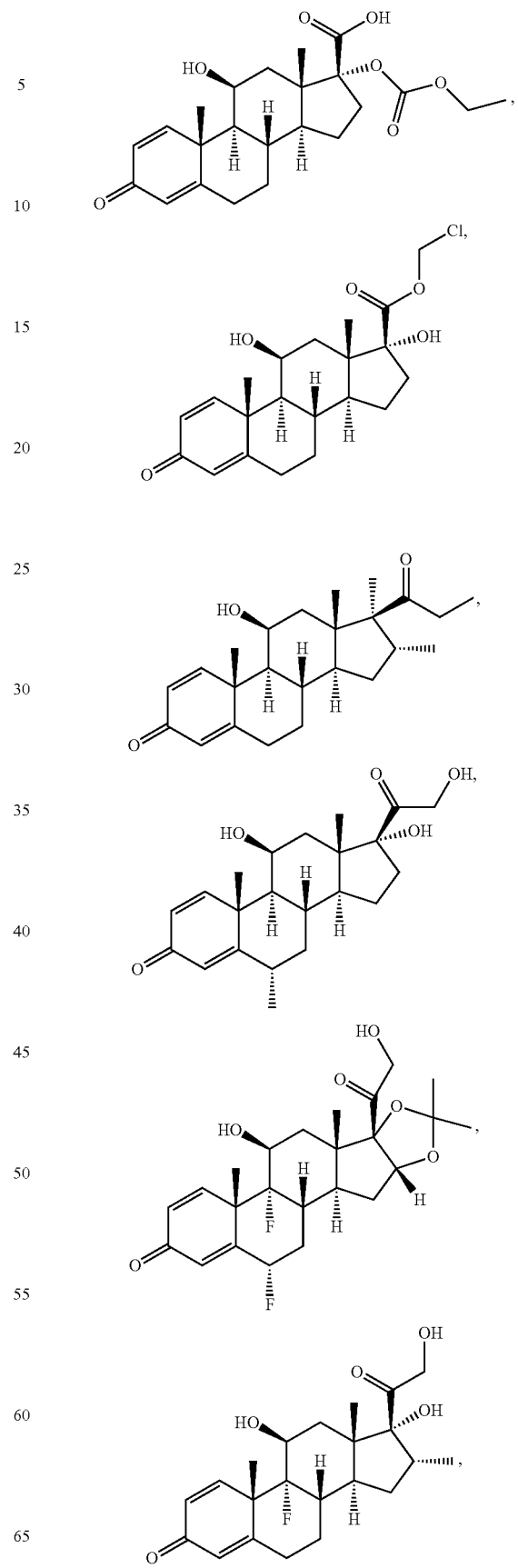

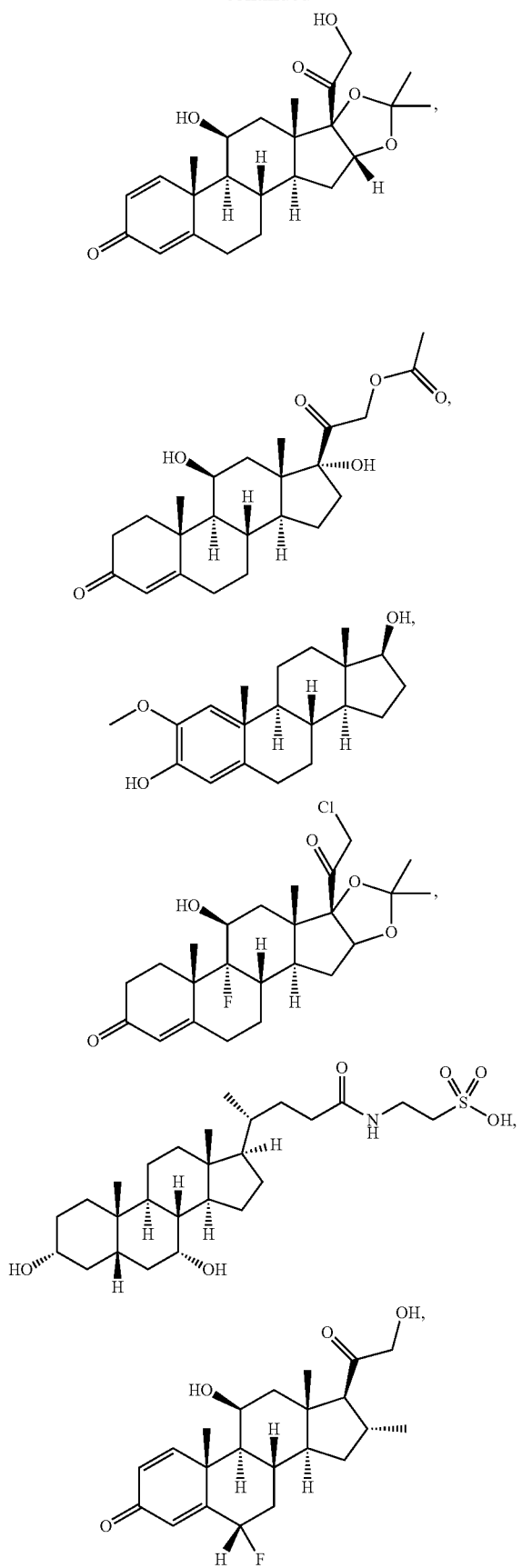
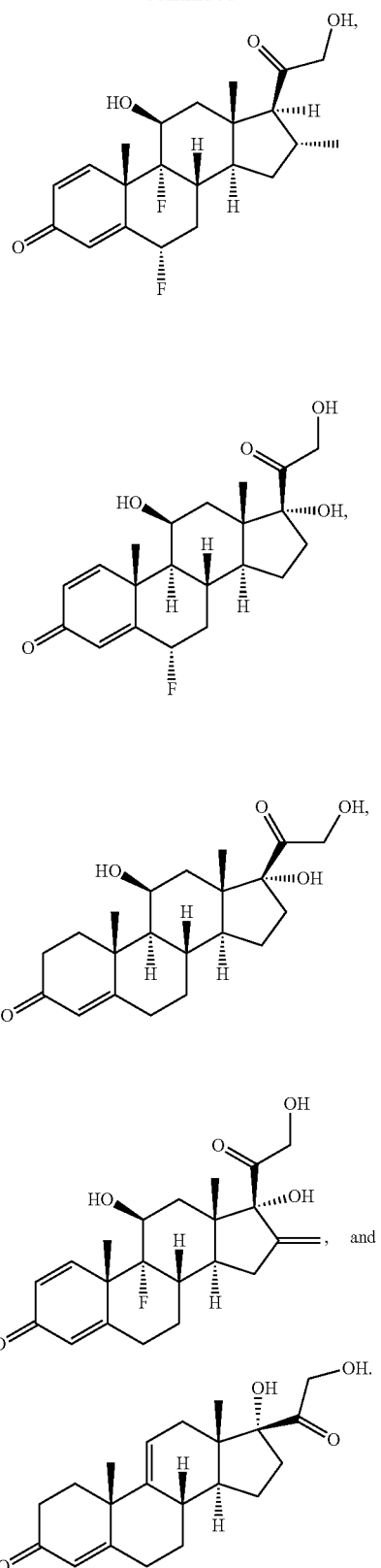
In some embodiments, the first radical is a (e.g., hydroxyl or carboxyl) radical of a compound selected from the group consisting of:

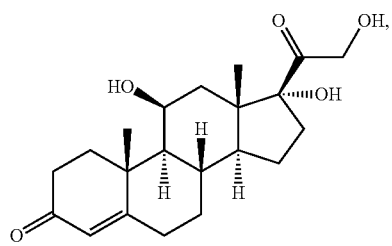
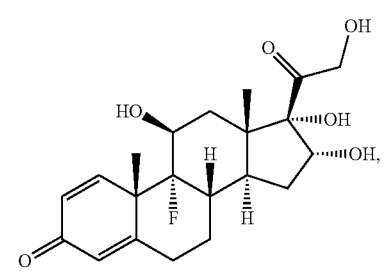
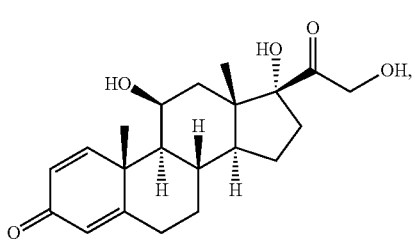
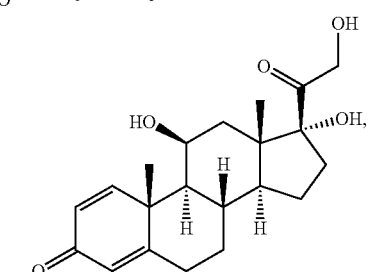
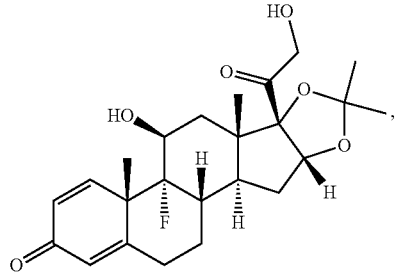
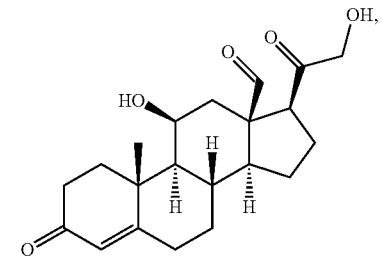
-continued
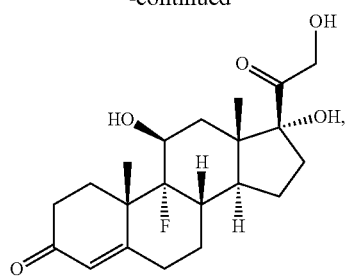
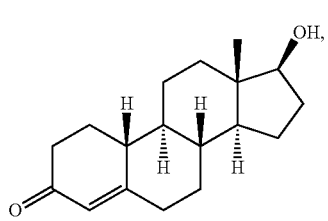
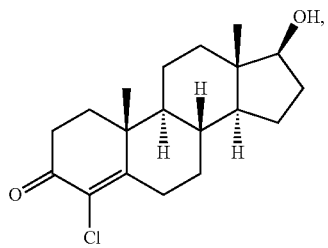
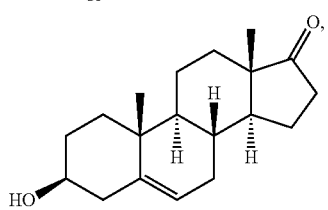
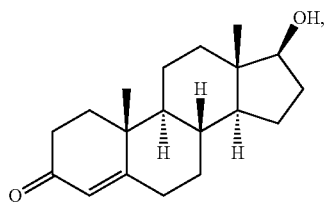
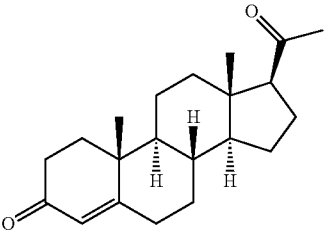
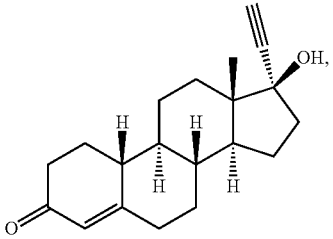

-continued
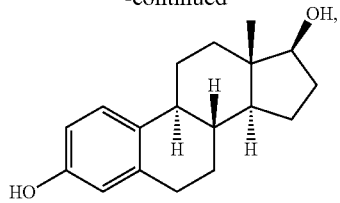
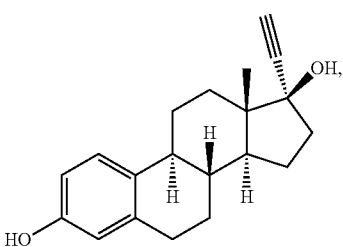
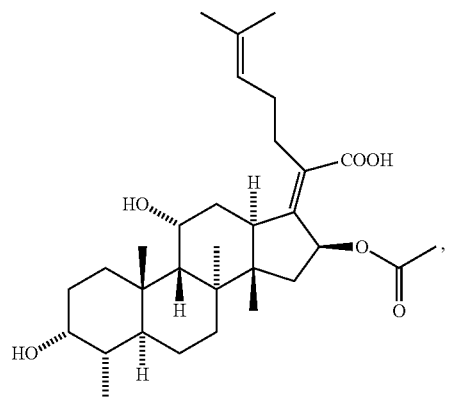
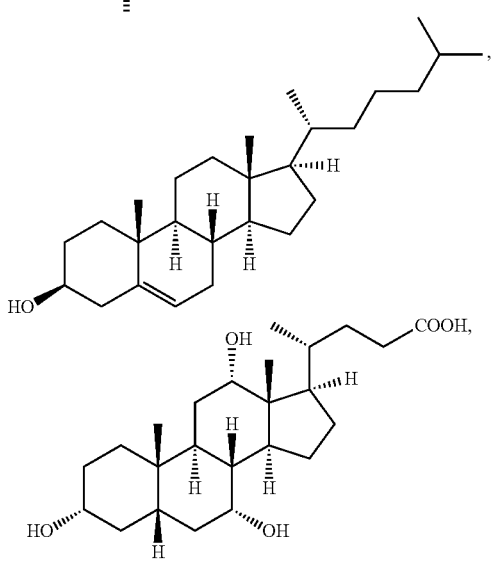
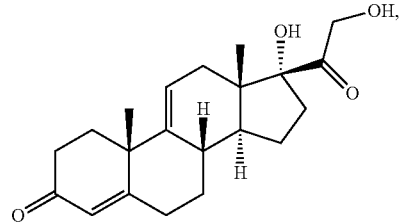
-continued
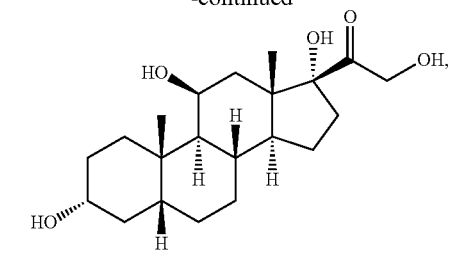
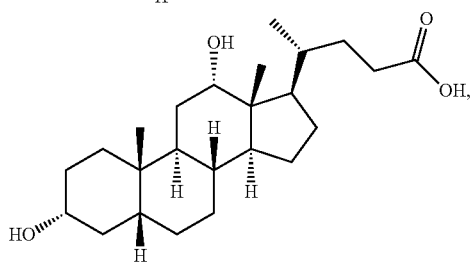
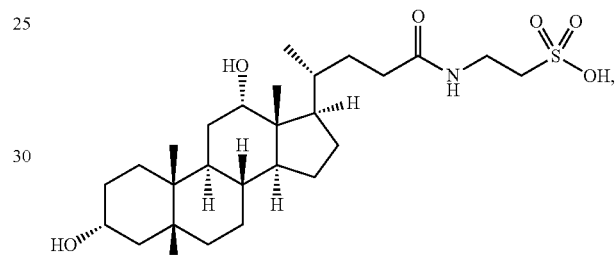
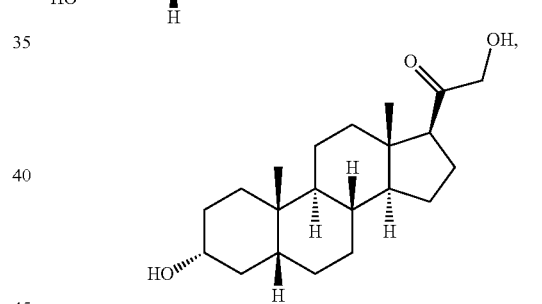
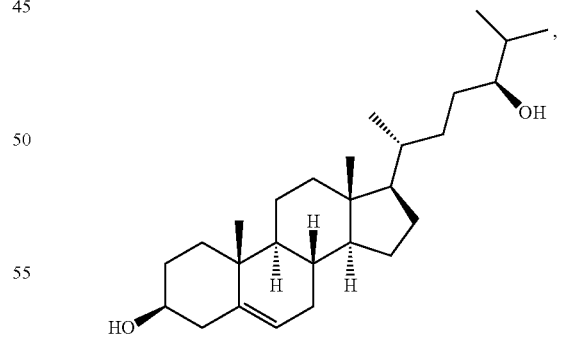
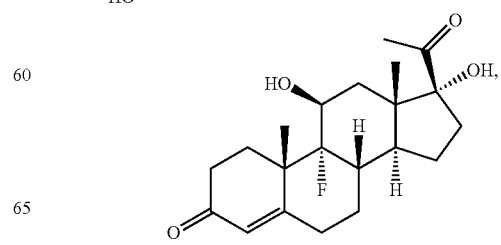

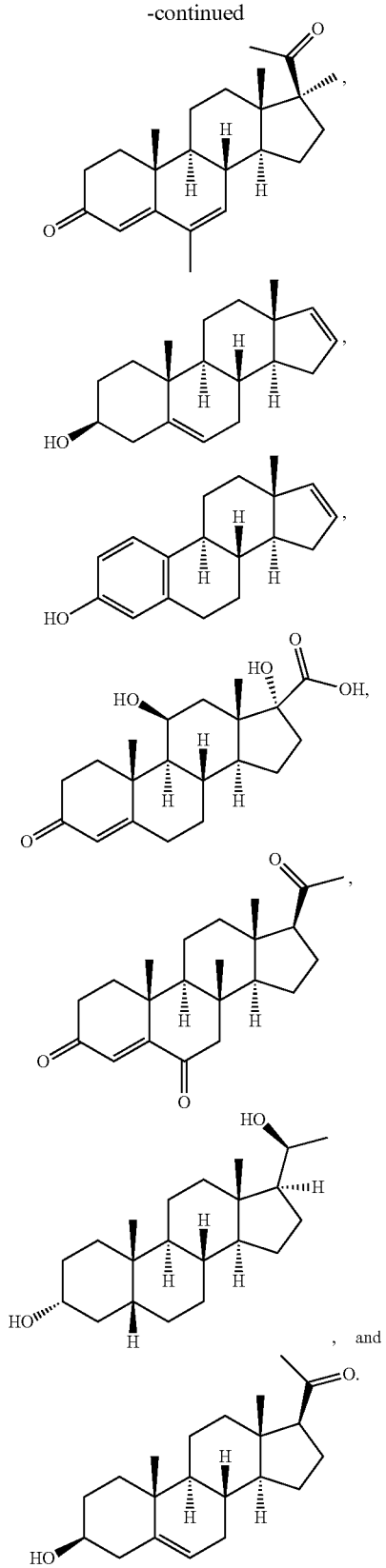
In some embodiments, the second radical is a (e.g., hydroxyl or carboxyl) radical of a compound selected from the group consisting of:

In some embodiments, the second radical is a (e.g., hydroxyl or carboxyl) radical of a compound selected from the group consisting of:

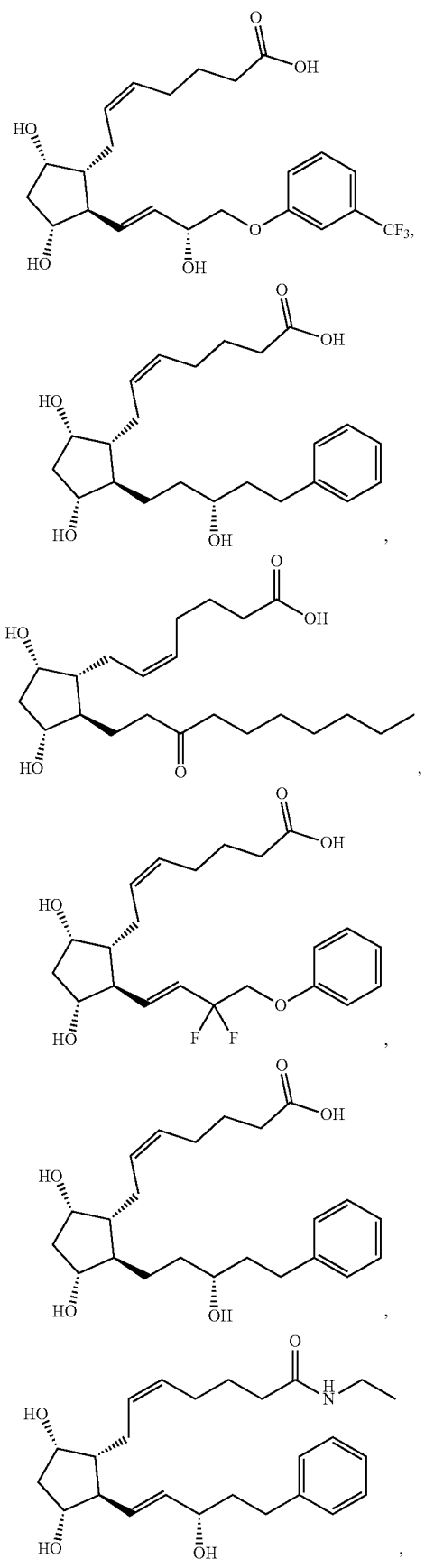

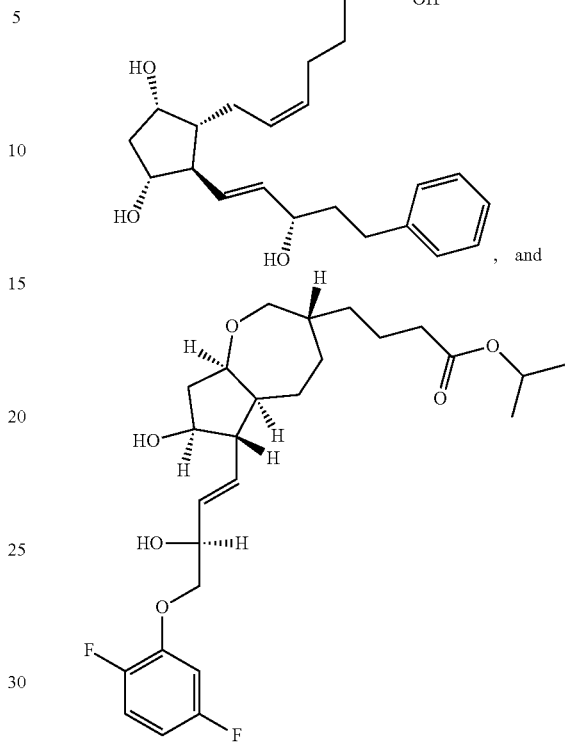

, and

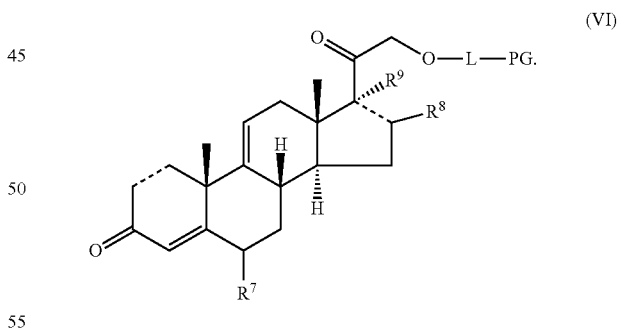

In some embodiments, the first radical is a hydroxyl radial. In some embodiments, the second radical is a hydroxyl radial. In some embodiments, the first radical is a carboxyl radical. In some embodiment, the second radical is a carboxyl radical.

In certain embodiments, provided herein is a compound having the structure of Formula (VI):

(VI)

In some embodiments, ⌒ is a single bond or a double bond. In some embodiments, $R^7$ is hydrogen or halogen. In some embodiments, $R^7$ is hydrogen. In some embodiments, $R^7$ is fluoro. In some embodiments, $R^8$ is a hydrogen or a $C_1$-$C_4$ alkyl. In some embodiments, $R^8$ is hydrogen. In some embodiments, $R^8$ is methyl, ethyl, propyl or butyl. In some embodiments, $R^8$ is methyl, ethyl, or butyl. In some embodiments, $R^8$ is methyl. In some embodiments, $R^7$ is hydrogen and $R^8$ is methyl. In some embodiments, $R^9$ is absent, hydrogen or hydroxyl. In some embodiments, $R^9$ is hydrogen. In some embodiments, $R^9$ is hydroxyl. In some embodiments, $R^9$ is absent. In some embodiments, L is a linker. In some embodiments, L is a linker described herein. In some embodiments, L is a bond. In some embodiments, L comprises one or more linker group, each linker group being independently selected from the group consisting of an alkylene, cycloalkylene and —O—. In some embodiments, PG is a prostaglandin radical. Also provided in certain embodiments herein are pharmaceutically-acceptable salts or solvates of a compound of Formula (VI).

In some embodiments, a compound provided herein has the structure of formula (VI-A):

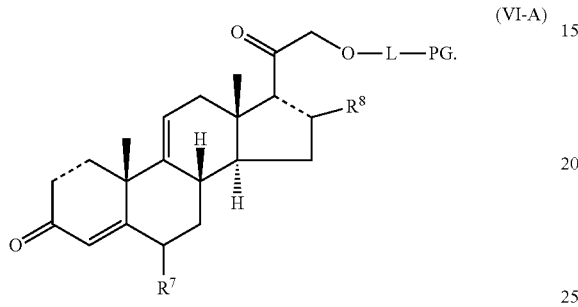

(VI-A)

In some embodiments, ⟶ is a single bond or a double bond. In some embodiments, $R^7$ is hydrogen or halogen. In some embodiments, $R^7$ is hydrogen. In some embodiments, $R^7$ is fluoro. In some embodiments, $R^8$ is a hydrogen or a $C_1$-$C_4$ alkyl. In some embodiments, $R^8$ is hydrogen. In some embodiments, $R^8$ is methyl, ethyl, propyl or butyl. In some embodiments, $R^8$ is methyl, ethyl, or butyl. In some embodiments, $R^8$ is methyl. In some embodiments, $R^7$ is hydrogen and $R^8$ is methyl. In some embodiments, L is a linker. In some embodiments, L is a bond. In some embodiments, L comprises one or more linker group, each linker group being independently selected from the group consisting of an alkylene, cycloalkylene or —O—. In some embodiments, PG is a prostaglandin radical. Also provided in certain embodiments herein are pharmaceutically-acceptable salts or solvates of a compound of Formula (VI-A).

In some embodiments, a compound provided herein has the structure of formula (VI-B):

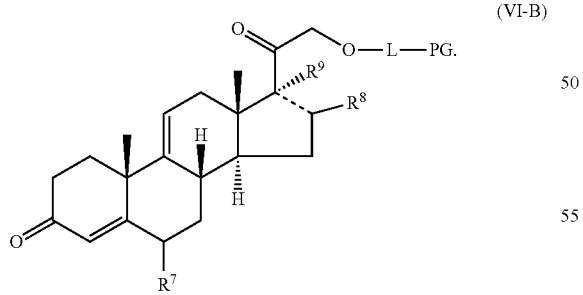

(VI-B)

In some embodiments, ⟶ is a single bond or a double bond. In some embodiments, $R^7$ is hydrogen or halogen. In some embodiments, $R^7$ is hydrogen. In some embodiments, $R^7$ is fluoro. In some embodiments, $R^8$ is a hydrogen or a $C_1$-$C_4$ alkyl. In some embodiments, $R^8$ is hydrogen. In some embodiments, $R^8$ is methyl, ethyl, propyl or butyl. In some embodiments, $R^8$ is methyl, ethyl, or butyl. In some embodiments, $R^8$ is methyl. In some embodiments, $R^7$ is hydrogen and $R^8$ is methyl. In some embodiments, $R^9$ is absent, hydrogen or hydroxyl. In some embodiments, $R^9$ is hydrogen. In some embodiments, $R^9$ is hydroxyl. In some embodiments, $R^9$ is absent. In some embodiments, L is a linker. In some embodiments, L is a bond. In some embodiments, L comprises one or more linker group, each linker group being independently selected from the group consisting of an alkylene, cycloalkylene or —O—. In some embodiments, PG is a prostaglandin radical. Also provided in certain embodiments herein are pharmaceutically-acceptable salts or solvates of a compound of Formula (VI-B).

In some embodiments, a compound provided herein has the structure of formula (VI-C):

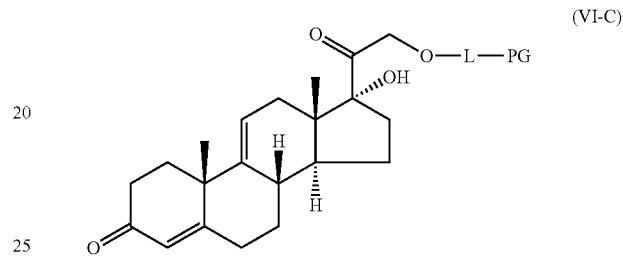

(VI-C)

In some embodiments, L is a linker. In some embodiments, L is a bond. In some embodiments, L comprises one or more linker group, each linker group being independently selected from the group consisting of an alkylene, cycloalkylene or —O—. In some embodiments, PG is a prostaglandin radical. Also provided in certain embodiments herein are pharmaceutically-acceptable salts or solvates of a compound of Formula (VI-B).

In certain embodiments, provided herein is a compound having a prostaglandin (PG) radical of the formula (VII).

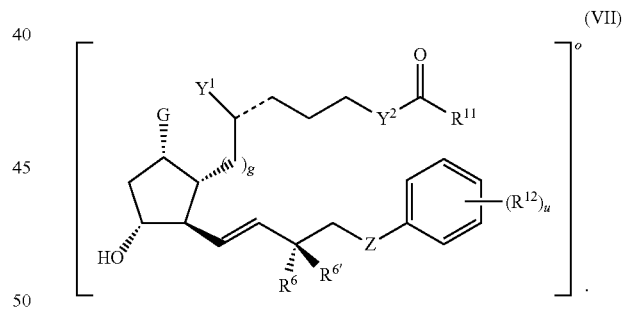

(VII)

In some embodiments, ⟶ is a single bond or a double bond. In some embodiments, G is OH and $Y^1$ is hydrogen. In some embodiments, G together with $Y^1$ form —O—$CH_2$—. In some embodiments, $Y^2$ is a bond or —$CH_2$—. In some embodiments, g is 1 or 2. In some embodiments, Z is —O— or —$CH_2$—. In some embodiments, $R^6$ and $R^{6'}$ are each independently hydrogen, halogen or OH. In some embodiments, $R^{11}$ is —$OR^{13}$, or —$NR^{13'}R^{13''}$. In some embodiments, $R^{13}$, $R^{13'}$ and $R^{13''}$ are each independently hydrogen or a $C_1$-$C_3$ alkyl. In some embodiments, each $R^{12}$ is independently halogen or haloalkyl. In some embodiments, u is 0-5. In some embodiments, $R^6$ and $R^{6'}$ are each fluoro. In some embodiments, $R^6$ is OH and $R^{6'}$ is hydrogen. In some embodiments, Z is —O—. In some embodiments, Z is —$CH_2$—. In some embodiments, each $R^{12}$ is F and u is 2. In some embodiments, $CF_3$ and u is 1. In some embodiments, u is 0. In some embodiments, u is 1. In some embodiments, u is 2. In some embodiments, u is 3. In some embodiments, u is 4. In some embodiments, u is 5. In some embodiments, $R^{11}$ is OH. In some embodiments, $R^{11}$ is —NHCH$_2$CH$_3$. In some embodiments, $R^{11}$ is —OCH(CH$_3$)$_2$.

In some embodiments, the prostaglandin (PG) radical provided herein has the formula (VII-A):

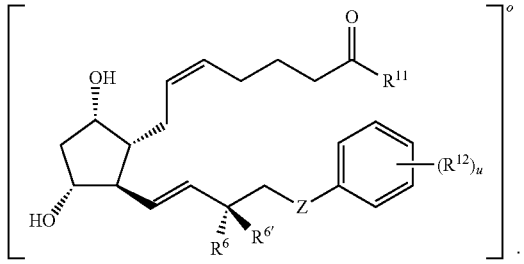

(VII-A)

In some embodiments, Z is —O— or —CH$_2$—. In some embodiments, $R^6$ and $R^{6'}$ are each independently hydrogen, halogen or OH. In some embodiments, $R^{11}$ is —OR$^{13}$, or —NR$^{13'}$R$^{13''}$. In some embodiments, $R^{13}$, $R^{13'}$ and $R^{13''}$ are each independently hydrogen or a C$_1$-C$_3$ alkyl. In some embodiments, each $R^{12}$ is independently halogen or haloalkyl. In some embodiments, u is 0-5. In some embodiments, $R^6$ and $R^{6'}$ are each independently fluoro. In some embodiments, $R^6$ is OH and $R^{6'}$ is hydrogen. In some embodiments, Z is —O—. In some embodiments, Z is —CH$_2$—. In some embodiments, $R^{12}$ is F and u is 2. In some embodiments, CF$_3$ and u is 1. In some embodiments, u is 0. In some embodiments, u is 1. In some embodiments, u is 2. In some embodiments, u is 3. In some embodiments, u is 4. In some embodiments, u is 5. In some embodiments, $R^{11}$ is OH. In some embodiments, $R^{11}$ is —NHCH$_2$CH$_3$. In some embodiments, $R^{11}$ is —OCH(CH$_3$)$_2$.

In some embodiments, the prostaglandin (PG) radical has the formula (VII-B):

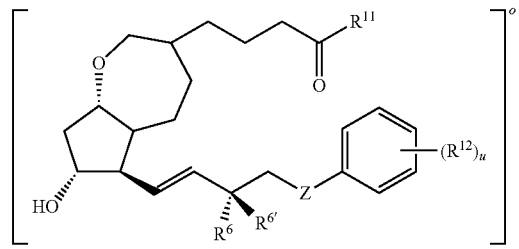

(VII-B)

In some embodiments, Z is —O— or —CH$_2$—. In some embodiments, $R^6$ and $R^{6'}$ are each independently hydrogen, halogen or OH. In some embodiments, $R^{11}$ is —OR$^{13}$, or —NR$^{13'}$R$^{13''}$. In some embodiments, $R^{13}$, $R^{13'}$ and $R^{13''}$ are each independently hydrogen or a C$_1$-C$_3$ alkyl. In some embodiments, each $R^{12}$ is independently halogen or haloalkyl. In some embodiments, u is 0-5. In some embodiments, $R^6$ and $R^{6'}$ are each independently fluoro. In some embodiments, $R^6$ is OH and $R^{6'}$ is hydrogen. In some embodiments, Z is —O—. In some embodiments, Z is —CH$_2$—. In some embodiments, $R^{12}$ is F and u is 2. In some embodiments, CF$_3$ and u is 1. In some embodiments, u is 0. In some embodiments, u is 1. In some embodiments, u is 2. In some embodiments, u is 3. In some embodiments, u is 4. In some embodiments, u is 5. In some embodiments, $R^{11}$ is OH. In some embodiments, $R^{11}$ is —NHCH$_2$CH$_3$. In some embodiments, $R^{11}$ is —OCH(CH$_3$)$_2$.

In some embodiments, the radical (e.g., a PG radical) is attached to a linker (e.g., L) provided herein. In some embodiments, the PG radical is attached to a linker (e.g., L) and the linker is further attached to a steroid radical (e.g., provided herein). In some embodiments, $R^{11}$ is a radical (e.g., a hydroxyl radical or an amino radical) attached to a linker (e.g., a radical of a linker) provided herein (e.g., and the linker (e.g., another radical of the linker) is further attached to a steroid radical provided herein). In some embodiments, $R^6$ or $R^{6'}$ is a radical (e.g., a hydroxyl radical) attached to a linker (e.g., a radical of a linker) provided herein (e.g., and the linker (e.g., another radical of the linker) is further attached to a steroid radical provided herein).

In certain embodiments, provided herein is a compound having the structure of Formula (VIII):

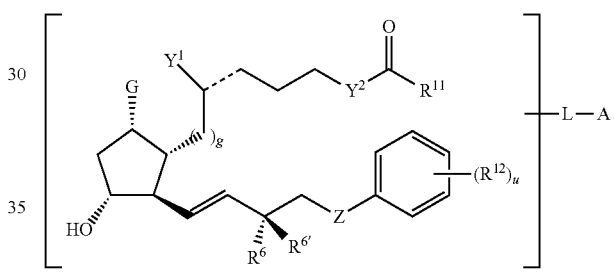

(VIII)

In some embodiments, ⌇ is a single bond or a double bond. In some embodiments, L is a linker. In some embodiments, A is a steroid radical. In some embodiments, G is OH and $Y^1$ is hydrogen. In some embodiments, G together with $Y^1$ form —O—CH$_2$—. In some embodiments, $Y^2$ is a bond or —CH$_2$—. In some embodiments, g is 1 or 2. In some embodiments, Z is —O— or —CH$_2$—. In some embodiments, $R^6$ and $R^{6'}$ are each independently hydrogen, halogen or OH. In some embodiments, $R^{11}$ is —OR$^{13}$ or —NR$^{13'}$R$^{13''}$. In some embodiments, each $R^{12}$ is independently halogen or haloalkyl. In some embodiments, $R^{13}$, $R^{13'}$ and $R^{13''}$ are each independently hydrogen or a C$_1$-C$_3$ alkyl. In some embodiments, u is 0-5. In some embodiments, $R^6$ and $R^{6'}$ are each independently fluoro. In some embodiments, $R^6$ is OH and $R^{6'}$ is hydrogen. In some embodiments, Z is —O—. In some embodiments, Z is —CH$_2$—. In some embodiments, $R^{12}$ is F and u is 2. In some embodiments, $R^{12}$ is CF$_3$ and u is 1. In some embodiments, u is 0. In some embodiments, u is 1. In some embodiments, u is 2. In some embodiments, u is 3. In some embodiments, u is 4. In some embodiments, u is 5. In some embodiments, $R^{11}$ is OH. In some embodiments, $R^{11}$ is —NHCH$_2$CH$_3$. In some embodiments, $R^{11}$ is —OCH(CH$_3$)$_2$. Provided in certain embodiments herein are pharmaceutically-acceptable salts or solvates of a compound of Formula (VIII).

In certain embodiments, provided herein is a compound having the structure of Formula (VIII-A):

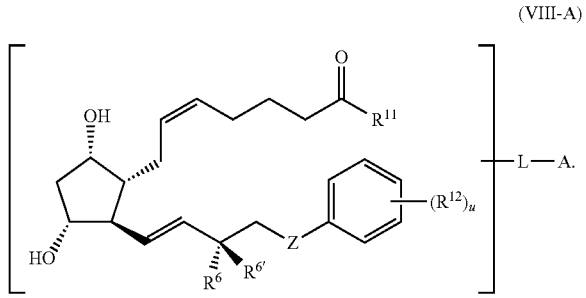

(VIII-A)

In some embodiments, L is a linker. In some embodiments, A is a steroid radical. In some embodiments, Z is —O— or —CH$_2$—. In some embodiments, R$^6$ and R$^{6'}$ are each independently hydrogen, halogen or OH; R$^{11}$ is —OR$^{13}$, or —NR$^{13'}$R$^{13''}$. In some embodiments, each R$^{12}$ is independently halogen or haloalkyl. In some embodiments, R$^{13}$, R$^{13'}$ and R$^{13''}$ are each independently hydrogen or a C$_1$-C$_3$ alkyl. In some embodiments, u is 0-5. In some embodiments, R$^6$ and R$^{6'}$ are each independently fluoro. In some embodiments, R$^6$ is OH and R$^{6'}$ is hydrogen. In some embodiments, Z is —O—. In some embodiments, Z is —CH$_2$—. In some embodiments, R$^{12}$ is F and u is 2. In some embodiments, R$^{12}$ is CF$_3$ and u is 1. In some embodiments, u is 0. In some embodiments, u is 1. In some embodiments, u is 2. In some embodiments, u is 3. In some embodiments, u is 4. In some embodiments, u is 5. In some embodiments, R$^{11}$ is OH. In some embodiments, R$^{11}$ is —NHCH$_2$CH$_3$. In some embodiments, R$^{11}$ is —OCH(CH$_3$)$_2$. Provided in certain embodiments herein are pharmaceutically-acceptable salts or solvates of a compound of Formula (VIII-A).

In certain embodiments, provided herein is a compound having the structure of Formula (VIII-B):

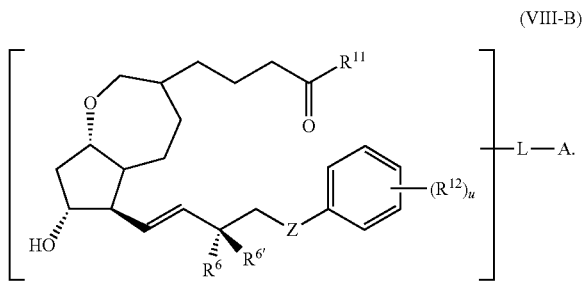

(VIII-B)

In some embodiments, L is a linker. In some embodiments, A is a steroid radical. In some embodiments, Z is —O— or —CH$_2$—. In some embodiments, R$^6$ and R$^{6'}$ are each independently hydrogen, halogen or OH. In some embodiments, R$^{11}$ is —OR$^{13}$, or —NR$^{13'}$R$^{13''}$. In some embodiments, each R$^{12}$ is independently halogen or haloalkyl. In some embodiments, R$^{13}$, R$^{13'}$ and R$^{13''}$ are each independently hydrogen or a C$_1$-C$_3$ alkyl. In some embodiments, u is 0-5. In some embodiments, R$^6$ and R$^{6'}$ are each independently fluoro. In some embodiments, R$^6$ is OH and R$^{6'}$ is hydrogen. In some embodiments, Z is —O—. In some embodiments, Z is —CH$_2$—. In some embodiments, R$^{12}$ is F and u is 2. In some embodiments, R$^{12}$ is CF$_3$ and u is 1. In some embodiments, u is 0. In some embodiments, u is 1. In some embodiments, u is 2. In some embodiments, u is 3. In some embodiments, u is 4. In some embodiments, u is 5. In some embodiments, R$^{11}$ is OH. In some embodiments, R$^{11}$ is —NHCH$_2$CH$_3$. In some embodiments, R$^{11}$ is —OCH(CH$_3$)$_2$. Provided in certain embodiments herein are pharmaceutically-acceptable salts or solvates of a compound of Formula (VIII-B).

In some embodiments, R$^{11}$ is a radical (e.g., a hydroxyl radical or an amino radical) attached to L. In some embodiments, R$^6$ or R$^{6'}$ is a radical (e.g., a hydroxyl radical) attached to L. In some embodiments, L is a bond. In some embodiments, L comprises one or more linker group, each linker group being independently selected from the group consisting of an alkylene, cycloalkylene or —O—.

In certain embodiments, A has the structure:

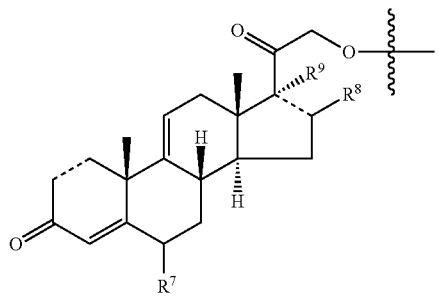

In some embodiments, ⟿ is a single bond or a double bond. In some embodiments, R$^7$ is hydrogen or halogen. In some embodiments, R$^8$ is a hydrogen or a C$_1$-C$_4$ alkyl. In some embodiments, R$^9$ is absent, hydrogen or hydroxyl. In some embodiments, R$^7$ is hydrogen. In some embodiments, R$^7$ is fluoro. In some embodiments, R$^8$ is hydrogen. In some embodiments, R$^8$ is methyl, ethyl, propyl or butyl. In some embodiments, R$^8$ is methyl, ethyl or butyl. In some embodiments, R$^8$ is methyl. In some embodiments, R$^9$ is hydroxyl.

In certain embodiments, A has the structure:

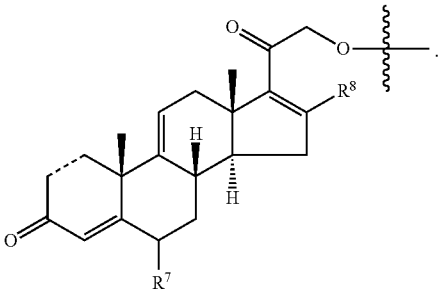

In some embodiments, ⟿ is a single bond or a double bond. In some embodiments, R$^7$ is hydrogen or halogen. In some embodiments, R$^8$ is a hydrogen or a C$_1$-C$_4$ alkyl. In some embodiments, R$^9$ is absent, hydrogen or hydroxyl. In some embodiments, R$^7$ is hydrogen. In some embodiments, R$^7$ is fluoro. In some embodiments, R$^8$ is hydrogen. In some embodiments, R$^8$ is methyl, ethyl, propyl or butyl. In some embodiments, R$^8$ is methyl, ethyl or butyl. In some embodiments, R$^8$ is methyl.

In certain embodiments, A has the structure:

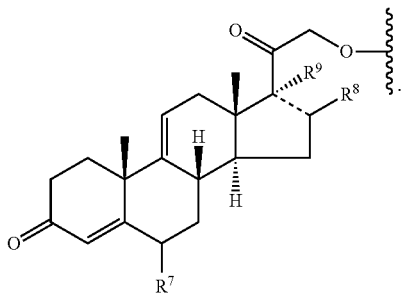

In some embodiments, ⌢ is a single bond or a double bond. In some embodiments, $R^7$ is hydrogen or halogen. In some embodiments, $R^8$ is a hydrogen or a $C_1$-$C_4$ alkyl. In some embodiments, $R^9$ is absent, hydrogen or hydroxyl. In some embodiments, $R^2$ is hydrogen. In some embodiments, $R^2$ is fluoro. In some embodiments, $R^8$ is hydrogen. In some embodiments, $R^8$ is methyl, ethyl, propyl or butyl. In some embodiments, $R^8$ is methyl, ethyl or butyl. In some embodiments, $R^8$ is methyl. In some embodiments, $R^9$ is hydroxyl.

In certain embodiments, A has the structure:

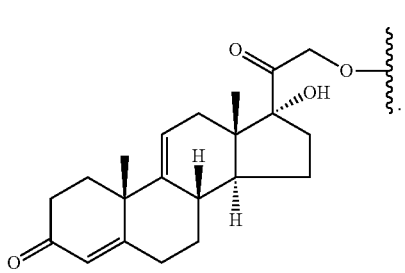

In certain embodiments, provided herein is a compound having the structure of Formula (IX):

(IX)

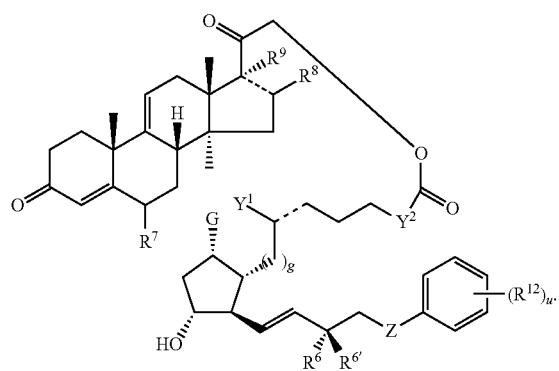

In certain embodiments, each ⌢ is independently a single bond or a double bond. In some embodiments, G is OH and $Y^1$ is hydrogen. In some embodiments, G together with $Y^1$ form —O—$CH_2$—. In some embodiments, $Y^2$ is a bond or —$CH_2$—. In some embodiments, g is 1 or 2. In some embodiments, Z is —O— or —$CH_2$—. In some embodiments, $R^6$ and $R^{6'}$ are each independently hydrogen, halogen or OH. In some embodiments, each $R^{12}$ is independently halogen or haloalkyl. In some embodiments, u is 0-5. In some embodiments, Z is —O— or —$CH_2$—. In some embodiments, $R^6$ and $R^{6'}$ are each independently hydrogen, halogen or OH. In some embodiments, each $R^{12}$ is independently halogen or haloalkyl. In some embodiments, $R^6$ and $R^{6'}$ are each fluoro. In some embodiments, $R^6$ is OH and $R^{6'}$ is hydrogen. In some embodiments, Z is —O—. In some embodiments, Z is —$CH_2$—. In some embodiments, $R^{12}$ is F and u is 2. In some embodiments, $R^{12}$ is $CF_3$ and u is 1. In some embodiments, u is 0. In some embodiments, u is 1. In some embodiments, u is 2. In some embodiments, u is 3. In some embodiments, u is 4. In some embodiments, u is 5. Also provided in certain embodiments herein are pharmaceutically-acceptable salts or solvates of a compound of Formula (IX).

In certain embodiments, provided herein is a compound having the structure of Formula (X):

(X)

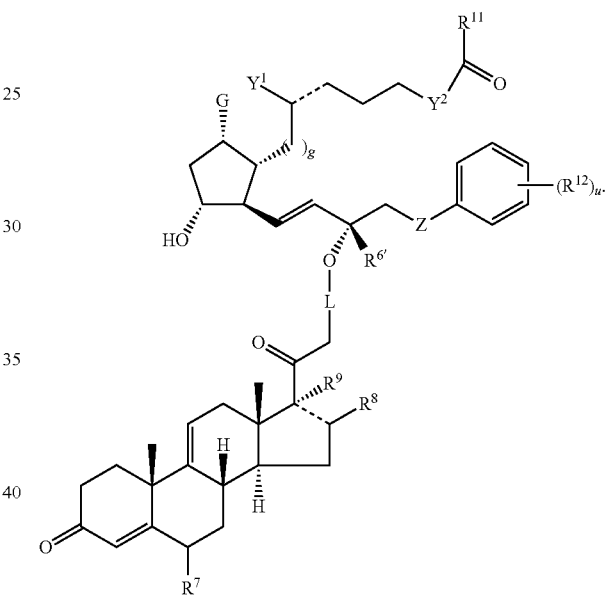

In certain embodiments, each ⌢ is independently a single bond or a double bond. In some embodiments, L is a linker. In some embodiments, L is a bond. In some embodiments, L is —(C=O)—, or —O—(C=O)—. In some embodiments, G is OH and $Y^1$ is hydrogen. In some embodiments, G together with $Y^1$ form —O—$CH_2$—. In some embodiments, $Y^2$ is a bond or —$CH_2$—. In some embodiments, g is 1 or 2. In some embodiments, Z is —O— or —$CH_2$—. In some embodiments, $R^6$ and $R^{6'}$ are each independently hydrogen, halogen or OH. In some embodiments, each $R^{12}$ is independently halogen or haloalkyl. In some embodiments, u is 0-5. In some embodiments, Z is —O— or —$CH_2$—. In some embodiments, $R^6$ and $R^{6'}$ are each independently hydrogen, halogen or OH. In some embodiments, each $R^{12}$ is independently halogen or haloalkyl. In some embodiments, $R^6$ and $R^{6'}$ are each independently fluoro. In some embodiments, $R^6$ is OH and $R^{6'}$ is hydrogen. In some embodiments, Z is —O—. In some embodiments, Z is —$CH_2$—. In some embodiments, $R^{12}$ is F and u is 2. In some embodiments, $R^{12}$ is $CF_3$ and u is 1. In some embodiments, u is 0. In some embodiments, u is 1. In some embodiments, u is 2. In some embodiments, u is 3.

In some embodiments, u is 4. In some embodiments, u is 5. Also provided in certain embodiments herein are pharmaceutically-acceptable salts or solvates of a compound of Formula (X).

In some embodiments, a compound provided herein comprises a steroid attached to a second agent (e.g., a prostaglandin) through an optional linker (e.g., travoprost-anecortave), as such, forming a heteroalkyl bond (e.g., an ester, a carbonate, etc.), such as, whereby upon cleavage (e.g., hydrolysis) of the heteroalkyl bond, the steroid and/or second agent are released in their free form. In some embodiments, a steroid radical (e.g., a first radical) provided herein (e.g., a hydroxyl radical (e.g., anecortave desacetate radical)) is attached to an optional linker or a second radical (e.g., a prostaglandin radical) (e.g., a hydroxyl radical, a carboxylic radical, etc.) provided herein to form a compound provided herein.

In some aspects, provided herein is a pharmaceutical composition comprising any compound provided herein, such as a compound having the structure of any one of Formula (I), Formula (IA), Formula (IB), Formula (IC), Formula (II), Formula (IIA), Formula (IIB), Formula (III), Formula (IV), Formula (V), Formula (VI), Formula (VI-A), Formula (VI-B), Formula (VI-C), Formula (VII), Formula (VII-A), Formula (VII-B), Formula (VIII), Formula (VIII-A), Formula (VIII-B), Formula (IX), or Formula (X), or a pharmaceutically-acceptable salt thereof. In some embodiments, the pharmaceutical composition comprises at least one pharmaceutically acceptable excipient. Another embodiment provides the pharmaceutical composition, wherein the pharmaceutical composition is suitable for ophthalmic administration. Another embodiment provides the pharmaceutical composition, wherein the pharmaceutical composition is suitable for intraocular ophthalmic administration. In some embodiments, intraocular ophthalmic administration is administration in the eye, such as intraocular, intracameral, intravitreal, suprachoroidal, punctal, retrobulbar, or subconjunctival.

Another embodiment provides the pharmaceutical composition, wherein the pharmaceutical composition is suitable for subcutaneous administration. Another embodiment provides the pharmaceutical composition, wherein the pharmaceutical composition is suitable for intraspinal administration.

Another embodiment provides a pharmaceutical implant or article comprising any compound provided herein, such as a compound having the structure of any one of Formula (I), Formula (IA), Formula (IB), Formula (IC), Formula (II), Formula (IIA), Formula (IIB), Formula (III), Formula (IV), or Formula (V), or a pharmaceutically acceptable salt thereof.

In some embodiments, the implant or article comprises at least 50 wt. % (at least 60 wt. %, at least 70 wt. %, at least 80 wt. %, at least 90 wt. %, at least 95 wt. %, at least 98 wt. %, or the like) of the compound and/or pharmaceutically acceptable salt thereof. In some instances, an article or implant provided herein comprises at least 50 wt. % of a compound as described herein. In some instances, an article or implant provided herein comprises at least 70 wt. % of a compound as described herein. In some instances, an article or implant provided herein comprises at least 90 wt. % of a compound as described herein. In some instances, an article or implant provided herein comprises at least 95 wt. % of a compound as described herein. In some instances, an article or implant provided herein comprises at least 99 wt. % of a compound as described herein. In some instances, an article or implant provided herein comprises an additional component, such as up to 20 wt. %, 15 wt. %, 10 wt. %, 5 wt. %, 1 wt. %, 0.1 wt. %, 0.01 wt. %, or less of the additional component. In some embodiments, an article or implant provided herein comprises up to 5 wt. % (e.g., up to 1 wt. %, up to 0.1 wt. %, or less) a first radical in its free form (e.g., a steroid (such as described herein)), a second radical in its free form (e.g., a prostaglandin (such as described herein), or a combination thereof (e.g., as an impurity, such as residual from a manufacturing process, such as provided herein). In some embodiments, an article or implant provided herein comprises up to 5 wt. % (e.g., up to 1 wt. %, up to 0.1 wt. %, or less) of an impurity, such as residual from a manufacturing process, such as provided herein. In some embodiments, an article or implant provided herein comprises up to 5 wt. % (e.g., up to 1 wt. %, up to 0.1 wt. %, or less) of a steroid (as described herein).

In certain embodiments, the implant or article releases a (e.g., active) group therefrom, such as when implanted into or otherwise administered to an individual (or when placed into an aqueous medium (e.g., aqueous buffer solution), serum, or other physiological medium, such as at a physiological temperature, such as 37° C.). In some instances, a (e.g., active) group released is the free form of the first radical and/or the second radical. In certain instances, a (e.g., active) group released from the compound is an active fragment or metabolite of the first and/or second radical. In some embodiments, the implant or article undergoes surface erosion to release the compound, the first radical, and/or the second radical (or an (e.g., active) fragment or radical thereof). In some embodiments, first radical and the second radical are released from the pharmaceutical implant or article at near zero-order in solution (e.g., buffer solution, serum, biological environment, in vivo, or the like). In some embodiments, the first radical and the second radical (or an (e.g., active) fragment or metabolite thereof) are released from the pharmaceutical implant or article at 37° C. in 100% bovine serum or at 37° C. in phosphate buffered saline (PBS) at a rate such that $t_{10}$ is greater than or equal to ⅒ of $t_{50}$.

In some embodiments, a compound or a pharmaceutical composition comprising any compound provided herein, such as a compound having the structure of any one of Formula (I), Formula (IA), Formula (IB), Formula (IC), Formula (II), Formula (IIA), Formula (IIB), Formula (III), Formula (IV), or Formula (V), or a pharmaceutically acceptable salt thereof. In certain embodiments, the composition further comprises an amount of a free form of any radical provided herein, or a combination thereof, such as a free form of a radical having the (e.g., steroid) structure of any one of Formula (I), Formula (IA), Formula (IB), Formula (IC), Formula (II), Formula (IIA), Formula (IIB), Formula (IC), Formula (II), Formula (IIA), Formula (IIB), Formula (III), Formula (IV), Formula (V), Formula (VI), Formula (VI-A), Formula (VI-B), Formula (VI-C), Formula (VII), Formula (VII-A), Formula (VII-B), Formula (VIII), Formula (VIII-A), Formula (VIII-B), Formula (IX), or Formula (X) (such as wherein the free form is the structure, wherein the free form (e.g., —COO— or —O— thereof) has a negative charge (e.g., as —O⁻) or an H (e.g., as —OH), rather than being connected to a linker and/or other (first or second) radical). In some embodiments, a composition provided herein comprises a (e.g., weight or molar) ratio of a compound provided herein to a free form of any radical provided herein, or a combination thereof, such as a free form of a radical having the structure of any one of Formula (I), Formula (IA), Formula (IB), Formula (IC), Formula (II), Formula (IIA), Formula (IIB), Formula (IC), Formula (II), Formula (IIA), Formula (IIB), Formula (III), Formula (IV), Formula (V), Formula (VI), Formula (VI-A), Formula (VI-B), Formula (VI-C), Formula (VII), Formula (VII-A), Formula (VII-B), Formula (VIII), Formula (VIII-A), Formula (VIII-B), Formula (IX), or Formula (X), or a pharmaceutically acceptable salt thereof (e.g., wherein the free form is the structure, wherein the free form (e.g., —COO— or —O— thereof) has a negative charge (e.g., as —O⁻) or an H (e.g., as —OH)), rather than being connected to a linker and/or other (first or second) radical, of about 1:99 to about 100:0 (e.g., the amount of the free form of the radical relative to the overall amount of free form of the radical plus the conjugate is between 0% (weight or molar) and 99%). In some embodiments, the relative amount of the free form of the radical is 0% to about 50%, such 0% to about 20%, 0% to about 10%, about 0.1% to about 10%, about 0.1% to about 5%, less than 5%, less than 2.5%, less than 2%, or the like (percentages being weight/weight or mole/mole percentages). Further, in some instances, compounds provided herein release free form of any radical provided herein, or a combination thereof, such as a free form of a structure of a compound having the structure of any one of Formula (I), Formula (IA), Formula (IB), Formula (IC), Formula (II), Formula (IIA), Formula (IIB), Formula (IC), Formula (II), Formula (IIA), Formula (IIB), Formula (III), Formula (IV), Formula (V), Formula (VI), Formula (VI-A), Formula (VI-B), Formula (VI-C), Formula (VII), Formula (VII-A), Formula (VII-B), Formula (VIII), Formula (VIII-A), Formula (VIII-B), Formula (IX), or Formula (X) (e.g., wherein the free form (e.g., —COO— or —O— thereof) has a negative charge (e.g., as —O⁻) or H (e.g., as —OH), rather than being connected to a linker and/or other (first or second) radical)), such as when administered to an individual (e.g., ocular (e.g., intraocular), subcutaneous, or intraspinal administration).

In certain embodiments, provided herein is a method of treating an ophthalmic disease or disorder in a patient in need thereof, comprising administering to the patient a composition comprising any compound provided herein, such as a compound having the structure of any one of Formula (I), Formula (IA), Formula (IB), Formula (IC), Formula (II), Formula (IIA), Formula (IIB), Formula (III), Formula (IV), or Formula (V), or a pharmaceutically acceptable salt thereof. Another embodiment provides the method wherein the ophthalmic disease or disorder is glaucoma. Another embodiment provides the method wherein the ophthalmic disease or disorder is selected from the group consisting of ocular inflammation, diabetic macular edema, posterior inflammation, anterior inflammation, macular degeneration (e.g., wet macular degeneration (AMD)), post-cataract surgery, and retinal vein occlusion.

In certain embodiments, provided herein is a method of treating a medical indication or abnormality (e.g., ocular or neurological disease and/or disorder), the method comprising administering a therapeutically effective amount of a compound or composition provided herein. In some embodiments, a composition provided herein (e.g., used in a method provided herein) comprises a compound provided herein in a therapeutically effective amount (e.g., at a concentration effective to treat an ophthalmic disease or disorder in an individual in need thereof, the method comprising administering to the individual a compound, pharmaceutically acceptable salt, implant, article, or composition having the structure of any one of Formula (I), Formula (IA), Formula (IB), Formula (IC), Formula (II), Formula (IIA), Formula (IIB), Formula (III), Formula (IV), Formula (V), Formula (VI), Formula (VI-A), Formula (VI-B), Formula (VI-C), Formula (VII), Formula (VII-A), Formula (VII-B), Formula (VIII), Formula (VIII-A), Formula (VIII-B), Formula (IX), or Formula (X). In some embodiments, a composition provided herein (e.g., used in a method provided herein) comprises a compound provided herein in a therapeutically effective amount (e.g., at a concentration effective to treat glaucoma, inflammation, and/or lower intraocular pressure) in the eye. In certain embodiments, a (e.g., pharmaceutical and/or ophthalmic) composition provided herein comprises about 0.1 wt. % to about 10 wt. % of a compound provided herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION OF THE INVENTION

Certain Definitions

Figure 1A:
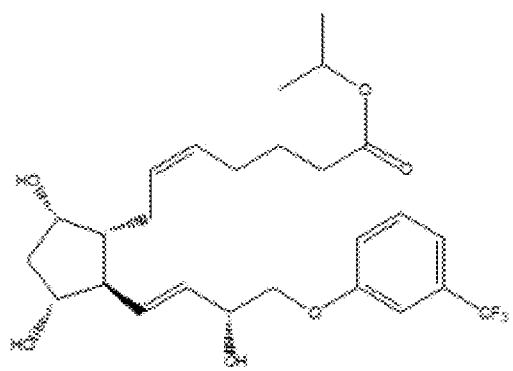
FIG. 1 shows the chemical structure for a prodrug ester and an active pharmaceutical ingredient for a prostaglandin (e.g., travaprost (FIG. 1A) and travoprost acid (FIG. 1B), respectively) and a steroid (e.g., anecortave acetate (FIG. 1C) and anecortave desacetate (FIG. 1D), respectively) exemplified herein.
Figure 1B:
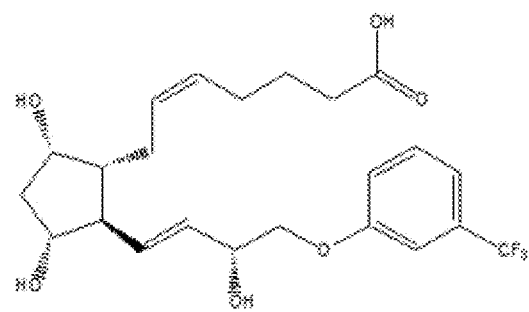
Figure 1C:
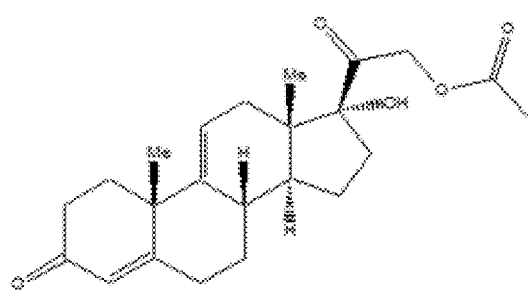

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Amino" refers to the —$NH_2$ radical (dihydroamino). "Alkylamino" refers to an amino group which is substituted by one or more alkyl groups as defined herein. "Arylamino" referrers to an amino group which substituted by one or more aryl groups as defined herein.

"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.
"Hydrogen" refers to the "H" radical.

"Alkyl" generally refers to a straight or branched hydrocarbon chain radical consisting solely of carbon and hydrogen atoms, such as having from one to fifteen carbon atoms (e.g., $C_1$-$C_{15}$ alkyl). Unless otherwise stated, alkyl is saturated or unsaturated (e.g., an alkenyl, which comprises at least one carbon-carbon double bond, or alkynyl, which comprises at least one carbon-carbon triple bond). Disclosures provided herein of an "alkyl" are intended to include independent recitations of a saturated "alkyl," or unsaturated alkyl (alkenyl, alkynyl), unless otherwise stated. Alkyl groups described herein are generally monovalent, but may also be divalent (which may also be described herein as "alkylene" or "alkylenylene", or alkynylene groups). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. In general, alkyl groups are each independently substituted or unsubstituted. Each recitation of "alkyl" provided herein, unless otherwise stated, includes a specific and explicit recitation of an unsaturated "alkyl" group. Similarly, unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is optionally substituted as described for "alkyl" groups.

"Alkynyl" refers to a straight or branched hydrocarbon chain radical group consisting solely of carbon and hydrogen atoms, containing at least one carbon-carbon triple bond, and having from two to twelve carbon atoms. In certain embodiments, an alkynyl comprises two to eight carbon atoms. In other embodiments, an alkynyl comprises two to four carbon atoms. The alkenyl is optionally substituted as described for "alkyl" groups.

"Alkylene" or "alkylene chain" generally refers to a straight or branched divalent alkyl group linking the rest of the molecule to a radical group, such as having from one to twelve carbon atoms, for example, methylene, ethylene, propylene, i-propylene, n-butylene, and the like. Unless stated otherwise specifically in the specification, an alkylene chain is optionally substituted as described for alkyl groups herein.

The term "article," as used herein, generally refers to a pharmaceutical composition that is machined, molded, heat-processed, emulsion-processed, electrospun, electrosprayed, blow molded, or extruded to form a fiber, fiber mesh, woven fabric, non-woven fabric, film, surface coating, pellet, cylinder, rod, microparticle, nanoparticle, or another shaped article.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" or "aryl-alkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" or "cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl or cycloalkyl is saturated (i.e., containing single C—C bonds only) or unsaturated (i.e., containing one or more double bonds or triple bonds). Examples of saturated cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkenyl" refers to a radical of the formula —$R^c$-carbocyclyl where $R^c$ is an alkenylene chain as defined above. The alkenylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

The term "heteroalkyl" refers to an alkyl group as defined above in which one or more skeletal carbon atoms of the alkyl are substituted with a heteroatom (with the appropriate number of substituents or valencies—for example, —$CH_2$— may be replaced with —NH— or —O—). For example, each substituted carbon atom is independently substituted with a heteroatom, such as wherein the carbon is substituted with a nitrogen, oxygen, selenium, or other suitable heteroatom. In some instances, each substituted carbon atom is independently substituted for an oxygen, nitrogen (e.g. —NH—, —N(alkyl)-, or —N(aryl)- or having another substituent contemplated herein), or sulfur (e.g. —S—, —S(=O)—, or —S(=O)$_2$—). In some embodiments, a heteroalkyl is attached to the rest of the molecule at a carbon atom of the heteroalkyl. In some embodiments, a heteroalkyl is attached to the rest of the molecule at a heteroatom of the heteroalkyl. In some embodiments, a heteroalkyl is a $C_1$-$C_{18}$ heteroalkyl. In some embodiments, a heteroalkyl is a $C_1$-$C_{12}$ heteroalkyl. In some embodiments, a heteroalkyl is a $C_1$-$C_6$ heteroalkyl. In some embodiments, a heteroalkyl is a $C_1$-$C_4$ heteroalkyl. Representative heteroalkyl groups include, but are not limited to —$OCH_2OMe$, or —$CH_2CH_2OMe$. In some embodiments, heteroalkyl includes alkoxy, alkoxyalkyl, alkylamino, alkylaminoalkyl, aminoalkyl, heterocycloalkyl, heterocycloalkyl, and heterocycloalkylalkyl, as defined herein. Unless stated otherwise specifically in the specification, a heteroalkyl group is optionally substituted as defined above for an alkyl group.

"Heteroalkylene" refers to a divalent heteroalkyl group defined above which links one part of the molecule to another part of the molecule. Unless stated specifically otherwise, a heteroalkylene is optionally substituted, as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

In general, optionally substituted groups are each independently substituted or unsubstituted. Each recitation of an optionally substituted group provided herein, unless otherwise stated, includes an independent and explicit recitation of both an unsubstituted group and a substituted group (e.g., substituted in certain embodiments, and unsubstituted in certain other embodiments). Unless otherwise stated, substituted groups may be substituted by one or more of the following substituents: halo, cyano, nitro, oxo, thioxo, imino, oximo, trimethylsilanyl, —$OR^a$, —$SR^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

The compounds disclosed herein, reference to any atom includes reference to isotopes thereof. For example, reference to H includes reference to any isotope thereof, such as a $^1$H, $^2$H, $^3$H, or mixtures thereof.

Figure 1D:
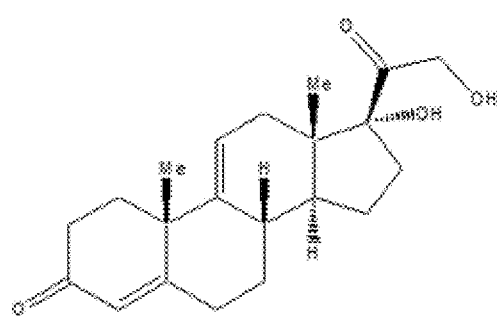
Figure 2A:
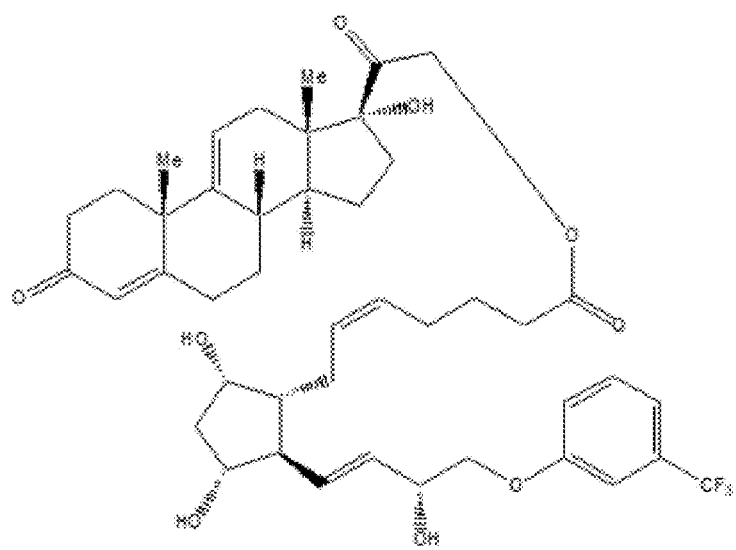
FIG. 2 shows the chemical structure (FIG. 2A) and the heat processed pellet (FIG. 2B) of a steroid-prostaglandin heterodimer (travoprost-anecortave, Compound 1) exemplified herein.
FIG. 2C shows the drug release profile for Compound 1 (pellet) in fetal bovine serum (FBS) over 15 days.
FIG. 2D represents the 15-day progression of the surface erosion drug release profile for the pellet of Compound 1 in FBS.
Figure 2B:
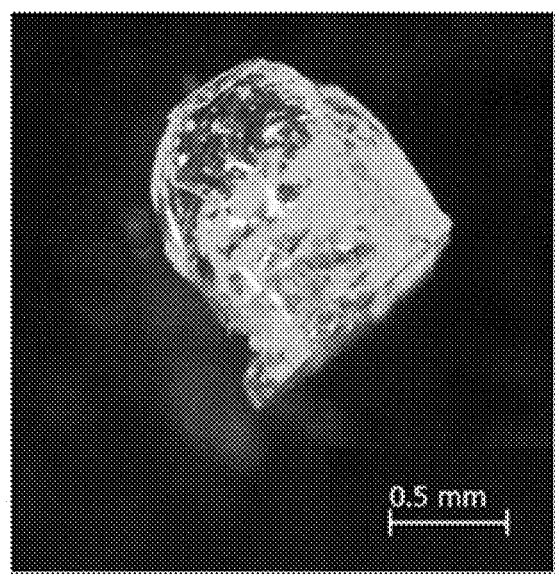
Figure 2C:
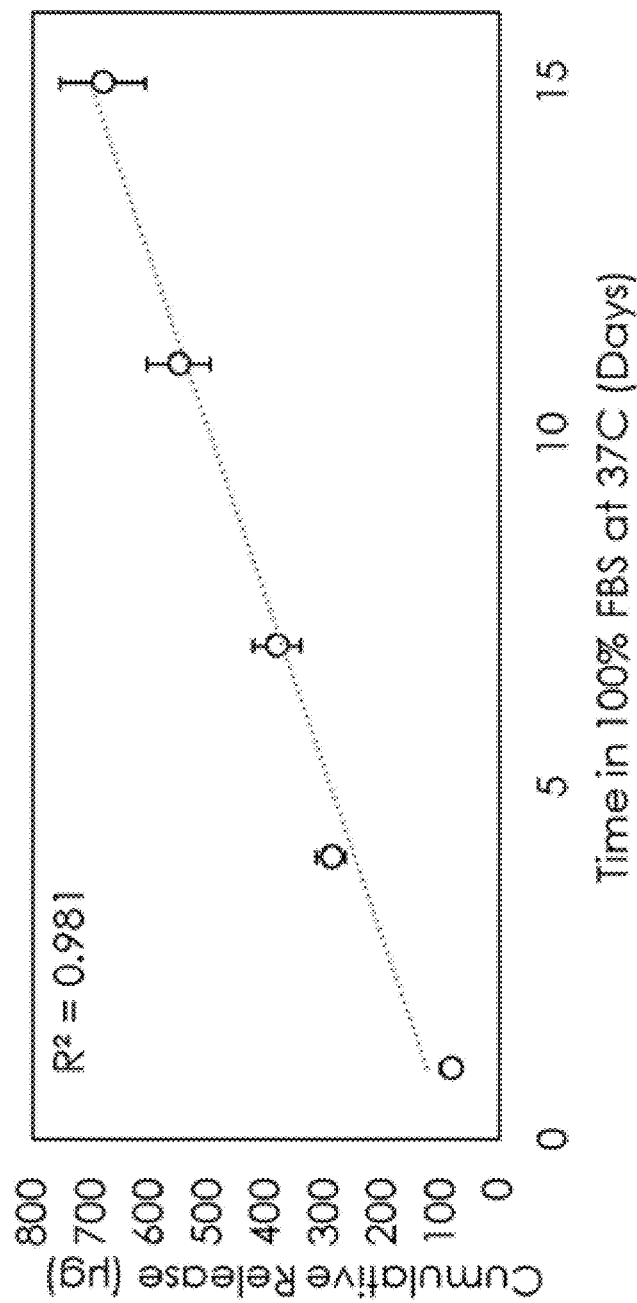
Figure 2D:
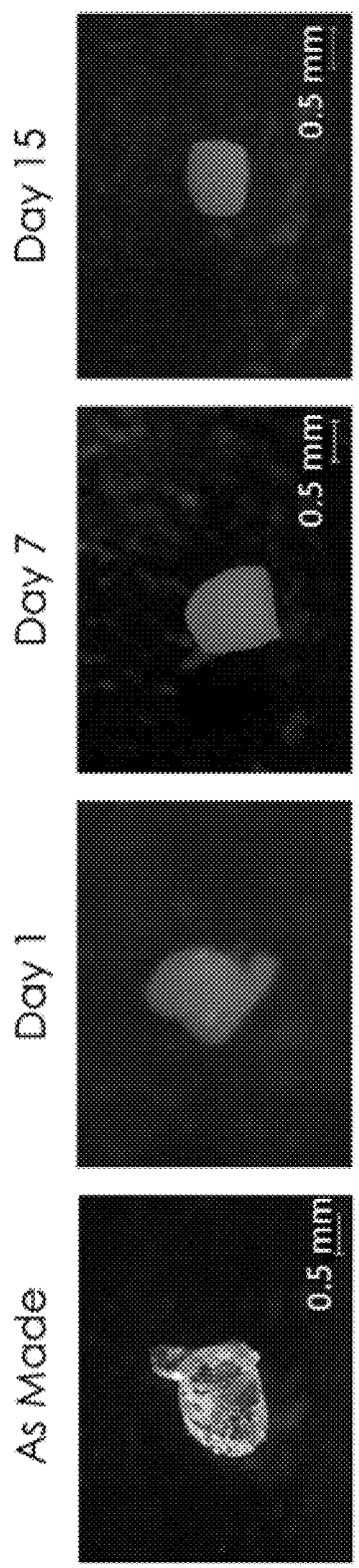
Figure 3A:
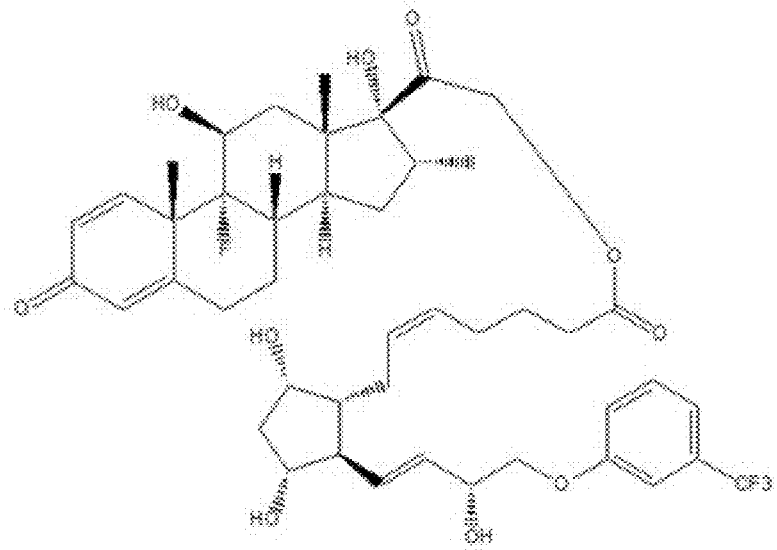
FIG. 3 shows the chemical structure (FIG. 3A) and the heat processed pellet (FIG. 3B) of a steroid-prostaglandin heterodimer (travoprost-dexamethasone, Compound 2) exemplified herein.
FIG. 3C shows the drug release profile for Compound 2 (pellet) in phosphate-buffered saline (PBS) over 30 days.
FIG. 3D represents the 30-day progression of the (e.g., surface erosion) drug release profile and swelling profile for the pellet of Compound 2 in PBS.
Figure 3B:
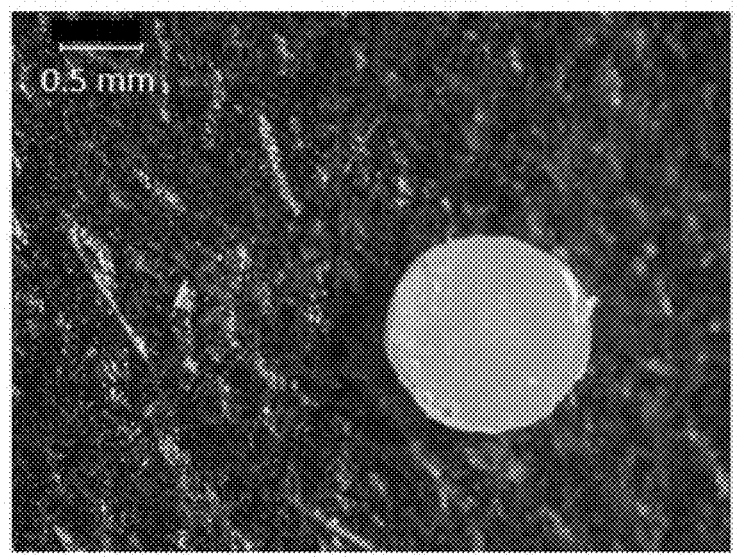
Figure 3C:
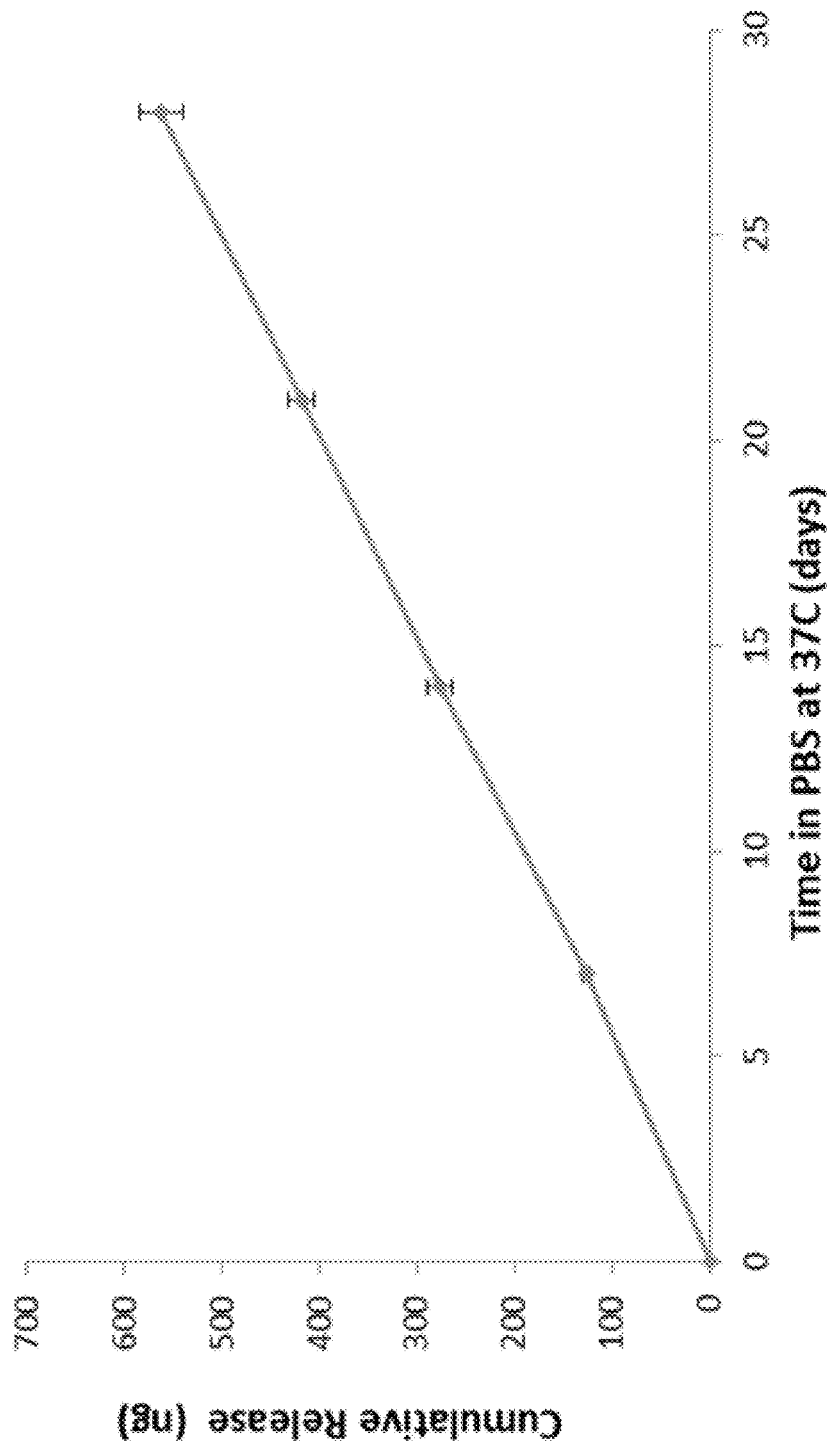
Figure 3D:
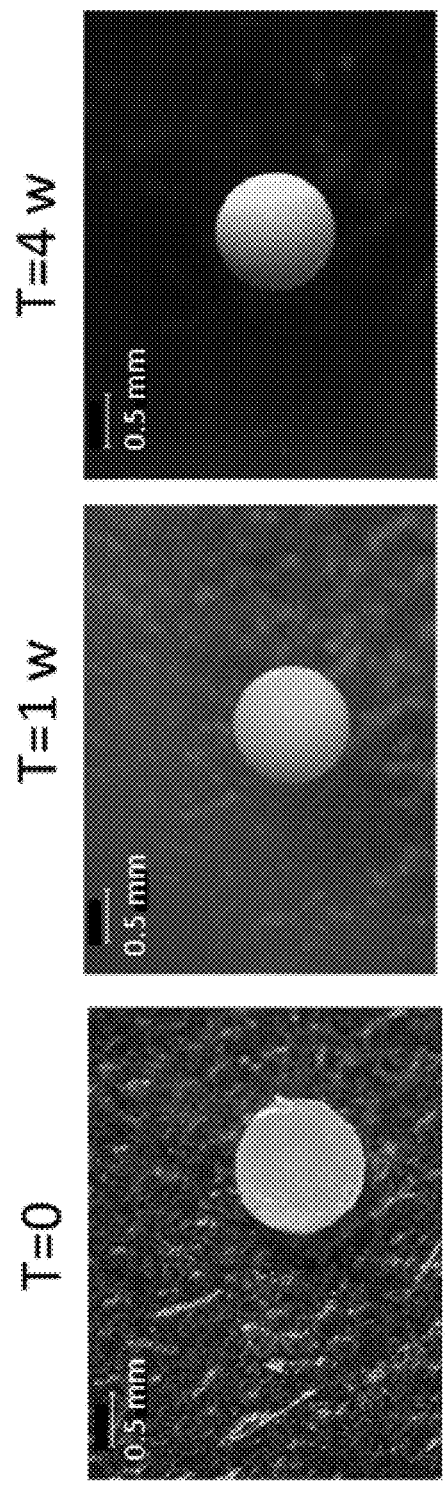
Figure 4A:
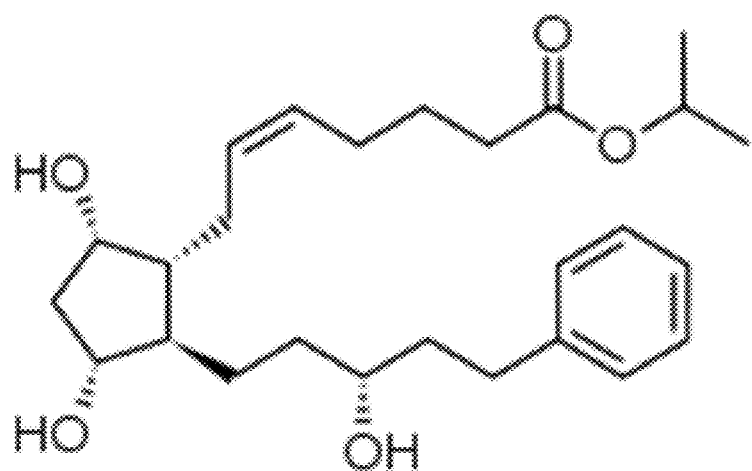
FIG. 4 shows the chemical structure for a prodrug ester and an active pharmaceutical ingredient for a prostaglandin (e.g., latanoprost (FIG. 4A) and latanoprost acid (FIG. 4B), respectively) exemplified herein.
Figure 4B:
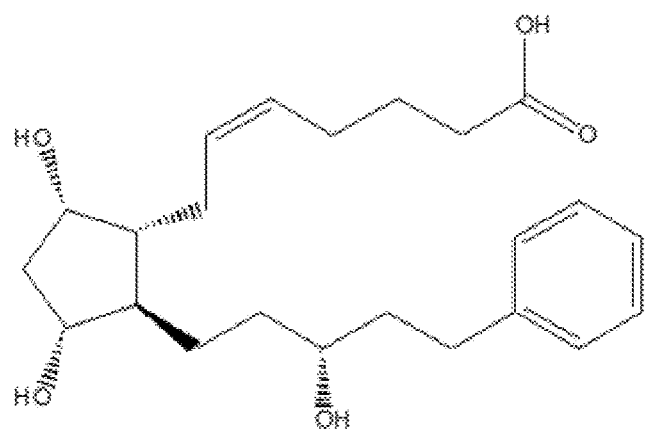
Figure 5A:
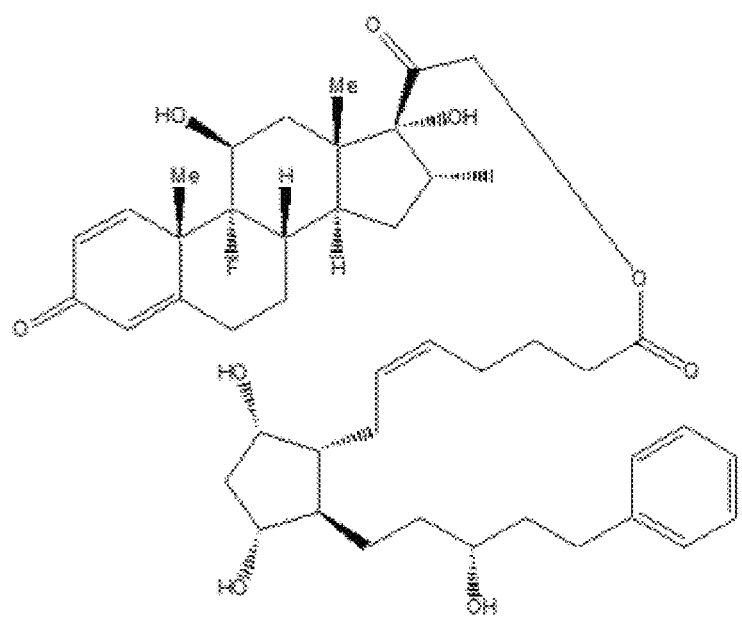
FIG. 5 shows the chemical structure (FIG. 5A) and the heat processed pellet (FIG. 5B) of a steroid-prostaglandin heterodimer (latanoprost-dexamethasone, Compound 3) exemplified herein.
FIG. 5C shows the drug release profile for Compound 3 (pellet) in fetal bovine serum (FBS) over 30 days.
FIG. 5D represents the 30-day progression of the (e.g., surface erosion) drug release profile and swelling profile for the pellet of Compound 3 in FBS.
Figure 5B:
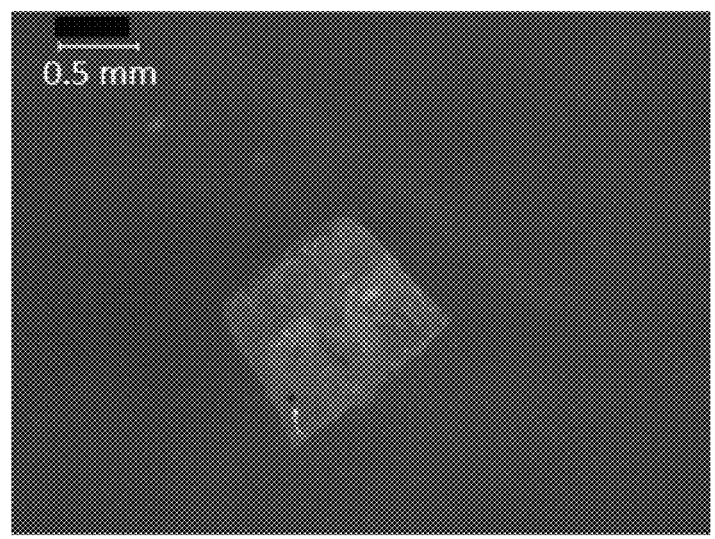
Figure 5C:
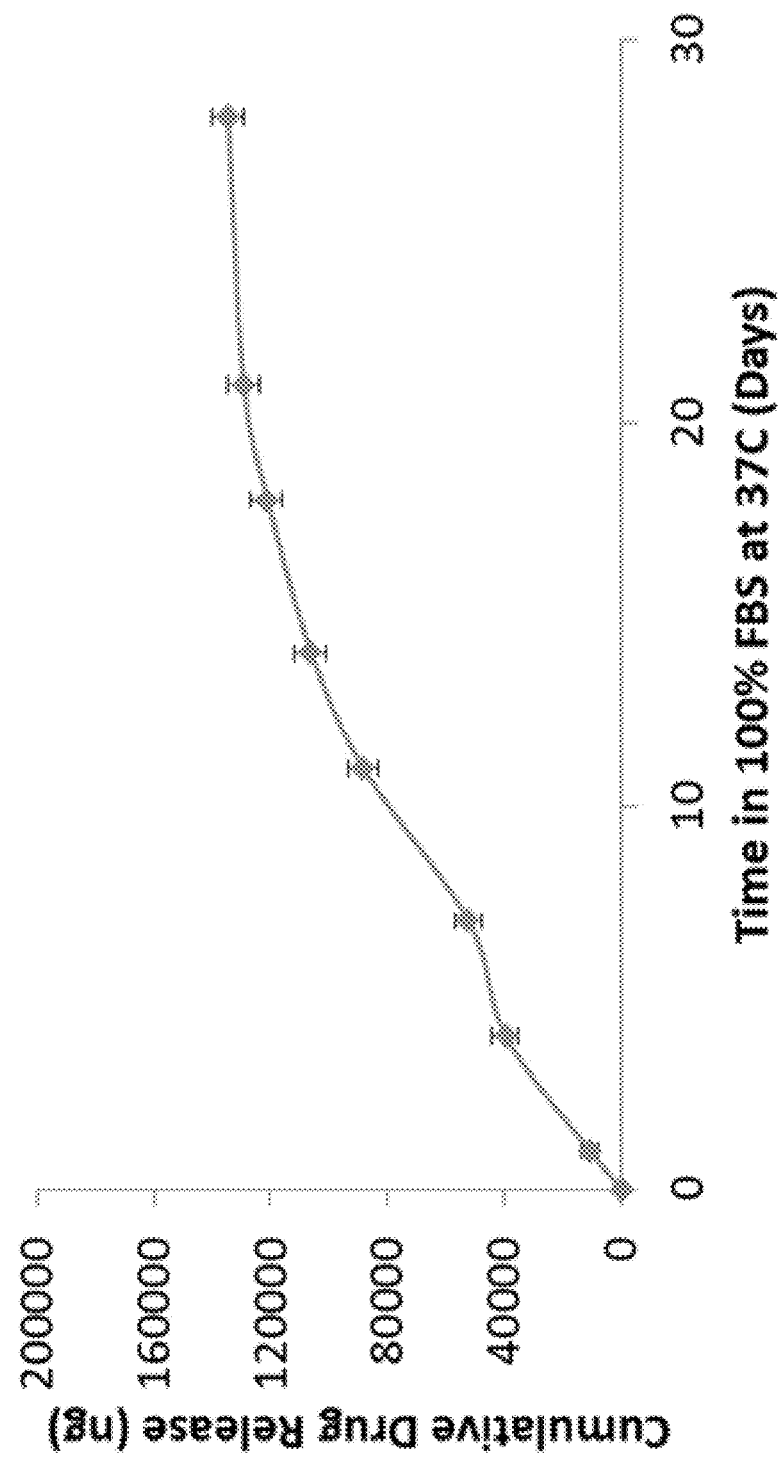
Figure 5D:
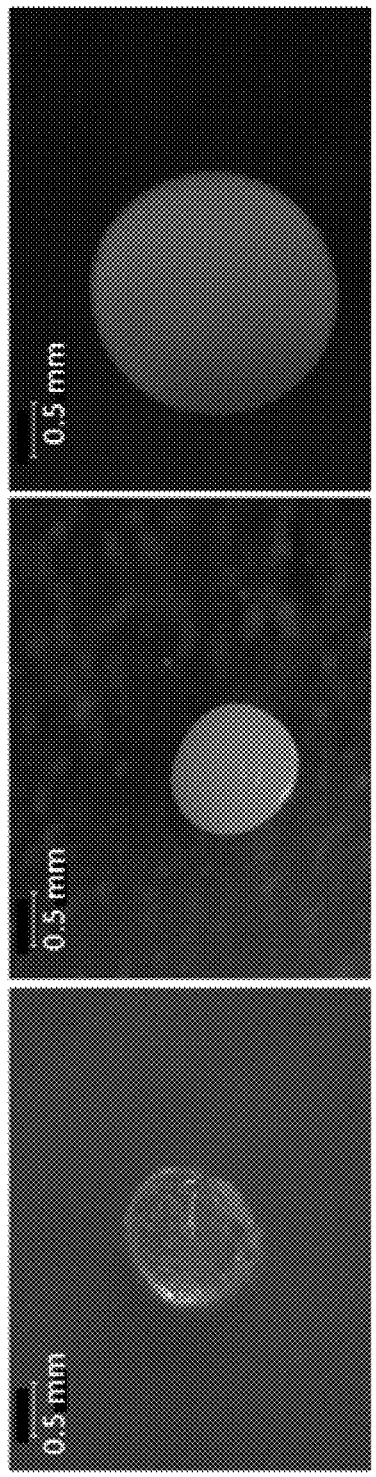
Figure 6A:
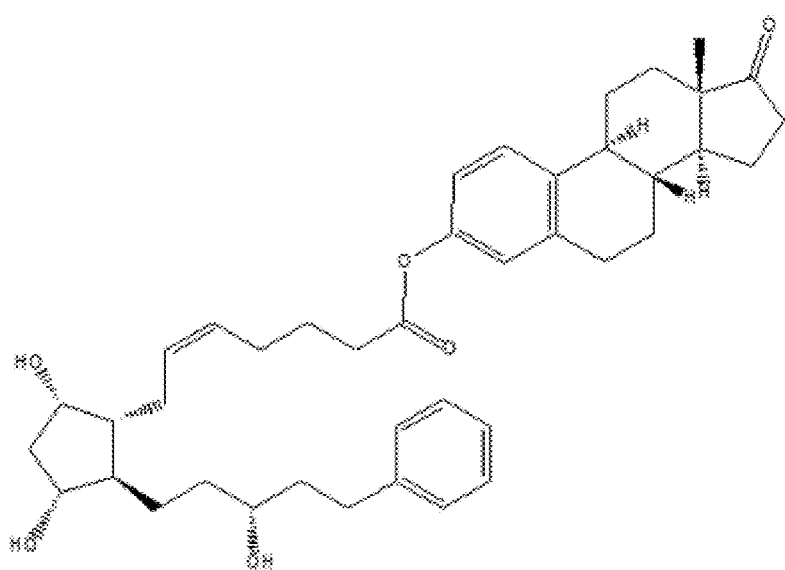
FIG. 6 shows the chemical structure (FIG. 6A) of a steroid-prostaglandin heterodimer (latanoprost-estrone, Compound 4) exemplified herein.
FIG. 6B shows the drug release profile for Compound 4 (coating on polymeric substrate) in fetal bovine serum (FBS) over 8 days.
FIG. 6C represents the 7-day progression of the surface coating drug release of Compound 4 in FBS.
Figure 6B:
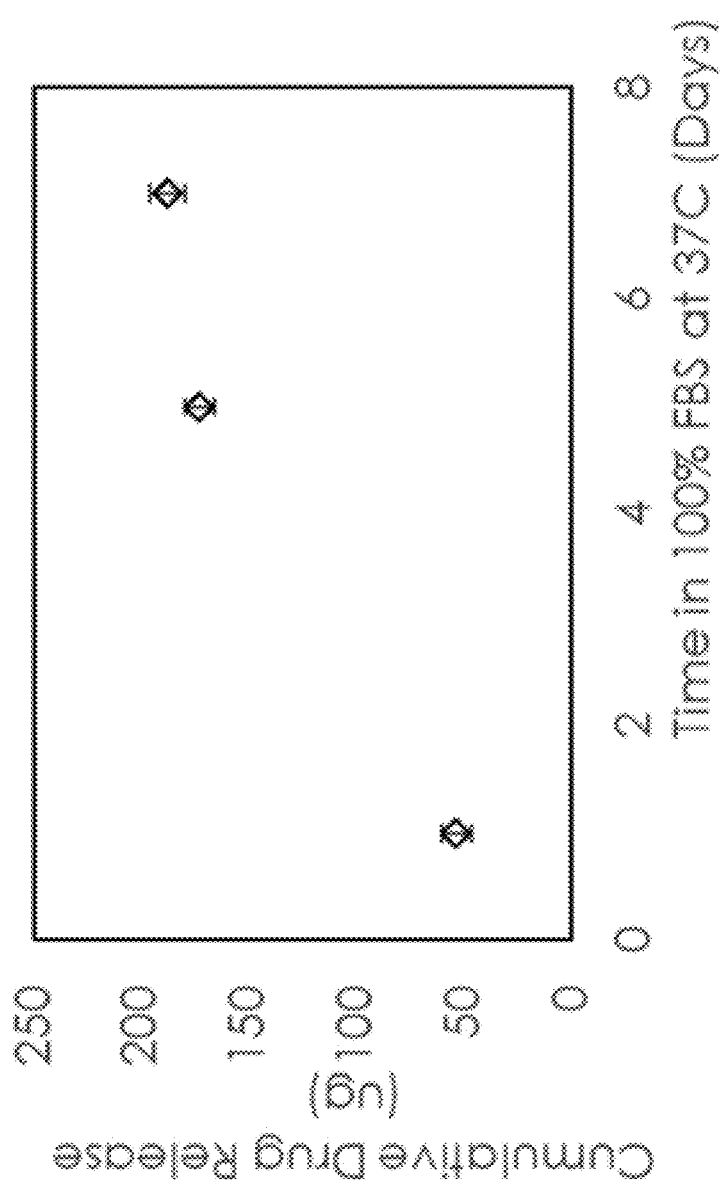
Figure 6C:
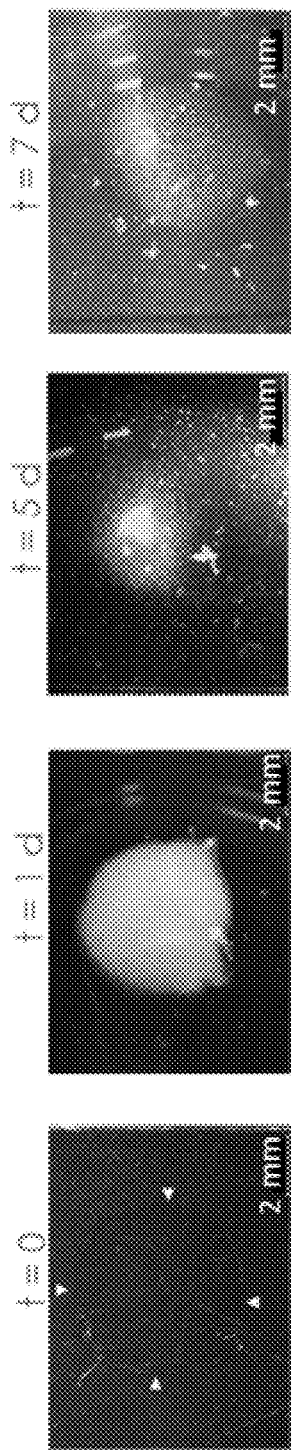
Figure 7A:
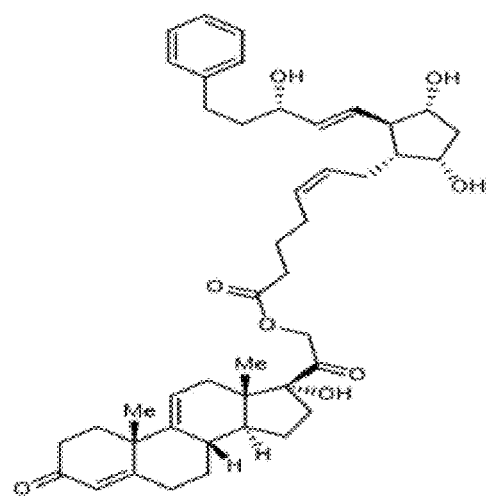
FIG. 7 shows the chemical structure (FIG. 7A) and the heat processed pellet (FIG. 7B) of a steroid-prostaglandin heterodimer (bimatoprost-anecortave, Compound 5) exemplified herein.
FIG. 7C shows the drug release profile for Compound 5 (pellet) in fetal bovine serum (FBS) over 25 days.
FIG. 7D represents the 28-day progression of the (e.g., surface erosion) drug release profile for the pellet of Compound 5 in FBS.
Figure 7B:
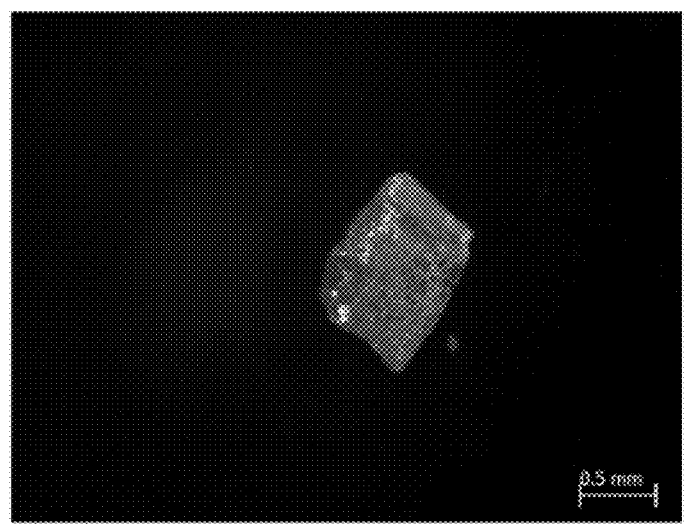
Figure 7C:
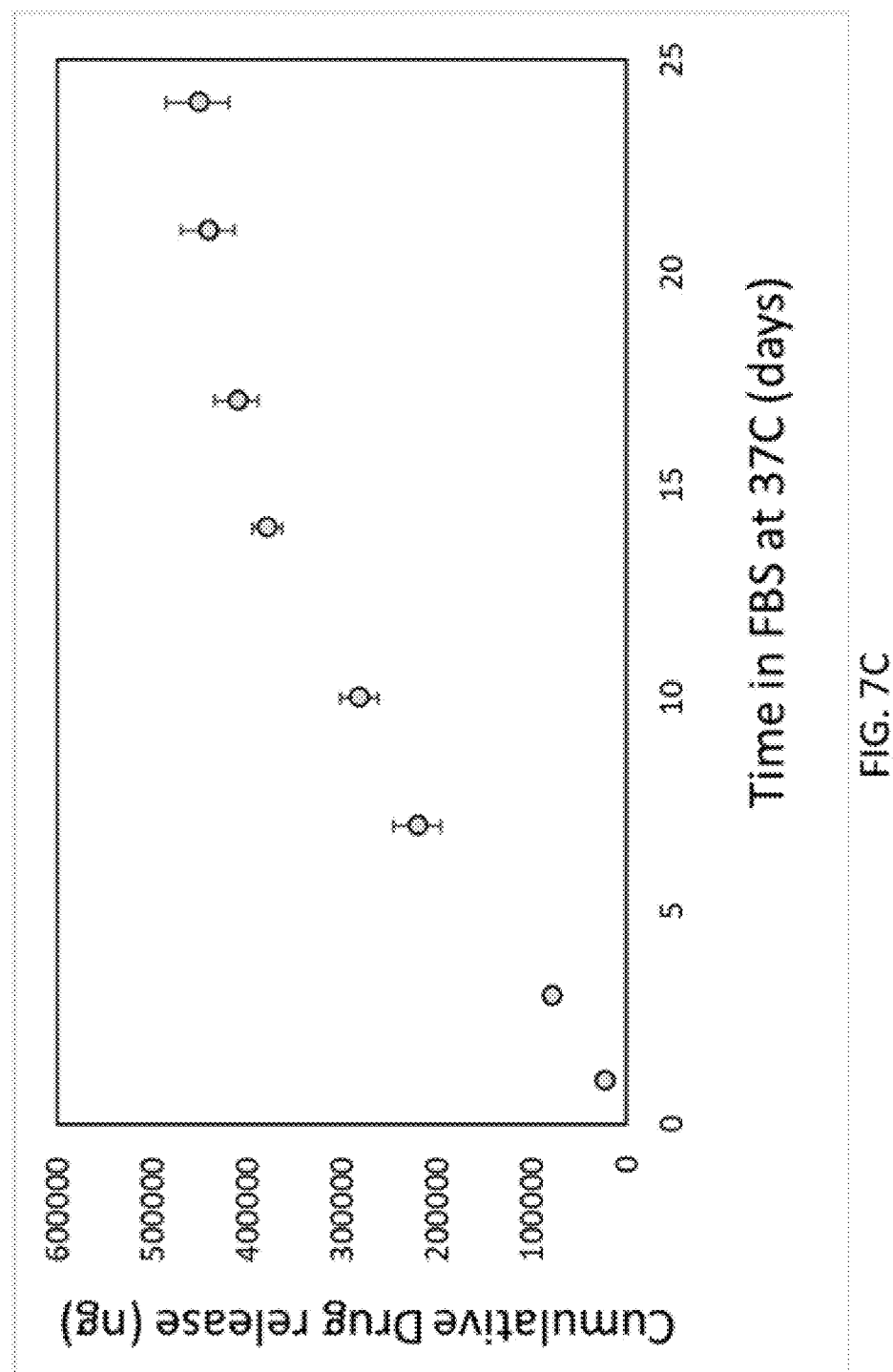
Figure 7D:
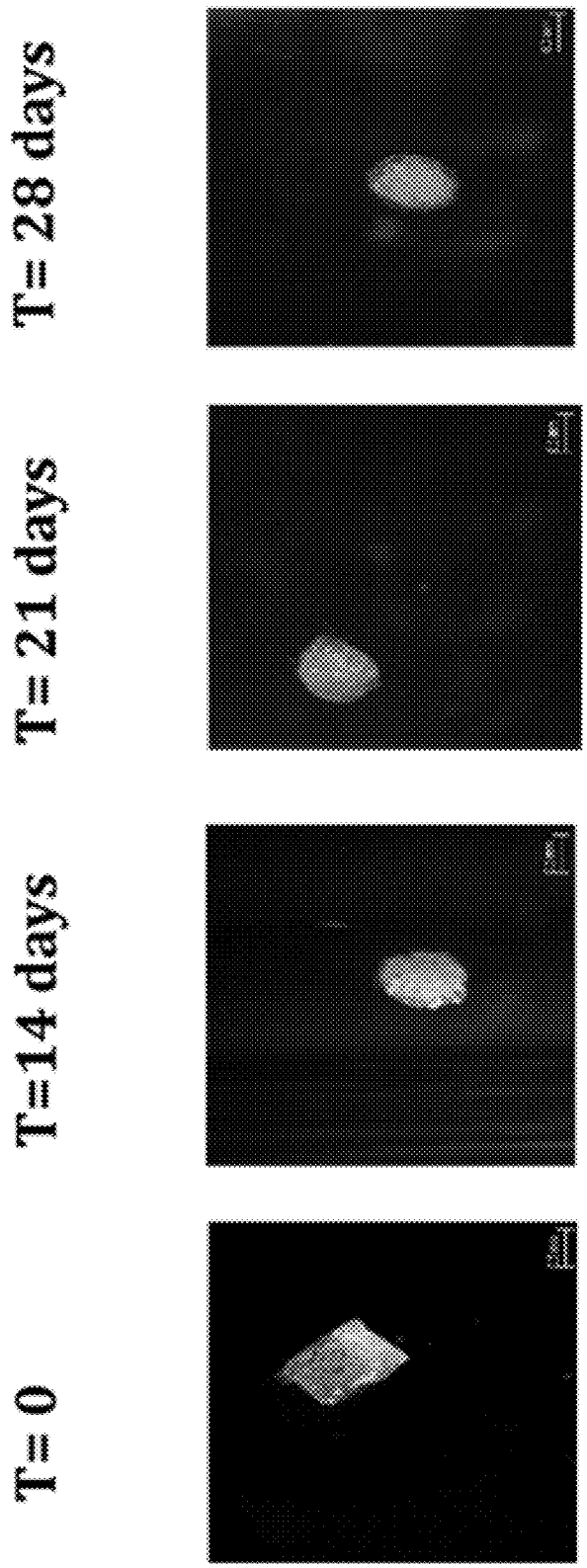

Generally, recitations of "anecortave" herein refer to "anecortave" in the desacetate form of FIG. 1D; however, where applicable, recitations of "anecortave" include disclosure of each of the "desacetate" and "acetate" forms.

The term "opioid" or "opiate," as used interchangeably herein, generally refers to a ligand that binds to an opioid receptor, such as, for example, the delta (δ)-opioid receptor (DOR), the kappa (κ)-opioid receptor (KOR), mu (μ)-opioid receptor (MOR), nociceptin opioid receptor (NOR), zeta (ζ)-opioid receptor (ZOR), or any combination thereof. In some embodiments, the opioid is an opioid agonist, an opioid antagonist, or a mixed opioid agonist/antagonist of an opioid receptor. In some embodiments, the opioid agonist is a partial opioid agonist or an inverse opioid agonist. In some embodiments, the opioid is an opioid radical. In some embodiments, the opioid radical is joined to a radical of a therapeutically active agent by a linker, as described herein, forming an opioid dimer. In some embodiments, the opioid dimer is a heterodimer as described above. In some embodiments, an opioid radical is joined to a second radical, which is not an opioid radical, such as, for example, a radical of a therapeutically active agent (e.g., a steroid), by a linker described herein, forming an opioid heterodimer. In some embodiments, a first opioid radical, such as, for example, a partial opioid agonist, is joined to a second opioid radical, which is a different opioid radical than the first opioid radical, such as, for example, an opioid antagonist, by a linker described herein, forming a heterodimer.

The term "pellet," as used herein, refers to the shape of the pharmaceutical compositions of the disclosure that is rounded, spherical, cylindrical, or a combination thereof. In some embodiments, the pellet has a mean diameter from about 0.2 to 5 mm, e.g., from about 0.2 to 1 mm, from about 0.2 to 2 mm, from about 0.3 to 3 mm, from about 1.5 to 5 mm, from about 2 to 5 mm, from about 2.5 to 5 mm, from about 3 to 5 mm, from about 3.5 to 5 mm, from about 4 to 5 mm, or from about 4.5 to 5 mm.

"Pharmaceutically acceptable salt" includes both acid and base addition salts. A pharmaceutically acceptable salt of any one of the pharmacological agents described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

The terms "treat," "treating," or "treatment" as used herein, include reducing, alleviating, abating, ameliorating, relieving, or lessening the symptoms associated with a disease, disease state, or indication (e.g., glaucoma) in either a chronic or acute therapeutic scenario. In one embodiment, treatment includes a reduction of intraocular pressure. Also, treatment of a disease or disease state described herein includes the disclosure of use of such compound or composition for the treatment of such disease, disease state, or indication.

Often the final hurdle of drug development, producing a final medicinal product from an active pharmaceutical ingredient (API) that is a solid or a liquid at room temperature is an extensive and costly process. Pharmaceutical formulation of an API that is a liquid at room temperature often requires, for example, excipients (e.g., stabilizers, additives, adjuvants, etc.) or conjugation to another molecule (e.g., a polymer) to stabilize and/or produce a processable and/or storable product. Instead, APIs that are solids at room temperature are often used for pharmaceutical formulations, avoiding the additional processing and formulation for producing medicinal products from liquid APIs; albeit, still incurring significant cost to formulation to a final medicinal product. Therefore, the cost of formulating solid or liquid APIs as well as the limited processability of liquid APIs limit the efficacy and/or adoption of potentially beneficial therapeutics.

Furthermore, patient compliance is an often unresolved issue in the clinic. In some instances, modified-release pharmaceuticals can improve patient compliance. For example, extended-release (ER) dosage forms, such as sustained-release (SR) or controlled-release (CR) dosage forms, may facilitate compliance with a therapeutic regimen in some instances. SR and CR dosage forms are generally designed to liberate an API at a certain rate, such as to maintain a particular drug concentration over a period of time. For example, SR maintains drug release over a sustained period but not at a constant rate, while CR maintains drug release over a sustained period at a more consistent (e.g., nearly constant) rate (e.g., zero-order). Despite their ability to extend the dosing of an active, such dosage forms can be difficult to develop. Moreover, such dosage forms often include controlled release excipients (e.g., polymers) and/or controlled release matrices to facilitate controlled release. In the case of liquid or otherwise low melting point active agents, controlled release formulations can be even more difficult to develop. Moreover, even in the best circumstances, many controlled release forms have limited durations of active release (e.g., 24-hour release windows), so patient compliance remains an issue.

Provided in certain embodiments herein are processable compounds that address the burden of medicinal product formulation as well as patient compliance. In certain embodiments, compounds described herein are solids at body temperature (e.g., about 37° C., or lower). In certain embodiments, compounds provided herein comprise a first group or radical (e.g., a structure provided in any one of Formula (I), Formula (IA), Formula (IB), Formula (IB') Formula (IC), Formula (II), Formula (IIA), Formula (IIB), Formula (III), Formula (IV), or Formula (V)) (e.g., covalently) joined (e.g., conjugated) to a second group. In some embodiments, the first group is a radical of Formula (I), Formula (IA), Formula (IB), Formula (IB') or Formula (IC). In some embodiments, the second group is a group that is itself not processable itself in free form (e.g., has a melting temperature that is higher than its degradation temperature, is generally insoluble, such as in aqueous media, or is otherwise not suited for processing). In certain embodiments, the second group is a group that is not processable in dimer form (e.g., when conjugated directly to itself or via a linker, such as described herein). In some embodiments, the second group is a group that has a melting point and/or glass transition temperature of less than 50° C., less than 40° C., less than 37° C., or the like. Generally, such compounds, even if solid at room temperature, may not be suitable for use as implants due to the possibility of melting or deformation in a physiological environment. In some embodiments, the compound is formed into an implantable article (e.g., a pellet), such as using methods described herein (e.g., as described in the examples). In some embodiments, the implantable article has a (e.g., zero-order) controlled release rate over an extended period (e.g., 1 week, 2 weeks, 3 weeks, 4 weeks, 6 weeks, 12 weeks, 52 weeks, or more) in an aqueous medium (e.g., a buffer solution, serum, biological environment (e.g., in the eye), in vivo, or the like). In some embodiments, a compound provided herein (or implant comprising such a compound) is administered to an individual suffering an acute or a chronic disease or condition (e.g., as a therapy for the acute or chronic disease or condition) in any suitable manner (e.g., route of administration, such as by implanting, and/or frequency of dosing), such as a single dose or a series of doses (e.g., once or twice every 1 week, 2 weeks, 3 weeks, 4 weeks, 6 weeks, 12 weeks, 52 weeks, or more).

In certain instances, compounds (e.g., conjugates) provided herein are used to improve treatment options and/or patient compliance for acute diseases and/or disorders. In some instances, processable compounds described herein are used to improve treatment options and/or patient compliance for chronic diseases and/or disorders. In some embodiments, the processable compounds described herein are used to improve treatment options and/or patient compliance for ophthalmology, neurology, post-surgical medicine, orthopedics, and pain management.

Provided herein are compounds (e.g., conjugates) that are processable (e.g., into an article). A processable compound is a compound that can be processed with heat or solvent to form a solid, such as with little (e.g., less than 20 wt. %, less than 10 wt. %, or less than 5 wt. %) or no addition of further excipient. In certain instances, the solid prepared following processing is an amorphous solid or a solid having a highly amorphous morphology (e.g., as discussed in more detail herein). In certain instances, a processable compound provided herein is a solid at room (e.g., 20° C.) and/or physiological temperature (e.g., 37° C.). In some instances, the compound is thermally processable, such as having a melt or glass transition temperature of at least 37° C., at least 40° C., at least 50° C., at least 60° C., at least 70° C., at least 100° C., or the like. In some embodiments, it is beneficial for the compound to be solid at room temperature, but processable at a temperature that is not prohibitively high. In some embodiments, a compound provided herein has a melt and/or glass transition temperature of less than 200° C., less than 150° C., less than 140° C., less than 130° C., less than 125° C., less than 120° C., or the like.

In some embodiments, the compounds have any suitable morphology, such as to facilitate processing and/or pharmacodynamic effects (e.g., release profile). In certain embodiments, the compound (or implant or pharmaceutical composition comprising the compound) is amorphous (or comprises a highly amorphous content). In some embodiments, a compound (e.g., morphology) provided herein is a solid, such as at a physiological temperature (e.g., having a melting point ($T_m$) and/or glass transition temperature ($T_g$) of at least 37° C.). In some embodiments, the compound is a crystalline solid, film, glass, or amorphous solid (e.g., at a temperature of at least 37° C.). In some embodiments, the compound (or composition, article, or coating comprising the compound) has a crystallinity of at most 15% (e.g., determined by PXRD, DSC, or polarized light microscopy). In some embodiments, the compound (or composition, article, or coating comprising the compound) is substantially non-crystalline (e.g., determined by PXRD, DSC, or polarized light microscopy). In some embodiments, the compound (or composition, article, or coating comprising the compound) is amorphous (e.g., determined by PXRD, DSC, or polarized light microscopy). In some embodiments, the compound (e.g., morphology) has a thermal melting point ($T_m$) that is greater than or equal to the glass transition temperature ($T_g$). In some embodiments, the compound has a melting point of at least 37° C. In some embodiments, the compound (e.g., morphology) has a melting point of at least 100° C. In some embodiments, either one or both of the first and/or second radicals (or (e.g., active) fragments or metabolites thereof) of the compounds (e.g., drug conjugates) and (e.g., active) agents are released (e.g., in their free form), the release being controlled release and/or extended release. In some embodiments, either one or both of the first and/or second radicals of the compounds and agents are released (e.g., in their free form) for at least 15 days (e.g., in solution, buffer solution, serum, biological environment, in vivo, or the like).

Described in certain embodiments herein are processable agents (e.g., compounds) formed from a processable group (e.g., a radical that makes a non-processable radical processable when linked or joined thereto) and a non-processable moiety (e.g., a radical that, if in its free form, would not be processable, such as by thermal techniques, e.g., because of a melting point that is below a physiological temperature). In some embodiments, the processable agents described herein are processable into a solid (e.g., at a temperature of at least 20° C., 25° C., 30° C., 37° C., or more). In some embodiments, provided herein are compounds useful in therapies for treating acute, chronic, or both disease or condition. In some instances, the conjugates provided herein represent a significant advance in the art, e.g., as processable compounds suitable for being formed into or formulated into controlled and/or extended release articles, coatings, or other pharmaceutical compositions that are beneficial for treating acute and/or chronic diseases or disorders, such as with infrequent (e.g., a single, or weekly, monthly, or less frequent) administration.

In certain aspects, provided herein is a compound comprising a first radical and a second radical, the first radical comprising the structure of Formula (I):

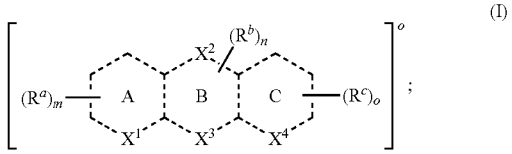

(I)

wherein:
⌢ is a single bond or a double bond;
each $R^a$, $R^b$, and $R^c$ are independently selected from the group consisting of oxo, halogen, —CN, —NO$_2$, alkyl, heteroalkyl, cycloalkyl, heterocycloalkyl, alkoxy, amino (e.g., dihydroamino, alkylamino, arylamino), hydroxy, or thiol, wherein the alkyl, heteroalkyl, cycloalkyl, or heterocycloalkyl is optionally substituted;
or any one of $R^a$, $R^b$, or $R^c$ are taken together with another of $R^a$, $R^b$, or $R^c$ to form a substituted or an unsubstituted cycloalkyl or heterocycloalkyl;
$X^1$, $X^2$, $X^3$, and $X^4$ are each independently selected from the group consisting of a bond and $Q_y$, wherein each Q is independently selected from the group consisting of —O—, —NR—, —S(R)$_x$—, and —C(R)$_z$—;
each of m, n, and o are independently 0-6;
each x is independently 0-5;
each y is independently 1-3;
each z is independently 1 or 2;
each R is independently selected from the group consisting of hydrogen, halogen, alkyl, heteroalkyl, cycloalkyl, heterocycloalkyl, alkoxy, amino (e.g., dihydroamino, alkylamino, arylamino), hydroxy, and thiol (e.g., wherein the alkyl, heteroalkyl, cycloalkyl, or heterocycloalkyl is optionally substituted), or one R is taken together with another R to form an oxo; and
the second radical being a therapeutically active agent (or drug) and the first radical (e.g., steroid) being different than the second radical (e.g., prostaglandin);
wherein, either the first radical, the second radical, or both the first radical and the second radical is not a steroid, or a pharmaceutically-acceptable salt or solvate thereof.

In some embodiments, provided herein is a compound comprising a first radical and a second radical, the first radical comprising a structure of Formula (IA):

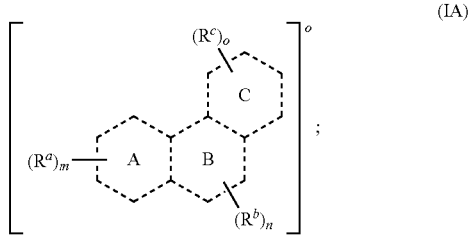

(IA)

wherein:
⌢ is a single bond or a double bond;
each $R^a$, $R^b$, and $R^c$ are independently selected from the group consisting of oxo, halogen, —CN, —NO$_2$, alkyl, heteroalkyl, cycloalkyl, heterocycloalkyl, alkoxy, amino (e.g., dihydroamino, alkylamino, arylamino), hydroxy, or thiol, wherein the alkyl, heteroalkyl, cycloalkyl, or heterocycloalkyl is optionally substituted;

or any one of $R^a$, $R^b$, or $R^c$ are taken together with another of $R^a$, $R^b$, or $R^c$ to form a substituted or an unsubstituted cycloalkyl or heterocycloalkyl;
each of m, n, and o are independently 0-6; and
the second radical being a therapeutically active agent (or drug) and the first radical (e.g., steroid) being different than the second radical (e.g., prostaglandin);
wherein, either the first radical, the second radical, or both the first radical and the second radical is not a steroid, or a pharmaceutically-acceptable salt or solvate thereof.

In some embodiments, provided herein is a compound comprising a first radical and a second radical, the first radical or the second radical comprising a structure of Formula (IB'):

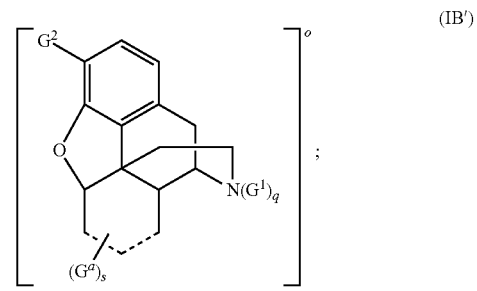

(IB')

wherein:
⌢ is a single bond or a double bond;
each $G^a$ is independently selected from the group consisting of oxo, halogen, —CN, —NO$_2$, azide, alkyl, heteroalkyl, cycloalkyl, heterocycloalkyl, alkoxy, aryloxy, ester, amino (e.g., dihydroamino, alkylamino, arylamino), hydroxy, hydrazone, oxime, or thiol, wherein the alkyl, heteroalkyl, cycloalkyl, alkoxy, aryloxy, hydrazone, or heterocycloalkyl is optionally substituted;
or a first $G^a$ is taken together with another $R^a$ to form an optionally substituted cycloalkyl, heterocycloalkyl, aryl, or heteroaryl;
each $G^1$ is independently hydrogen, alkyl, heteroalkyl, cycloalkyl, or heterocycloalkyl, wherein the alkyl, heteroalkyl, cycloalkyl, or heterocycloalkyl are optionally substituted;
$G^2$ is hydrogen, hydroxy, alkyl, heteroalkyl, alkoxy, cycloalkyl, or heterocycloalkyl, wherein the alkyl, heteroalkyl, cycloalkyl, alkoxy, or heterocycloalkyl are optionally substituted;
s is 0-8; and
q is 1 or 2,
or a pharmaceutically-acceptable salt or solvate thereof.

In some embodiments, provided herein is a compound comprising a first radical and a second radical, the first radical comprising a structure of Formula (IB):

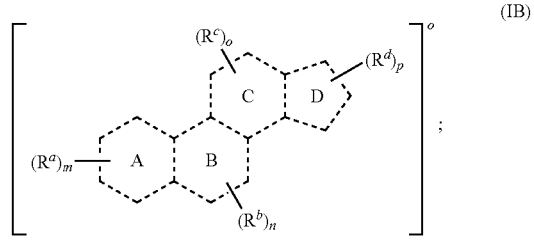

(IB)

wherein:

is a single bond or a double bond;

each $R^a$, $R^b$, $R^c$, and $R^d$ are independently selected from the group consisting of oxo, halogen, —CN, —NO$_2$, alkyl, heteroalkyl, cycloalkyl, heterocycloalkyl, alkoxy, amino (e.g., dihydroamino, alkylamino, arylamino), hydroxy, or thiol, wherein the alkyl, heteroalkyl, cycloalkyl, or heterocycloalkyl is optionally substituted;

or any one of $R^a$, $R^b$, $R^c$, and $R^d$ are taken together with another of $R^a$, $R^b$, $R^c$, and $R^d$ to form a substituted or an unsubstituted cycloalkyl or heterocycloalkyl;

each of m, n, o, and p are independently 0-6; and the second radical being a therapeutically active agent (or drug) and the first radical (e.g., steroid) being different than the second radical (e.g., prostaglandin);

wherein, either the first radical, the second radical, or both the first radical and the second radical is not a steroid, or a pharmaceutically-acceptable salt or solvate thereof.

In some embodiments, Ring A, B, C, or D of Formula (I), Formula (IA), or Formula (IB), each optionally and independently comprise one or more heteroatom (e.g., O, S, or N) within the ring.

In some embodiments, provided herein is a compound comprising a first radical and a second radical, the first radical comprising a structure of Formula (IC):

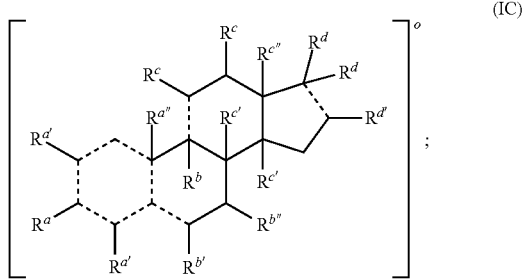

wherein:

is a single bond or a double bond;

$R^a$ is hydrogen, —OH, or oxo;

each $R^{a'}$ is independently selected from hydrogen, —OH, halogen, C$_1$-C$_3$ alkyl, and alkoxy;

$R^{a''}$ is absent, hydrogen, or C$_1$-C$_3$ alkyl;

$R^b$ is absent, hydrogen, halogen, or C$_1$-C$_3$ alkyl;

$R^{b'}$ is hydrogen, halogen, —OH, oxo, or C$_1$-C$_3$ alkyl;

$R^{b''}$ is hydrogen or —OH;

each $R^c$ is independently hydrogen, —OH, oxo, or C$_1$-C$_3$ alkyl;

each $R^{c'}$ is independently hydrogen or C$_1$-C$_3$ alkyl;

$R^{c''}$ is hydrogen, —OH, C$_1$-C$_3$ alkyl, or —C(=O)H;

each $R^d$ is independently hydrogen, —OH, —COOH, alkyl (e.g., alkylene, alkenyl, or alkynyl), heteroalkyl, or each $R^d$ is taken together to form an oxo, wherein the alkyl or heteroalkyl is optionally substituted;

$R^{d'}$ is hydrogen, —OH, C$_1$-C$_3$ alkyl (e.g., alkylene or alkenyl), or heteroalkyl;

or one $R^d$ is taken together with $R^{d'}$ to form a substituted or unsubstituted cycloalkyl or heterocycloalkyl; and the second radical being a therapeutically active agent (or drug) and the first radical (e.g., steroid) being different than the second radical (e.g., prostaglandin);

wherein, either the first radical, the second radical, or both the first radical and the second radical is not a steroid, or a pharmaceutically-acceptable salt or solvate thereof.

In some embodiments, the alkyl or heteroalkyl of $R^d$ is substituted with one or more of the group consisting of —SH, —OH, —COOH, oxo, halogen, amino, alkyl (e.g., alkenyl, alkynyl), heteroalkyl, ester, amide, sulfonic acid, and sulfone. In some embodiments, one $R^d$ is taken together with $R^{d'}$ to form substituted heterocycloalkyl.

In some embodiments, the first radical and the second radical are joined by a linker (e.g., a bond). In some embodiments, the first radical is joined to the second radical through any one of $R^a$, $R^b$, $R^c$, or $R^d$ of the first radical. In some embodiments, the first radical is joined to the second radical through any one of $R^a$, $R^b$, $R^c$, or $R^d$, and the $R^a$, $R^b$, $R^c$, or $R^d$ through which the first radical is joined to the second radical comprises a hydroxyl radical (e.g., when together with the linker or second radical (where the linker is a bond), forms an ether), a thiol radical (e.g., when together with the linker or second radical (where the linker is a bond), forms a thioether), or a carboxylate radical (e.g., when taken together with the linker or second radical (where the linker is a bond), forms an ester or carbonate).

In some embodiments, the $R^a$, $R^b$, $R^c$, or $R^d$ through which the first radical is joined to the second radical comprises a hydroxyl radical which together with the linker or with the second radical forms an ether. In some embodiments, the $R^a$, $R^b$, $R^c$, or $R^d$ through which the first radical is joined to the second radical comprises a thiol radical which together with the linker or the second radical forms a thioether. In some embodiments, the $R^a$, $R^b$, $R^c$, or $R^d$ through which the first radical is joined to the second radical comprises a carboxylate radical which together with the linker or the second radical forms an ester or a carbonate.

In some embodiments, both the first radical and the second radical have the structure of any one of Formula (I), Formula (IA), Formula (IB'), Formula (IB), or Formula (IC). In some embodiments, both the first radical and the second radical have the structure of any one of Formula (I), Formula (IA), or Formula (IB'). In some embodiments, both the first radical and the second radical have the structure of Formula (I) or Formula (IA). In some embodiments, both the first radical and the second radical have the structure of Formula (I). In some embodiments, both the first radical and the second radical have the structure of Formula (IA). In some embodiments, the first radical and the second radical (e.g., that have the structure of any one of Formula (I), Formula (IA), Formula (IB'), Formula (IB), or Formula (IC)) are joined by a linker (e.g., a hydrolysable linker). In some embodiments, the linker (e.g., a hydrolysable linker) is a bond.

In some embodiments, the first radical has a structure of any one of Formula (I), Formula (IA), Formula (IB'), Formula (IB), or Formula (IC). In some embodiments, the second radical has a structure of any one of Formula (I), Formula (IA), Formula (IB'), Formula (IB), or Formula (IC). In some embodiments, the second radical (e.g., which is not processable in its free form, not processable in dimer form, and/or is liquid or malleable at physiological temperature) does not have a structure of any one of a structure of any one of Formula (I), Formula (IA), Formula (IB'), Formula (IB), or Formula (IC).

In some embodiments, the radical of Formula (I), Formula (IA), Formula (IB'), Formula (IB), or Formula (IC) is a steroid, an opioid agonist, an opioid antagonist, an adrenergic receptor antagonist (e.g., β-blocker, α-1 blocker), or a serotonergic antagonist (e.g., serotonin 5-HT3 receptor antagonist). In some embodiments, the first radical and/or the second radical is an anti-inflammatory agent, an anti-psychotic agent (e.g., typical anti-psychotic, atypicalantipsychotic, schizophrenia, or the like), or the like.

In some embodiments, the first radical and/or the second radical is a beta-blocker, which may be used to treat intraocular pressure in the eye. In some embodiments, the beta-blocker is timolol. In other embodiments, the beta-blocker is levobunolol, metipranolol or carteolol. In some embodiments, the beta-blocker is selected from the group consisting of Dichloroisoprenaline, Propranolol, Bucindolol, Carteolol, Carvedilol, Labetalol, Nadolol, Oxprenolol, Penbutolol, Pindolol, Sotalol, Timolol, Acebutolol, Atenolol, Betaxolol, Bisoprolol, Celiprolol, Metoprolol, Nebivolol, Esmolol, Butaxamine, ICI-118,551, SR 59230A, Nebivolol, Acebutolol, pindolol, labetalol, mepindolol, oxprenolol, celiprolol, and penbutolol. In some embodiments, the beta-blocker is selected from the group consisting of Betaxolol, carteolol, levobunolol, timolol, metipranolol.

In some embodiments, the first radical is a solid (e.g., having a melting point of at least 30° C.) in its free form. In some embodiments, the second radical is a liquid (e.g., having a melting point of less than 30° C.) in its free form.

In some embodiments, the first radical or the second radical is a steroid (e.g., dexamethasone, anecortave (e.g., anecortave desacetate), etc.). In some embodiments, the first radical is or is derived from anecortave (e.g., anecortave acetate or anecortave desacetate). In some embodiments, the first radical is a steroid (e.g., dexamethasone, anecortave (e.g., anecortave desacetate), etc.). In some embodiments, the steroid is a corticosteroid (e.g., glucocorticoid or mineralcorticoid), a sex steroid, a neurosteroid, an aminosteroid, or a secosteroid. In some embodiments, the second radical is not a steroid. In certain embodiments, the second radical is a radical that does not have a structure of Formula (I), Formula (IA), Formula (IB'), Formula (IB), or Formula (IC).

In some embodiments, the steroid is a glucocorticoid. In some embodiments, the glucocorticoid is selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, loprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide, and ulobetasol, or the like.

In some embodiments, the steroid is a mineralocorticoid. In some embodiments, the mineralocorticoid is selected from the group consisting of aldosterone, fludrocortisone, deoxycorticosterone, and corticosterone, or the like. In some embodiments, the mineralocorticoid is canrenone (e.g., potassium canrenoate), drospirenone, eplerenone, spirolactone, or a metabolite thereof (e.g., 7α-thionnethylspironolactone, canrenone, 6β-hydroxy-7α-thionnethylspironolactone, and 7α-thiospironolactone).

In some embodiments, the steroid is an anabolic steroid. In some embodiments, the anabolic steroid is selected from the group consisting of androisoxazole, androstenediol, bolandiol, bolasterone, clostebol, ethylestrenol, formyldienolone, 4-hydroxy-19-nortestosterone, methandriol, methenolone, methyltrienolone, nandrolone, norbolethone, oxymesterone, stenbolone, and trenbolone, or the like.

In some embodiments, the steroid is an androgenic steroid. In some embodiments, the androgenic steroid is selected from the group consisting of boldenone, fluoxymesterone, mestanolone, mesterolone, methandrostenolone, 17-methyltestosterone, 17-α-methyltestosterone 3-cyclopentyl enol ether, norethandrolone, normethandrone, oxandrolone, oxymesterone, oxymetholone, prasterone, stanlolone, stanozolol, testosterone, testosterone 17-chloral hemiacetal, testosterone proprionate, testosterone enanthate tiomesterone dehydroepiandrosterone (DHEA), androstenedione, androstenediol, androsterone, dihydrotestosterone (DHT), and androstanolone, or the like.

In some embodiments, the steroid is a progestin steroid. In some embodiments, the progestin steroid is selected from the group consisting of progesterone, norethisterone, norethisterone acetate, gestodene, levonorgestrel, allylestrenol, anagestone, desogestrel, dimethisterone, dydrogesterone, ethisterone, ethynodiol, ethynodiol diacetate, etonogestrel, gestodene, ethinylestradiol, haloprogesterone, 17-hydroxy-16-methylene-progesterone, 17-alpha-hydroxyprogesterone, lynestrenol, medroxyprogesterone, melengestrol, norethindrone, norethynodrel, norgesterone, gestonorone, norgestimate, norgestrel, levonorgestrel, norgestrienone, norvinisterone, pentagestrone, MENT (7-methyl-19-testosterone); norelgestromin, and trimigestone drospirenone, tibolone, and megestrol, or the like.

In some embodiments, the steroid is an estrogen steroid. In some embodiments, the estrogen steroid is selected from the group consisting of estradiol, estrone, eguilenin, equilin, estradiol benzoate, estriol, ethinyl estradiol, mestranol, moxestrol, mytatrienediol, quinestradiol, and quinestrol, or the like.

In some embodiments, the steroid is selected from the group consisting of abiraterone, cyproterone acetate, dutasteride, enzalutamide, finasteride, galeterone, fusidic acid, cholesterol, 11-deoxycortisol, 11-deoxycorticosterone, pregnenolone, cholic acid, chenodeoxycholic acid, ursodeoxycholic acid, obeticholic acid, tetrahydrocortisone, tetrahydrodeoxycortisol, tetrahydrocorticosterone, 5α-dihydrocorticosterone, 5α-dihydropregesterone, flugestone, prebediolone, chlormadinone acetate, medrogestone, and segesterone acetate, or the like.

In some embodiments, the steroid is an anti-angiogenic or an intraocular pressure (IOP) lowering steroid. In some embodiments, the anti-angiogenic or intraocular pressure (IOP) lowering steroid is selected from the group consisting of anecortave acetate, anecortave (e.g., anecortave desacetate), 11-epicortisol, 17α-hydroxyprogesterone, tetrahydrocortexolone, and tetrahydrocortisol, or the like. In some embodiments, the anti-angiogenic or IOP lowering steroid is anecortave desacetate.

In some embodiments, the steroid is a cholic acid-related bile acid steroid. In some embodiments, the cholic acid-related bile acid steroid is selected from the group consisting of deoxycholic acid, apocholic acid, dehydrocholic acid, glycochenodeoxycholic acid, glycocholic acid, glycodeoxycholic acid, hyodeoxycholic acid, lithocholic acid, α-muricholic acid, β-muricholic acid, γ-muricholic acid, ω-muricholic acid, taurochenodeoxycholic acid, taurocholic acid, taurodeoxycholic acid, taurolithocholic acid, and tauroursodeoxycholic acid, or the like.

In some embodiments, the steroid is a neurosteroid. In some embodiments, the neurosteroid is selected from the group consisting of alphaxalone, alphadolone, hydroxydione, minaxolone, tetrahydrodeoxycorticosterone, allopregnanolone, pregnanolone, ganoxolone, 3α-androstanediol, epipregnanolone, isopregnanolone, and 24(S)-hydroxycholesterol, or the like.

In some embodiments, the steroid is a steroid pheromone. In some embodiments, the steroid pheromone is selected from the group consisting of androstadienol, androstadienone, androstenol, androstenone, estratetraenol, 5-dehydroprogesterone, 6-dehydro-retroprogesterone, allopregnanolone, and hydroxyprogesterone caproate, or the like.

In some embodiments, the steroid is a steroid metabolite. In some embodiments, the steroid metabolite is selected from the group consisting of tetrahydrotriamcinolone, cortienic acid, 11-dehydrocorticosterone, 11β-hydroxypregnenolone, ketoprogesterone, 17-hydroxypregnenolone, 17,21-dihydroxypregnenolone, 18-hydroxycorticosterone, deoxycortisone, 21-hydroxypregnenolone, and progesterone, or the like.

In some embodiments, the steroid is a progestin. In some embodiments, the progestin is selected from the group consisting of allopregnone-3α,20α-diol, allopregnone-3β,20β-diol, allopregnane-3β,21-diol-11,20-dione, allopregnane-3β,17α-diol-20-one, 3,20-allopregnanedione, 3β,11β,17α,20β,21-pentol, allopregnane-3β,17α,20β,21-tetrol, allopregnane-3α,11β,17α,21-tetrol-20-one, allopregnane-3β,11β,17α,21-tetrol-20-one, allopregnane-3β,17α,20β-triol, allopregnane-3β,17α,21-triol-11,20-dione, allopregnane-3β,11β,21-triol-20-one, allopregnane-3β,17α,21-triol-20-one, allopregnane-3α-ol-20-one, allopregnane-3β-ol-20-one, pregnanediol, 3,20-pregnanedione, 4-pregnene-20,21-diol-3,11-dione, 4-pregnene-11β,17α,20β,21-tetrol-3-one, 4-pregnene-17α,20β,21-triol-3,11-dione, 4-pregnene-17α,20β,21-triol-3-one, and pregnenolone, or the like.

In some embodiments, the first radical and the second radical are joined by a linker (e.g., hydrolyzable linker). In some embodiments, the first radical and the second radical are joined by a bond.

In some embodiments, the linker is a bond, alkyl, heteroalkyl, or alkoxy, wherein the alkyl, heteroalkyl, or alkoxy is optionally substituted. In some embodiments, the alkyl, heteroalkyl, or alkoxy are each independently substituted with one or more groups, each group being independently selected from the group consisting of a bond, —O—, —S—, silicone, amino, optionally substituted alkyl (e.g., alkenyl, alkynyl, branched (e.g., polypropylene), haloalkyl), optionally substituted heteroalkyl (e.g., polyTHF), and optionally substituted cycloalkyl. In some embodiments, the linker is a bond. In some embodiments, the linker is alkyl (alkylene) and the alkyl (alkylene) is substituted with one or more groups selected from —OH, halo, oxo, alkyl, heteroalkyl, cycloalkyl, and heterocycloalkyl. In some embodiments, the linker is alkyl (alkylene) and the alkyl (alkylene) is an unsubstituted alkylene. In some embodiments, the linker is heteroalkyl (heteroalkylene) and the heteroalkyl (heteroalkylene) is substituted with one or more groups selected from halo or alkyl. In some embodiments, the linker is heteroalkyl (heteroalkylene) and is the heteroalkyl (heteroalkylene) an unsubstituted heteroalkylene. In some embodiments, the linker comprises one or more linker groups selected from a bond, —O—, —S—, unsubstituted alkylene, C=O (CH$_2$CH$_2$)$_n$C=O, C=O(CHCH)$_n$C=O, C=O(OCH$_2$CH$_2$O)$_n$C=O, O(CH$_2$CH$_2$O)$_n$, and C=O(CH$_2$CH$_2$O)$_n$, (CH(CH$_3$)C(=O)O)$_n$, wherein n is 1-20. In some embodiments, the linker is a bond, unsubstituted alkylene, C=O(CH$_2$CH$_2$)$_n$C=O, C=O(CHCH)$_n$C=O, C=O(OCH$_2$CH$_2$O)$_n$C=O, O(CH$_2$CH$_2$O)$_n$, and C=O(CH$_2$CH$_2$O)$_n$, (CH(CH$_3$)C(=O)O)$_n$, C=O(CH$_2$CH$_2$)$_n$ C=O(CH(CH$_3$)C(=O)O)$_n$, wherein n is 1-20. In some embodiments, the linker is a bond.

In some embodiments, the linker is hydrolyzed in a buffered solution. In some embodiments, the linker is hydrolyzed by an enzyme. In some embodiments, the enzyme is a hydrolase (e.g., a protease or an esterase).

In some embodiments, the first radical is a (e.g., hydroxyl or carboxyl) radical of a compound selected from the group consisting of:

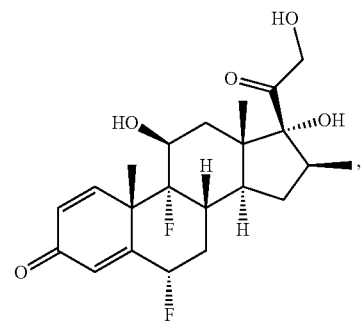

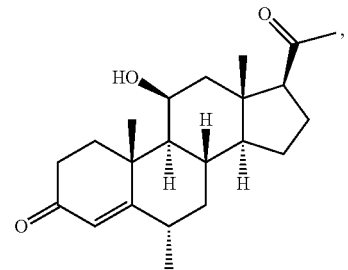

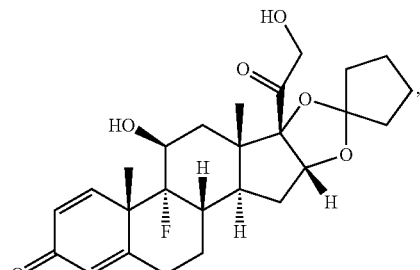

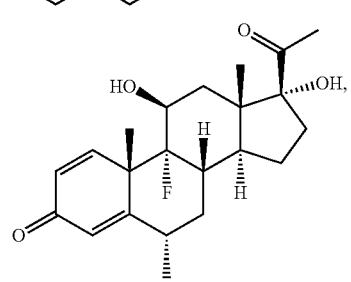

71
-continued
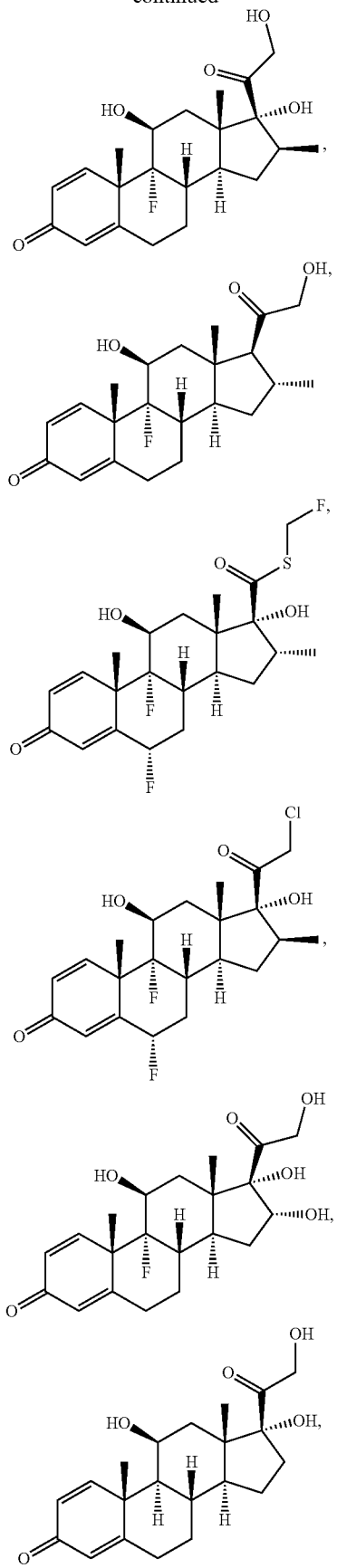
72
-continued
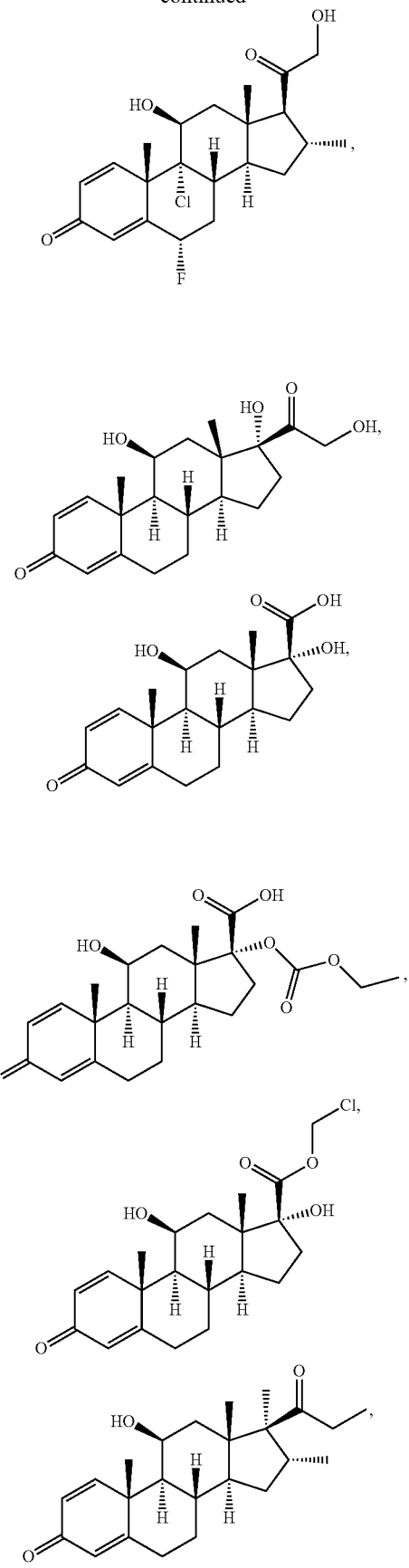

73
-continued
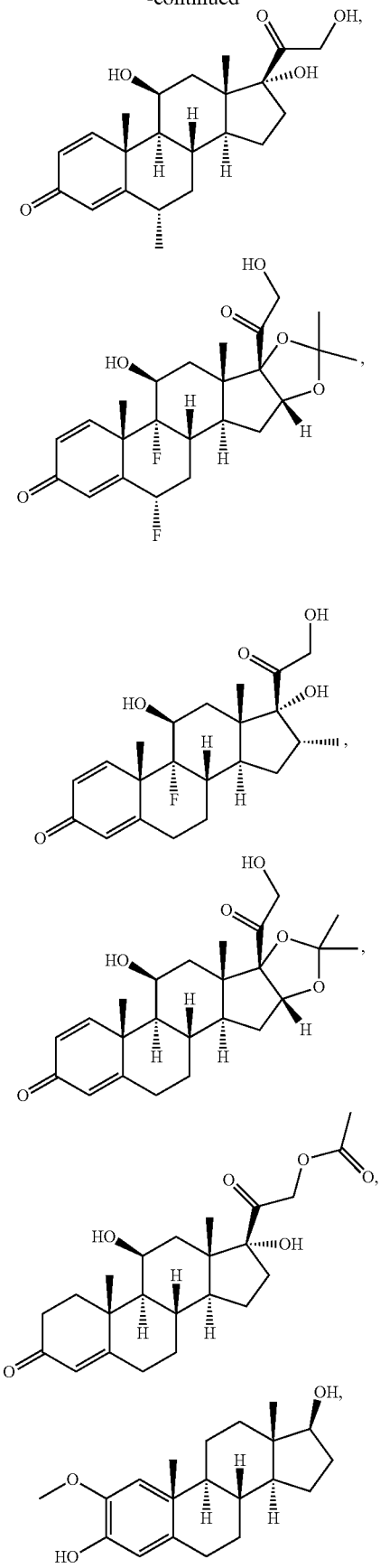
74
-continued
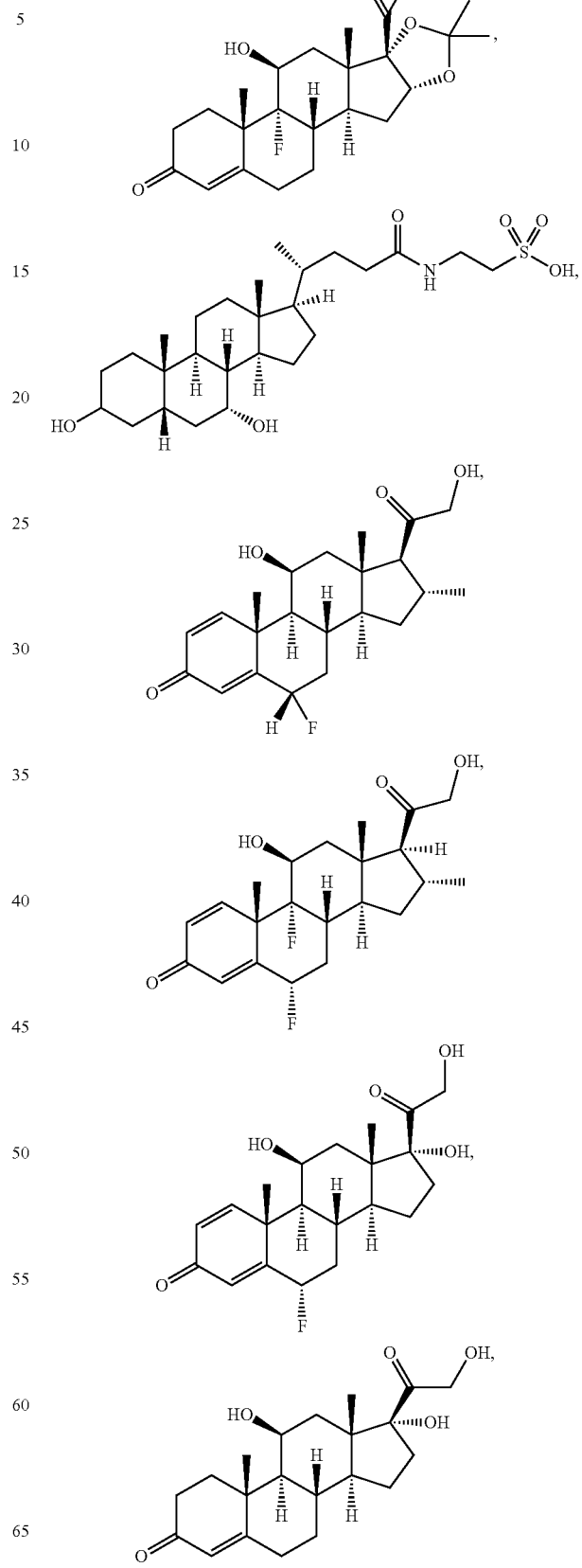

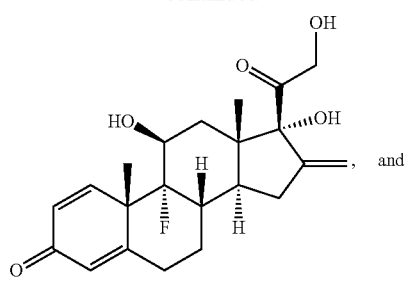
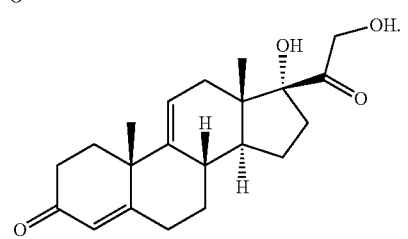
In some embodiments, the first radical is a (e.g., hydroxyl or carboxyl) radical of a compound selected from the group consisting of:
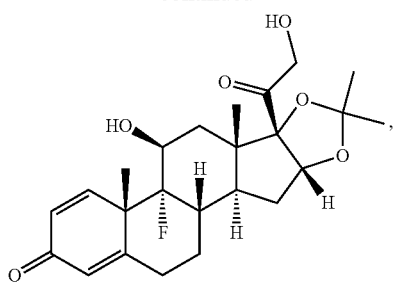
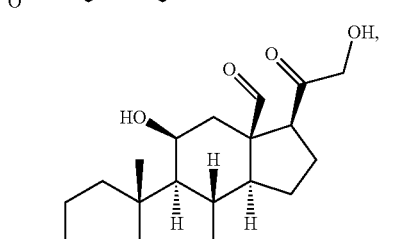
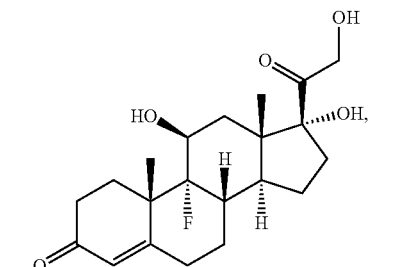
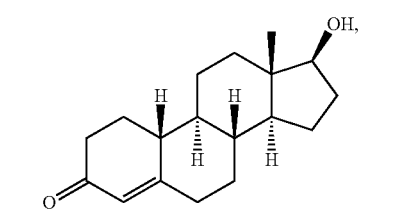
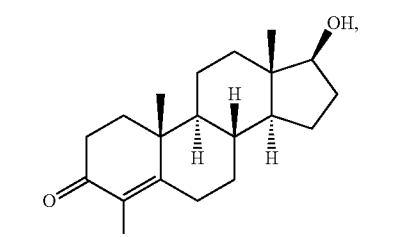
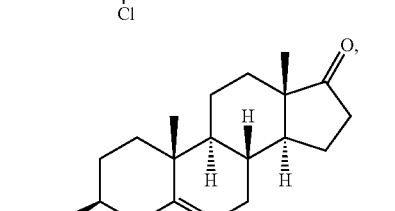
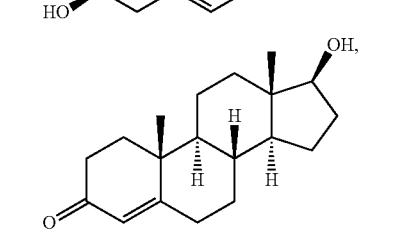

77
-continued
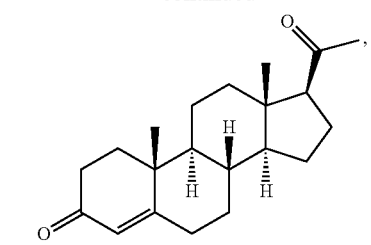
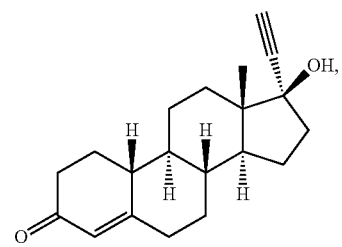
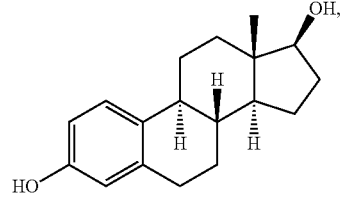
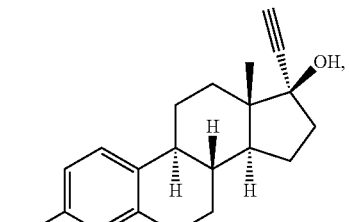
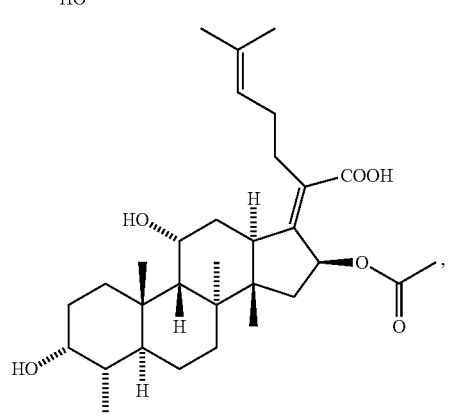
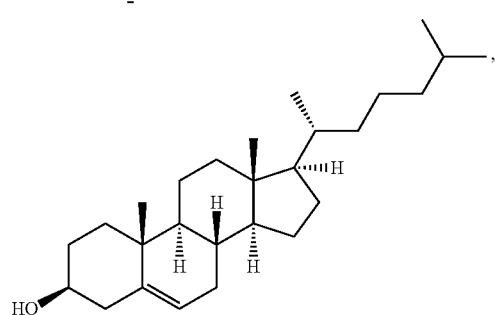
78
-continued
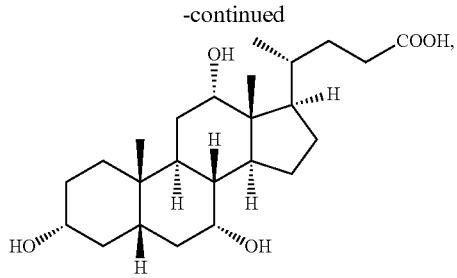
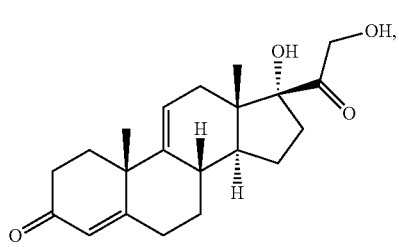
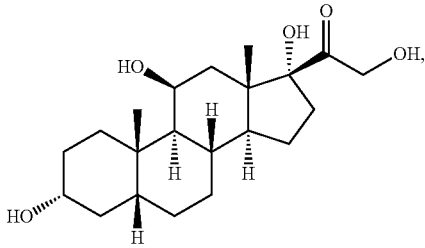
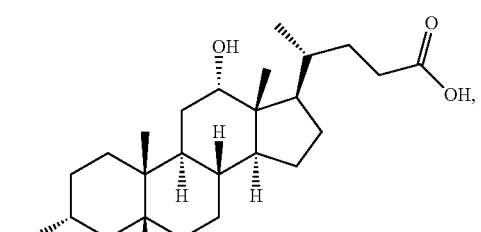
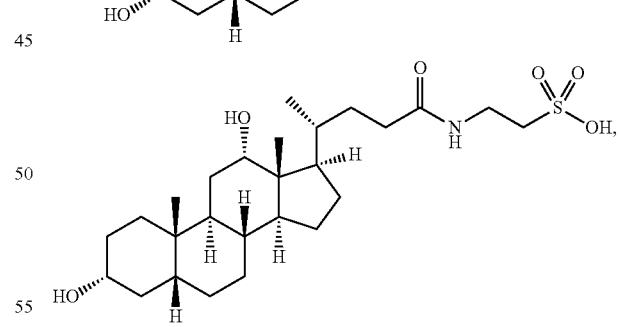
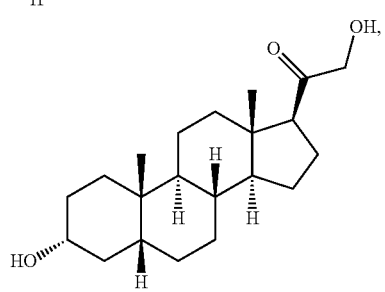

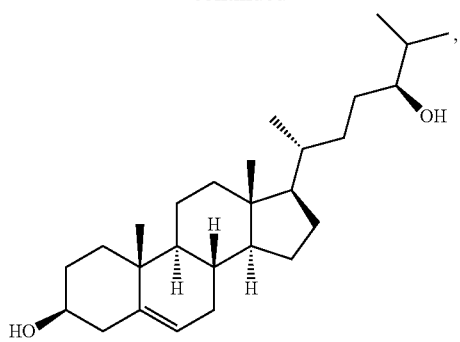

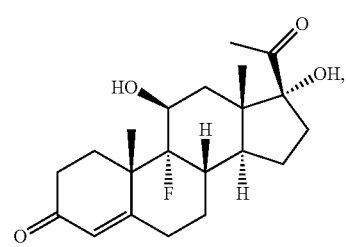

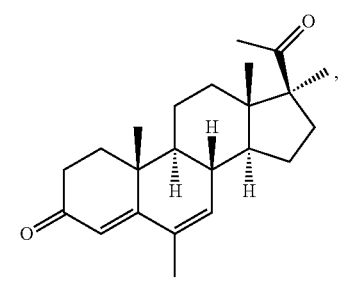

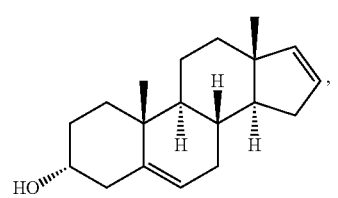

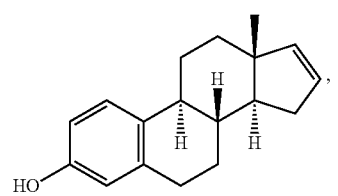

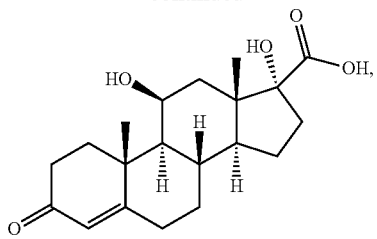

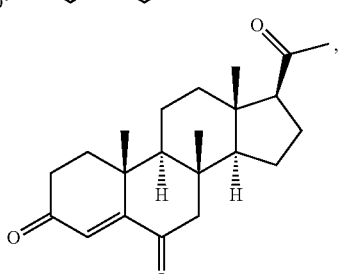

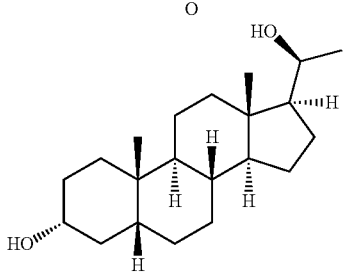

, and

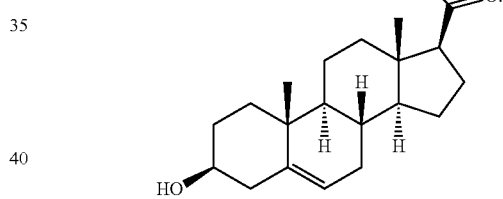

In certain embodiments, the disclosure provides a compound, or pharmaceutically acceptable salt thereof, having a structure provided in Table 1. In some embodiments, the compound, or pharmaceutically acceptable salt thereof, provided in Table 1 is a solid at a temperature of at least 20° C. (e.g., at least 30 C, at least 37 C, at least 40 C, at least 50 C, at least 70 C, at least 100 C, or the like). In some embodiments, the compound, or pharmaceutically acceptable salt thereof, provided in Table 1 is processable at a temperature of at least 20° C. (e.g., as described in the examples). In some embodiments, the compound, or pharmaceutically acceptable salt thereof, provided in Table 1 is processable into an article (e.g., machined, molded, emulsion-processed, electrospun, electrosprayed, blow molded, or extruded to form a fiber, fiber mesh, woven fabric, non-woven fabric, film, surface coating, pellet, cylinder, rod, microparticle, nanoparticle, or another shaped article) at a temperature of at least 20° C. In some embodiments, the compound, or pharmaceutically acceptable salt thereof, provided in Table 1 comprises both a first radical and a second radical. In some embodiments, the compound in Table 1 is processable when the first radical, and the second radical are joined by a linker. In some embodiments, the linker is a bond.

TABLE 1

| Compound Number | Structure | Name |
|---|---|---|
| 1 | 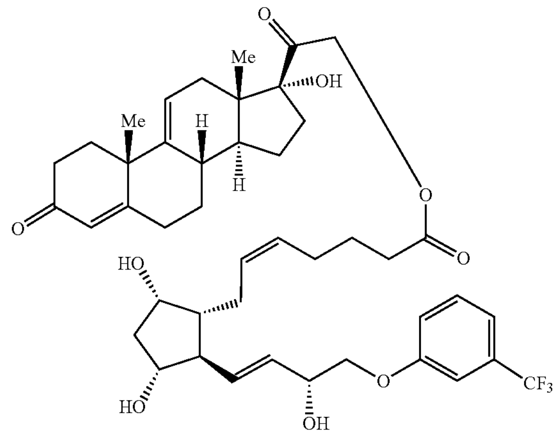 | 2-((8S,10S,13S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate |
| 2 | 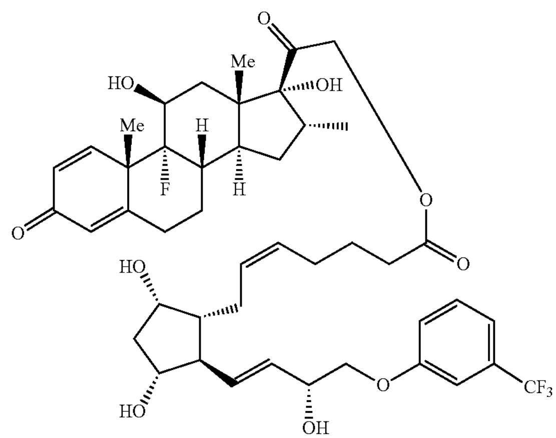 | 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate |
| 3 | 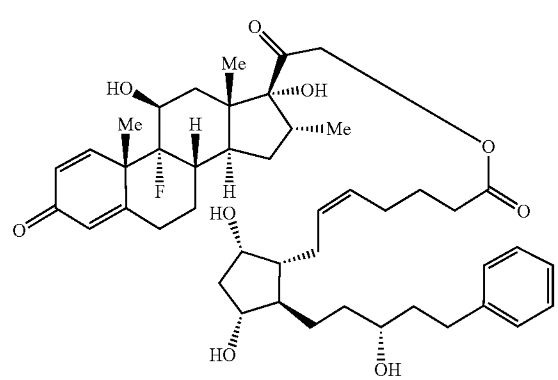 | 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl (Z)-7-((1R,2R,3R,5S)-3,5-dihydroxy-2-((R)-3-hydroxy-5-phenylpentyl)cyclopentyl)hept-5-enoate |

TABLE 1-continued

| Compound Number | Structure | Name |
|---|---|---|
| 4 | 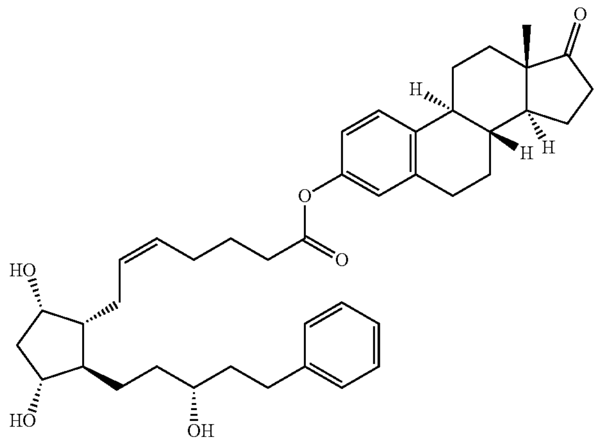 [SMILES: C[C@]12CC[C@@H]3c4ccc(OC(=O)CCC/C=C\C[C@@H]5[C@@H](CC[C@@H](O)CCc6ccccc6)[C@H](O)C[C@@H]5O)cc4CC[C@H]3[C@@H]1CCC2=O] | (8R,9S,13S,14S)-13-methyl-17-oxo-7,8,9,11,12,13,14,15,16,17-decahydro-6H-cyclopenta[a]phenanthren-3-yl (Z)-7-((1R,2R,3R,5S)-3,5-dihydroxy-2-((R)-3-hydroxy-5-phenylpentyl)cyclopentyl)hept-5-enoate |
| 5 | 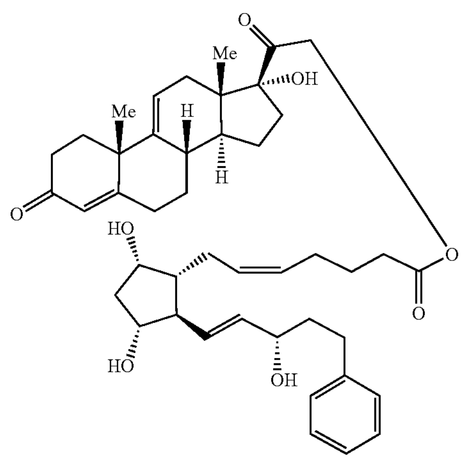 | 2-((8S,10S,13S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl (Z)-7-((1R,2R,3R,5S)-3,5-dihydroxy-2-((S,E)-3-hydroxy-5-phenylpent-1-en-1-yl)cyclopentyl)hept-5-enoate |
| 6 | 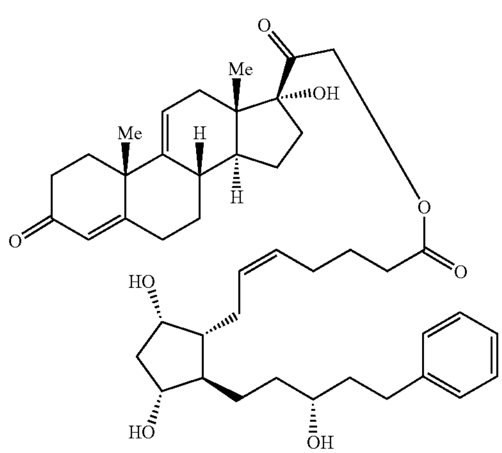 | 2-((8S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl (Z)-7-((1R,2R,3R,5S)-3,5-dihydroxy-2-((R)-3-hydroxy-5-phenylpentyl)cyclopentyl)hept-5-enoate |

TABLE 1-continued

| Compound Number | Structure | Name |
|---|---|---|
| 7 | 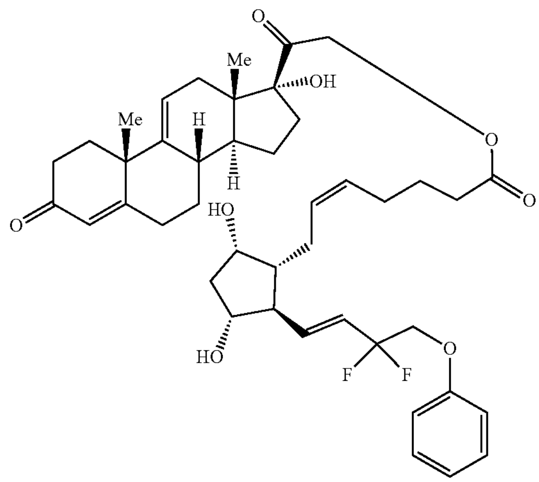 | 2-((8S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl (Z)-7-((1R,2R,3R,5S)-2-((E)-3,3-difluoro-4-phenoxybut-1-en-1-yl)-3,5-dihydroxycyclopentyl)hept-5-enoate |
| 8 | 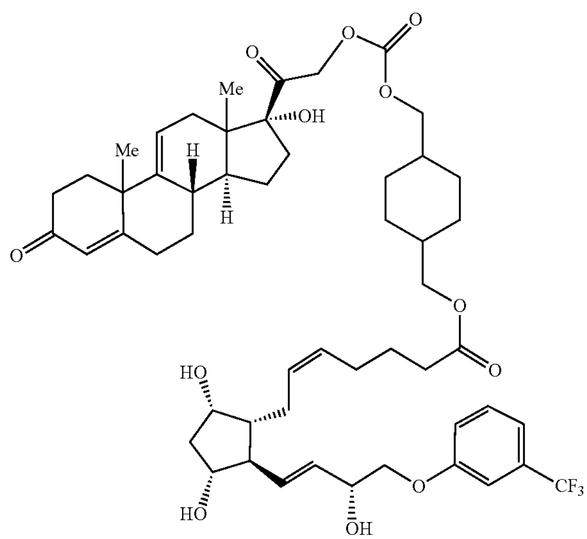 | (4-((((2-((8S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethoxy)carbonyl)oxy)methyl)cyclohexyl)methyl (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate |
| 9 | 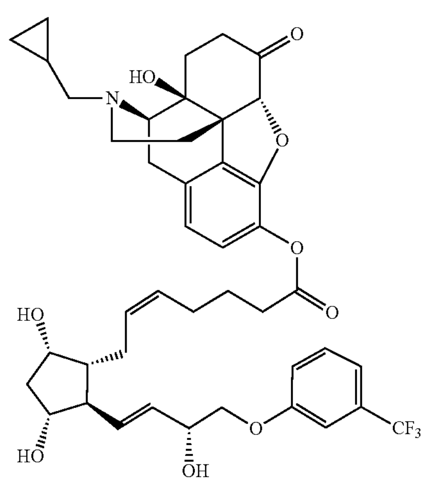 [SMILES: O=C(CCC/C=C\C[C@@H]1[C@@H](/C=C/[C@@H](O)COc2cccc(C(F)(F)F)c2)[C@H](O)C[C@@H]1O)Oc1ccc2c3c1O[C@H]1C(=O)CC[C@@]4(O)[C@@H](C2)N(CC2CC2)CC[C@]314] | (4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate |

TABLE 1-continued

| Compound Number | Structure | Name |
|---|---|---|
| 10 | 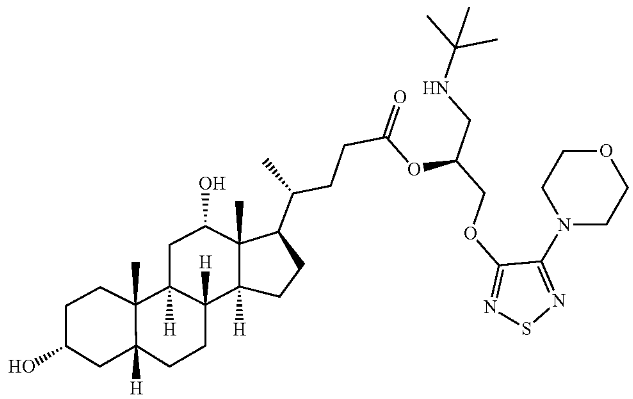 | (S)-1-(tert-butylamino)-3-((4-morpholino-1,2,5-thiadiazol-3-yl)oxy)propan-2-yl (R)-4-((3R,5R,8R,9S,10S,12S,13R,14S,17R)-3,12-dihydroxy-10,13-dimethylhexadecahydro-1H-cyclopenta[a]phenanthren-17-yl)pentanoate |
| 11 | 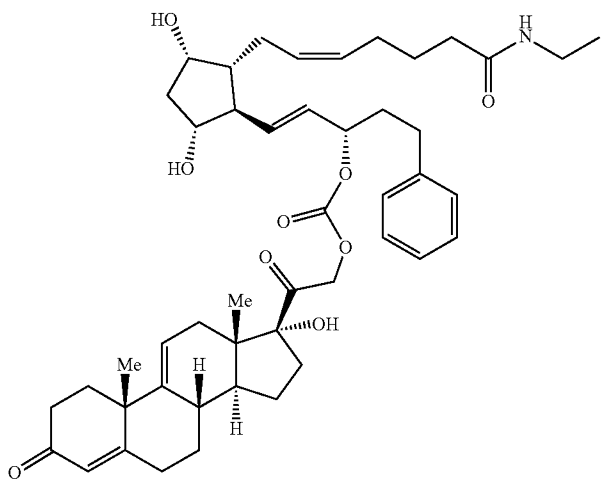 | (S,E)-1-((1R,2R,3S,5R)-2-((Z)-7-(ethylamino)-7-oxohept-2-en-1-yl)-3,5-dihydroxycyclopentyl)-5-phenylpent-1-en-3-yl (2-((8S,10S,13S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl) carbonate |
| 12 | 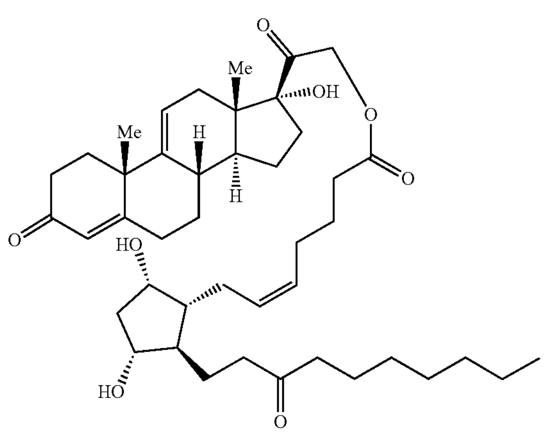 | 2-((8S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl (Z)-7-((1R,2R,3R,5S)-3,5-dihydroxy-2-(3-oxodecyl)cyclopentyl)hept-5-enoate |

TABLE 1-continued

| Compound Number | Structure | Name |
|---|---|---|
| 13 | 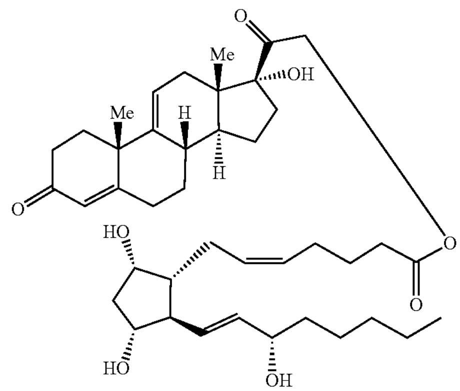 | 2-((8S,10S,13S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl (Z)-7-((1R,2R,3R,5S)-3,5-dihydroxy-2-((S,E)-3-hydroxyoct-1-en-1-yl)cyclopentyl)hept-5-enoate |
| 14 | 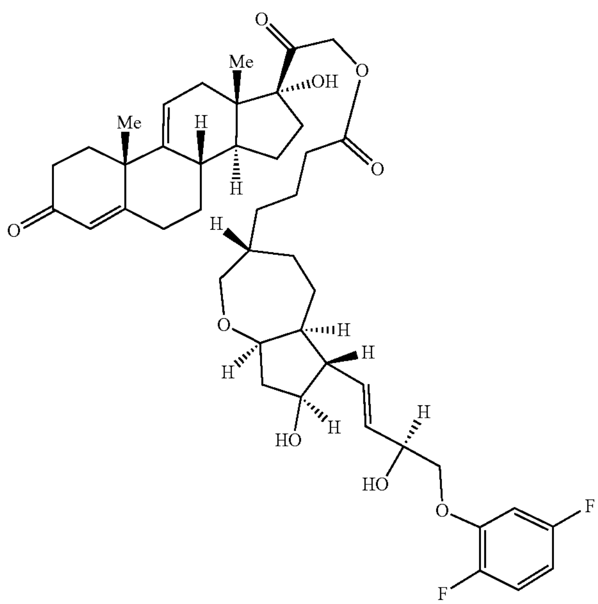 | 2-((8S,10S,13S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl 4-((3R,5aS,6S,7S,8aR)-6-((S,E)-4-(2,5-difluorophenoxy)-3-hydroxybut-1-en-1-yl)-7-hydroxyoctahydro-2H-cyclopenta[b]oxepin-3-yl)butanoate |
| 15 | 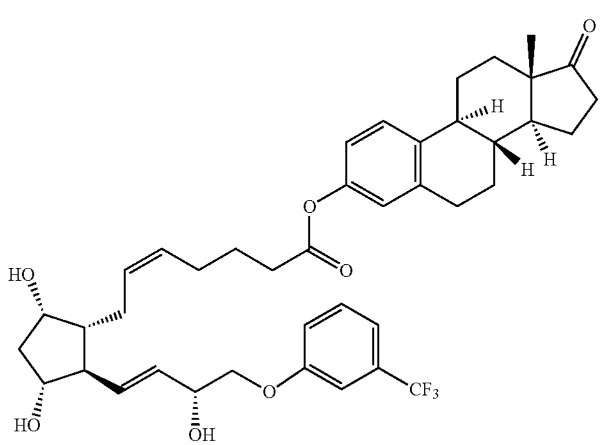 | (8R,9S,13S,14S)-13-methyl-17-oxo-7,8,9,11,12,13,14,15,16,17-decahydro-6H-cyclopenta[a]phenanthren-3-yl (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate |

TABLE 1-continued

| Compound Number | Structure | Name |
|---|---|---|
| 16 | 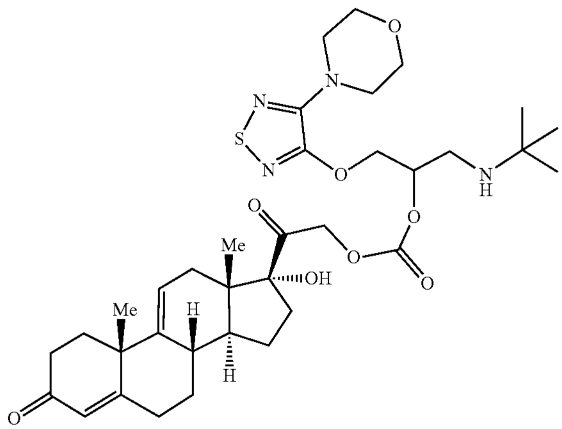 | 1-(tert-butylamino)-3-((4-morpholino-1,2,5-thiadiazol-3-yl)oxy)propan-2-yl (2-((8S,10S,13S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl) carbonate |
| 17 | 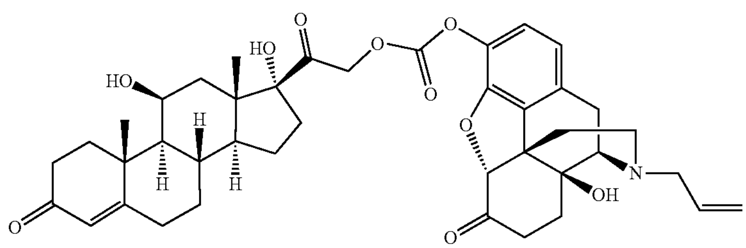 | (4R,4aS,7aR,12bS)-3-allyl-4a-hydroxy-7-oxo-2,3,4,4a,5,6,7,7a-octahydro-1H-4,12-methanobenzofuro[3,2-e]isoquinolin-9-yl (2-((8S,9S,10R,11S,13S,14S,17R)-11,17-dihydroxy-10,13-dimethyl-3-oxo-2,3,6,7,8,9,10,11,12,13,14,15,16,17-tetradecahydro-1H-cyclopenta[a]phenanthren-17-yl)-2-oxoethyl) carbonate |
| 18 | 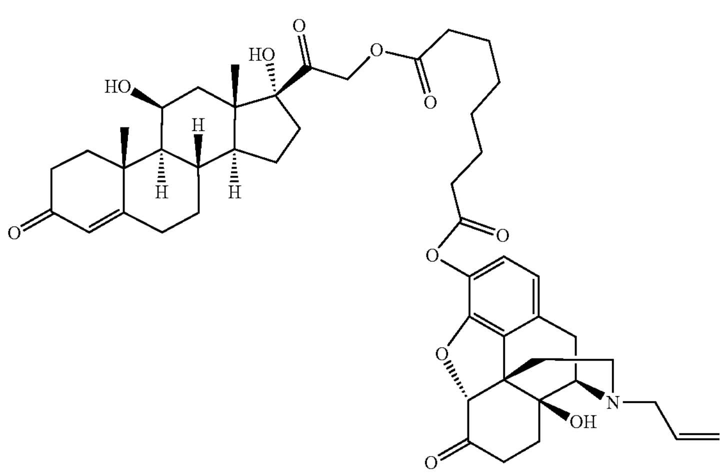 | 1-((4R,4aS,7aR,12bS)-3-allyl-4a-hydroxy-7-oxo-2,3,4,4a,5,6,7,7a-octahydro-1H-4,12-methanobenzofuro[3,2-e]isoquinolin-9-yl) 8-(2-((8S,9S,10R,11S,13S,14S,17R)-11,17-dihydroxy-10,13-dimethyl-3-oxo-2,3,6,7,8,9,10,11,12,13,14,15,16,17-tetradecahydro-1H-cyclopenta[a]phenanthren-17-yl)-2-oxoethyl) octanedioate |

TABLE 1-continued

| Compound Number | Structure | Name |
|---|---|---|
| 19 | 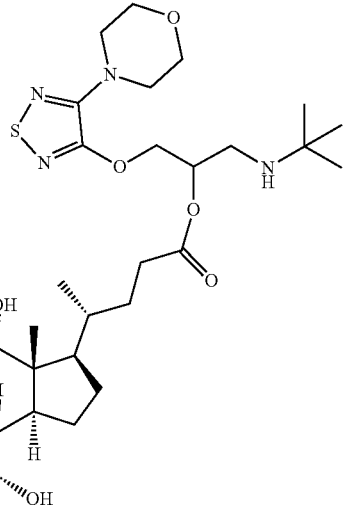 | 1-(tert-butylamino)-3-((4-morpholino-1,2,5-thiadiazol-3-yl)oxy)propan-2-yl (4R)-4-((3R,5S,7R,8R,9S,10S,12S,13R,14S,17R)-3,7,12-trihydroxy-10,13-dimethylhexadecahydro-1H-cyclopenta[a]phenanthren-17-yl)pentanoate |
| 20 | 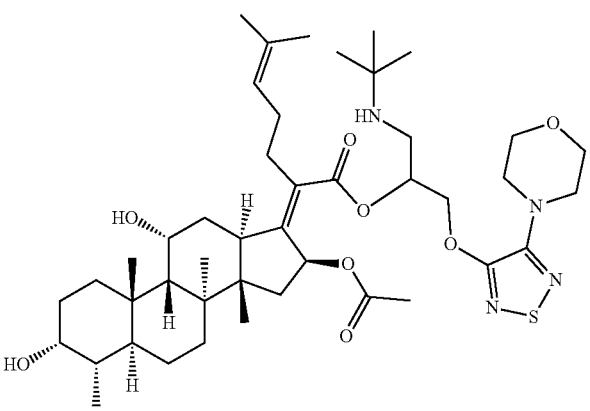 | 1-(tert-butylamino)-3-((4-morpholino-1,2,5-thiadiazol-3-yl)oxy)propan-2-yl (Z)-2-((3R,4S,5S,8S,9S,10S,11R,13R,14S,16S)-16-acetoxy-3,11-dihydroxy-4,8,10,14-tetramethylhexadecahydro-17H-cyclopenta[a]phenanthren-17-ylidene)-6-methylhept-5-enoate |
| 21 | 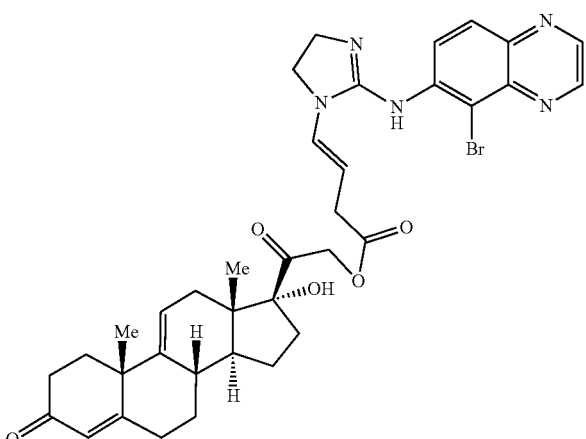 | 2-((8S,10S,13S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl (E)-4-(2-((5-bromoquinoxalin-6-yl)amino)-4,5-dihydro-1H-imidazol-1-yl)but-3-enoate |

TABLE 1-continued
| Compound Number | Structure | Name |
|---|---|---|
| 22 | 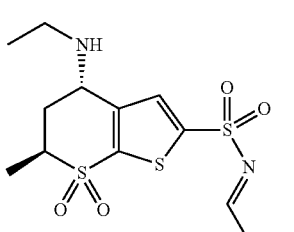 | 2-((8S,10S,13S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl (E)-4-((((4S,6S)-4-(ethylamino)-6-methyl-7,7-dioxido-5,6-dihydro-4H-thieno[2,3-b]thiopyran-2-yl)sulfonyl)imino)butanoate |
| 23 | 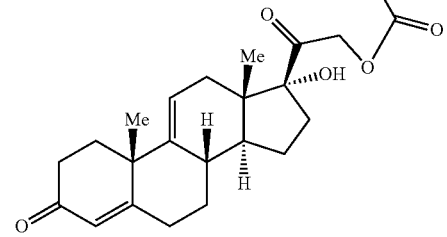 | 2-((8S,10S,13S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl (E)-4-(4-(isoquinolin-5-ylsulfonyl)-1,4-diazepan-1-yl)but-3-enoate |

TABLE 1-continued

| Compound Number | Structure | Name |
|---|---|---|
| 24 | 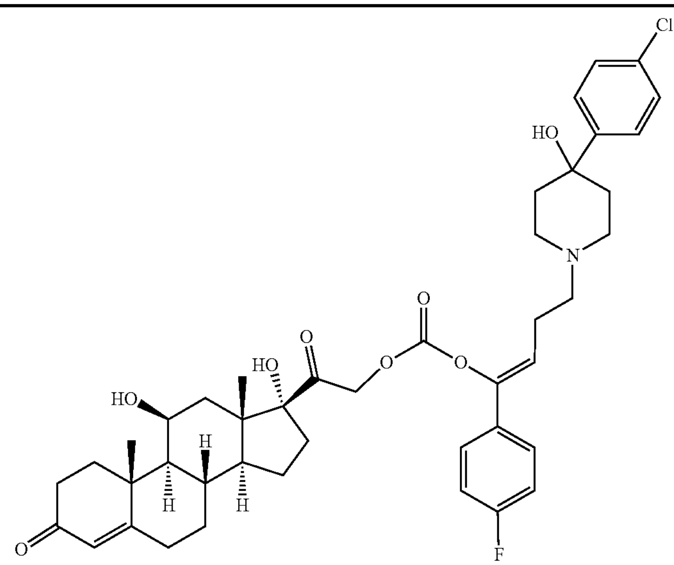 | (Z)-4-(4-(4-chlorophenyl)-4-hydroxypiperidin-1-yl)-1-(4-fluorophenyl)but-1-en-1-yl (2-((8S,9S,10R,11S,13S,14S,17R)-11,17-dihydroxy-10,13-dimethyl-3-oxo-2,3,6,7,8,9,10,11,12,13,14,15,16,17-tetradecahydro-1H-cyclopenta[a]phenanthren-17-yl)-2-oxoethyl) carbonate |

In some embodiments, the disclosure provides a compound (e.g., conjugate, such as a heterodimeric conjugate), or pharmaceutically acceptable salt thereof, having a structure provided in Table 2. In other embodiments, parent conjugate compounds that do not form a processable solid are shown in Table 2. In some embodiments, the compound, or pharmaceutically acceptable salt thereof, provided in Table 2 is not a solid at a temperature of at least 20° C. In some embodiments, the compound, or pharmaceutically acceptable salt thereof, provided in Table 2 is not processable at a temperature of at least 20° C. In some embodiments, the compound, or pharmaceutically acceptable salt thereof, provided in Table 2 is not processable into an article, as described herein, at a temperature of at least 20° C.

In some embodiments, the compound, or pharmaceutically acceptable salt thereof, provided in Table 2 comprises both a first radical and a second radical. In some embodiments, the heterodimeric conjugate in Table 2 is not processable when the first radical and the second radical are joined by a linker. In some embodiments, the linker is not a bond. In some embodiments, the linker is alkyl, heteroalkyl, or alkoxy, wherein the alkyl, heteroalkyl, or alkoxy is optionally substituted with one or more groups, each group being independently selected from the group consisting of a bond, —O—, —S—, silicone, amino, optionally substituted alkyl (e.g., alkenyl, alkynyl, branched (e.g., polypropylene), haloalkyl), optionally substituted heteroalkyl (e.g., poly-THF), and optionally substituted cycloalkyl.

TABLE 2

| Compound Number | Structure | Name |
|---|---|---|
| 25 | 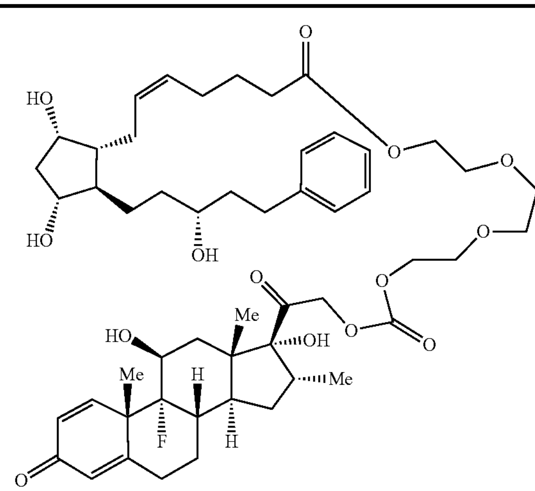 | 1-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-1,4-dioxo-3,5,8,11-tetraoxatridecan-13-yl (Z)-7-((1R,2R,3R,5S)-3,5-dihydroxy-2-((R)-3-hydroxy-5-phenylpentyl)cyclopentyl)hept-5-enoate |

TABLE 2-continued

| Compound Number | Structure | Name |
|---|---|---|
| 26 | 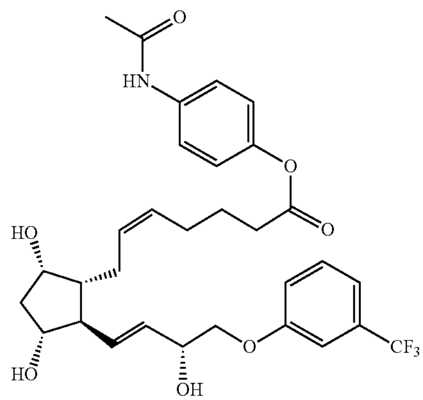 [SMILES: CC(=O)Nc1ccc(OC(=O)CCC/C=C\C[C@@H]2[C@@H](/C=C/[C@@H](O)COc3cccc(C(F)(F)F)c3)[C@H](O)C[C@@H]2O)cc1] | 4-acetamidophenyl (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate |
| 27 | 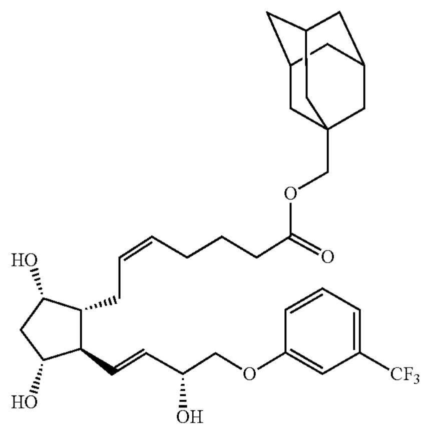 [SMILES: O=C(CCC/C=C\C[C@@H]1[C@@H](/C=C/[C@@H](O)COc2cccc(C(F)(F)F)c2)[C@H](O)C[C@@H]1O)OCC12CC3CC(CC(C3)C1)C2] | ((3R,5R,7R)-adamantan-1-yl)methyl (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate |
| 28 | 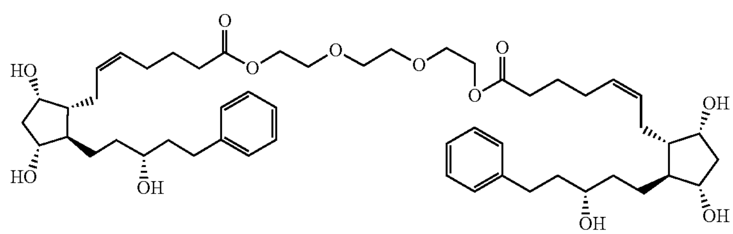 [SMILES: O=C(CCC/C=C\C[C@@H]1[C@@H](CC[C@@H](O)CCc2ccccc2)[C@H](O)C[C@@H]1O)OCCOCCOCCOC(=O)CCC/C=C\C[C@H]1[C@H](CC[C@H](O)CCc2ccccc2)[C@@H](O)C[C@H]1O] | 2-(2-(2-(((Z)-7-((1R,2R,3R,5S)-3,5-dihydroxy-2-((R)-3-hydroxy-5-phenylpentyl)cyclopentyl)hept-5-enoyl)oxy)ethoxy)ethoxy)ethyl (Z)-7-((1S,2S,3S,5R)-3,5-dihydroxy-2-((S)-3-hydroxy-5-phenylpentyl)cyclopentyl)hept-5-enoate |
| 29 | 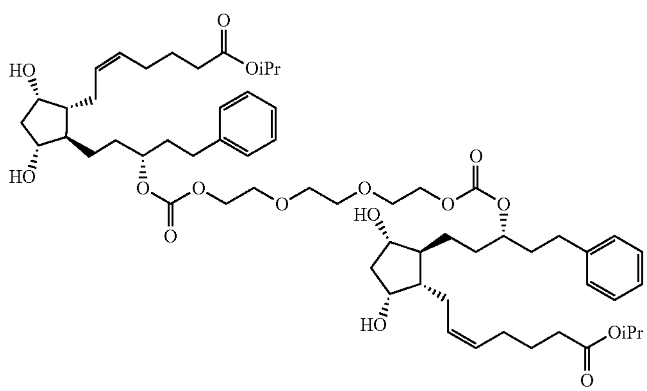 [SMILES: CC(C)OC(=O)CCC/C=C\C[C@@H]1[C@@H](CC[C@H](CCc2ccccc2)OC(=O)OCCOCCOCCOC(=O)O[C@H](CCc2ccccc2)CC[C@H]2[C@H](C/C=C\CCCC(=O)OC(C)C)[C@H](O)C[C@@H]2O)[C@H](O)C[C@@H]1O] | propyl (Z)-7-((1R,2R,3R,5S)-2-((3R,18S)-20-((1S,2S,3R,5S)-3,5-dihydroxy-2-((Z)-7-oxo-7-propoxyhept-2-en-1-yl)cyclopentyl)-5,16-dioxo-3,18-diphenethyl-4,6,9,12,15,17-hexaoxaicosyl)-3,5-dihydroxycyclopentyl)hept-5-enoate |

TABLE 2-continued

| Compound Number | Structure | Name |
|---|---|---|
| 30 | (structure) | propyl (Z)-7-((1R,2R,3R,5S)-2-((R)-3-((ethoxycarbonyl)oxy)-5-phenylpentyl)-3,5-dihydroxycyclopentyl)hept-5-enoate |

Ocular Diseases or Disorders

Intraocular diseases are a group of diseases including, but not limited to, glaucoma, ocular inflammation, diabetic macular edema, posterior inflammation, anterior inflammation, macular degeneration (e.g., wet macular degeneration (AMD) and dry AMD), post-cataract surgery, and retinal vein occlusion. Prominent aspects of intraocular diseases are increased intraocular pressure and inflammation. In some embodiments, the intraocular disease is a macular degeneration. In some embodiments, the intraocular disease is wet AMD. In some embodiments, the intraocular disease is dry AMD.

Glaucoma

In some embodiments, glaucoma is a group of eye diseases, which result in damage to the optic nerve and cause vision loss. Glaucoma is one of the leading causes of blindness globally, and there is currently no cure for glaucoma. Glaucoma management is limited to avoiding glaucomatous damage and nerve damage as well as preserving visual field and total quality of life. This management system relies on diagnostic techniques and follow-up examinations as well as judicious selection of treatments for the individual patient.

Therapeutic strategies for glaucoma are limited to pharmaceutical agents (e.g., intraocular pressure (IOP) lowering agents, e.g., prostaglandins), surgery (e.g., implants), laser therapy, or any combination thereof. The reported rates of nonadherence to topical glaucoma medication vary widely from 16% to 67%, and it is estimated that less than a third of patients remained on their initial therapy after 12 months (Robin et al, Exp. Rev. Ophth. (2019); 14:4-5, 199-210). Poor compliance with medications and follow-up visits is a major reason for vision loss in glaucoma patients.

Ocular hypertension (increased intraocular pressure (IOP)) is one of the major risk factors for glaucoma, and lowering it is a major goal of glaucoma treatment. Intraocular pressure is a function of the production of aqueous humor by the ciliary processes of the eye as well as it's drainage through the trabecular meshwork. In glaucoma, the drainage mechanisms are hindered and/or blocked, causing an increase in IOP. Furthermore, inflammation blocks outflow of aqueous humor through the trabecular meshwork, causing secondary glaucoma. This inflammation is often difficult to treat because anti-inflammatory steroids (e.g., corticosteroids), which restrict blood flow to the eye, often raise the IOP further. Described herein are compounds that navigate the balance between reducing the IOP (e.g., with an IOP lowering agent such as a prostaglandin or an IOP lowering steroid) as well as reducing inflammation (e.g., with a corticosteroid). In some embodiments, described herein are compounds that significantly increase patient compliance by reducing the number of administrations of API (e.g., once per month).

Described herein are processable agents for glaucoma formed from a processable moiety and a non-processable moiety. The processable agents for glaucoma described herein are processable into a solid (e.g., at a temperature of at least 20° C., 25° C., 30° C., 37° C., or more). The processable agents for glaucoma described herein have a controlled release profile (e.g., zero order) and/or an extended release profile (e.g., at least 1 day, 2 days, 3 days, 4 days, 5 days, 6 days, 7 days, 15 days, 30 days, or more) in solution (e.g., buffer solution, serum, biological environment, in vivo, or the like). The compounds for glaucoma described herein are useful to treat both acute and chronic diseases or disorders. The compounds for glaucoma are tested, in certain embodiments, using the assays and methods described herein (e.g., as described in the examples). The compounds for glaucoma described herein represent a significant advance in the art as the processable agents produce a controlled and extended release profile that is beneficial for treating acute and/or chronic forms of glaucoma with a single administration.

Provided herein is a heteromeric conjugate comprising a first radical and a second radical. In some embodiments, both the first radical and the second radical have the structure of any one of Formula (I), Formula (IA), Formula (IB'), Formula (IB), or Formula (IC). In some embodiments, the first radical is an anti-inflammatory agent. In some embodiments, the second radical is selected from the group consisting of a non-steroidal anti-inflammatory (NSAID), an intraocular pressure (IOP) lowering agent, a beta blocker, a Rho kinase inhibitor, a carbonic anhydrase inhibitor, an α-adrenergic agonist, tyrosine kinase inhibitor, neuroprotective agent, anti-oxidant, anti-microbial, anti-viral, or the like. In some embodiments, the second radical is an IOP lowering agent. In some embodiments, the first radical is an anti-inflammatory agent and the second radical is an IOP lowering agent. In some embodiments, the first radical is an IOP lowering steroid (e.g., anecortave (e.g., anecortave desacetate)) or benign steroid (e.g., cholesterol) and the second radical is an IOP lowering agent. In some embodiments, the IOP lowering agent is a prostaglandin. In some embodiments, the first radical is a steroid and the second radical is a prostaglandin.

In certain aspects, the first radical has the structure of any one of Formula (I), Formula (IA), Formula (IB'), Formula (IB), or Formula (IC).

In some embodiments, the second radical has a structure of Formula (II):

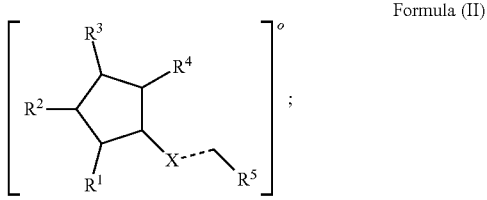

Formula (II)

wherein:
$R^1$, $R^2$, $R^3$, $R^4$, and $R^5$ are each independently selected from one or more of the group consisting of hydrogen, oxo, halo, alkyl, heteroalkyl, cycloalkyl, heterocycloalkyl, alkoxy, amino (e.g., dihydroamino, alkylamino, arylamino), hydroxyl, and thiol, wherein the alkyl, heteroalkyl, cycloalkyl, and heterocycloalkyl is optionally substituted;
or any one of $R^1$, $R^2$, $R^3$, $R^4$, or $R^5$ are taken together to form an optionally substituted cycloalkyl or heterocycloalkyl;
X is selected from the group consisting of —O—, —NR—, —S(R)$_a$—, and —C(R)$_b$—;
a is independently 0-2; and
b is independently 1 or 2,
or a pharmaceutically acceptable salt or solvate thereof.

In some embodiments, $R^4$ is alkyl substituted with one or more of —COOH, —CONH$_2$, and alkyl (e.g., alkylene or alkenyl). In some embodiments, X is S, —C(R)$_1$—, or —C(R)$_2$—. In some embodiments, X is —CH— or —CH$_2$—.

In some embodiments, the second radical has a structure of Formula (IIA):

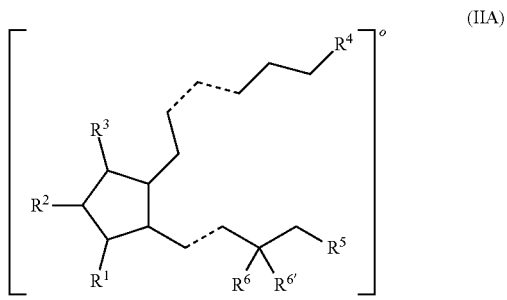

(IIA)

wherein:
$R^1$, $R^2$, $R^3$, $R^4$, and $R^5$ are each independently selected from one or more of the group consisting of hydrogen, oxo, halo, alkyl, heteroalkyl, cycloalkyl, heterocycloalkyl, alkoxy, amino (e.g., dihydroamino, alkylamino, arylamino), hydroxyl, and thiol, wherein the alkyl, heteroalkyl, cycloalkyl, and heterocycloalkyl is optionally substituted; and
$R^6$ and $R^{6'}$ are each independently hydrogen, halogen, alkyl, or $R^6$ and $R^{6'}$ are taken together to form an oxo, or a pharmaceutically acceptable salt or solvate thereof.

In some embodiments, $R^6$ and $R^{6'}$ are each independently fluoro. In some embodiments, $R^6$ is H or methyl and $R^{6'}$ is —OH. In some embodiments, $R^6$ and $R^{6'}$ are taken together to form an oxo. In some embodiments, $R^1$ and $R^3$ are each independently —OH or oxo. In some embodiments, $R^3$ and $R^4$ are taken together to form a heterocycloalkyl substituted with alkyl (e.g., alkenyl) substituted with —COOH.

In some embodiments, the second radical has a structure of Formula (IIB):

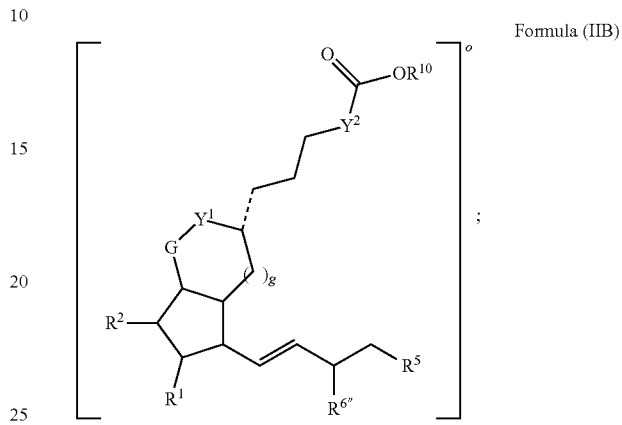

Formula (IIB)

wherein:
$R^1$, $R^2$, and $R^5$ are each independently selected from one or more of the group consisting of hydrogen, oxo, halo, alkyl, heteroalkyl, cycloalkyl, heterocycloalkyl, alkoxy, amino (e.g., dihydroamino, alkylamino, arylamino), hydroxyl, and thiol, wherein the alkyl, heteroalkyl, cycloalkyl, and heterocycloalkyl is optionally substituted;
$R^{6''}$ is oxo or —OH;
and $Y^2$ are each independently a bond or alkylene;
G is O or CH$_2$;
g is 1 or 2; and
$R^{10}$ is alkyl or hydrogen,
or a pharmaceutically acceptable salt or solvate thereof.

In some embodiments, $R^1$ is oxo or —OH. In some embodiments, $R^2$ is hydrogen. In some embodiments, $R^5$ is selected from one or more of the group consisting of —O—, —OH, halogen, alkyl (e.g., alkynyl), aryl, wherein the alkyl (e.g., alkynyl) and aryl are optionally substituted with one or more of alkyl (e.g., fluoroalkyl), halogen, and —OH. In some embodiments, $R^5$ is optionally substituted aryl or optionally substituted —O-aryl.

In some embodiments, the first radical and the second radical are joined by a linker (e.g., hydrolyzable linker). In some embodiments, the first radical and the second radical are joined by a bond.

In certain aspects, provided herein is a compound comprising:
a) a steroid;
b) a prostaglandin; and
c) a linker (e.g., hydrolyzable linker), wherein the linker adjoins (e.g., covalently) the steroid and the prostaglandin, or a pharmaceutically acceptable salt or solvate thereof.

In certain aspects, provided herein is a compound having the structure of Formula (III):

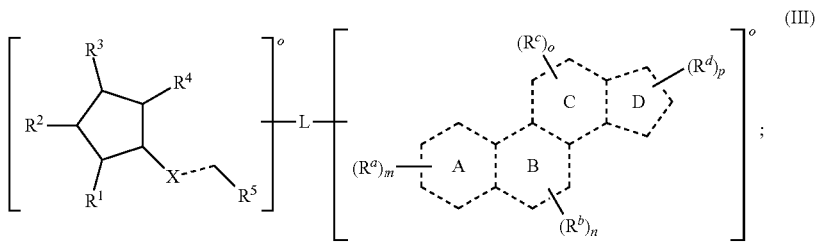

wherein:
⁓ is a single bond or a double bond;
each $R^a$, $R^b$, $R^c$, and $R^d$ are independently selected from the group consisting of oxo, halogen, —CN, —NO$_2$, alkyl, heteroalkyl, cycloalkyl, heterocycloalkyl, alkoxy, amino (e.g., dihydroamino, alkylamino, arylamino), hydroxy, or thiol, wherein the alkyl, alkynyl, heteroalkyl, cycloalkyl, or heterocycloalkyl is optionally substituted;
or any one of $R^a$, $R^b$, $R^c$, and $R^d$ are taken together with another of $R^a$, $R^b$, $R^c$, and $R^d$ to form an substituted or unsubstituted cycloalkyl or heterocycloalkyl;
each of m, n, o, and p are independently 0-6;
each R is independently selected from the group consisting of hydrogen, halogen, alkyl, heteroalkyl, cycloalkyl, heterocycloalkyl, alkoxy, amino (e.g., dihydroamino, alkylamino, arylamino), hydroxy, and thiol, or is taken together with another R to form an oxo;
$R^1$, $R^2$, $R^3$, $R^4$, and $R^5$ are each independently selected from one or more of the group consisting of hydrogen, oxo, halo, alkyl, heteroalkyl, cycloalkyl, heterocycloalkyl, alkoxy, amino (e.g., dihydroamino, alkylamino, arylamino), hydroxyl, and thiol, wherein the alkyl, heteroalkyl, cycloalkyl, and heterocycloalkyl is optionally substituted; and
L is a linker,
or a pharmaceutically-acceptable salt or solvate thereof.

In certain aspects, provided herein is a compound having the structure of Formula (IV):

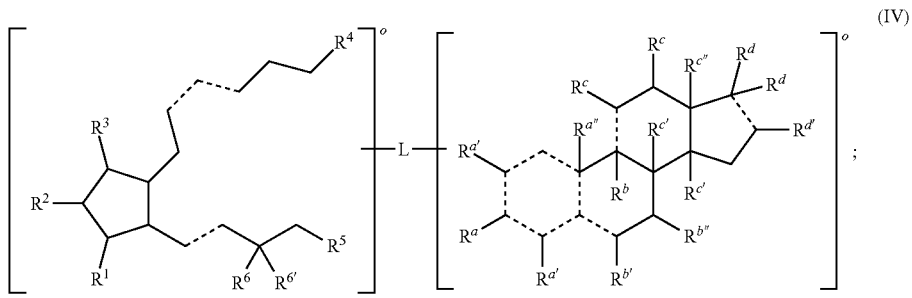

wherein:

⟋⟋ is a single bond or a double bond;

$R^a$ is hydrogen, —OH, or oxo;

each $R^{a'}$ is independently selected from hydrogen, —OH, halogen, $C_1$-$C_3$ alkyl, and alkoxy;

$R^{a''}$ is absent, hydrogen, or $C_1$-$C_3$ alkyl;

$R^b$ is absent, hydrogen, halogen, or $C_1$-$C_3$ alkyl;

$R^{b'}$ is hydrogen, halogen, —OH, oxo, or $C_1$-$C_3$ alkyl;

$R^{b''}$ is hydrogen or —OH;

each $R^c$ is independently hydrogen, —OH, oxo, or $C_1$-$C_3$ alkyl;

each $R^{c'}$ is independently hydrogen or $C_1$-$C_3$ alkyl;

$R^{c''}$ is hydrogen, —OH, $C_1$-$C_3$ alkyl, or —C(=O)H;

each $R^d$ is independently hydrogen, —OH, —COOH, alkyl (e.g., alkylene, alkenyl, or alkynyl), heteroalkyl, or each $R^d$ is taken together to form an oxo, wherein the alkyl or heteroalkyl is optionally substituted;

$R^{d'}$ is hydrogen, —OH, $C_1$-$C_3$ alkyl (e.g., alkylene or alkenyl), or heteroalkyl;

or one $R^d$ is taken together with $R^{d'}$ to form a substituted or unsubstituted cycloalkyl or heterocycloalkyl;

$R^1$, $R^2$, $R^3$, $R^4$, and $R^5$ are each independently selected from one or more of the group consisting of hydrogen, oxo, halo, alkyl, heteroalkyl, cycloalkyl, heterocycloalkyl, alkoxy, amino (e.g., dihydroamino, alkylamino, arylamino), hydroxyl, and thiol, wherein the alkyl, heteroalkyl, cycloalkyl, and heterocycloalkyl is optionally substituted; and $R^6$ and $R^{6'}$ are each independently hydrogen, halogen, alkyl, or $R^6$ and $R^{6'}$ are taken together to form an oxo, or a pharmaceutically acceptable salt or solvate thereof.

In certain aspects, provided herein is a compound having the structure of Formula (V):

each $R^d$ is independently hydrogen, —OH, —COOH, alkyl (e.g., alkylene, alkenyl, or alkynyl), heteroalkyl, or each $R^d$ is taken together to form an oxo, wherein the alkyl or heteroalkyl is optionally substituted;

$R^{d'}$ is hydrogen, —OH, $C_1$-$C_3$ alkyl (e.g., alkylene or alkenyl), or heteroalkyl;

or one $R^d$ is taken together with $R^{d'}$ to form a substituted or unsubstituted cycloalkyl or heterocycloalkyl;

$R^1$, $R^2$, and $R^5$ are each independently selected from one or more of the group consisting of hydrogen, oxo, halo, alkyl, heteroalkyl, cycloalkyl, heterocycloalkyl, alkoxy, amino (e.g., dihydroamino, alkylamino, arylamino), hydroxyl, and thiol, wherein the alkyl, heteroalkyl, cycloalkyl, and heterocycloalkyl is optionally substituted;

$R^{6''}$ is oxo or —OH;

and $Y^2$ are each independently a bond or alkylene;

G is O or $CH_2$;

g is 1 or 2;

$R^{10}$ is alkyl or H; and

L is a linker, or a pharmaceutically acceptable salt or solvate thereof.

In some embodiments, any one of $R^a$, $R^{a'}$, $R^b$, $R^{b'}$, $R^{b''}$, $R^c$, $R^{c''}$, $R^d$, or $R^{d'}$ is an ester radical, a hydroxyl radical, or a carboxylate radical, and any one of $R^1$, $R^2$, $R^3$, $R^4$, $R^5$, $R^6$, $R^{6'}$, $R^{6''}$, or $R^{10}$ is a thiol radical, a hydroxyl radical, or a carboxylate radical. In some embodiments, any one of $R^a$, $R^{a'}$, $R^b$, $R^{b'}$, $R^{b''}$, $R^c$, $R^{c''}$, $R^d$, or $R^{d'}$ is adjoined to any one of $R^1$, $R^2$, $R^3$, $R^4$, $R^5$, $R^6$, $R^{6'}$, $R^{6''}$, or by a linker. In some embodiments, any one of $R^a$, $R^{a'}$, $R^b$, $R^{b'}$, $R^{b''}$, $R^c$, $R^{c''}$, $R^d$, or $R^{d'}$ is adjoined to any one of $R^4$, $R^5$, $R^6$, $R^{6'}$, $R^{6''}$, or $R^{10}$ by a linker. In some embodiments, any one of $R^d$ or $R^{d'}$ is Formula (V)

wherein:

⟋⟋ is a single bond or a double bond;

$R^d$ is hydrogen, —OH, or oxo;

each $R^{a'}$ is independently selected from hydrogen, —OH, halogen, $C_1$-$C_3$ alkyl, and alkoxy;

$R^{a''}$ is absent, hydrogen, or $C_1$-$C_3$ alkyl;

$R^b$ is absent, hydrogen, halogen, or $C_1$-$C_3$ alkyl;

$R^{b'}$ is hydrogen, halogen, —OH, oxo, or $C_1$-$C_3$ alkyl;

$R^{b''}$ is hydrogen or —OH;

each $R^c$ is independently hydrogen, —OH, oxo, or $C_1$-$C_3$ alkyl;

each $R^{c'}$ is independently hydrogen or $C_1$-$C_3$ alkyl;

$R^{c''}$ is hydrogen, —OH, $C_1$-$C_3$ alkyl, or —C(=O)H;

adjoined to any one of $R^4$, $R^5$, $R^6$, $R^{6'}$, $R^{6''}$, or $R^{10}$ by a linker. In some embodiments, the linker is a bond.

In some embodiments, the linker is a bond, alkyl, heteroalkyl, or alkoxy, wherein the alkyl, heteroalkyl, or alkoxy is optionally substituted. In some embodiments, the alkyl, heteroalkyl, or alkoxy are each independently substituted with one or more groups, each group being independently selected from the group consisting of a bond, —O—, —S—, silicone, amino, optionally substituted alkyl (e.g., alkenyl, alkynyl, branched (e.g., polypropylene), haloalkyl), optionally substituted heteroalkyl (e.g., polyTHF), and optionally substituted cycloalkyl. In some embodiments, the linker is a bond. In some embodiments, the linker is alkyl (alkylene) and the alkyl (alkylene) is substituted with one or more groups selected from —OH, halo, oxo, alkyl, heteroalkyl, cycloalkyl, and heterocycloalkyl. In some embodiments, the linker is alkyl (alkylene) and the alkyl (alkylene) is an unsubstituted alkylene. In some embodiments, the linker is heteroalkyl (heteroalkylene) and the heteroalkyl (heteroalkylene) is substituted with one or more groups selected from halo or alkyl. In some embodiments, the linker is heteroalkyl (heteroalkylene) and is the heteroalkyl (heteroalkylene) an unsubstituted heteroalkylene. In some embodiments, the linker comprises one or more linker groups selected from a bond, —O—, —S—, unsubstituted alkylene, C=O(CH$_2$CH$_2$)$_n$C=O, C=O(CHCH)$_n$C=O, C=O(OCH$_2$CH$_2$O)$_n$C=O, O(CH$_2$CH$_2$O)$_n$, and C=O(CH$_2$CH$_2$O)$_n$, (CH(CH$_3$)C(=O)O)$_n$, wherein n is 1-20. In some embodiments, the linker is a bond, unsubstituted alkylene, C=O(CH$_2$CH$_2$)$_n$C=O, C=O(CHCH)$_n$C=O, C=O(OCH$_2$CH$_2$O)$_n$C=O, O(CH$_2$CH$_2$O)$_n$, and C=O(CH$_2$CH$_2$O)$_n$, (CH(CH$_3$)C(=O)O)$_n$, C=O(CH$_2$CH$_2$)$_n$C=O(CH(CH$_3$)C(=O)O)$_n$, wherein n is 1-20.

In some embodiments, the linker comprises one or more linker group, each linker group being independently selected from the group consisting of a bond, alkyl, cycloalkyl, heteroalkyl, or alkoxy, wherein the alkyl, cycloalkyl, heteroalkyl, or alkoxy is optionally substituted. In some embodiments, the alkyl, cycloalkyl, heteroalkyl, or alkoxy are each independently substituted with one or more substituent, each substituent being independently selected from the group consisting of —O— (e.g., —OH), —S— (e.g., —SH), silicone, amino, optionally substituted alkyl (e.g., alkenyl, alkynyl, branched (e.g., polypropylene), haloalkyl), optionally substituted heteroalkyl (e.g., polyTHF), and optionally substituted cycloalkyl. In some embodiments, the linker comprises one or more linker group, each linker group being independently selected from the group consisting of alkyl (alkylene) and cycloalkyl (cycloalkylene), and the alkyl (alkylene) or cycloalkyl (cycloalkylene) is unsubstituted or substituted (e.g., with one or more substituent each substituent being independently selected from the group consisting of —OH, halo, oxo, alkyl, heteroalkyl, cycloalkyl, and heterocycloalkyl). In some embodiments, the linker comprises an unsubstituted or substituted alkylene-cycloalkylene-alkylene. In some embodiments, the linker comprises one or more linker group, each linker group being independently selected from the group consisting of a bond, —O—, —O(C=O)—, —O(C=O)—O—, —S—, unsubstituted alkylene, unsubstituted cycloalkylene, C=O(CH$_2$CH$_2$)$_n$C=O, C=O(CHCH)$_n$C=O, C=O(OCH$_2$CH$_2$O)$_n$C=O, O(CH$_2$CH$_2$O)$_n$, and C=O(CH$_2$CH$_2$O)$_n$, and (CH(CH$_3$)C(=O)O)$_n$, wherein n is 1-20. In some embodiments, the linker is a bond, unsubstituted alkylene, unsubstituted alkylene-cycloalkylene-alkylene, C=O(CH$_2$CH$_2$)$_n$C=O, C=O(CHCH)$_n$C=O, C=O(OCH$_2$CH$_2$O)$_n$C=O, O(CH$_2$CH$_2$O)$_n$, and C=O(CH$_2$CH$_2$O)$_n$, (CH(CH$_3$)C(=O)O)$_n$, C=O(CH$_2$CH$_2$)$_n$C=O(CH(CH$_3$)C(=O)O)$_n$, wherein n is 1-20. In some embodiments, n is 1-10. In some embodiments, n is 6. In some embodiments, n is 5. In some embodiments, n is 4. In some embodiments, n is 3. In some embodiments, n is 2. In some embodiments, n is 1.

In some embodiments, the linker is hydrolyzed in a buffered solution. In some embodiments, the linker is hydrolyzed by an enzyme. In some embodiments, the enzyme is a hydrolase (e.g., a protease or an esterase).

In some embodiments, the first radical is a (e.g., hydroxyl or carboxyl) radical of a compound selected from the group consisting of:

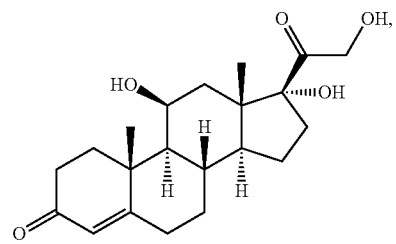

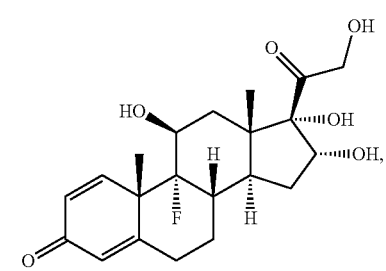

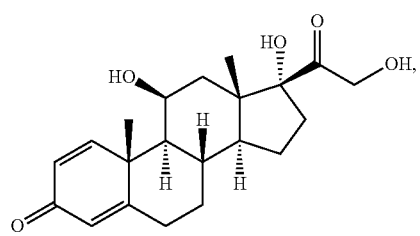

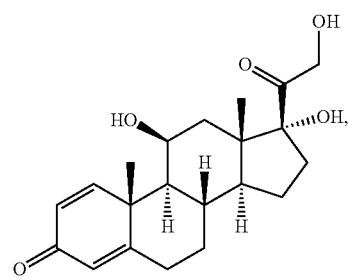

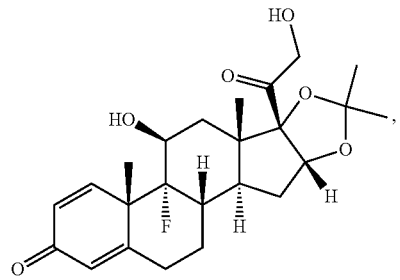

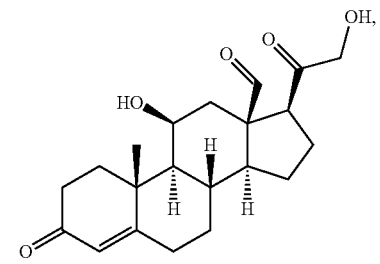

-continued
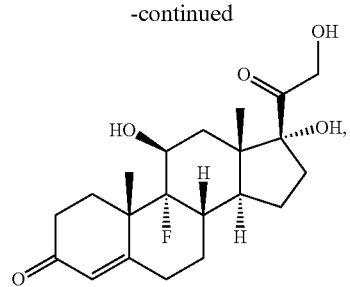
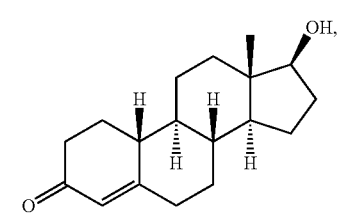
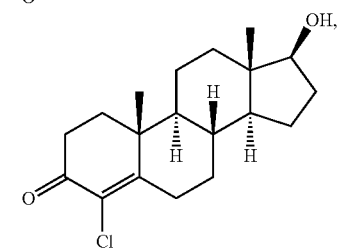
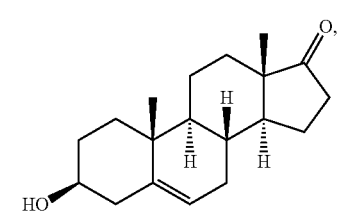
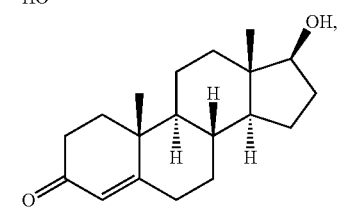
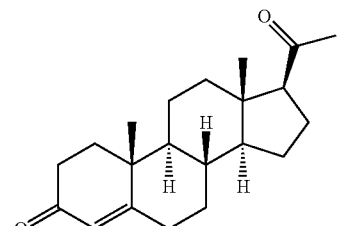
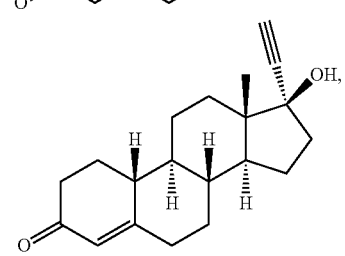
-continued
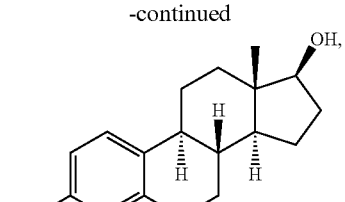
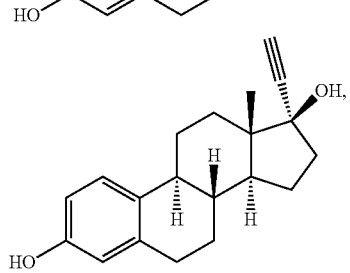
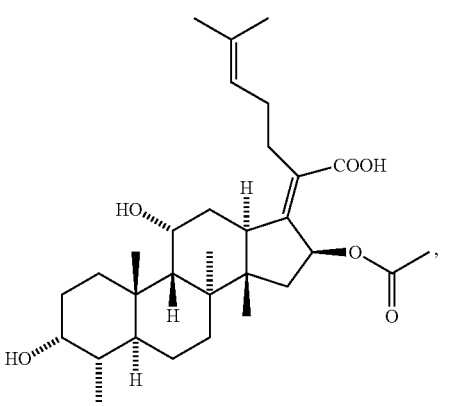
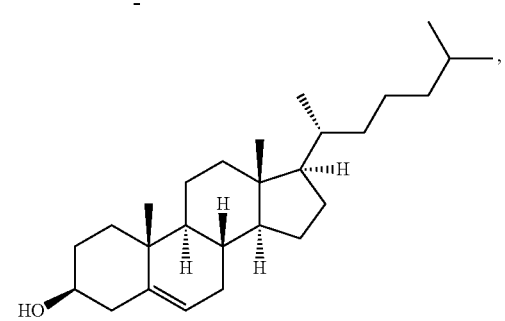
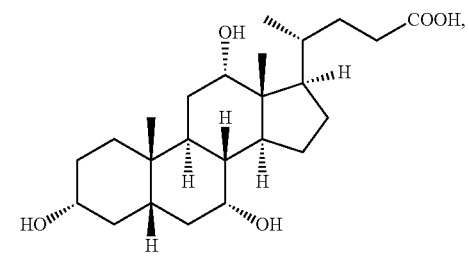
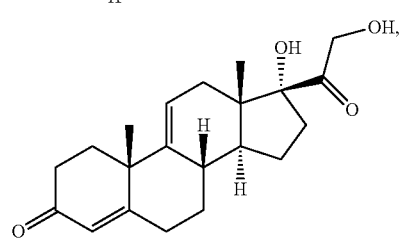

113
-continued
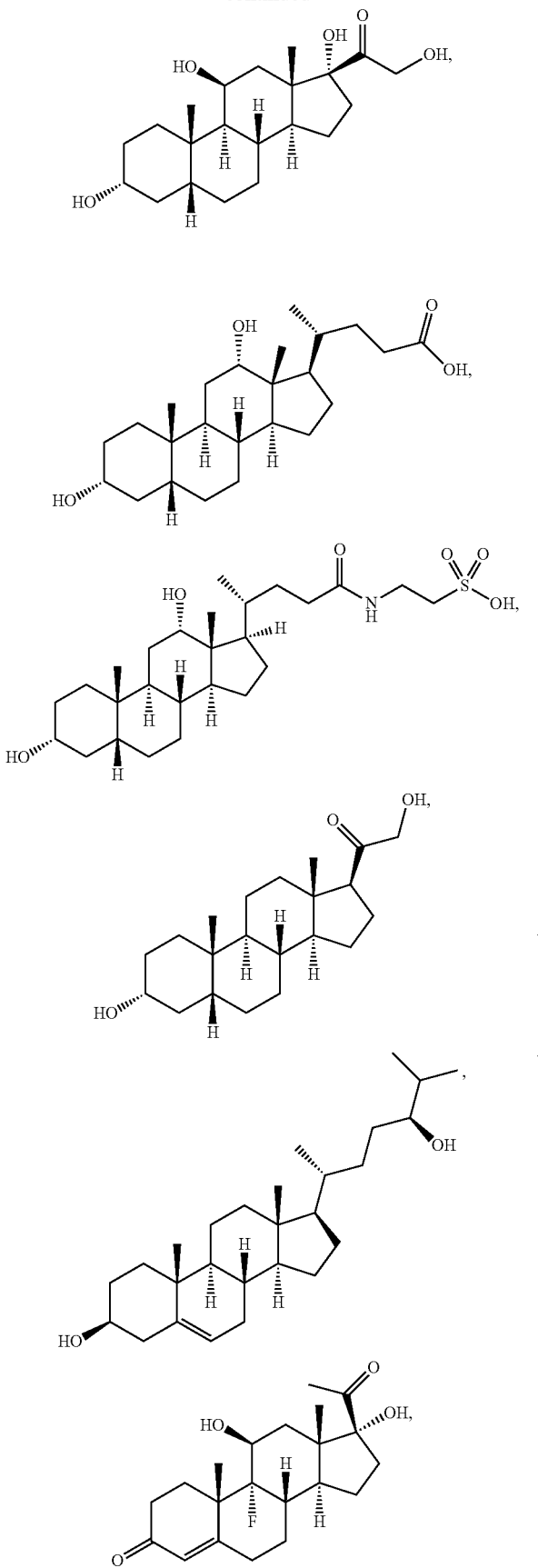
114
-continued
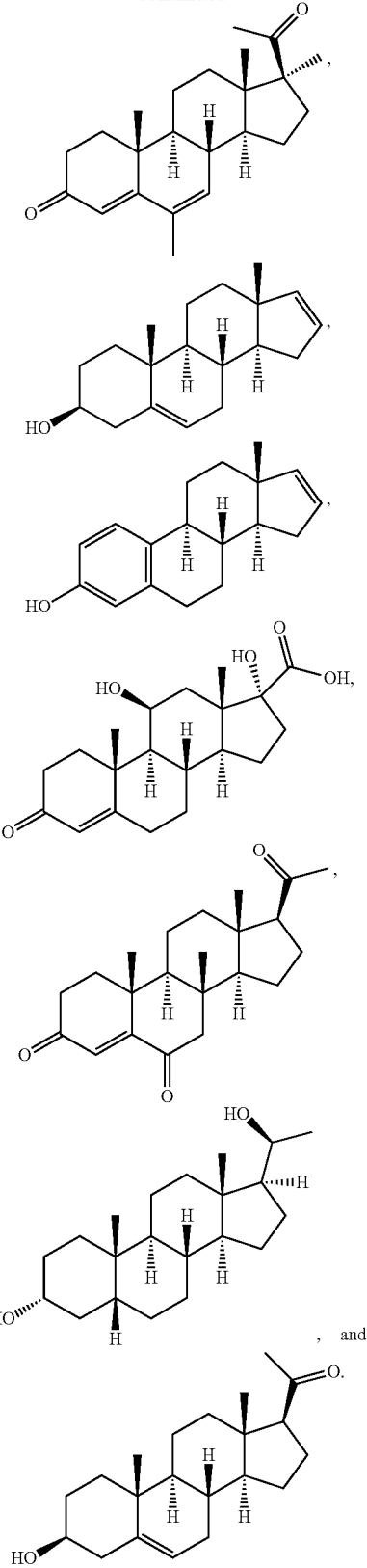
In some embodiments, the second radical is a (e.g., hydroxyl or carboxyl) radical of a compound selected from the group consisting of:

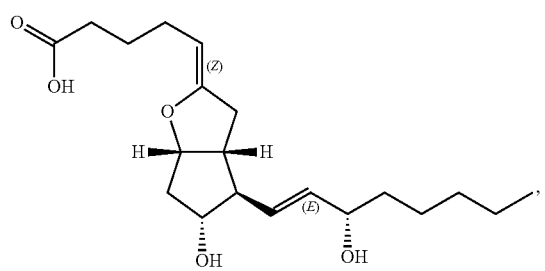
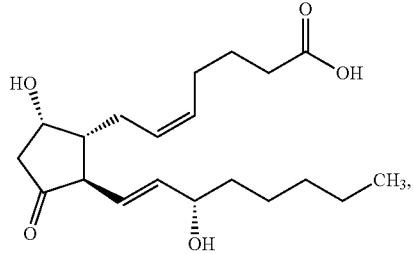
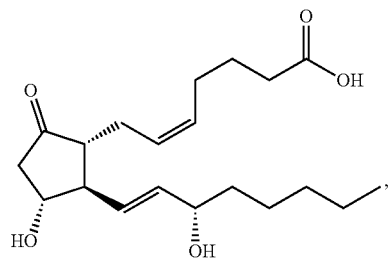
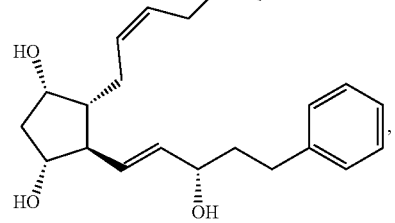
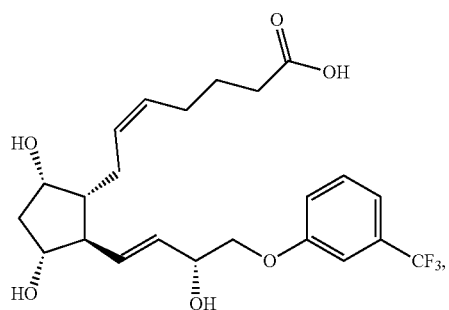
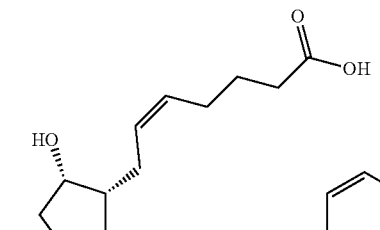
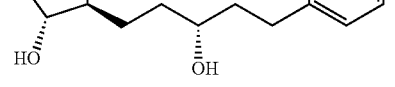
-continued
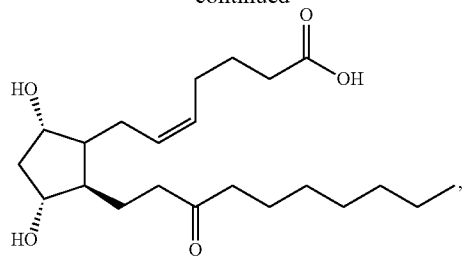
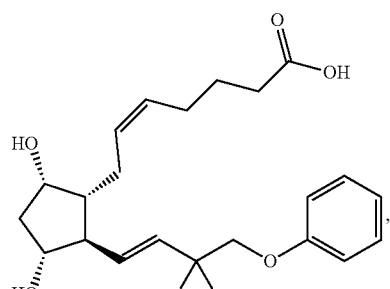
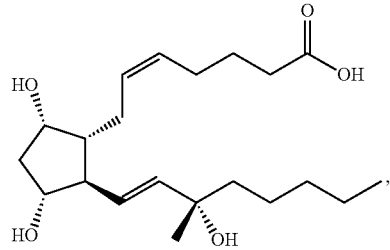
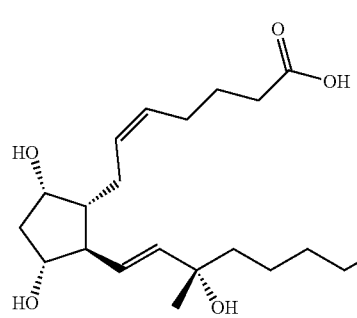
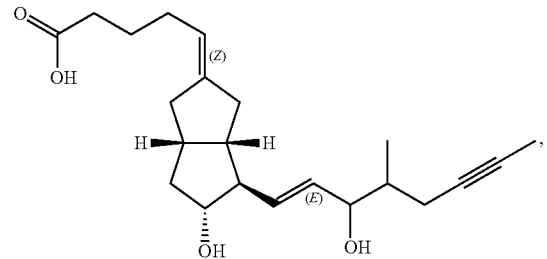
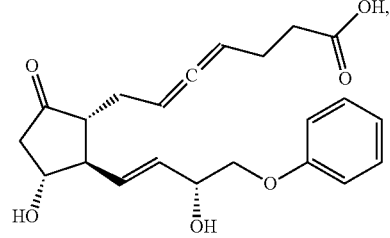

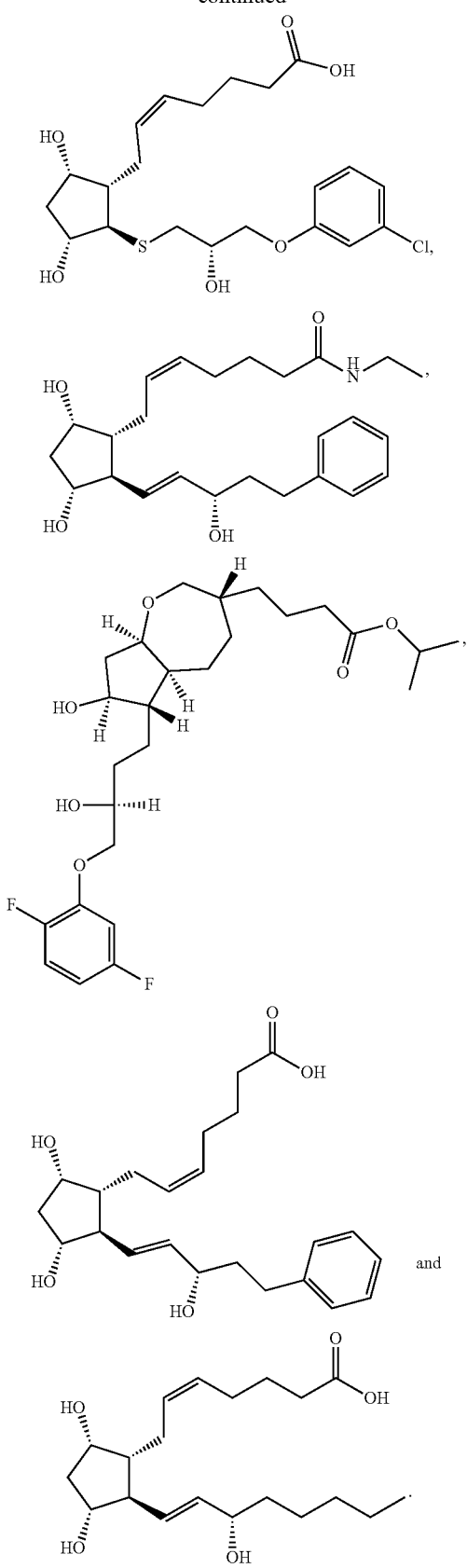
In some embodiments, the second radical is a (e.g., hydroxyl or carboxyl) radical of a compound selected from the group consisting of:
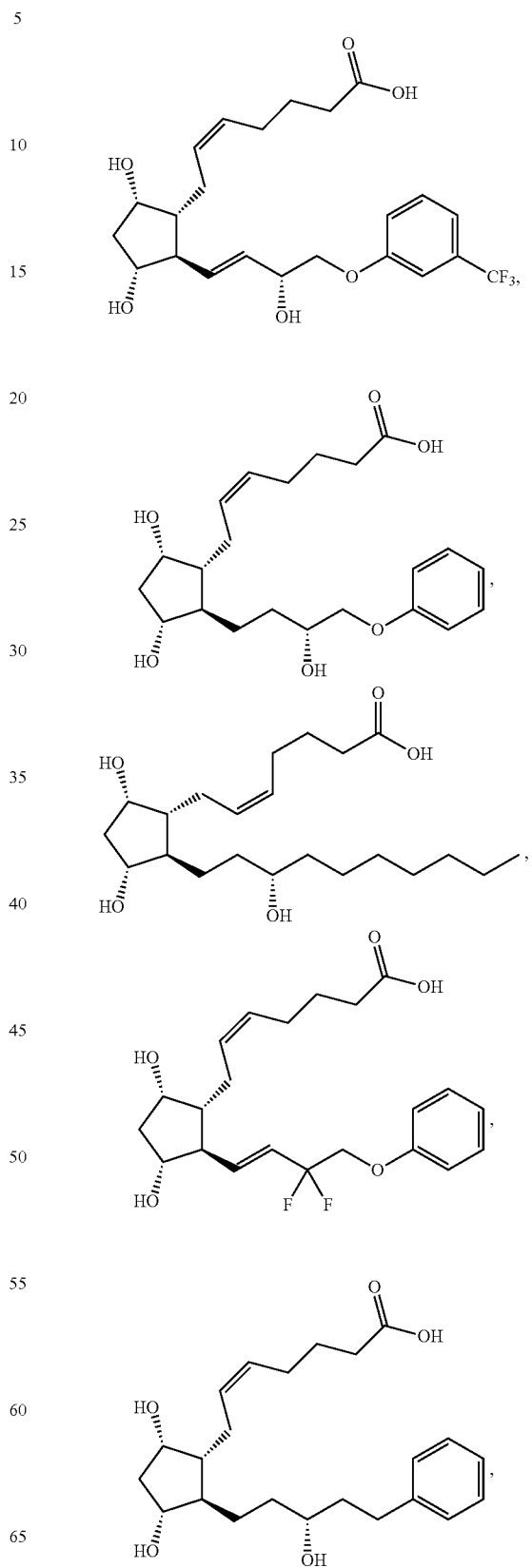
and

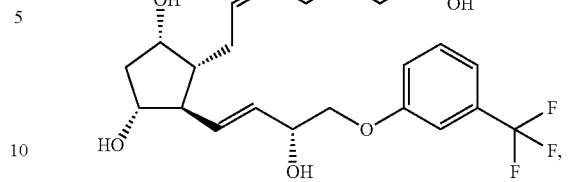

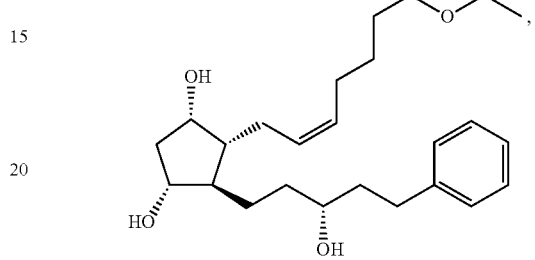

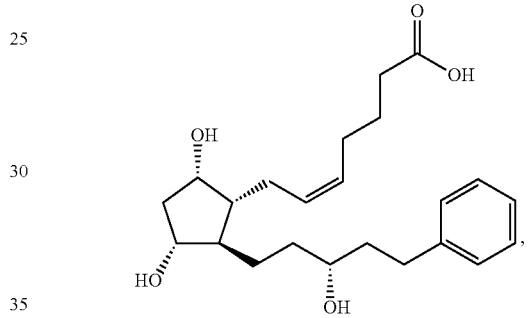

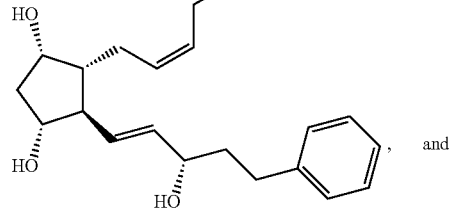

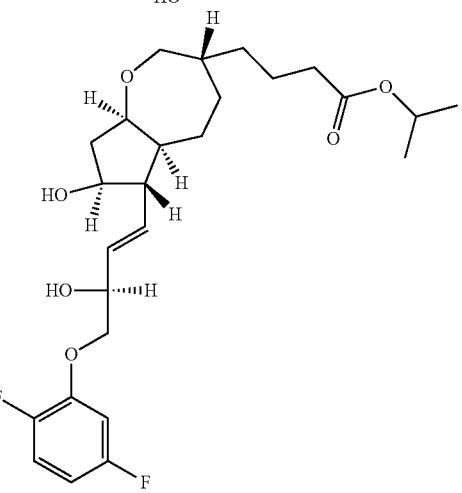

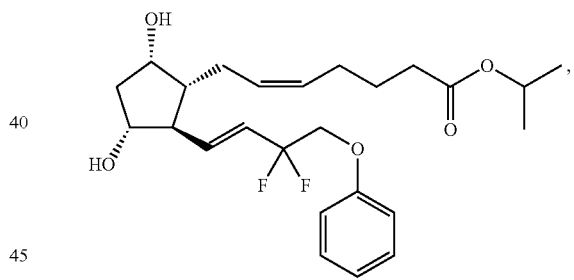

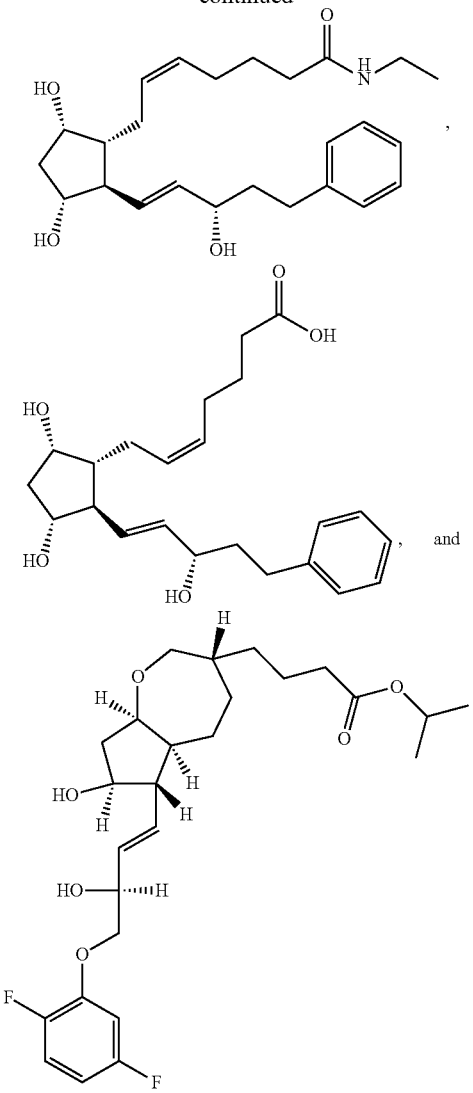

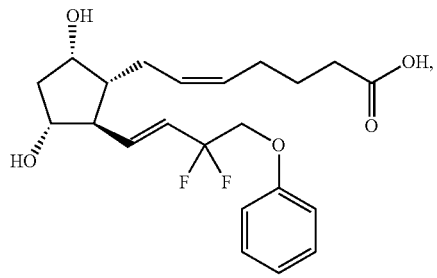

In some embodiments, the second radical is a radical of a drug. In some embodiments, the drug is a prostaglandin. In some embodiments, the prostaglandin is selected from the group consisting of latanoprost, latanoprost acid, travoprost, travoprost acid, tafluprost, tafluprost acid, bimatoprost, bimatoprost acid, sepetaprost, and sepetaprost acid, or a fragment or radical of any of the foregoing.

In some embodiments, the second radical is a (e.g., hydroxyl or carboxyl) radical of a compound selected from the group consisting of:

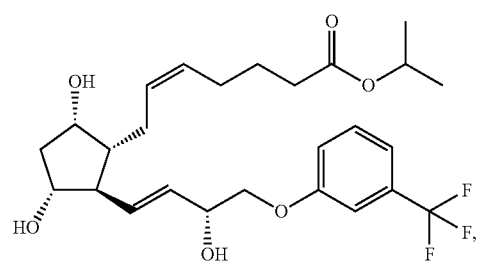

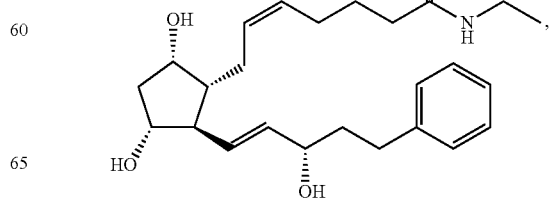

-continued

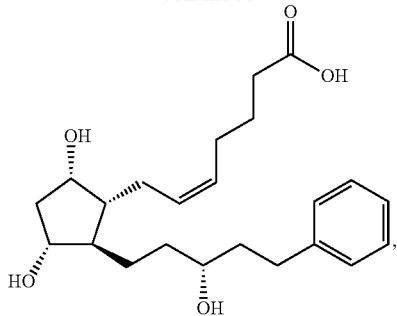

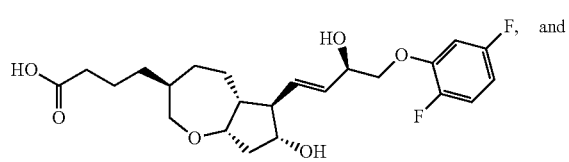

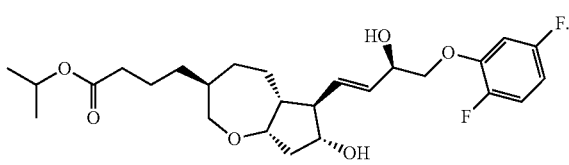

In some embodiments, the disclosure provides a compound for glaucoma, or pharmaceutically acceptable salt thereof, having a structure provided in Table 3. In some embodiments, parent conjugate compounds that form articles (e.g., pellets), using methods described in the examples herein, are shown in Table 3. In some embodiments, the compound for glaucoma, or pharmaceutically acceptable salt thereof, provided in Table 3 is a solid at a temperature of at least 20° C. In some embodiments, the compound for glaucoma, or pharmaceutically acceptable salt thereof, provided in Table 3 is processable at a temperature of at least 20° C. In some embodiments, the compound for glaucoma, or pharmaceutically acceptable salt thereof, provided in Table 3 is processable into an article, as described herein, at a temperature of at least 20° C. In some embodiments, the compound for glaucoma, or pharmaceutically acceptable salt thereof, provided in Table 3 comprises a first radical that is processable in its free form and a second radical that is not processable in its free form. In some embodiments, the compound for glaucoma in Table 3 is processable when the first radical that is processable in its free form and the second radical that is not processable in its free form are joined by a linker. In some embodiments, the linker is a bond. In some embodiments, the linker comprises one more linker group, each linker group being independently selected from the group consisting of a bond, alkyl or cycloalkyl, wherein the alkyl or cycloalkyl may optionally be substituted. In some embodiment the linker forms, together with the first and/or the second radical, an ether. In some embodiment the linker forms, together with the first and/or the second radical, an ester. In some embodiment the linker forms, together with the first and/or second radical, a carbonate.

TABLE 3

| Compound Number | Structure | Name |
| --- | --- | --- |
| 1 | 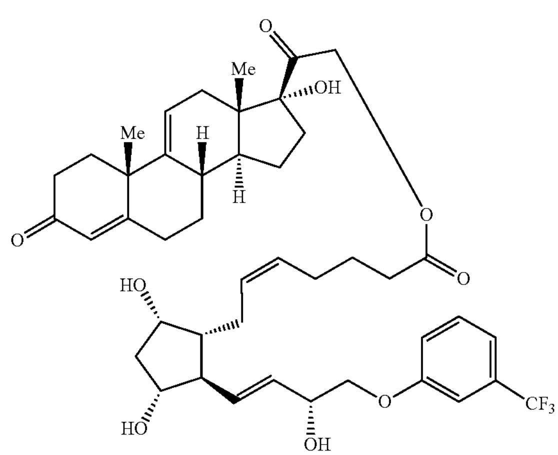 | 2-((8S,10S,13S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate |

TABLE 3-continued

| Compound Number | Structure | Name |
|---|---|---|
| 2 | 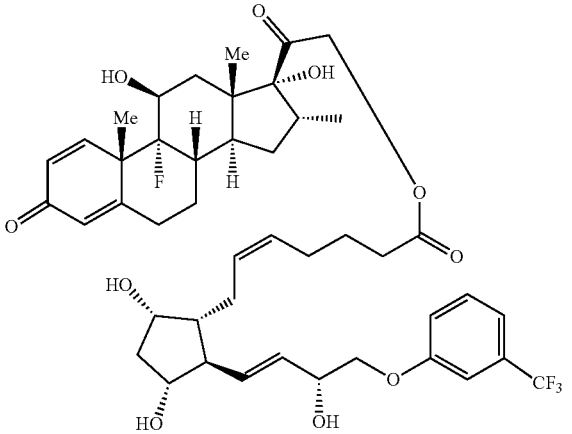 | 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate |
| 3 | 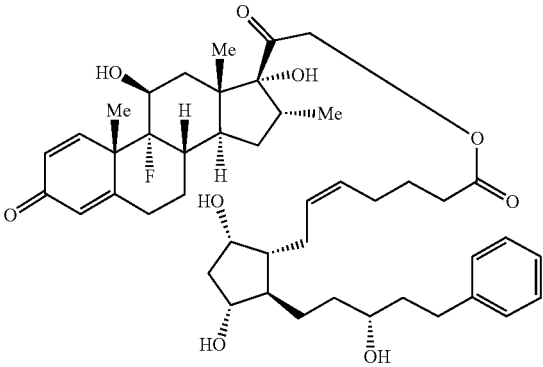 | 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl (Z)-7-((1R,2R,3R,5S)-3,5-dihydroxy-2-((R)-3-hydroxy-5-phenylpentyl)cyclopentyl)hept-5-enoate |
| 4 | 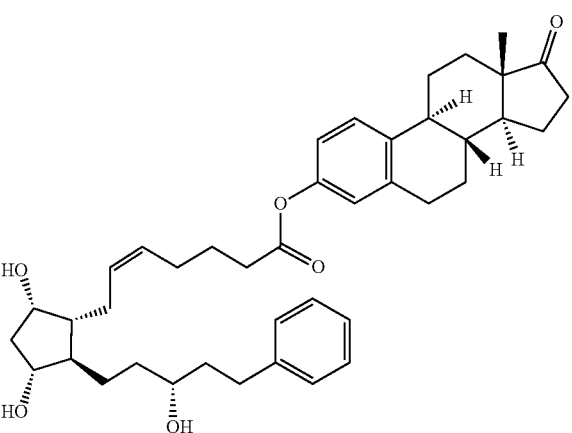 | (8R,9S,13S,14S)-13-methyl-17-oxo-7,8,9,11,12,13,14,15,16,17-decahydro-6H-cyclopenta[a]phenanthren-3-yl (Z)-7-((1R,2R,3R,5S)-3,5-dihydroxy-2-((R)-3-hydroxy-5-phenylpentyl)cyclopentyl)hept-5-enoate |

TABLE 3-continued

| Compound Number | Structure | Name |
|---|---|---|
| 5 | 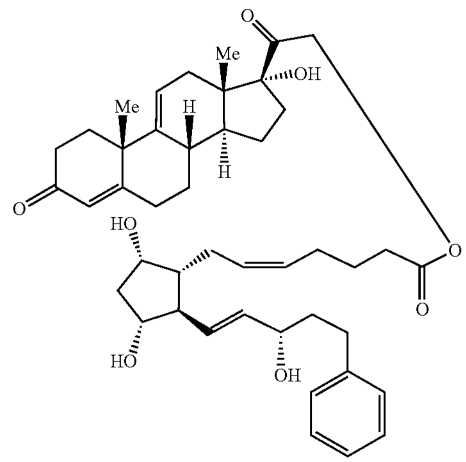 | 2-((8S,10S,13S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl (Z)-7-((1R,2R,3R,5S)-3,5-dihydroxy-2-((S,E)-3-hydroxy-5-phenylpent-1-en-1-yl)cyclopentyl)hept-5-enoate |
| 6 | 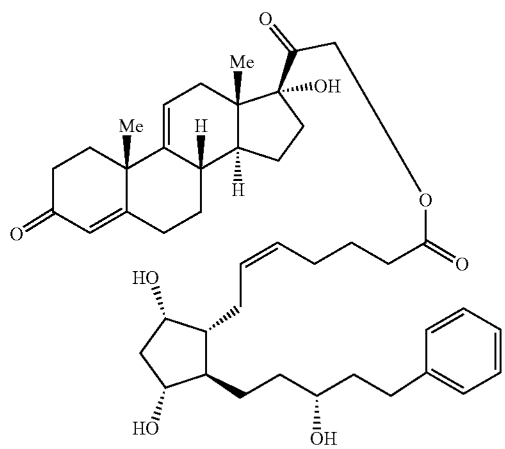 | 2-((8S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl (Z)-7-((1R,2R,3R,5S)-3,5-dihydroxy-2-((R)-3-hydroxy-5-phenylpentyl)cyclopentyl)hept-5-enoate |
| 7 | 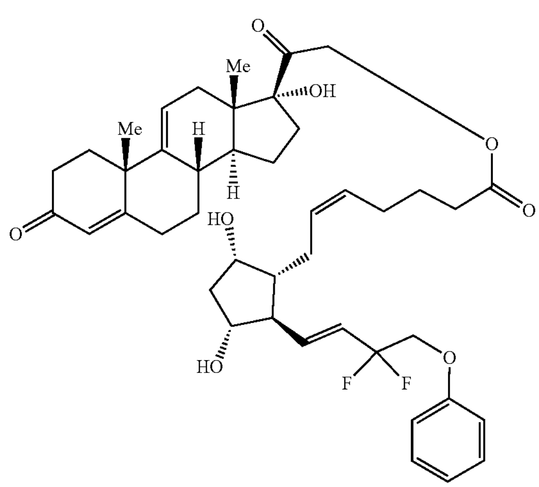 | 2-((8S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl (Z)-7-((1R,2R,3R,5S)-2-((E)-3,3-difluoro-4-phenoxybut-1-en-1-yl)-3,5-dihydroxycyclopentyl)hept-5-enoate |

TABLE 3-continued

| Compound Number | Structure | Name |
|---|---|---|
| 8 | 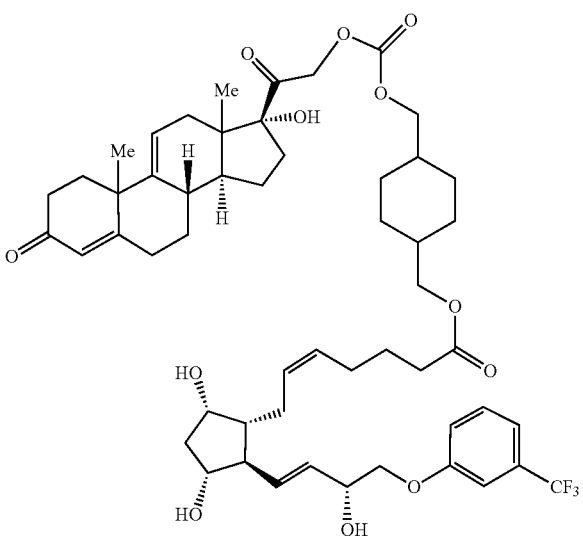 | (4-((((2-((8S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethoxy)carbonyl)oxy)methyl)cyclohexyl)methyl (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate |
| 9 | 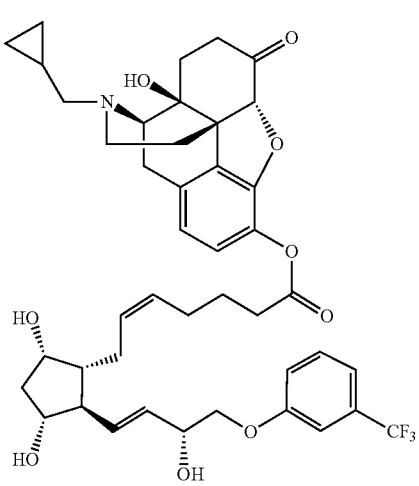 [SMILES: O=C(CCC/C=C\C[C@@H]1[C@@H](/C=C/[C@@H](O)COc2cccc(C(F)(F)F)c2)[C@H](O)C[C@@H]1O)Oc1ccc2c3c1O[C@H]1C(=O)CC[C@@]4(O)[C@@H](C2)N(CC2CC2)CC[C@]314] | (4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate |
| 10 | 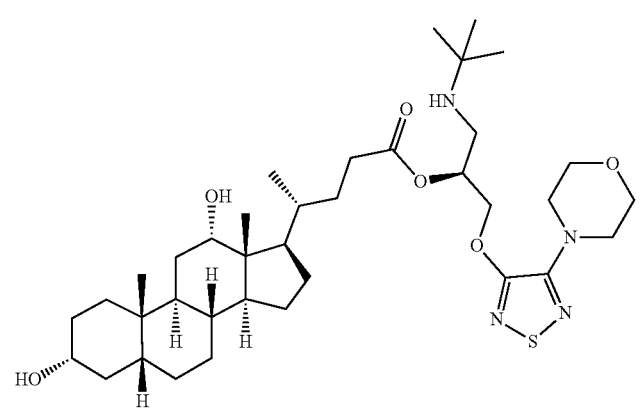 | (S)-1-(tert-butylamino)-3-((4-morpholino-1,2,5-thiadiazol-3-yl)oxy)propan-2-yl (R)-4-((3R,5R,8R,9S,10S,12S,13R,14S,17R)-3,12-dihydroxy-10,13-dimethylhexadecahydro-1H-cyclopenta[a]phenanthren-17-yl)pentanoate |

TABLE 3-continued

| Compound Number | Structure | Name |
|---|---|---|
| 11 | 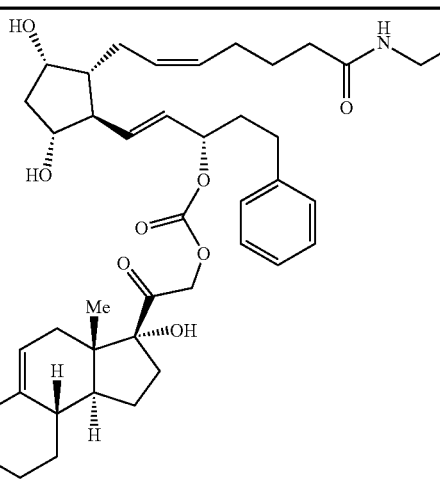 | (S,E)-1-((1R,2R,3S,5R)-2-((Z)-7-(ethylamino)-7-oxohept-2-en-1-yl)-3,5-dihydroxycyclopentyl)-5-phenylpent-1-en-3-yl (2-((8S,10S,13S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl) carbonate |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the dual-acting meibomian gland dysfunction pharmacological agent described herein is P. H. Stahl & C. G. Wermuth "Handbook of Pharmaceutical Salts", Verlag Helvetica Chimica Acta, Zurich, 2002.

Pharmaceutical Compositions

In some embodiments, the compound described herein has a structure provided in any one of Formula (I), Formula (IA), Formula (IB'), Formula (IB), Formula (IC), Formula (II), Formula (IIA), Formula (IIB), Formula (III), Formula (IV), or Formula (V). In certain embodiments, the compounds as described herein is administered as a pure chemical. In other embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

One embodiment provides a pharmaceutical composition comprising any compound provided herein, such as a compound that has the structure of any one of Formula (I), Formula (IA), Formula (IB'), Formula (IB), Formula (IC), Formula (II), Formula (IIA), Formula (IIB), Formula (III), Formula (IV), Formula (V), Formula (VI), Formula (VI-A), Formula (VI-B), Formula (VI-C), Formula (VII), Formula (VII-A), Formula (VII-B), Formula (VIII), Formula (VIII-A), Formula (VIII-B), Formula (IX), or Formula (X), or a pharmaceutically acceptable salt thereof, and at least one pharmaceutically acceptable excipient. Another embodiment provides the pharmaceutical composition, wherein the pharmaceutical composition is suitable for ophthalmic administration. Another embodiment provides the pharmaceutical composition, wherein the pharmaceutical composition is suitable for intraocular ophthalmic administration. In some embodiments, intraocular ophthalmic administration is intraocular, subretinal, superciliary, forniceal, into Schlemm's canal, inside a bleb, intracameral, intravitreal, suprachoroidal, punctal, retrobulbar, or subconjunctival.

In some embodiments, any composition provided herein, such as containing a compound as described by any one of Formula (I), Formula (IA), Formula (IB'), Formula (IB), Formula (IC), Formula (II), Formula (IIA), Formula (IIB), Formula (III), Formula (IV), Formula (V), Formula (VI), Formula (VI-A), Formula (VI-B), Formula (VI-C), Formula (VII), Formula (VII-A), Formula (VII-B), Formula (VIII), Formula (VIII-A), Formula (VIII-B), Formula (IX), or Formula (X), (or pharmaceutically acceptable salt thereof) comprises an optional additional component, in that it contains less than about 5%, or less than about 1%, or less than about 0.1%, of other molecules, such as, for example, impurities, synthetic materials (e.g., unreacted starting materials (e.g., a steroid provided herein in its free form), hydrolyzed materials (e.g., a steroid provided herein in its free form), unreacted intermediates, or the like) or byproducts (e.g., synthesis by-products or processing by-products, such as produced by heat processing, solvent processing, and/or sterilization).

In some embodiments, any article or implant provided herein, such as containing a compound as described by any one of Formula (I), Formula (IA), Formula (IB'), Formula (IB), Formula (IC), Formula (II), Formula (IIA), Formula (IIB), Formula (III), Formula (IV), Formula (V), Formula (VI), Formula (VI-A), Formula (VI-B), Formula (VI-C), Formula (VII), Formula (VII-A), Formula (VII-B), Formula (VIII), Formula (VIII-A), Formula (VIII-B), Formula (IX), or Formula (X), (or pharmaceutically acceptable salt thereof) is substantially pure, in that it contains less than about 5%, or less than about 1%, or less than about 0.1%, of other organic small molecules, such as, for example, impurities, synthetic materials (e.g., unreacted starting materials (e.g., a steroid provided herein in its free form), hydrolyzed materials (e.g., a steroid provided herein in its free form), unreacted intermediates, or the like) or byproducts (e.g., synthesis by-products or processing by-products, such as produced by heat processing, solvent processing, and/or sterilization).

In certain embodiments, any compound provided herein, such as the compound as described by any one of Formula (I), Formula (IA), Formula (IB'), Formula (IB), Formula (IC), Formula (II), Formula (IIA), Formula (IIB), Formula (III), Formula (IV), Formula (V), Formula (VI), Formula (VI-A), Formula (VI-B), Formula (VI-C), Formula (VII), Formula (VII-A), Formula (VII-B), Formula (VIII), Formula (VIII-A), Formula (VIII-B), Formula (IX), or Formula (X), (or pharmaceutically acceptable salt thereof) is substantially pure, in that it contains less than about 5%, or less than about 1%, or less than about 0.1%, of other organic small molecules, such as impurities, unreacted intermediates or byproducts (e.g., synthesis by-products or processing by-products, such as produced by heat processing, solvent processing, and/or sterilization).

In certain embodiments, any compound provided herein, such as the compound as described by any one of Formula (I), Formula (IA), Formula (IB'), Formula (IB), Formula (IC), Formula (II), Formula (IIA), Formula (IIB), Formula (III), Formula (IV), Formula (V), Formula (VI), Formula (VI-A), Formula (VI-B), Formula (VI-C), Formula (VII), Formula (VII-A), Formula (VII-B), Formula (VIII), Formula (VIII-A), Formula (VIII-B), Formula (IX), or Formula (X), (or pharmaceutically acceptable salt thereof) is a pharmaceutical implant or article. In some embodiments, the implant or article comprises at least 50 wt. % (at least 60 wt. %, at least 70 wt. %, at least 80 wt. %, at least 90 wt. %, at least 95 wt. %, at least 98 wt. %, or the like) of the compound and/or pharmaceutically acceptable salt thereof. In some embodiments, the implant or article releases (such as by surface erosion) the compound, the first radical, and/or the second radical (and/or other (e.g., active) fragment or metabolite of the compound). In some embodiments, release is at or near zero-order (e.g., in an aqueous medium, such as in a buffer solution, serum, biological environment, in vivo, or the like, such as at a physiological temperature (e.g., 37° C.). In some embodiments, the first radical and the second radical are released from the pharmaceutical implant or article at 37° C. in 100% bovine serum or at 37° C. in phosphate buffered saline (PBS) at a rate such that $t_{10}$ is greater than or equal to ⅒ of $t_{50}$. In some embodiments, the first radical and the second radical are released from the pharmaceutical implant or article at 37° C. in mixture of fetal bovine serum (FBS) and phosphate buffered saline (PBS) (e.g., 1% FBS in PBS) at a rate such that $t_{10}$ is greater than or equal to ⅒ of $t_{50}$.

In some embodiments, certain forms of pharmaceutical compositions described herein (e.g., fibers, fiber meshes, woven fabrics, non-woven fabrics, pellets, cylinders, rods, hollow tubes, microparticles (e.g., microbeads), nanoparticles (e.g., nanobeads), or other shaped articles) provide a controllable surface area. In some embodiments, the controllable surface area is injected, does not require removal after completion of drug release, and allows for tailoring of drug release rates for a given indication. In certain embodiments, methods provided herein do not require (or comprise) removal of an article or implant, or residual materials or components thereof (e.g., because the implant is completely or almost completely (e.g., bio- or physiologically) degraded or degradable (e.g., at least 80 wt. %, at least 85 wt. %, at least 90 wt. %, at least 95 wt. %, at least 98 wt. %, at least 99 wt. %, or the like)).

In some embodiments, the implants, articles, or compositions described herein are amorphous. In some embodiments, the implants, articles, or compositions described herein are formed by heat-based and solvent based processing methods. Non-limiting examples of heat processing methods include heat molding, injection molding, extrusion, 3D printing, melt electrospinning, fiber spinning, fiber extrusion, and/or blow molding. Non-limiting examples of solvent processing include coating, micro printing, dot printing, micropatterning, fiber spinning, solvent blow molding, emulsions, electrospraying, and electrospinning. In some embodiments, processing methods to form an intermediate glassy state of any of the above heat and solvent based methods as well as heat and solvent based methods that lead to glassy state material with no defined shape (e.g. spray drying, lyophilization, powder melting, etc.).

The term "glassy state," as used herein, generally refers to an amorphous solid including greater than 70%, 80%, 90%, 95%, 98%, or 99% (w/w) of compositions, articles, or implants described herein. In some embodiments, the compositions, articles, or implants described herein exhibit a glass transition temperature above 38° C. In the glassy state, as measured by differential scanning calorimetry (DSC), X-ray powder diffraction (XRD), or polarized light microscopy (PLM), the level of crystallinity is, for example, from 0-15% (e.g., less than 1%, 0-1%, 0-3%, 0-5%, 0-7%, 0-9%, 0-10%, or 0-13%). In some embodiments, glass formulations are formed using heat processing or solvent processing methods described herein (e.g., in the examples).

In some embodiments, the pharmaceutical compositions described herein are prepared by electrospinning. In some embodiments, the pharmaceutical compositions of the disclosure are dissolved in a solvent (e.g., acetone) at concentrations ranging from, e.g., 10-30% w/v, and are electrosprayed to form micro- and nanoparticles. In some embodiments, the solution is loaded into a syringe and injected at a rate (e.g., 0.5 mL/h) onto a stationary collection plate. In some embodiments, a potential difference (e.g., 18 kV) is maintained between the needle and collecting surface. For example, in certain embodiments, a concentration of 10% w/v is used to obtain nanoparticles. In other embodiments, a concentration of 30% w/v is used to obtain micro particles.

The pharmaceutical compositions of the disclosure are dissolved in a solvent (e.g., THF, or 1:1 ratio of DCM/THF). In some embodiments, the solution is loaded into a syringe and injected at a rate (e.g., 0.5 mL/h) onto a cylindrical mandrel rotating at a particular rotational speed, e.g., 1150 rpm, to obtain aligned fibers, or onto a stationary collector surface to obtain unaligned fibers. In some embodiments, a potential difference (e.g., 18 kV or 17 kV) is maintained between the needle and collecting surface for aligned and random fibers.

In other embodiments, fibers are prepared from the melt at elevated temperatures, the glassy state intermediate, or from the solution by dissolving the pharmaceutical compositions described herein in a solvent (e.g., DCM, THF, or chloroform). As used herein, "melt spinning" describes heat processing from the melt state, "heat spinning" describes heat processing from the glassy state, and "wet", "dry", and "gel" spinning describe solution processing.

In some embodiments, the viscous melt, intermediate, or solution is fed through a spinneret and fibers are formed upon cooling (melt or heat spinning) or following solvent evaporation with warm air as the compound exits the spinneret (dry spinning). In some embodiments, wet spinning and gel spinning are used to produce the fibers disclosed herein. "Heat spinning," as used herein, describes a process that is similar to the melt spinning, but performed with a glassy state intermediate and heated above the glass transition temperature ($T_g$), obtaining the viscous fluid to extrude/spin instead of the melt. Alternatively, tweezers may be dipped into melted material or concentrated solutions and retracted slowly in order to pull fibers. The rate of pulling and distance pulled may be varied to yield fibers and columnar structures of different thickness.

In some embodiments, micro-particles or nano-particles made from the pharmaceutical composition are formed using an emulsion process. In some embodiments, the pharmaceutical composition is dissolved in an organic solvent (e.g. DCM, THF, etc.). In some embodiments, a surfactant (e.g. SDS, PVA, etc.) is added (e.g. 1%) to the solution/mixture. In some embodiments, the resulting mixture is stirred for the appropriate time at room temperature to form an emulsion. In some embodiments, the emulsion is subsequently added to Milli-Q water under stirring for an appropriate time (e.g., 1 h) to remove residual solvent. The resulting micro- or nano-particles may be collected by centrifugation and dried.

In some embodiments, injectable cylinders or rods made from a pharmaceutical composition described herein is formed by heat extrusion. In some embodiments, the pharmaceutical composition is loaded into a hot melt extruder, heated to a temperature above the melting point (e.g., for crystalline compositions) or glass transition temperature (e.g., for pre-melted or amorphous compositions), and extruded using (i) a compressive force to push the material through the nozzle and (ii) a tensile force (or gravity) to pull the material out of the extruder. The extrudate may be cut to the desired length for suitable drug dosing for a medical indication.

In some embodiments, a milling process is used to reduce the size of an article described to form sized particles, e.g., beads, in the micrometer (microbeads) to nanometer size range (nanobeads). The milling process may be performed using a mill or other suitable apparatus. In some embodiments, dry and wet milling processes, such as, for example, jet milling, cryo-milling, ball milling, media milling, sonication, and homogenization are used in methods described herein. In some embodiments, heating of the milled microparticle above the $T_g$ is performed to achieve a spherical shape. In some embodiments, particles with non-spherical shapes are used as milled.

In certain embodiments, a composition described herein has a limited window (e.g., short timeframe of seconds to minutes) of thermal stability, whereby the purity of the dimer is affected (e.g., minimally) at elevated temperatures. In some embodiments, an intermediate glassy state form (e.g., film, surface coating, pellet, micro-particles, or other shaped article) is made to avoid decomposition. In some embodiments, heat or solvent processing is used to remove or reduce the crystallinity of the material to form a glassy state composition. In some embodiments, the glassy state composition is heat processed at a lower temperature (e.g., processing just above the glass transition temperature ($T_g$), and below the melt temperature ($T_m$)). In some embodiments, the lower temperature allows for a longer timeframe for heat processing the glassy state material into the final shaped article, while reducing the impact of processing conditions on the purity of the prodrug dimer in the article.

Exemplary processing details are provided in the Examples.

In some embodiments, the processable compound as described by any one of Formula (I), Formula (IA), Formula (IB'), Formula (IB), Formula (IC), Formula (II), Formula (IIA), Formula (IIB), Formula (III), Formula (IV), Formula (V), Formula (VI), Formula (VI-A), Formula (VI-B), Formula (VI-C), Formula (VII), Formula (VII-A), Formula (VII-B), Formula (VIII), Formula (VIII-A), Formula (VIII-B), Formula (IX), or Formula (X), is formulated for administration by injection. In some instances, the injection formulation is an solid formulation. In some instances, the injection formulation is a non-aqueous formulation.

In certain aspects, the pharmaceutical compositions described herein provide an article (e.g., as described herein) with a controlled release profile (e.g., by surface erosion). In some embodiments, the surface erosion allows the article to maintain its physical form, while gradually decreasing in size as the surface erodes (e.g., at a constant rate), rather than by, for example, bulk erosion that is characteristic of some polymer-based drug release vehicles (e.g., polylactic/glycolic acid). In some embodiments, the surface erosion inhibits burst release and/or reduces the formation of inflammatory particulates (e.g., no or minimal crystalline particulates are formed or released from the articles when drug is released as described herein). In some embodiments, compositions described herein are delivered over a period of time. For example, a slower and steadier rate of delivery (e.g., release of less than 10% of the first radical or the second radical in their free form (as a percentage of the total drug, the first radical or the second radical in their free form, present in the article) at 37° C. in 100% bovine serum over 5 days) results in a reduction in the frequency with which the pharmaceutical composition is administered to a subject and/or improve the safety profile of the drug. In some embodiments, the drug release is tailored to avoid side effects of slower and longer release of the drug by engineering the article to provide constant release over a comparatively shorter period of time. In some embodiments, the drug release is tailored for dose and duration suitable for the indication or administration method.

In some embodiments, the release rate is related to, for example, the drug configuration of the dimer. In some embodiments, the drug release rate from an article described herein is modulated by the cleavage of dimer-linker bond through hydrolysis or enzymatic degradation. In some embodiments, the linking moiety (e.g., the linker) affects drug release rate. In some embodiments, the drug release rate is controlled by a functional group on the composition described herein to conjugate through to the linker, for example, a primary vs. a secondary hydroxyl group. In some embodiments, the release rate from a dimer is related to percentage of the loaded dimer compared to the final drug dimer formulation (e.g., by using a pharmaceutical excipient (e.g., bulking agent/excipient). In some embodiments, the release rate is controlled by the size of a microbead. In some embodiments, drug release is tailored based on the solubility of drug dimer (e.g., through selection of appropriate drug and/or linker) that will influence the rate of surface erosion (e.g., dissolution/degradation) from the article. In other embodiments, drug release is affected by changes in surface area of the formulation, e.g., by changing the diameter of the microbeads. By adjusting the vide supra factors, dissolution, degradation, diffusion, and controlled release may be varied over wide ranges. For example, release may be designed to be initiated over minutes to hours, and may extend over the course of days, weeks, months, or years.

Figure 8A:
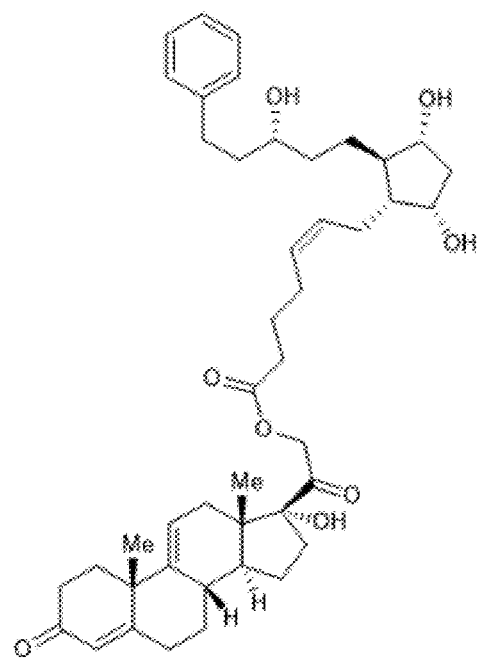
FIG. 8 shows the chemical structure (FIG. 8A) and the heat processed pellet (FIG. 8B) of a steroid-prostaglandin heterodimer (latanoprost-anecortave, Compound 6) exemplified herein.
FIG. 8C shows the drug release profile for each of latanoprost acid (●) and anecortave desacetate (o) (pellet) in fetal bovine serum (FBS) over 30 days.
FIG. 8D represents the 28-day progression of the (e.g., surface erosion) drug release profile for the pellet of Compound 6 in FBS.
Figure 8B:
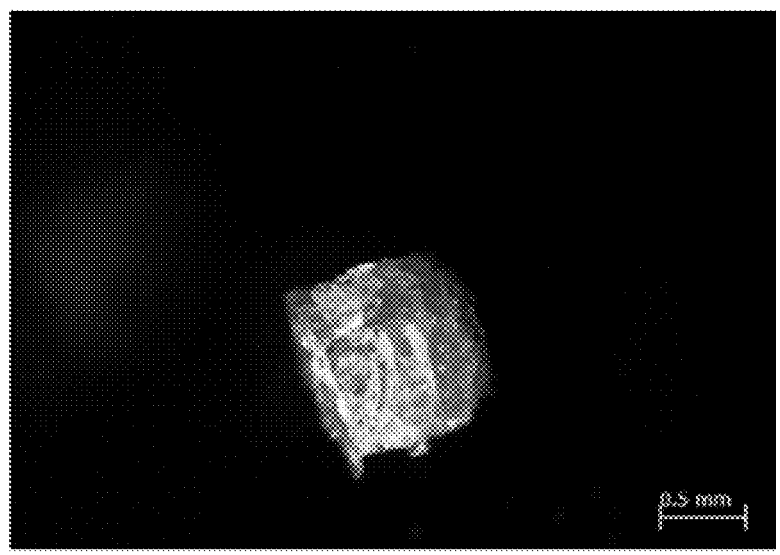
Figure 8C:
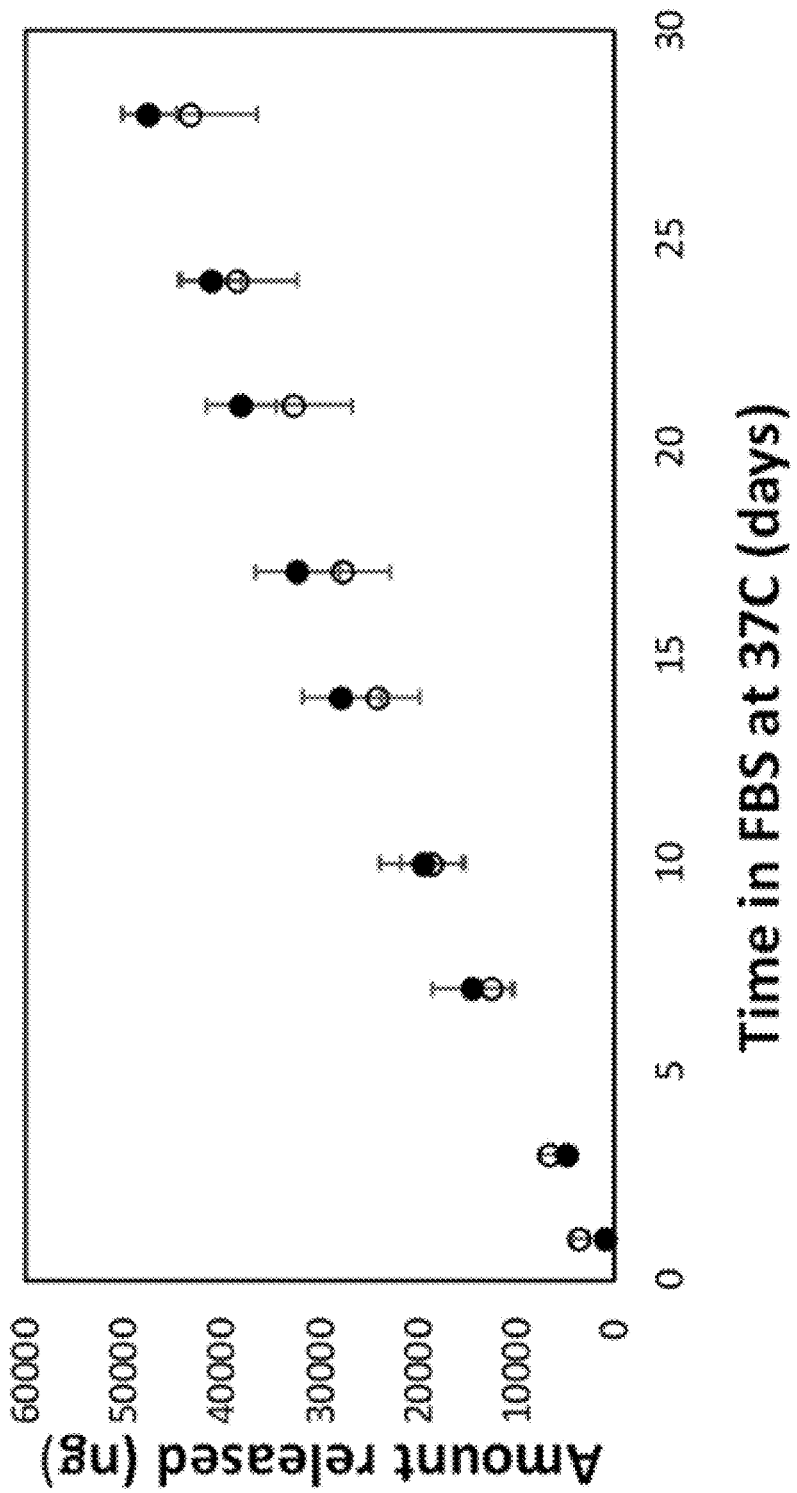
Figure 8D:
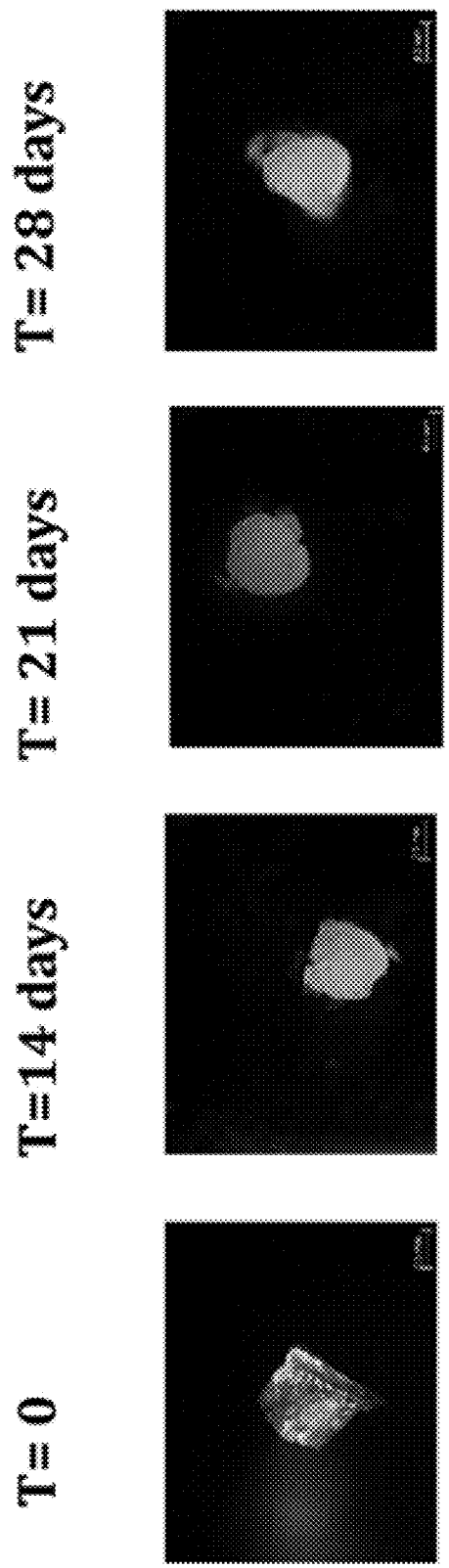
Figure 9A:
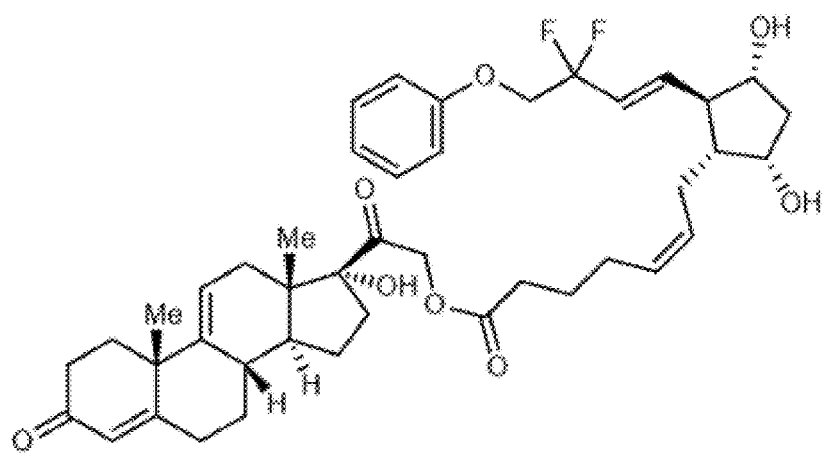
FIG. 9 shows the chemical structure (FIG. 9A) and the heat processed pellet (FIG. 9B) of a steroid-prostaglandin heterodimer (tafluprost-anecortave, Compound 7) exemplified herein.
FIG. 9C shows the drug release profile for Compound 7 (pellet) in fetal bovine serum (FBS) over 30 days.
FIG. 9D represents the 28-day progression of the (e.g., surface erosion) drug release profile for the pellet of Compound 7 in FBS.
Figure 9B:
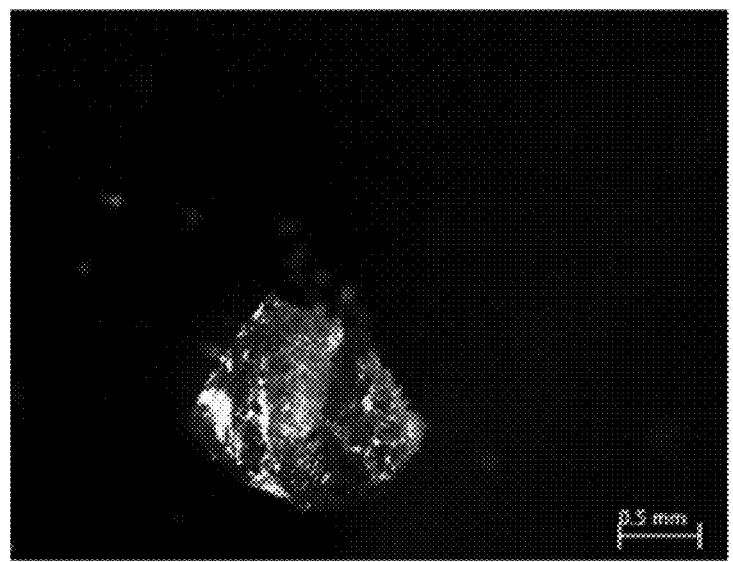
Figure 9C:
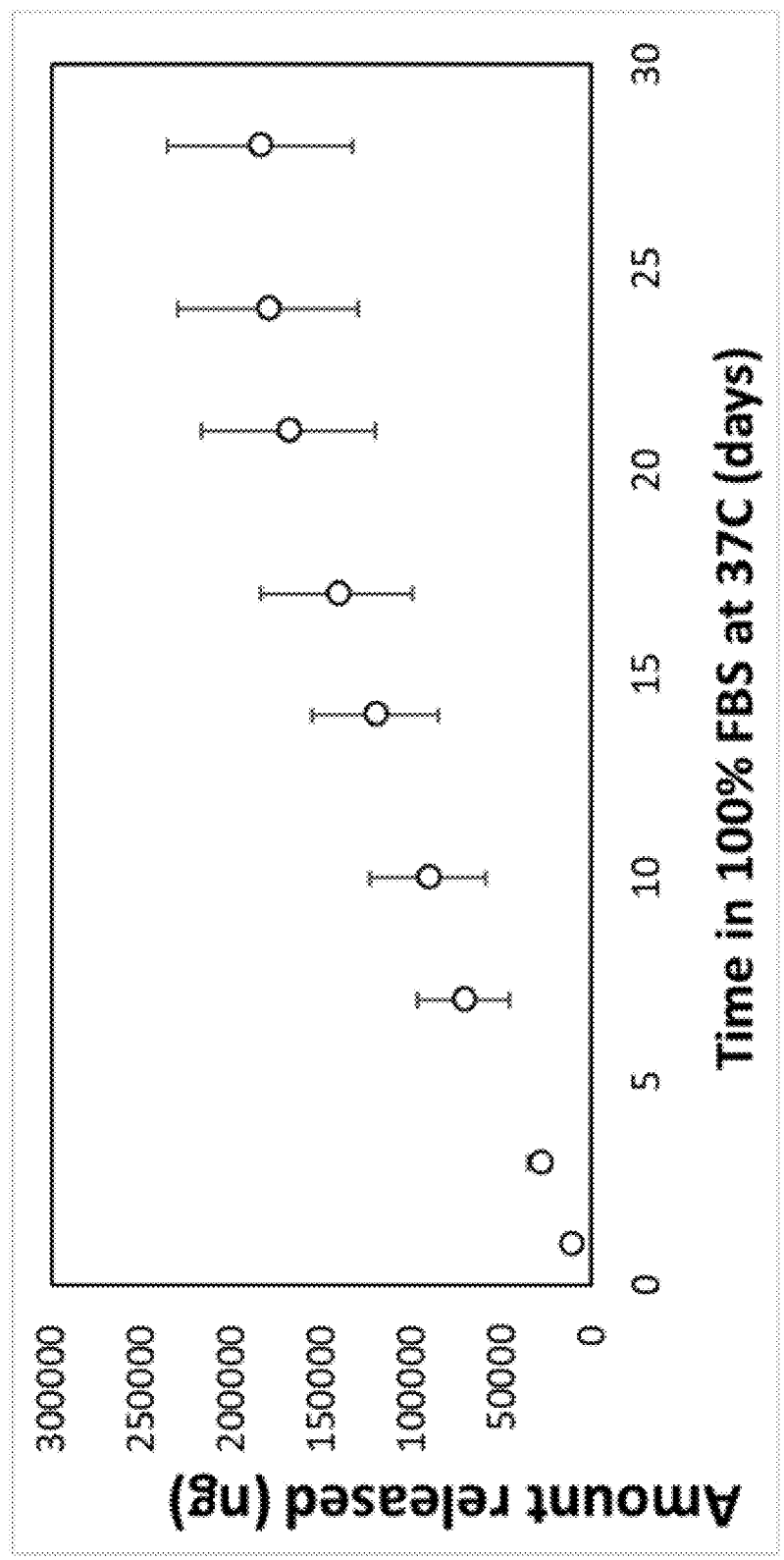
Figure 9D:
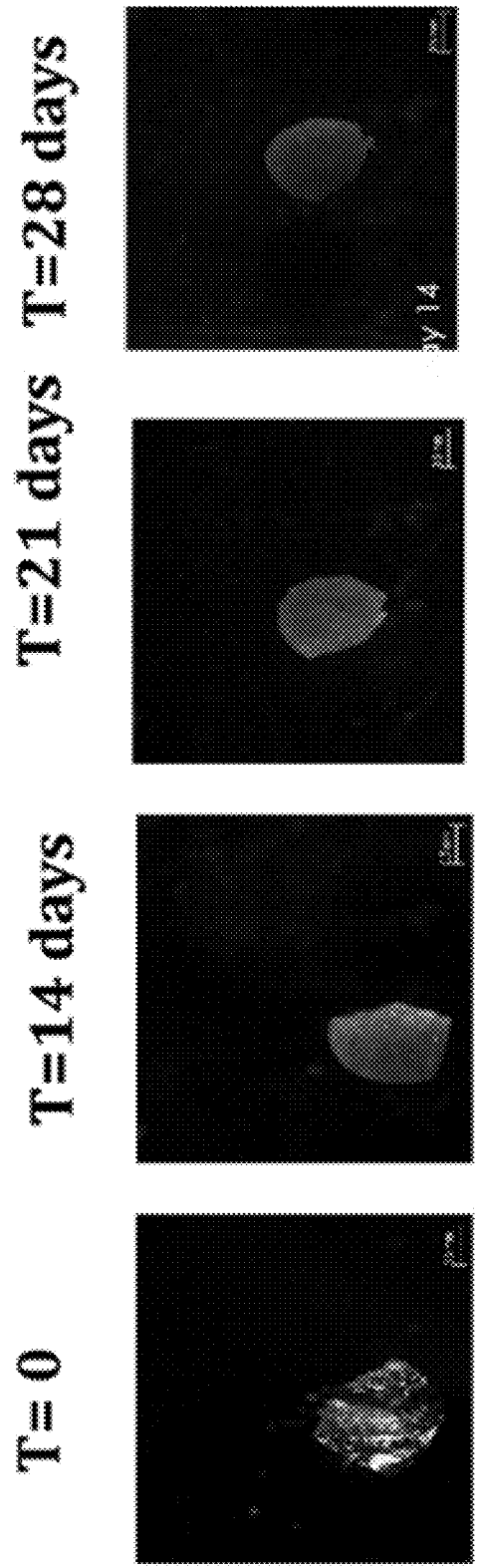
Figure 10A:
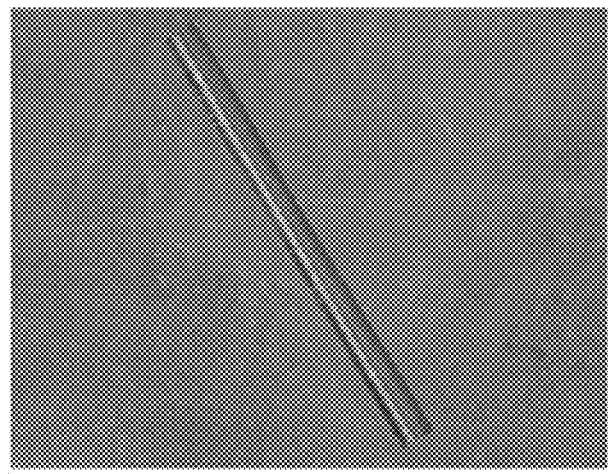
FIG. 10 shows an extruded rod of a steroid-prostaglandin heterodimer (bimatoprost-anecortave, Compound 5) exemplified herein (FIG. 10A).
FIG. 10B shows the drug release profile of Compound 5 (extruded rod) in fetal bovine serum (FBS) over 30 days.
FIG. 10C represents the 30-day progression of the (e.g., surface erosion) drug release profile for the extruded rod of Compound 5 in FBS.
Figure 10B:
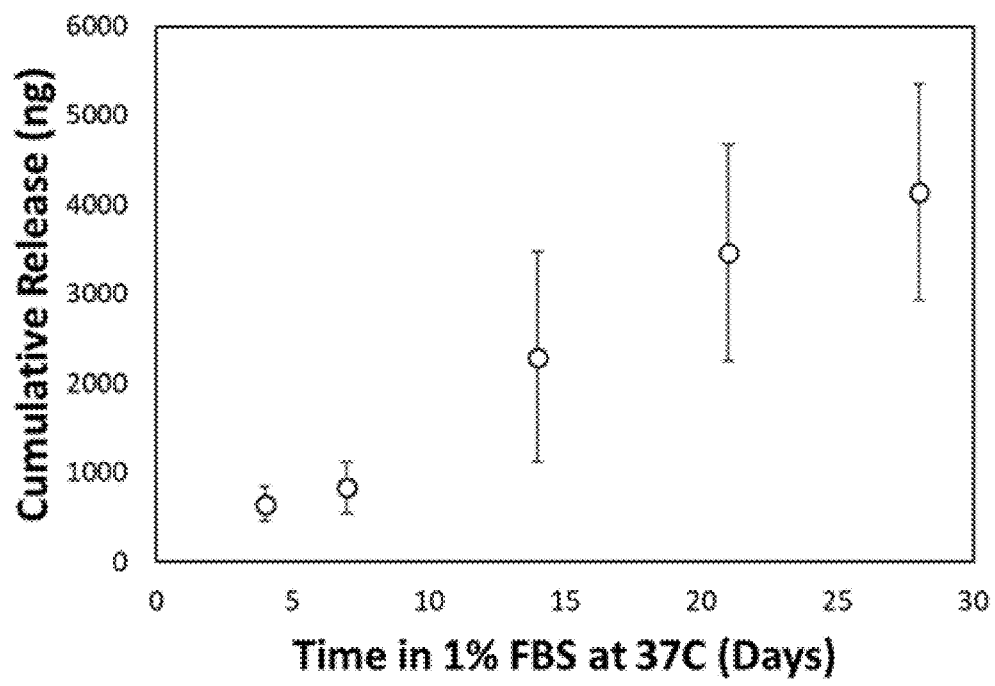
Figure 10C:
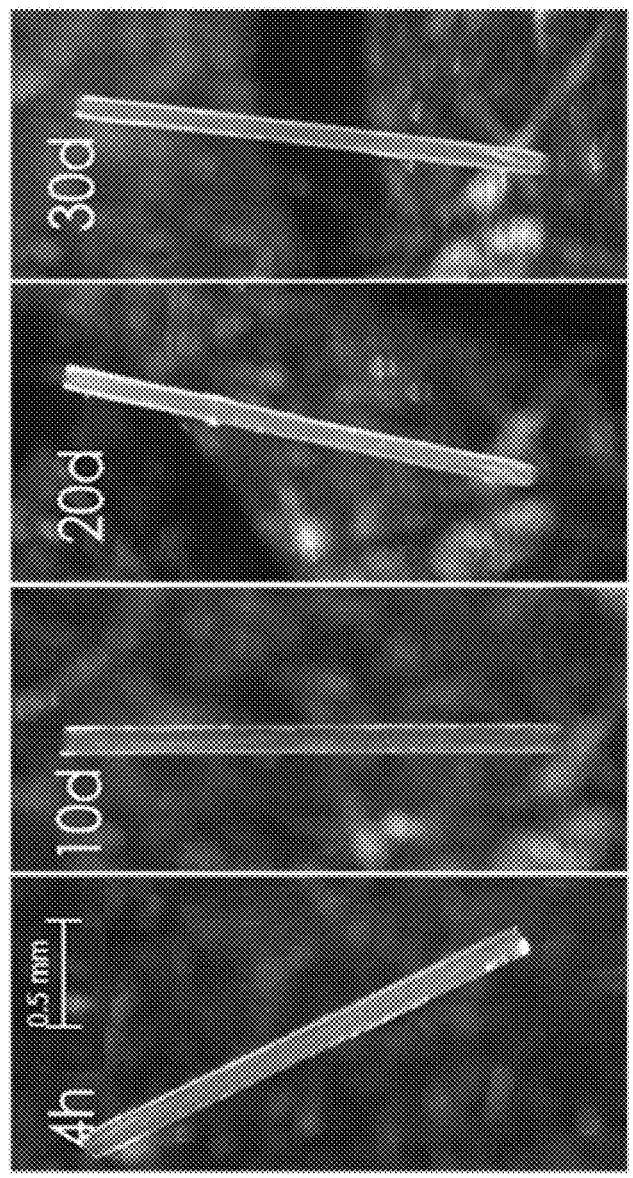
Figure 11A:
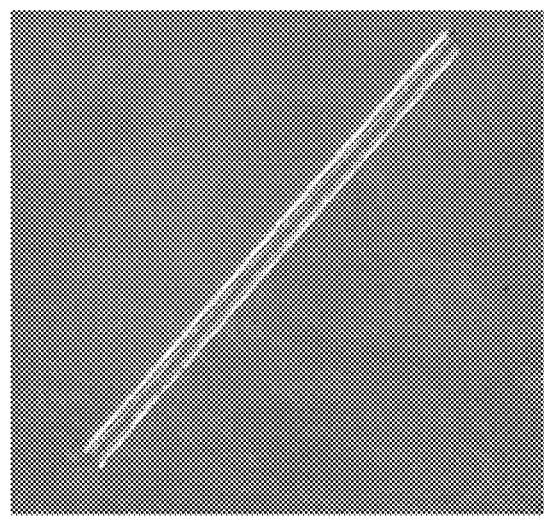
FIG. 11 shows an extruded rod of a steroid-prostaglandin heterodimer (travoprost-anecortave, Compound 1) exemplified herein (FIG. 11A).
FIG. 11B shows the drug release profile of Compound 1 (extruded rod) in fetal bovine serum (FBS) over 30 days.
Figure 11B:
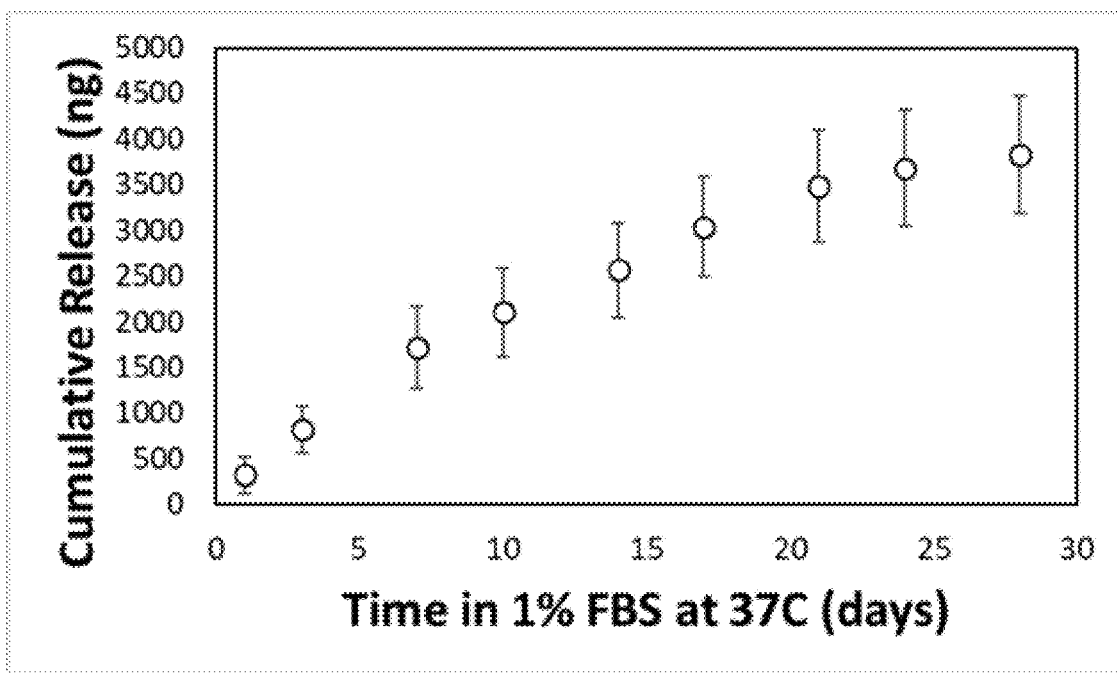
Figure 12A:
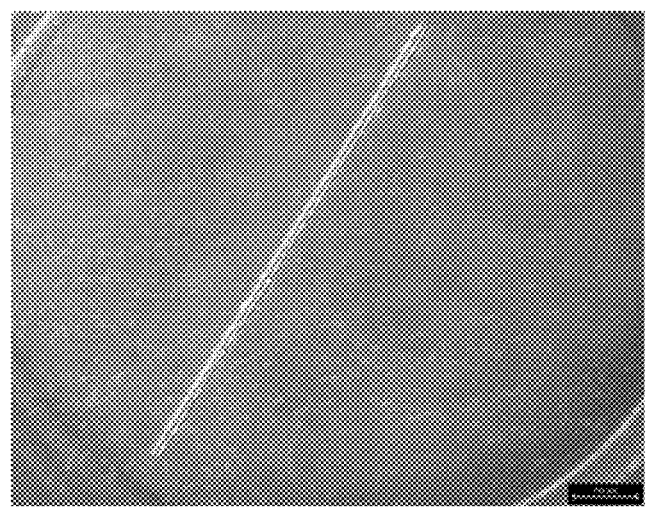
FIG. 12 shows an extruded rod of a steroid-prostaglandin heterodimer (latanoprost-anecortave, Compound 6) exemplified herein (FIG. 12A).
FIG. 12B shows the drug release profile of Compound 6 (extruded rod) in fetal bovine serum (FBS) over 70 days.
FIG. 12C represents the 70-day progression of the (e.g., surface erosion) drug release profile for the extruded rod of Compound 6 in FBS.
Figure 12B:
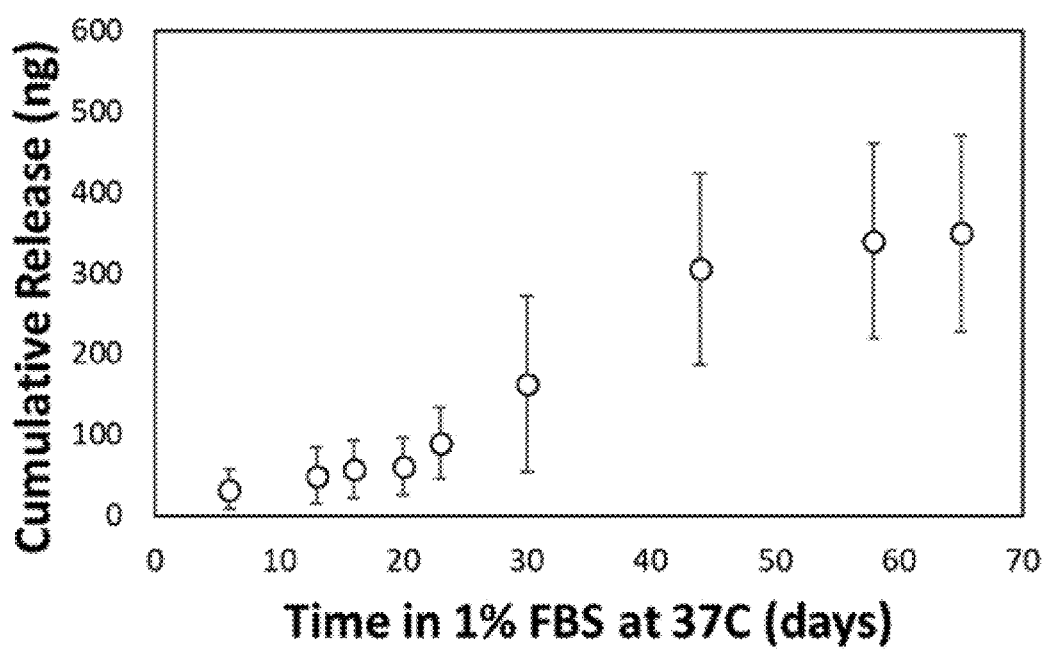
Figure 12C:
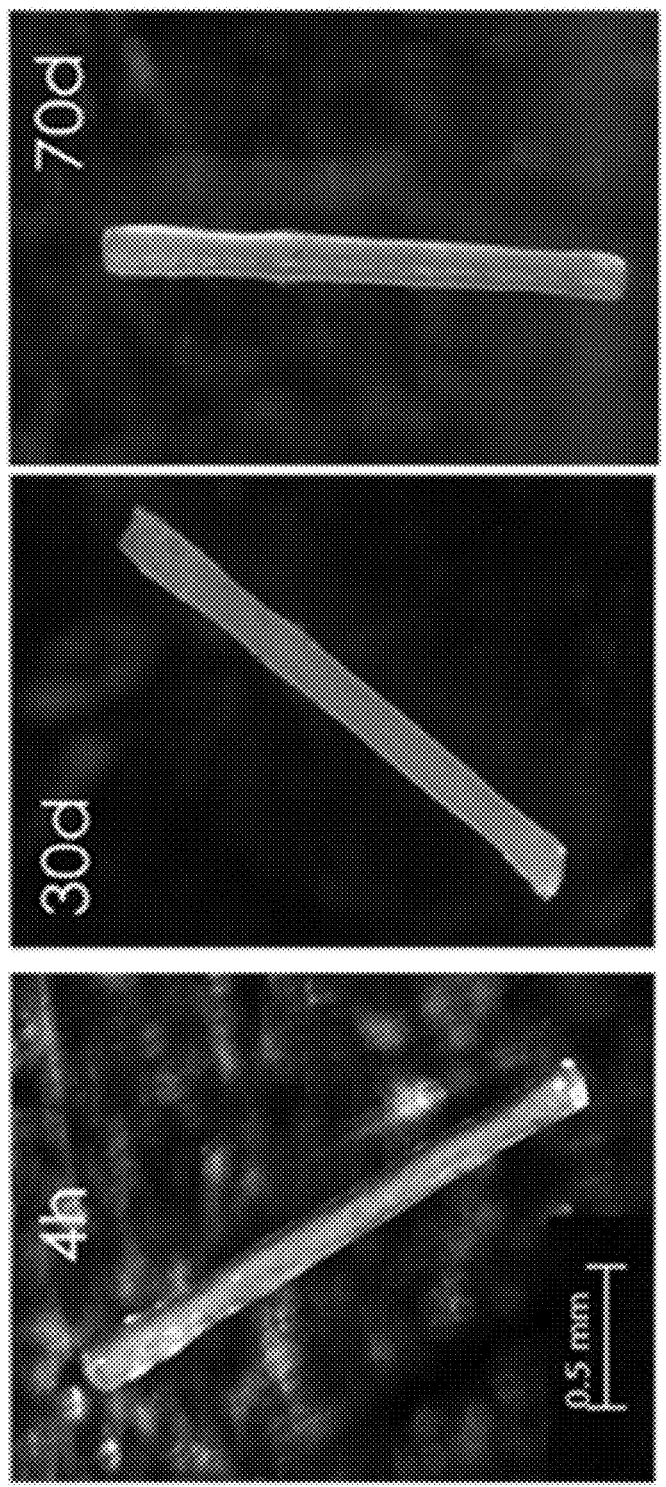
Figure 13A:
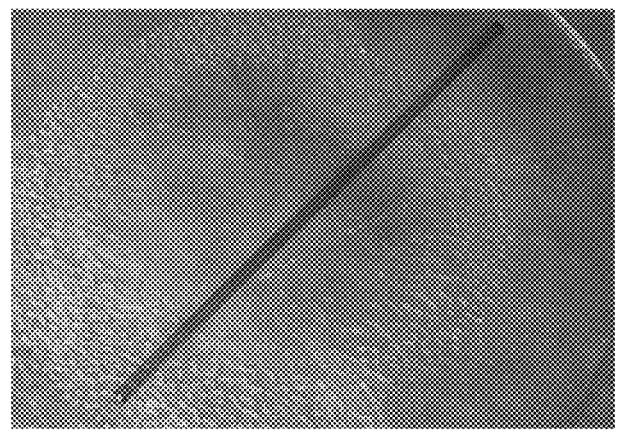
FIG. 13 shows an extruded rod of a steroid-prostaglandin heterodimer (tafluprost-anecortave, Compound 7) exemplified herein (FIG. 13A).
FIG. 13B shows the drug release profile of Compound 7 (extruded rod) in fetal bovine serum (FBS) over 100 days.
FIG. 13C represents the 100-day progression of the (e.g., surface erosion) drug release profile for the extruded rod of Compound 7 in FBS.
Figure 13B:
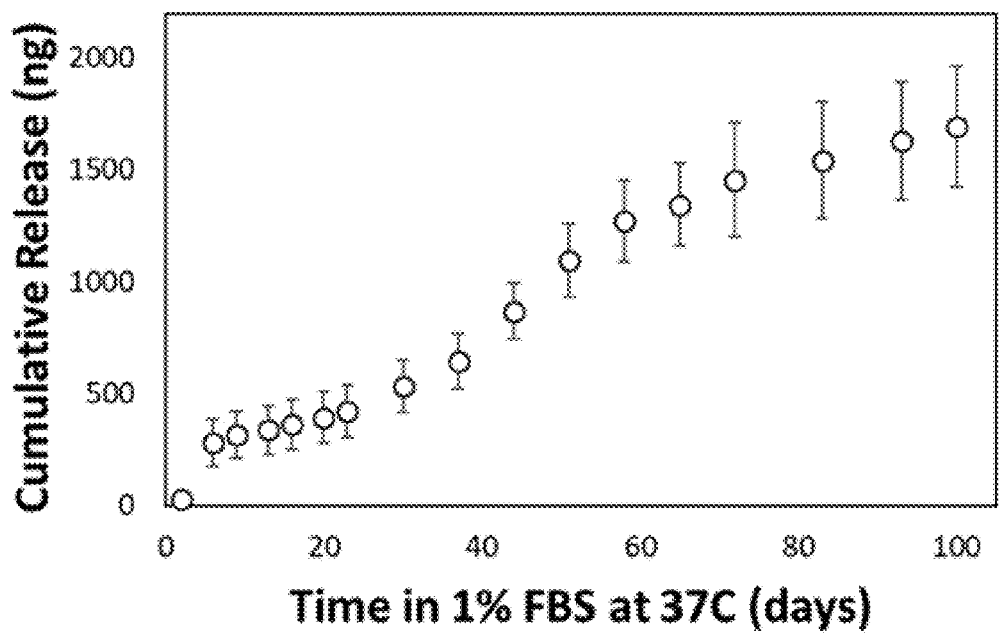
Figure 13C:
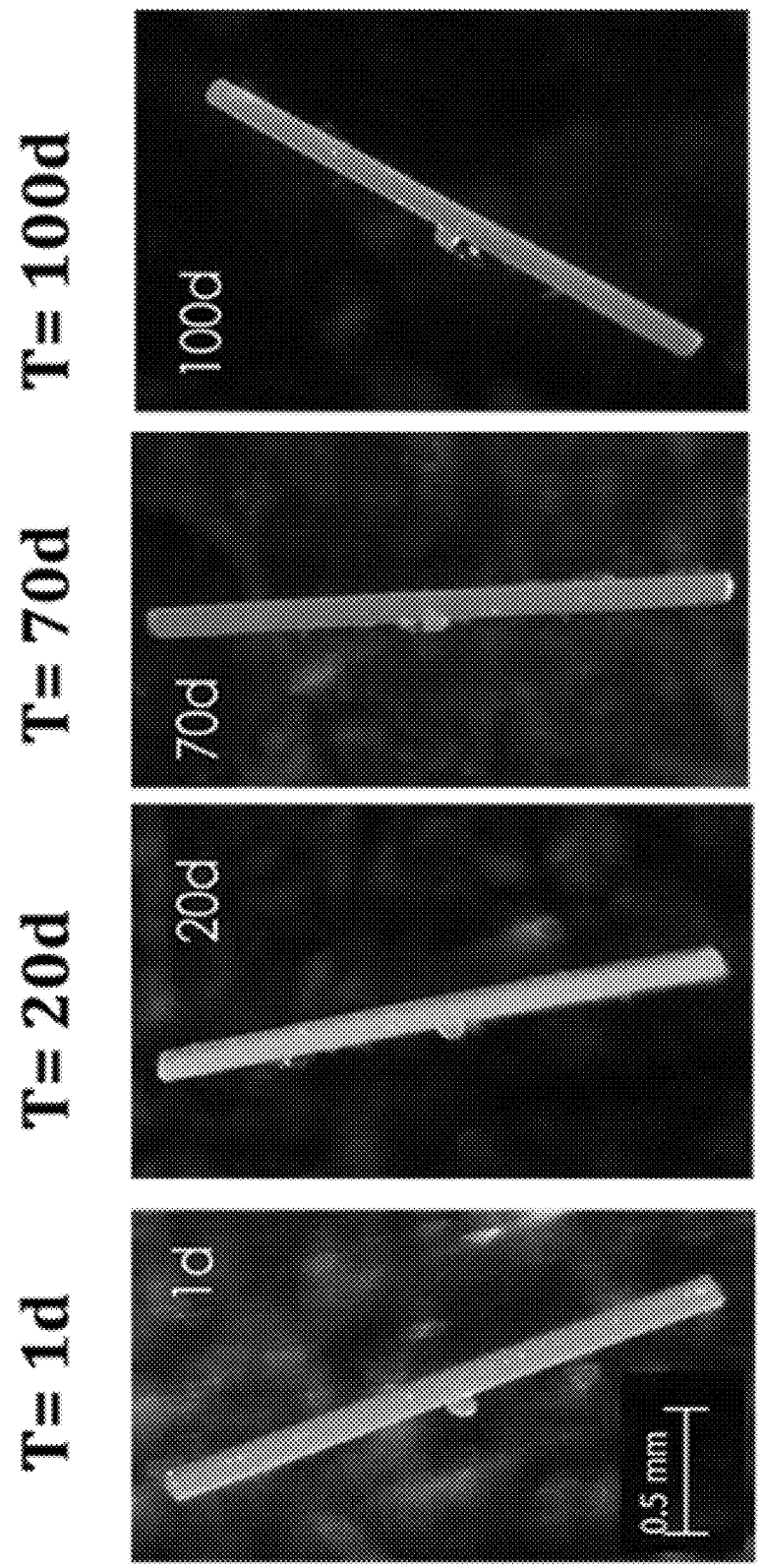

In some instances, provided herein is a heat processed pellet (e.g., FIGS. 2B, 3B, 5B, 7B, 8B, 9B, 15B, and 19B) or rod (e.g., FIGS. 10A, 11A, 12A, and 13A) of a heterodimer (e.g., a steroid-prostaglandin heterodimer) (e.g., FIGS. 2A, 3A, 5A, 6A, 7A, 8A, 9A, 15A, and 19A) exemplified herein. In some instances, provided herein is a drug release profile of a pellet (e.g., FIGS. 2C, 2D, 3C, 3D, 5C, 5D, 6B, 6C, 7C, 7D, 8C, 8D, 9C, 9D, and 15C) or a rod (FIGS. 10B, 10C, 11B, 12B, 12C, 13B, and 13C) provided herein in fetal bovine serum (FBS), phosphate-buffered saline (PBS), or a combination thereof over a period (e.g., an extended period is time) of time (e.g., 15 days, 30 days, 60 days, 90 days, 120 days, 365 days, or more). In some instances, the release profile of a composition provided herein (e.g., a steroid-prostaglandin heterodimer derived pellet) is measured as the change (e.g., increase) in concentration of one or more drug (e.g., a steroid and/or a prostaglandin) in a solution over a period of time. In some instances, the release profile of a composition provided herein (e.g., a steroid-prostaglandin heterodimer derived pellet) is measured as an increase in concentration of a steroid over a period of time. FIG. 8C illustrates release of both steroid and prostaglandin in FBS. As is illustrated, both steroid and prostaglandin have similar release profiles. It is expected that because steroid and prostaglandin are directly linked, there should be an identical release profile. However, the steroid and prostaglandin appear to have slightly differing release profile at many time points, e.g., as a function of greater difficulty in detecting one of the chromophores (e.g., prostaglandin or steroid) over the other of the chromophores (e.g., steroid or prostaglandin). Other figures demonstrating drug release illustrate release of prostaglandins, which may be overestimated or underestimated as a result of detection methods. However, other figures demonstrate that the various compounds provided herein and illustrated therein demonstrate release of prostaglandin (and, implicitly, steroid). As such this data demonstrates a platform for providing compounds and implants (e.g., with high drug content, low excipient content (e.g., that needs to be removed), and other benefits, such as described herein) that provide long-lasting release of prostaglandins (and steroid) under desirable conditions. In some instances, the release profile of a composition provided herein (e.g., a steroid-prostaglandin heterodimer derived pellet) is measured as an increase in concentration of a prostaglandin over a period of time. In some instances, the release profile of a composition provided herein (e.g., a steroid-prostaglandin heterodimer derived pellet) is measured as an increase in concentration of a steroid and a prostaglandin over a period of time (e.g., FIG. 8B). In some instances, the increase in concentration of one drug (e.g., a steroid) over a period of time corresponds with the increase in concentration of another drug (e.g., a prostaglandin) over a period of time. In some instances, drug release (e.g., of prostaglandins) is difficult to analyze by HPLC and UV techniques (e.g., poor chromophores), which may, for instance, result in over- or under estimation of released amounts (e.g., in particular for sustained release applications where released amounts of prostaglandin analogs are present at low amounts). In some instances, an increase of steroid concentration in solution over a period of time is used to quantify a drug (e.g., prostaglandin) release profile.

In some embodiments, a pharmaceutical composition containing a dimer described herein is administered to a subject by the following non-limiting examples oral, sublingual, nasal, intradermal, subcutaneous, intramuscular, rectal, vaginal, intravenous, intraarterial, intracisternal, intraperitoneal, intravitreal, periocular, topical (as by powders, creams, ointments, or drops), buccal and inhalational administration. In certain instances, the articles described herein are administered parenterally as injections (intravenous, intramuscular, or subcutaneous), or locally as injections (intraocularly or into a joint space). In some embodiments, the formulations described herein are admixed under sterile conditions with a pharmaceutically acceptable carrier, preservatives and/or buffers.

In some embodiments, the implant, article, or composition described herein is suitable for ophthalmic administration, subcutaneous administration, or intraspinal administration. In some embodiments, the ophthalmic administration is intraocular, subretinal, superciliary, forniceal, into Schlemm's canal, inside a bleb, intracameral, intravitreal, suprachoroidal, punctal, retrobulbar, or subconjunctival.

In some instances, the implant, article, or composition described herein is a coating on a device. In some instances, the device is a contact lenses, a microshunt device, microinvasive glaucoma surgery (MIGS) device, an intraocular lenses, or the like.

The dose of the composition comprising at least one compound as described herein differ, depending upon the patient's (e.g., human) condition, that is, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form and/or potency of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. The optimal dose depends upon the body mass, weight, or blood volume of the patient.

In other embodiments, the compositions described herein are combined with a pharmaceutically suitable or acceptable carrier (e.g., a pharmaceutically suitable (or acceptable) excipient, physiologically suitable (or acceptable) excipient, or physiologically suitable (or acceptable) carrier. Exemplary excipients are described, for example, in *Remington: The Science and Practice of Pharmacy* (Gennaro, 21$^{st}$ Ed. Mack Pub. Co., Easton, Pa. (2005)).

In certain aspects, provided herein is a method of treating an ophthalmic, neurological, orthopedic, acute or chronic pain, or post-operative disease or disorder in a patient in need of thereof, comprising administering to the patient any compound provided herein, or a pharmaceutically acceptable salt thereof, or a (e.g., pharmaceutical) composition comprising any compound provided herein, or a pharmaceutically acceptable salt thereof, such as a compound having a structure of any one of Formula (I), Formula (IA), Formula (IB'), Formula (IB), Formula (IC), Formula (II), Formula (IIA), Formula (IIB), Formula (III), Formula (IV), Formula (V) Formula (VI), Formula (VI-A), Formula (VI-B), Formula (VI-C), Formula (VII), Formula (VII-A), Formula (VII-B), Formula (VIII), Formula (VIII-A), Formula (VIII-B), Formula (IX), or Formula (X). In certain aspects, provided herein is a method of treating an ophthalmic disease or disorder in a patient in need of thereof, comprising administering to the patient any compound provided herein, or a pharmaceutically acceptable salt thereof, or a (e.g., pharmaceutical) composition comprising any compound provided herein, or a pharmaceutically acceptable salt thereof, such as a compound having a structure of any one of Formula (I), Formula (IA), Formula (IB'), Formula (IB), Formula (IC), Formula (II), Formula (IIA), Formula (IIB), Formula (III), Formula (IV), Formula (V) Formula (VI), Formula (VI-A), Formula (VI-B), Formula (VI-C), Formula (VII), Formula (VII-A), Formula (VII-B), Formula (VIII), Formula (VIII-A), Formula (VIII-B), Formula (IX), or Formula (X). Another embodiment provides the method wherein the pharmaceutical composition is in the form of a solid suitable for intraocular ophthalmic administration (e.g., injection). In some embodiments, intraocular ophthalmic administration is intraocular, subretinal, superciliary, forniceal, into Schlemm's canal, inside a bleb, intracameral, intravitreal, suprachoroidal, punctal, retrobulbar, or subconjunctival.

Methods involving treating a subject may include preventing a disease, disorder or condition from occurring in the subject which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected (e.g., such treating the pain of a subject by administration of an agent even though such agent does not treat the cause of the pain).

Another embodiment provides the method wherein the ophthalmic disease or disorder is selected from glaucoma, ocular inflammation, diabetic macular edema, posterior inflammation, anterior inflammation, macular degeneration (e.g., wet macular degeneration (AMD) or dry AMD), post-cataract surgery, and retinal vein occlusion. In some embodiments, the ocular disease or disorder is glaucoma.

EXAMPLES

Example 1: Analytical Methods

Analytical Example 1: High Performance Liquid Chromatography (HPLC)

Samples (20.0 mg) are dissolved in acetonitrile (10.0 mL) to make 2 mg/mL solution. For the system: solvent A was Water+0.05% trifluoroacetic acid (TFA); solvent B was Acetonitrile+0.05% TFA; the flow rate was 1.0 mL/min; and the detection method was UV @242 nm and UV Spectra from 190 to 400 nm. The samples were loaded onto an Agilent 1100 series HPLC with either (i) a Phenomenex Gemini-NX C18 Column (5 µm; 110 Å; 250×4.6 mm; 00G-4454-E0) or (ii) Phenomenex SecurityGuard Analytical Guard Column (KJO-4282) with Gemini C18 4×3.0 mm Guard Cartridge (AJO-7597). The solvent gradient profile is shown in Table 4:

TABLE 4

| Time (min) | % A Solvent | % B Solvent |
| --- | --- | --- |
| 0 | 80 | 20 |
| 40 | 16 | 84 |
| 42 | 0 | 100 |
| 50 | 0 | 100 |

Analytical Example 2: Nuclear Magnetic Resonance (NMR)

Compounds (10 mg) were dissolved in 666 uL of either CDCl$_3$ or DMSO-d6 and loaded in an 8-inch length, 5 mm diameter NMR tube. The instrument was a Varian Mercury 400 NMR spectrometer. Proton NMR spectra were obtained with 16 scans using the default method. FIDs were processed with MestRe-C software.

Analytical Example 3: Mass Spectrometry (MS)

Compounds were dissolved in acetonitrile at 1 mg/ml and used directly for analysis on an Agilent 6538 QTOF, using ESI MS+ as ion source.

Analytical Example 4: Melting Point

Compound powder was prepared neat in a glass capillary tube, and melting temperature was measured manually with standard glass capillary tube melting point apparatus.

Analytical Example 5: Differential Scanning Calorimetry (DSC)

5-10 mg of compounds were weighed in an aluminum pan. Using a Hitachi Differential Scanning calorimeter DSC7020, samples were heated from room temperature to 110-150° C. at 10° C./min, cooled to −30° C. at 10° C./min, and heated again to 110-150° C. at 10° C./min.

Example 2: Chemical Synthesis

Solvents, reagents and starting materials were purchased from commercial vendors and used as received unless otherwise described. All reactions were performed at room temperature unless otherwise stated. Starting materials were purchased from commercial sources or synthesized according to the methods described herein or using literature procedures.

Chemical Synthesis Example 1

(Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoic acid (Travoprost Acid)

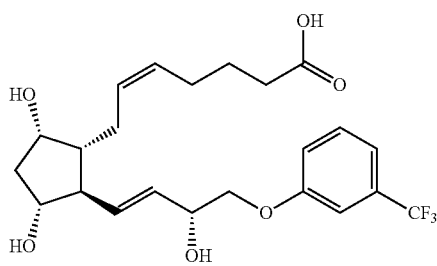 [SMILES: O=C(O)CCC/C=C\C[C@@H]1[C@@H](/C=C/[C@@H](O)COc2cccc(C(F)(F)F)c2)[C@H](O)C[C@@H]1O]

To a stirred solution of travoprost (1 g, 2.00 mmol) in MeOH (16 mL) was added 1M NaOH$_{(aq)}$ (16 mL, 16 mmol) and the mixture stirred for 16 h. The mixture was quenched into 0.5M HCl$_{(aq)}$ (32 mL, 16 mmol) and the aqueous extracted with DCM (2×100 mL). The DCM layers were combined dried (MgSO$_4$) and concentrated to give travoprost acid (916 mg, 100%) as a colorless oil. $^1$H NMR (400 MHz, CDCl$_3$) δ 7.39 (1H, t, J=8 Hz), 7.22 (1H, d, J=8 Hz), 7.15 (1H, s), 7.08 (1H, d, J=8 Hz), 5.70 (2H, m), 5.40 (2H, m), 4.98 (1H, heptet, J=6.5 Hz), 4.52 (1H, m), 3.97 (3H, m), 3.25 (2H, br s), 2.60 (1H, br s), 2.38 (1H, m), 2.30-1.96 (7H, m), 1.76 (1H, dd, J=16, 4 Hz), 1.65 (2H, quintet, J=7), 1.55 (1H, m).

Chemical Synthesis Example 2

(8S,10S,13S,14S,17R)-17-hydroxy-17-(2-hydroxyacetyl)-10,13-dimethyl-1,2,6,7,8,10,12,13,14,15,16,17-dodecahydro-3H-cyclopenta[a]phenanthren-3-one (Anecortave Desacetate)

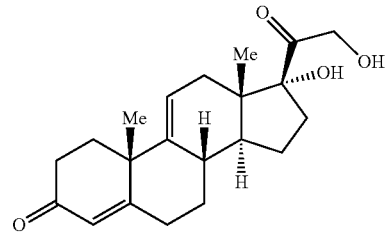

To a stirred suspension of anecortave acetate (3.0 g, 7.76 mmol) in methanol (80 mL) was added potassium hydroxide solution (77.5 mL of a 0.2M solution, 15.52 mmol) and the mixture stirred overnight. The reaction mixture was quenched into ice water (400 mL), stirred and filtered to collect the precipitate which was dissolved in DCM (300 mL), washed with water (300 mL) and dried over sodium sulfate to give anecortave desacetate (1.0 g, 37%). $^1$H NMR (400 MHz, DMSO-d6) δ 5.66 (s, 1H); 5.52 (d, 1H, J=5 Hz), 5.28 (s, 1H, OH), 4.60 (t, J=5 Hz, 1H, OH), 4.31 (AB, 2H, J=19 Hz, Δv=82.5 Hz, further split (J=5 Hz) by OH), 2.60 (m, 3H), 2.50 (m, 1H), 2.25 (m, 3H), 2.05 (m, 3H), 1.80 (m, 2H), 1.55 (m, 2H), 1.22 (m, 1H), 1.20 (s, 3H), 1.02 (q, 1H, J=12 Hz), 0.49 (s, 3H).

Chemical Synthesis Example 3

2-((8S,10S,13S,14S,17R)-17-hydroxy-10,13-dimethyl-3-oxo-2,3,6,7,8,10,12,13,14,15,16,17-dodecahydro-1H-cyclopenta[a]phenanthren-17-yl)-2-oxoethyl (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate (Compound 1)

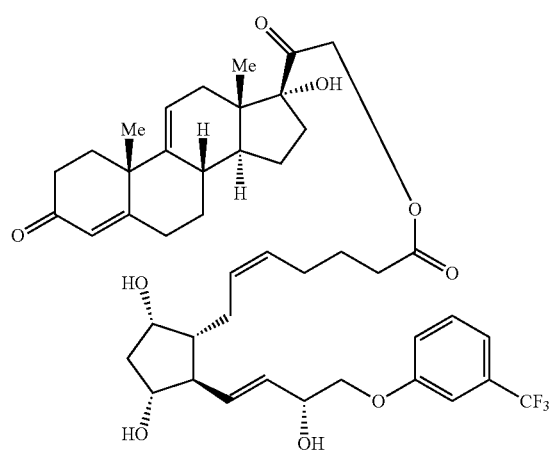

To a stirred solution of travoprost acid (180 mg, 0.393 mmol) in dry pyridine (20 mL) under nitrogen was added anecortave desacetate (406 mg, 1.18 mmol), 4-(dimethylamino)pyridine (96 mg, 0.786 mmol) and N-(3-Dimethylaminopropyl)-N'-ethylcarbodiimide hydrochloride (150 mg, 0.786 mmol) and the mixture was stirred overnight. The mixture was concentrated and the residue dissolved in DCM (100 mL), the solution washed with 0.5 M hydrochloric acid (100 mL), water (100 mL), dried (MgSO$_4$) and concentrated onto 5 g reverse phase silica. Purification was performed by reverse phase Biotage automated chromatography (aqueous-MeCN gradient). Product containing fractions were combined, extracted with DCM, dried (MgSO$_4$) and concentrated to give the product as an off-white solid (102 mg, 33%). Melting point: 78-80° C. HPLC retention time: 31.7 min, ESI MS+ Found, $C_{44}H_{55}F_3NaO_9^+$ Exact Mass: 807.3684. $^1$H NMR (400 MHz, DMSO-d6) δ 7.45 (1H, t, J=8 Hz), 7.20 (3H, m), 5.62 (1H, s), 5.55-5.40 (6H, m), 5.20 (1H, s, OH), 5.11 (1H, br s), 4.95 (1H, d, J=12 Hz), 4.80 (1H, d, J=12 Hz), 4.48 (1H, br s), 4.31 (2H, m), 3.85 (3H, m), 3.64 (1H, m), 2.60 (2H, m), 2.38 (1H, m), 2.25 (3H, m), 2.20 (3H, m), 2.05 (3H, m), 1.95 (3H, m), 1.80 (6H, m), 1.55 (3H, m), 1.41 (1H, m), 1.22 (1H, m), 1.20 (3H, s), 1.02 (1H, q, J=12 Hz), 0.49 (3H, s).

Chemical Synthesis Example 4

2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate (Compound 2)

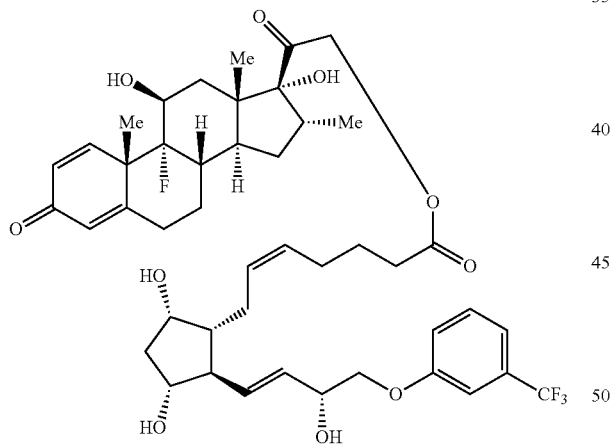

To a stirred solution of travoprost acid (180 mg, 0.393 mmol) and dexamethasone (1.54 g, 3.93 mmol) in dry THF (50 mL) under nitrogen was added 4-(dimethylamino)pyridine (96 mg, 0.786 mmol) and N-(3-Dimethylaminopropyl)-N'-ethylcarbodiimide hydrochloride (150 mg, 0.786 mmol) and the mixture was stirred overnight. The mixture was concentrated onto 10 g reverse phase silica. Purification was performed by reverse phase Biotage automated chromatography (aqueous-MeCN gradient), product containing fractions were combined, extracted with DCM, dried (MgSO$_4$) and concentrated to give a solid which was further purified by normal phase Biotage automated chromatography (hexane-ethyl acetate gradient). Product containing fractions were combined and concentrated to give the product as an off-white solid (120 mg, 37%). Melting point: 80° C. HPLC retention time: 30.5 min, ESI MS+ Found, $C_{45}H_{56}F_4NaO_{10}^+$ Exact Mass: 855.3707. $^1$H NMR (400 MHz, DMSO-d6) δ 7.45 (1H, t, J=8 Hz), 7.20 (4H, m), 6.20 (1H, d), 5.99 (1H, s), 5.60-5.35 (4H, m), 5.20 (1H, m), 5.11 (1H, d), 4.95 (1H, d, J=12 Hz), 4.76 (1H, d, J=12 Hz), 4.50 (1H, d), 4.31 (2H, m), 4.05 (1H, m), 3.89 (3H, m), 3.64 (1H, m), 3.59 (1H, m), 2.83 (1H, m), 2.60 (1H, m), 2.38 (1H, m), 2.25 (3H, m), 2.20 (3H, m), 2.05 (3H, m), 1.95 (3H, m), 1.78 (2H, m), 1.60-1.40 (4H, m), 1.30 (1H, m), 1.21 (3H, s), 1.02 (1H, q, J=12 Hz), 0.82 (3H, s), 0.78 (3H, d).

Chemical Synthesis Example 5

(Z)-7-((1R,2R,3R,5S)-3,5-dihydroxy-2-((R)-3-hydroxy-5-phenylpentyl)cyclopentyl)hept-5-enoic acid (Latanoprost Acid)

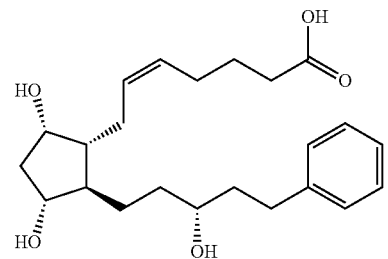 [SMILES: O=C(O)CCC/C=C\C[C@@H]1[C@@H](CC[C@@H](O)CCc2ccccc2)[C@H](O)C[C@@H]1O]

To a stirred solution of latanoprost (1 g, 2.31 mmol) in MeOH (16 mL) was added 1M NaOH$_{(aq)}$ (18.5 mL, 18.5 mmol) and the mixture stirred for 16 h. The mixture was quenched into 0.5M HCl$_{(aq)}$ (37 mL, 18.5 mmol) and the aqueous extracted with DCM (2×100 mL). The DCM layers were combined dried (MgSO$_4$) and concentrated to give latanoprost acid (902 mg, 100%) as a colorless oil. $^1$H NMR (400 MHz, DMSO-d6) δ 11.98 (1H, br s), 7.23 (2H, m), 7.12 (3H, m), 5.42 (1H, m), 5.23 (1H, m), 4.39 (2H, m), 4.20 (1H, m), 3.82 (1H, m), 3.60 (1H, m), 3.36 (1H, m), 2.60 (1H, m), 2.52 (1H, m), 2.15 (3H, m), 1.98 (4H, m), 1.60-1.25 (10H, m), 1.20 (1H, m).

Chemical Synthesis Example 6

2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl (Z)-7-((1R,2R,3R,5S)-3,5-dihydroxy-2-((R)-3-hydroxy-5-phenylpentyl)cyclopentyl)hept-5-enoate (Compound 3)

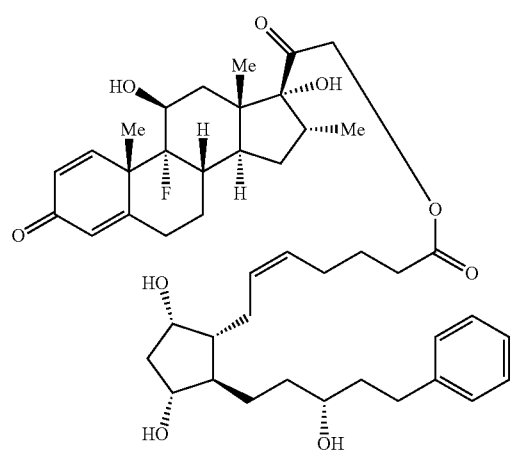

To a stirred solution of latanoprost acid (153 mg, 0.393 mmol) and dexamethasone (1.54 g, 3.93 mmol) in dry THF (50 mL) under nitrogen was added 4-(dimethylamino)pyridine (96 mg, 0.786 mmol) and N-(3-Dimethylaminopropyl)-N'-ethylcarbodiimide hydrochloride (150 mg, 0.786 mmol) and the mixture was stirred overnight. The mixture was concentrated onto 10 g reverse phase silica. Purification was performed by reverse phase Biotage automated chromatography (aqueous-MeCN gradient), product containing fractions were combined, extracted with DCM, dried (MgSO$_4$) and concentrated to give a solid which was further purified by normal phase Biotage automated chromatography (hexane-ethyl acetate gradient). Product containing fractions were combined and concentrated to give the product as an off-white solid (102 mg, 34%). Melting point: 78° C. HPLC retention time: 30.8 min, ESI MS+ Found, $C_{45}H_{62}FO_9+$ Exact Mass: 765.4378 $^1$H NMR (400 MHz, DMSO-d6) δ 7.35-7.05 (6H, m), 6.20 (1H, d), 5.99 (1H, s), 5.50-5.25 (3H, m), 5.10 (1H, s), 5.00 (1H, d), 4.80 (1H, d), 4.40 (2H, d), 4.21 (2H, m), 3.85 (1H, m), 3.61 (1H, m), 2.83 (2H, m), 2.60 (4H, m), 2.38 (4H, m), 2.11 (6H, m), 1.75 (1H, m), 1.60-1.20 (18H, m), 1.02 (1H, q, J=12 Hz), 0.82 (3H, s), 0.78 (3H, d).

Chemical Synthesis Example 7

(8R,9S,13S,14S)-13-methyl-17-oxo-7,8,9,11,12,13,14,15,16,17-decahydro-6H-cyclopenta[a]phenanthren-3-yl (Z)-7-((1R,2R,3R,5S)-3,5-dihydroxy-2-((R)-3-hydroxy-5-phenylpentyl)cyclopentyl)hept-5-enoate (Compound 4)

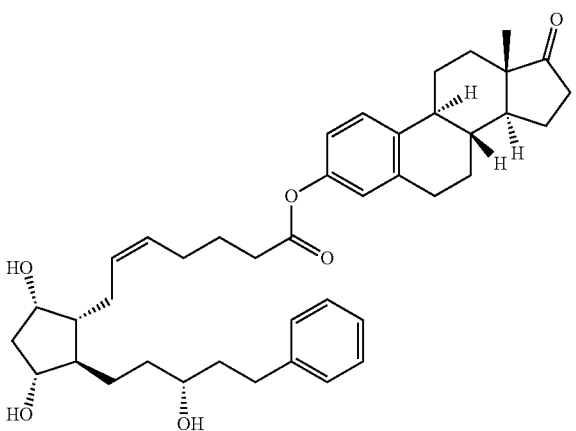

To a stirred solution of latanoprost acid (153 mg, 0.393 mmol) and estrone (318 mg, 1.179 mmol) in dry THF (50 mL) under nitrogen was added 4-(dimethylamino)pyridine (96 mg, 0.786 mmol) and N-(3-Dimethylaminopropyl)-N'-ethylcarbodiimide hydrochloride (150 mg, 0.786 mmol) and the mixture was stirred overnight. The mixture was concentrated onto 10 g reverse phase silica. Purification was performed by reverse phase Biotage automated chromatography (aqueous-MeCN gradient), product containing fractions were combined, extracted with DCM, dried (MgSO4) and concentrated to give a solid which was further purified by normal phase Biotage automated chromatography (hexane-ethyl acetate gradient). Product containing fractions were combined and concentrated to give the product as an off-white solid (28 mg, 11%). Melting point: 65° C. HPLC retention time: 35.9 min, ESI MS+ Found, C41H54NaO6+ Exact Mass: 665.3818 $^1$H NMR (400 MHz, DMSO-d6) δ 7.23 (2H, m), 7.12 (3H, m), 7.04 (1H, d), 6.51 (1H, m), 6.45 (1H, m), 5.42 (1H, m), 5.23 (1H, m), 4.39 (2H, m), 4.20 (1H, m), 3.82 (1H, m), 3.60 (1H, m), 3.36 (1H, m), 2.75 (2H, m), 2.60 (1H, m), 2.52 (1H, m), 2.42 (1H, m), 2.30 (1H, m), 2.15 (4H, m), 2.05 (1H, m), 1.98 (4H, m), 1.92 (2H, m), 1.74 (1H, m), 1.60-1.25 (16H, m), 1.20 (1H, m), 0.81 (3H, s).

Chemical Synthesis Example 8

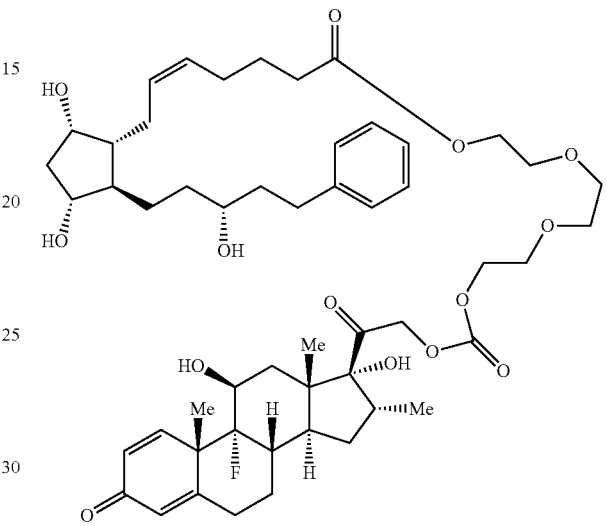

Dexamethasone (314 mg, 0.80 mmol, 1.0 equiv) was dissolved in THF (20 mL) under nitrogen and phosgene solution (2.86 mL of a 1.4 M solution in toluene, 4.0 mmol, 5 equiv) was added dropwise with stirring. The mixture was stirred at room temperature overnight. Concentration of the mixture afforded the dexamethasone chloroformate as a thick oil which was dissolved in DCM (50 mL). Triethylene glycol (1.07 mL, 1.20 g, 8 mmol, 10 equiv) and pyridine (130 µL, 126 mg, 1.60 mmol, 2.0 equiv) were added and the mixture stirred for 2 h. The reaction solution was washed with water (2×50 mL) and the DCM layer concentrated onto normal phase silica (2 g) and purified by automated normal phase chromatography (ethyl acetate-hexane). The product containing fractions were combined and concentrated in vacuo to give the dexamethasone-triethyleneglycol ester intermediate as an off-white glassy solid (296 mg, 0.52 mmol, 65%). This was dissolved in DCM (50 mL) and latanoprost acid (202 mg, 0.52 mmol), 4-(dimethylamino)pyridine (127 mg, 1.04 mmol) and N-(3-Dimethylaminopropyl)-N'-ethylcarbodiimide hydrochloride (198 mg, 1.04 mmol) were added and the mixture was stirred overnight. The reaction solution was washed with water (2×50 mL) and the DCM layer concentrated onto reverse phase silica (2 g) and purified by automated reverse phase chromatography (acetonitrile-water). The product containing fractions were concentrated in vacuo to give the dexamethasone-triethyleneglycol-latanoprost as a colourless oil (49 mg, 0.052 mmol, 10%). HPLC retention time: 33.9 min, ESI MS+ Found, C52H74FO14+ Exact Mass: 941.5063 $^1$H NMR (400 MHz, DMSO-d6) δ 7.35-7.05 (6H, m), 6.20 (1H, d), 5.99 (1H, s), 5.50-5.25 (3H, m), 5.10 (1H, s), 5.00 (1H, d), 4.80 (1H, d), 4.40 (2H, d), 4.21 (6H, m), 3.85 (1H, m), 3.65 (4H, m), 3.61 (1H, m), 3.57 (4H, s), 2.83 (2H, m), 2.60 (4H, m), 2.38 (4H, m), 2.11 (6H, m), 1.75 (1H, m), 1.60-1.20 (18H, m), 1.02 (1H, q, J=12 Hz), 0.82 (3H, s), 0.78 (3H, d).

Chemical Synthesis Example 9

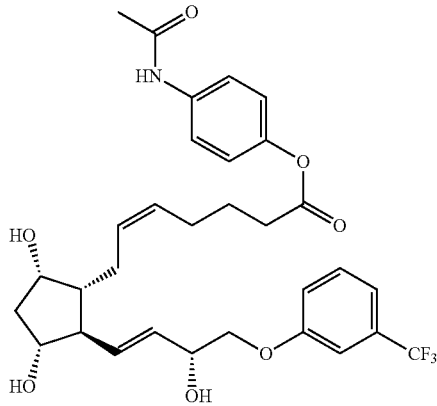 [SMILES: CC(=O)Nc1ccc(OC(=O)CCC/C=C\C[C@@H]2[C@@H](/C=C/[C@@H](O)COc3cccc(C(F)(F)F)c3)[C@H](O)C[C@@H]2O)cc1]

To a stirred solution of travoprost acid (180 mg, 0.393 mmol) and acetaminophen (297 mg, 1.97 mmol) in dry THF (50 mL) under nitrogen was added 4-(dimethylamino)pyridine (96 mg, 0.786 mmol) and N-(3-Dimethylaminopropyl)-N'-ethylcarbodiimide hydrochloride (150 mg, 0.786 mmol) and the mixture was stirred overnight. The mixture was concentrated onto 5 g reverse phase silica. Purification was performed by reverse phase Biotage automated chromatography (aqueous-MeCN gradient), product containing fractions were combined, extracted with DCM, dried (MgSO$_4$) and concentrated to give travoprost-acetaminophen ester (139 mg, 60%) as a colourless oil. HPLC retention time: 22.6 min, ESI MS+ Found, $C_{31}H_{37}F_3NO_7^+$ Exact Mass: 592.2522. $^1$H NMR (400 MHz, DMSO-d6) δ 9.97 (1H, s, NH), 7.57 (2H, d, J=8 Hz), 7.45 (1H, t, 0.1=8 Hz), 7.22 (2H, m), 7.15 (1H, s), 6.98 (2H, d), 5.70 (2H, m), 5.40 (2H, m), 4.98 (1H, heptet, J=6.5 Hz), 4.52 (1H, m), 3.97 (3H, m), 3.25 (2H, br s), 2.60 (1H, br s), 2.38 (1H, m), 2.30-1.96 (10H, m), 1.76 (1H, dd, J=16, 4 Hz), 1.65 (2H, quintet, J=7), 1.55 (1H, m).

Chemical Synthesis Example 10

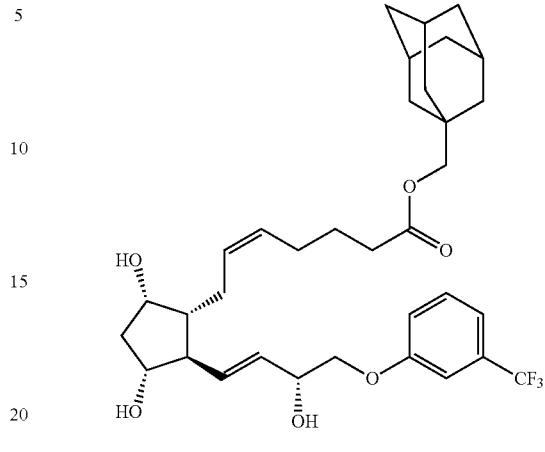

To a stirred solution of travoprost acid (180 mg, 0.393 mmol) and 1-Adamantanemethanol (327 mg, 1.97 mmol) in dry THF (50 mL) under nitrogen was added 4-(dimethylamino)pyridine (96 mg, 0.786 mmol) and N-(3-Dimethylaminopropyl)-N'-ethylcarbodiimide hydrochloride (150 mg, 0.786 mmol) and the mixture was stirred overnight. The mixture was concentrated onto 5 g reverse phase silica. Purification was performed by reverse phase Biotage automated chromatography (aqueous-MeCN gradient), product containing fractions were combined, extracted with DCM, dried (MgSO$_4$) and concentrated to give travoprost-acetaminophen ester (71 mg, 30%) as a colourless oil. HPLC retention time: 40.3 min, ESI MS+ Found, $C_{34}H_{46}F_3O_6^+$ Exact Mass: 607.3246. $^1$H NMR (400 MHz, DMSO-d6) δ 7.60 (1H, t, J=8 Hz), 7.22 (2H, m), 7.15 (1H, s), 5.60-5.40 (3H, m), 5.20 (1H, m), 5.10 (1H, d J=8.0 Hz), 4.52 (1H, m), 4.30 (2H, m), 3.88 (3H, m), 3.63 (1H, m), 3.56 (2H, s), 2.93 (1H, m), 2.20-1.80 (10H, m), 1.70-1.40 (15H, m), 1.25 (1H, m).

Chemical Synthesis Example 11

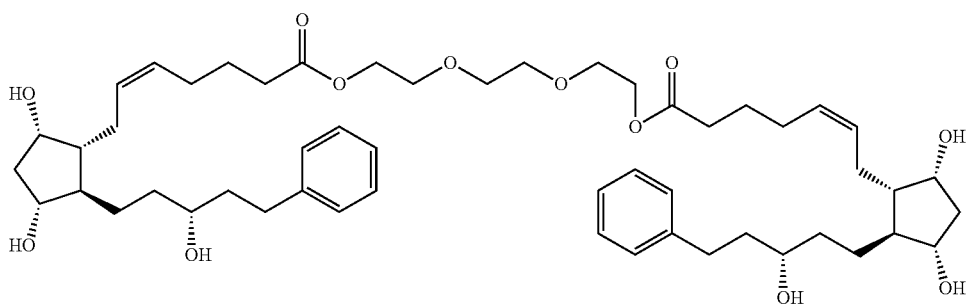 [SMILES: O=C(CCC/C=C\C[C@@H]1[C@@H](CC[C@@H](O)CCc2ccccc2)[C@H](O)C[C@@H]1O)OCCOCCOCCOC(=O)CCC/C=C\C[C@H]1[C@H](CC[C@H](O)CCc2ccccc2)[C@@H](O)C[C@H]1O]

To a solution of latanoprost acid (202 mg, 0.52 mmol) and triethylene glycol (42 uL, 39 mg, 0.26 mmol) in DCM (50 mL) was added 4-(dimethylamino)pyridine (127 mg, 1.04 mmol) and N-(3-Dimethylaminopropyl)-N'-ethylcarbodiimide hydrochloride (198 mg, 1.04 mmol) were added and the mixture was stirred overnight. The reaction solution was washed with water (2×50 mL) and the DCM layer concentrated onto reverse phase silica (2 g) and purified by automated reverse phase chromatography (acetonitrile-water). The product containing fractions were concentrated in vacuo to give the latanoprost-triethyleneglycol-latanoprost as a colourless oil (37 mg, 0.042 mmol, 8%). HPLC retention time: 30.2 min, ESI MS+ Found, C52H79O12+ Exact Mass: 895.5972 $^1$H NMR (400 MHz, DMSO-d6) δ 7.23 (4H, m), 7.12 (6H, m), 5.42 (2H, m), 5.23 (2H, m), 4.39 (4H, m), 4.25-4.20 (6H, m), 3.82 (2H, m), 3.65 (4H, m), 3.60-3.55 (6H, m), 3.36 (2H, m), 2.60 (2H, m), 2.52 (2H, m), 2.15 (6H, m), 1.98 (8H, m), 1.60-1.25 (20H, m), 1.20 (2H, m).

Chemical Synthesis Example 12

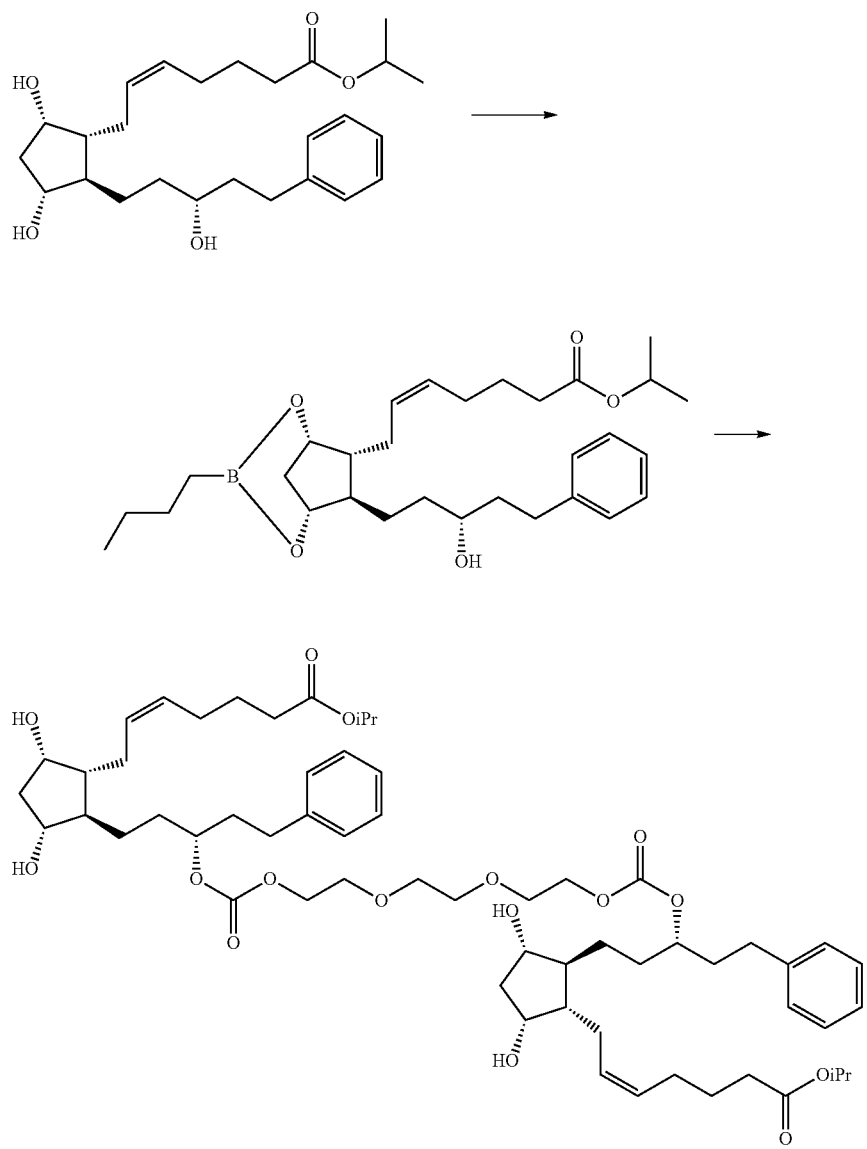

To a stirred solution of latanoprost (222.0 mg, 0.51 mmol) in dry DCM (20 mL) was added n-butylboronic acid (60.1 mg, 0.59 mmol) and the mixture stirred at reflux for 1 h under nitrogen atmosphere. The mixture was concentrated and the residue redissolved in dry DCM, the mixture heated to reflux for 3 h, concentrated to give the 9,11-boronate of latanoprost (254 mg, 100%) as a clear colourless oil which was and used directly without further purification. 1H NMR (400 MHz, CDCl3) δ (ppm): 7.28-7.17 (m, 2H), 7.17-7.03 (m, 3H), 5.49-5.27 (m, 2H), 4.93 (ddd, J=15.2, 7.6, 4.9 Hz, 1H), 4.28-4.13 (m, 1H), 4.07-3.90 (m, 1H), 3.65-3.46 (m, 1H), 2.78-2.67 (m, 1H), 2.67-2.41 (m, 1H), 2.28-2.11 (m, 4H), 2.09-1.98 (m, 2H), 1.91-1.79 (m, 1H), 1.79-1.53 (m, 7H), 1.53-1.38 (m, 3H), 1.38-1.07 (m, 12H), 0.89-0.75 (m, 3H), 0.64-0.52 (m, 2H). To a solution of 9,11-boronate of latanoprost (254 mg, 0.51 mmol) in dry DCM (25 mL) was added pyridine (164 uL, 162 mg, 2.04 mmol) and triethylene glycol bis(chloroformate) (52 uL, 70 mg, 0.255 mmol, 0.5 equiv) and the mixture stirred for 4 h, methanol (5 mL) was added and the mixture stirred overnight. The mixture was concentrated onto 1 g reverse phase silica. Purification was performed by reverse phase Biotage automated chromatography (aqueous-MeCN gradient), product containing fractions were combined, extracted with DCM, dried (MgSO₄) and concentrated to give latanoprost-TEG-latanoprost carbonate dimer (68 mg, 25%) as a colourless oil. HPLC retention time: 48.2 min, ESI MS+ Found, C60H91O16+ Exact Mass: 1067.6307 ¹H NMR (400 MHz, DMSO-d6) δ 7.23 (4H, m), 7.12 (6H, m), 5.42 (2H, m), 5.23 (2H, m), 4.39 (4H, m), 4.25-4.20 (6H, m), 3.82 (2H, m), 3.65 (4H, m), 3.60-3.55 (6H, m), 3.36 (2H, m), 2.60 (2H, m), 2.52 (2H, m), 2.15 (6H, m), 1.98 (8H, m), 1.60-1.25 (20H, m), 1.20 (2H, m), 1.00 (12H, d).

Chemical Synthesis Example 13

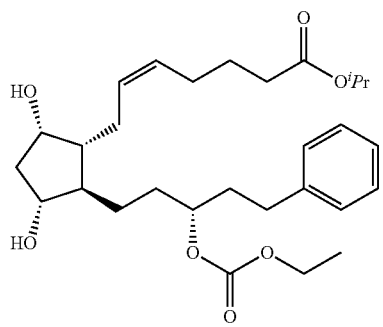 [SMILES: CCOC(=O)O[C@@H](CCc1ccccc1)CC[C@@H]1[C@@H](C/C=C\CCCC(=O)OC(C)C)[C@@H](O)C[C@H]1O]

To a solution of 9,11-boronate of latanoprost (254 mg, 0.51 mmol) in dry DCM (25 mL) was added pyridine (82 uL, 81 mg, 1.02 mmol) and ethylchloroformate (48 uL, 55 mg, 0.51 mmol) and the mixture stirred for 4 h, methanol (5 mL) was added and the mixture stirred overnight. The mixture was concentrated onto 1 g reverse phase silica. Purification was performed by reverse phase Biotage automated chromatography (aqueous-MeCN gradient), product containing fractions were combined, extracted with DCM, dried (MgSO₄) and concentrated to give latanoprost-15-ethyl carbonate (154 mg, 60%) as a colourless oil. HPLC retention time: 34.8 min, ESI MS+ Found, C29H45O7+ Exact Mass: 505.3165 ¹H NMR (400 MHz, DMSO-d6) δ 7.23 (2H, m), 7.12 (3H, m), 5.42 (1H, m), 5.23 (1H, m), 4.80 (1H, m), 4.60 (1H, m), 4.39 (2H, m), 4.20 (1H, m), 4.03 (2H, m), 3.82 (1H, m), 3.60 (1H, m), 2.60 (1H, m), 2.52 (1H, m), 2.15 (2H, m), 1.98 (4H, m), 1.80-1.25 (10H, m), 1.20 (4H, m), 1.16 (6H, d).

Chemical Synthesis Example 14:
(Bimatoprost-Anecortave Ester; Compound 5)

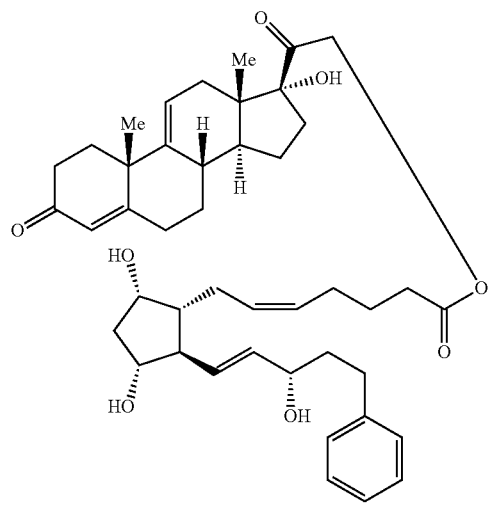

To a stirred solution of bimatoprost acid (1.0 g, 2.57 mmol) in dry pyridine (120 mL) under nitrogen was added anecortave desacetate (1.77 g, 5.14 mmol), 4-(dimethylamino)pyridine (0.62 g, 5.14 mmol) and N-(3-Dimethylaminopropyl)-N'-ethylcarbodiimide hydrochloride (0.99 g, 5.14 mmol) and the mixture was stirred for 4 d at 37° C. The mixture was concentrated and the residue dissolved in DCM (150 mL), the solution washed with 0.5 M hydrochloric acid (150 mL), water (100 mL), dried (MgSO₄) and concentrated onto 5 g reverse phase silica. Purification was performed by reverse phase Biotage automated chromatography (aqueous-MeCN gradient) followed by normal phase Biotage automated chromatography (hexanes-ethyl acetate). Product containing fractions were combined, concentrated, redissolved in MeCN (50 mL) and concentrated to give the product as an off-white solid (445 mg, 24%). Melting point: 110-115° C. HPLC retention time: 29.7 min, ESI MS+ Calculated for C₄₄H₅₈NaO₈⁺; 737.4024, Found: 737.4020. ¹H NMR (400 MHz, DMSO-d6) δ 7.25 (t, J=7.5 Hz, 2H), 7.20-7.10 (m, 3H), 5.66 (d, J=1.5 Hz, 1H), 5.58-5.17 (m, 6H), 4.97 (d, J=17.6 Hz, 1H), 4.84 (d, J=17.6 Hz, 1H), 4.65 (d, J=4.6 Hz, 1H), 4.49 (d, J=5.8 Hz, 1H), 4.34 (d, J=5.0 Hz, 1H), 3.92 (td, J=6.4, 3.5 Hz, 2H), 3.67 (ddd, J=13.6, 6.9, 4.0 Hz, 1H), 2.72-2.42 (m, 4H), 2.37-1.92 (m, 16H), 1.88-1.75 (m, 3H), 1.75-1.62 (m, 2H), 1.62-1.49 (m, 3H), 1.44 (ddd, J=14.1, 5.7, 2.4 Hz, 1H), 1.40-1.21 (m, 5H), 1.07-0.93 (m, 1H), 0.48 (s, 3H).

Chemical Synthesis Example 15:
(Latanoprost-Anecortave Ester; Compound 6)

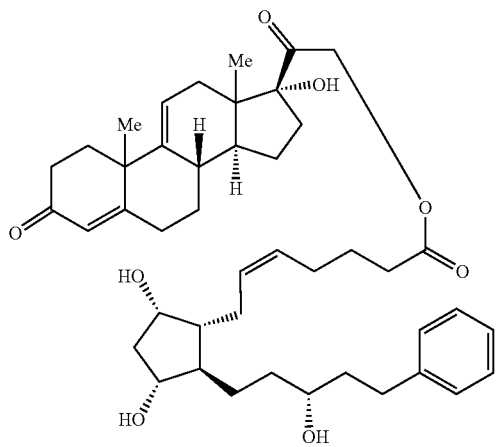

To a stirred solution of latanoprost acid (1.0 g, 2.56 mmol) in dry pyridine (60 mL) under nitrogen was added anecortave desacetate (1.76 g, 5.12 mmol), 4-(dimethylamino)pyridine (0.62 g, 5.12 mmol) and N-(3-Dimethylaminopropyl)-N'-ethylcarbodiimide hydrochloride (0.99 g, 5.14 mmol) and the mixture was stirred for 4 d at 37° C. The mixture was concentrated and the residue dissolved in DCM (150 mL), the solution washed with 0.5 M hydrochloric acid (150 mL), water (100 mL), dried (MgSO$_4$) and concentrated onto 4 g reverse phase silica. Purification was performed by reverse phase Biotage automated chromatography (aqueous-MeCN gradient) followed by normal phase Biotage automated chromatography (hexanes-ethyl acetate). Product containing fractions were combined, concentrated, redissolved in MeCN (50 mL) and concentrated to give the product as an off-white solid (415 mg, 23%). Melting point: 122-124° C. HPLC retention time: 31.4 min, ESI MS+ Calculated for C$_{44}$H$_{60}$NaO$_8^+$; 739.4180, Found: 737.4183. $^1$H NMR (400 MHz, DMSO-d6) δ 7.25 (t, J=7.5 Hz, 2H), 7.21-7.10 (m, 3H), 5.65 (d, J=1.6 Hz, 1H), 5.55-5.42 (m, 3H), 5.36-5.25 (m, 1H), 4.99 (d, J=17.6 Hz, 1H), 4.85 (d, J=17.6 Hz, 1H), 4.45-4.34 (m, 2H), 4.20 (d, J=5.4 Hz, 1H), 3.94-3.84 (m, 1H), 3.68-3.57 (m, 1H), 3.38 (d, J=9.8 Hz, 1H), 2.75-2.51 (m, 5H), 2.50-2.42 (m, 4H), 2.41-1.91 (m, 10H), 1.83 (dt, J=11.7, 7.5 Hz, 3H), 1.69-1.31 (m, 12H), 1.30 (s, 3H), 1.23 (tt, J=9.3, 5.5 Hz, 1H), 1.07-0.93 (m, 1H), 0.48 (s, 3H).

Chemical Synthesis Example 16:
(Tafluprost-Anecortave Ester; Compound 7)

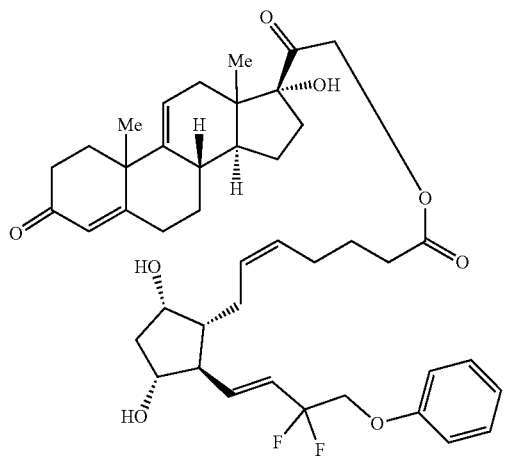

To a solution of tafluprost acid (800 mg, 1.95 mmol) and anecortave desacetate (1.34 g, 3.90 mmol) in dry pyridine (50 mL) was added DMAP (476 mg, 3.90 mmol) and EDCl (747 mg, 3.90 mmol) at 0° C., then stirred at 20° C. for 10 h. The reaction mixture was poured into DCM (50 mL), washed with 1M aqueous HCl (3×100 mL), the organic layer was dried over Na$_2$SO$_4$, filtered and concentrated to give a residue. The residue was purified by prep-HPLC (column: Phenomenex luna C18 (250*70 mm, 15 um); mobile phase: [water (0.225% FA)-ACN]; B %: 35%-80%, 23 min) to give the product (600 mg, 42%) as an off-white solid. Melting point: 107-110° C. HPLC retention time: 33.8 min, ESI MS+ Calculated for C$_{43}$H$_{54}$F$_2$NaO$_8^+$; 759.3684, Found: 759.3690. $^1$H NMR (400 MHz, DMSO-d6) δ 7.30 (t, J=7.8 Hz, 2H) 6.92-7.05 (m, 3H) 6.09 (br dd, J=15.7, 8.9 Hz, 1H) 5.77 (dt, J=15.7, 11.2 Hz, 1H) 5.65 (s, 1H) 5.49-5.55 (m, 2H) 5.39-5.48 (m, 1H) 5.22-5.31 (m, 1H) 4.93-5.02 (m, 1H) 4.79-4.89 (m, 1H) 4.73 (d, J=5.9 Hz, 1H) 4.47 (d, J=4.8 Hz, 1H) 4.33 (br t, J=12.9 Hz, 2H) 3.92 (br d, J=3.8 Hz, 1H) 3.75 (quin, J=6.9 Hz, 1H) 2.53-2.69 (m, 3H) 1.90-2.37 (m, 15H) 1.74-1.87 (m, 3H) 1.55 (quin, J=7.2 Hz, 3H) 1.39-1.49 (m, 2H) 1.25-1.37 (m, 4H) 0.92-1.07 (m, 1H) 0.48 (s, 3H)

Chemical Synthesis Example 18:
(Travoprost-Cyclohexanedimethanol-Anecortave; Compound 8)

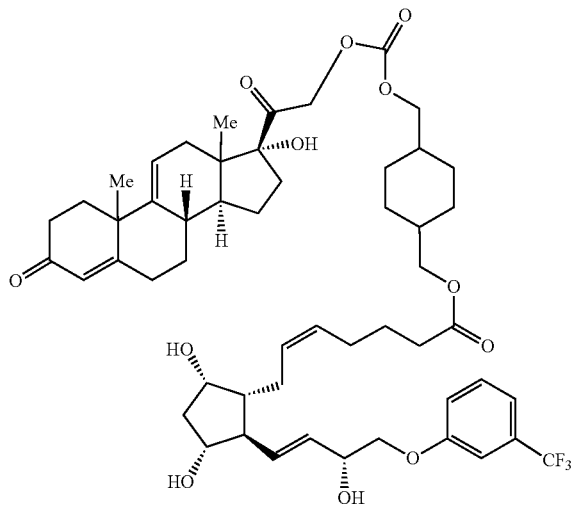

Anecortave desacetate (640 mg, 1.86 mmol) was dissolved in dry THF (40 mL) under nitrogen and phosgene solution (6.64 mL of a 1.4 M solution in toluene, 9.29 mmol) was added dropwise with stirring. The mixture was stirred at room temperature overnight. Concentration of the mixture afforded anecortave chloroformate as a pale yellow solid (740 mg, 98%) that was used without further purification or analysis.

To a stirred suspension of 1,4-cyclohexanedimethanol (2.48 g, 1.72 mmol) in dry $CH_2Cl_2$ (30 mL) was added anecortave chloroformate (700 mg, 1.72 mmol) and dry pyridine (1.08 mL, 13.4 mmol). The solution was stirred at room temperature for 16 h, concentrated and the yellow residue re-dissolved in $CH_2Cl_2$ (50 mL). The solution was washed with 0.5 M hydrochloric acid (2×50 mL), water (50 mL), dried ($MgSO_4$) and evaporated to give anecortave-CDM as a pale yellow solid (701 mg, 79%). HPLC retention time: 27.4 min. ESI MS+ calculated for $C_{30}H_{42}NaO_7^+$; 537.2823, Found: 537.2830. $^1$H NMR (400 MHz, DMSO-d6) δ 5.66 (1H, s), 5.54-5.51 (2H, m), 5.04 (1H, d, J=17.8, Hz), 4.83 (1H, d, J=17.8 Hz), 4.37-4.29 (1H, m), 4.02 (1H, d, J=7.2 Hz), 3.92 (1H, d, J=6.4 Hz), 3.30-3.25 (1H, m), 3.22-3.17 (1H, m), 2.68-2.43 (3H, m), 2.36-2.18 (3H, m), 2.12-1.94 (4H, m), 1.87-1.69 (5H, m), 1.61-1.48 (2H, m), 1.45-1.28 (5H, m), 1.30 (3H, s), 1.06-0.79 (3H, m), 0.52-0.46 (3H, m).

A stirred solution of travoprost acid (200 mg, 0.436 mmol) in dry MeCN (10 mL) under nitrogen was stirred at −15° C. (ice/salt bath). N-Methylmorpholine (96.8 μL, 0.872 mmol) and isobutyl chloroformate (57.8 μL, 0.436 mmol) were added and the solution stirred for 10 mins. The solution was then added dropwise to a suspension of anecortave-CDM (453 mg, 0.872 mmol) in dry MeCN (20 mL) under nitrogen at −15° C. (ice/salt bath). After 10 mins stirring, the mixture was warmed to room temperature and stirred for 3 hours. The mixture was concentrated onto reverse phase silica (3 g) and purified by automated reverse phase chromatography (aqueous-MeCN). The product containing fractions were concentrated in vacuo to give the product as a colorless solid (53 mg, 13%). For thermal property measurements, the solid was dissolved in DCM and concentrated in vacuo to give a colorless solid. Melting point: not observed (Tg=~43° C.). HPLC retention time: 37.8 min. ESI MS+ calculated for $C_{53}H_{69}F_3NaO_{12}^+$; 977.4633, Found: 977.4640. $^1$H NMR (400 MHz, DMSO-d6) δ 7.49 (1H, t, J=8.0 Hz), 7.26-7.19 (2H, m), 7.18 (1H, s), 5.65 (1H, s), 5.58-5.38 (5H, m), 5.26-5.18 (1H, m), 5.10 (1H, d, J=4.8 Hz), 5.02 (1H, dd, J=17.8, 1.79 Hz), 4.82 (1H, d, J=17.8 Hz), 4.52 (1H, d, J=5.8 Hz), 4.35-4.26 (2H, m), 4.01 (1H, d, J=7.2 Hz), 3.96-3.86 (5H, m), 3.78 (1H, d, J=6.5 Hz), 3.71-3.63 (1H, m), 2.66-2.42 (3H, m), 2.35-2.25 (2H, m), 2.25-2.10 (6H, m), 2.10-2.03 (2H, m), 2.00-1.92 (5H, m), 1.83-1.65 (5H, m), 1.60-1.26 (12H, m), 1.29 (3H, s), 1.05-0.81 (3H, m), 0.47 (3H, s).

Chemical Synthesis Example 19:
(Travoprost-Naltrexone; Compound 9)

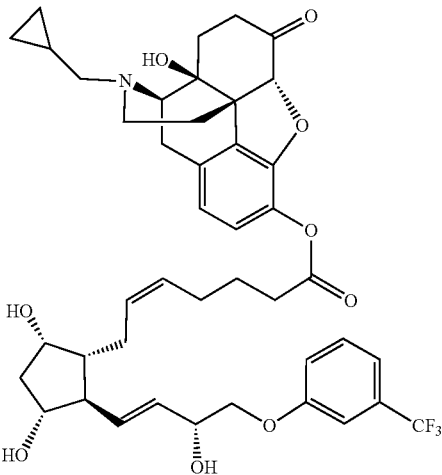 [SMILES: O=C(CCC/C=C\C[C@@H]1[C@@H](/C=C/[C@@H](O)COc2cccc(C(F)(F)F)c2)[C@H](O)C[C@@H]1O)Oc1ccc2c3c1O[C@H]1C(=O)CC[C@@]4(O)[C@@H](C2)N(CC2CC2)CC[C@]314]

To a stirred solution of travoprost acid (122 mg, 0.27 mmol) and naltrexone.HCl (100 mg, 0.27 mmol) in dry DCM (20 mL) under nitrogen was added 4-(dimethylamino) pyridine (132 mg, 1.08 mmol) and N-(3-Dimethylaminopropyl)-N'-ethylcarbodiimide hydrochloride (104 mg, 0.54 mmol) and the mixture was stirred overnight. The mixture was concentrated onto 2 g reverse phase silica. Purification was performed by reverse phase Biotage automated chromatography (aqueous-MeCN gradient), product containing fractions were combined and concentrated, the residue dissolved in MTBE (20 mL) and concentrated to give travoprost-naltrexone ester (84 mg, 40%) as a glassy white solid. Melting point: 56° C. HPLC retention time: 17.6 min, ESI MS+ Calculated for $C_{43}H_{51}F_3NO_9^+$; 782.3516, Found: 782.3512. $^1$H NMR (400 MHz, DMSO-d6) δ 7.50 (t, J=7.9 Hz, 1H), 7.32-7.15 (m, 3H), 6.80 (d, J=8.2 Hz, 1H), 6.70 (d, J=8.3 Hz, 1H), 5.64-5.39 (m, 3H), 5.34-5.23 (m, 1H), 5.11 (d, J=4.8 Hz, 2H), 4.90 (s, 1H), 4.53 (d, J=5.8 Hz, 1H), 4.36 (d, J=4.9 Hz, 1H), 4.31 (p, J=5.3 Hz, 1H), 3.93 (dq, J=8.9, 4.8 Hz, 2H), 3.69 (p, J=7.4 Hz, 1H), 3.16 (d, J=5.6 Hz, 1H), 3.09-3.06 (m, 1H), 2.97-2.84 (m, 2H), 2.70-2.53 (m, 2H), 2.43-2.30 (m, 4H), 2.26-1.89 (m, 8H), 1.77 (td, J=9.7, 5.8 Hz, 1H), 1.62 (p, J=7.3 Hz, 2H), 1.49-1.20 (m, 4H), 1.10 (s, 1H), 0.87 (dtd, J=14.1, 6.9, 4.0 Hz, 1H), 0.58-0.42 (m, 2H), 0.19-0.09 (m, 2H).

Chemical Synthesis Example 20:
(Timolol-Deoxycholic Acid; Compound 10)

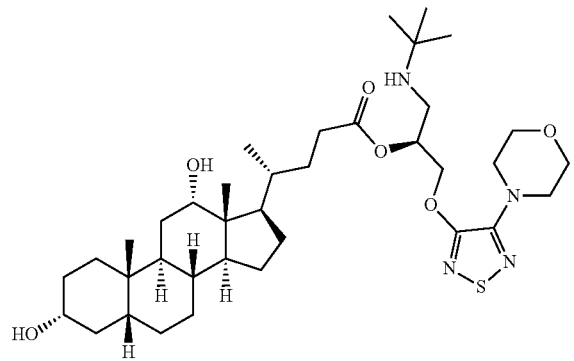

To a stirred solution of timolol free base (316 mg, 1.0 mmol) and deoxycholic acid (393 mg, 1.0 mmol) in dry DCM (20 mL) under nitrogen was added 4-(dimethylamino)pyridine (244 mg, 2.0 mmol) and N-(3-Dimethylaminopropyl)-N'-ethylcarbodiimide hydrochloride (384 mg, 2.0 mmol) and the mixture was stirred for 2 d. The mixture was concentrated onto 1 g reverse phase silica. Purification was performed by reverse phase Biotage automated chromatography (aqueous-MeCN gradient), product containing fractions were combined and concentrated, the residue dissolved in MTBE (20 mL) and concentrated to give timolol-deoxycholic ester (242 mg, 35%) as a glassy white solid. Melting point: 73'C. HPLC retention time: 36.2 min, ESI MS+ Calculated for $C_{37}H_{63}N_4O_6^+$; 691.4463, Found: 691.4464 $^1$H NMR (400 MHz, DMSO-d6) δ 5.11 (qd, J=6.3, 2.8 Hz, 1H), 4.61 (dd, J=11.4, 2.8 Hz, 1H), 4.51-4.41 (m, 2H), 4.19 (d, J=4.1 Hz, 1H), 3.77 (d, J=3.8 Hz, 1H), 3.68 (t, J=4.8 Hz, 4H), 3.48-3.34 (m, 5H), 2.70 (d, J=6.3 Hz, 2H), 2.33 (ddd, J=14.4, 9.0, 4.9 Hz, 1H), 2.16 (dq, J=15.5, 8.1 Hz, 1H), 1.86-1.41 (m, 11H), 1.38-1.11 (m, 11H), 1.11 (s, 1H), 1.08-0.93 (m, 11H), 0.90 (d, J=6.2 Hz, 3H), 0.84 (s, 3H), 0.55 (s, 3H).

Chemical Synthesis Example 21:
(Bimatoprost($C_{15}$)-Anecortave Carbonate; Compound 11)

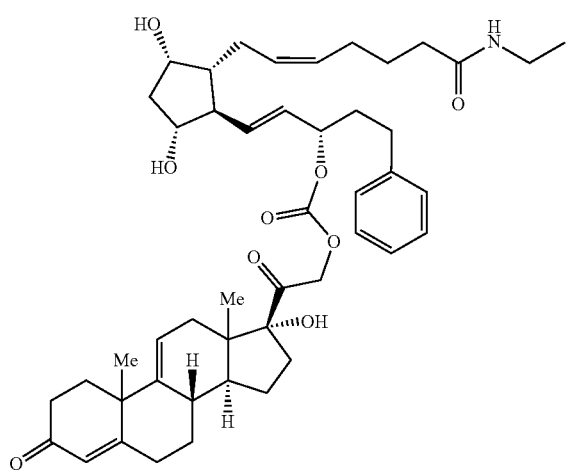

To a stirred solution of bimatoprost amide (100 mg, 0.241 mmol) in dry pyridine (3 mL) under nitrogen was added anecortave chloroformate (196 mg, 0.482 mmol). The yellow solution was stirred for 4 days, concentrated and re-dissolved in $CH_2Cl_2$ (5 mL). The mixture was concentrated onto reverse phase silica (2 g) and purified by automated reverse phase chromatography (aqueous-MeCN). The product containing fractions were concentrated to give a solid that was further purified by normal phase Biotage automated chromatography (hexane-ethyl acetate gradient). The product containing fractions were concentrated in vacuo to give the product as a colorless solid (23 mg, 12%). Melting point: not observed (Tg=~60° C.). HPLC retention time: 30.5 min. ESI MS+ calculated for $C_{47}H_{63}NNaO_9^+$; 808.4395, Found: 808.4397. $^1$H NMR (400 MHz, DMSO-d6) 7.68 (1H, t, J=5.7 Hz, NH), 7.30-7.22 (2H, m), 7.19-7.12 (3H, m), 5.65 (1H, s), 5.55-5.38 (5H, m), 5.33-5.26 (1H, m), 5.03 (1H, d, J=17.8 Hz), 4.82-4.76 (2H, m), 4.70-4.64 (2H, m), 3.98-3.89 (2H, m), 3.07-2.99 (2H, qd, J=7.2, 5.7 Hz), 2.67-2.43 (6H, m), 2.38-2.15 (5H, m), 2.15-1.89 (10H, m), 1.86-1.63 (3H, m), 1.59-1.21 (8H, m), 1.29 (3H, s), 0.98 (3H, t, J=7.2 Hz), 0.47 (3H, s).

Example 3: Formation and Evaluation of Processable Conjugates

Process Example 1: Heat Processing Pellets

A compound of the disclosure was formed into a pellet in the glassy state by heat molding. Crystalline powder of the conjugate compound was melted between 85° C. to 110° C. and pressed into a cylindrical mold of ~1 mm height×1 mm diameter.

Process Example 2: Solvent Processing for Compound 4

Compound 4 was formed into a thin film coating on a polymer surface by solvent casting. Compound 4 was dissolved in acetone at 50 mg/ml. 20 μl was cast onto a Dacron coupon and left to air dry at room temperature overnight followed by 2 h under vacuum at 50'C.

Process Example 3: Heat Processing Rods

A compound of the disclosure was formed into a rod in the glassy state by heat extrusion. The conjugate compound was initially melted at a temperature up to 140° C. The resulting material was then loaded into a heat extruder with a 30 G die head, heated between 70° C. to 125° C., and pressure was applied to a piston to form extrudate from the extruder. The extrudate was cut to different lengths.

Example 4: Drug Release Evaluation from Pellets or Extruded Rods

Drug release from heat-molded pellets or extruded rods of Compounds of the disclosure were assessed in either fetal bovine serum (FBS), phosphate buffered saline (PBS), or 1% FBS in PBS (v/v). Heat-molded pellets or extruded rods were placed in 20 ml glass vials, to which was added 2 ml of release buffer. Samples were incubated at 37° C. with constant agitation at 115 rpm. At intervals up to 14 days in length, release buffer was assessed for released drug and then fully replaced with 2 ml of fresh buffer. For FBS release conditions, acetonitrile was added to precipitate proteins and extract drug release products. Samples were analyzed by high performance liquid chromatography (HPLC) to quantify drug products.

Example 5. Sterilization of a Heat Processed Rod of Compound 5

Compound 5 was formed into rods by melt extrusion and cut to length. The resulting implants were loaded into the lumen of needles and terminally sterilized by ethylene oxide, gamma irradiation, and E-beam. Following sterilization, samples were dissolved in a suitable solvent and assessed for changes in purity due to sterilization by HPLC.

Figure 18:
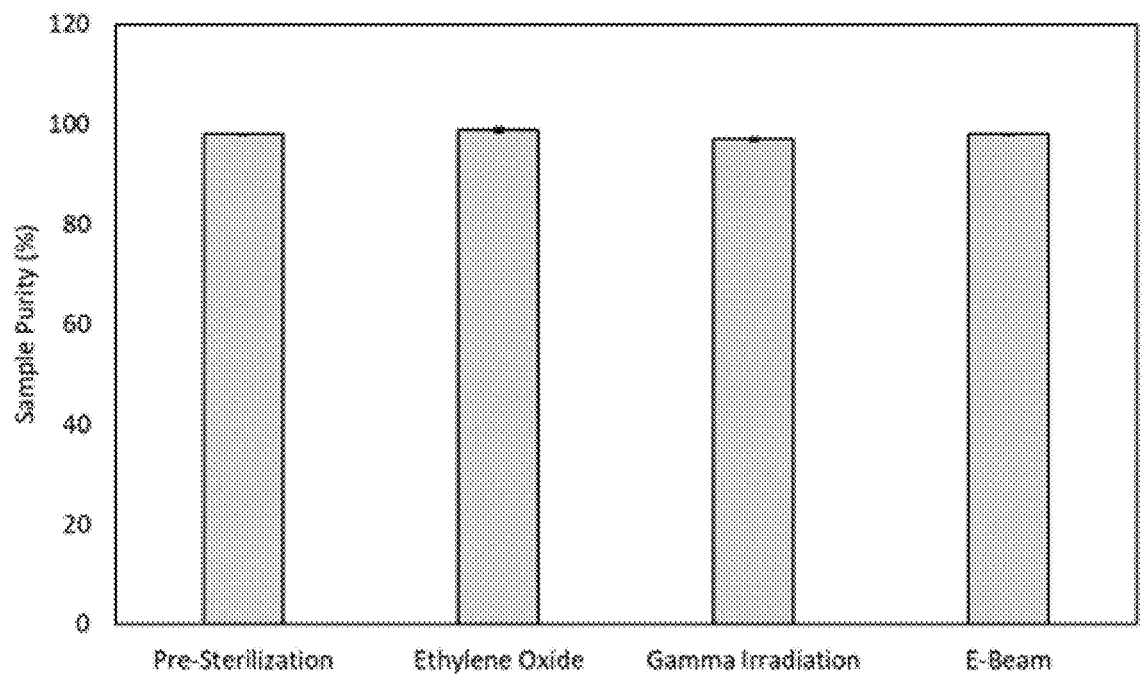
FIG. 18 shows purity of Compound 5 before (pre-sterilization) or post sterilization of Compound 5 in ethylene oxide, or by gamma-radiation or E-beam.
Figure 19A:
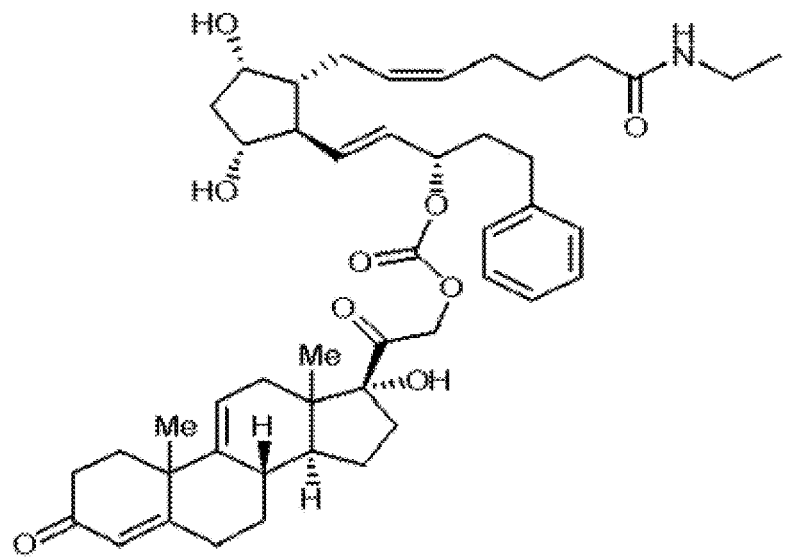
FIG. 19 shows the chemical structure (FIG. 19A) and the heat processed pellet (FIG. 19B) of a steroid-prostaglandin heterodimer (Bimatoprost ($C_{15}$)-anecortave, Compound 11) exemplified herein.
Figure 19B:
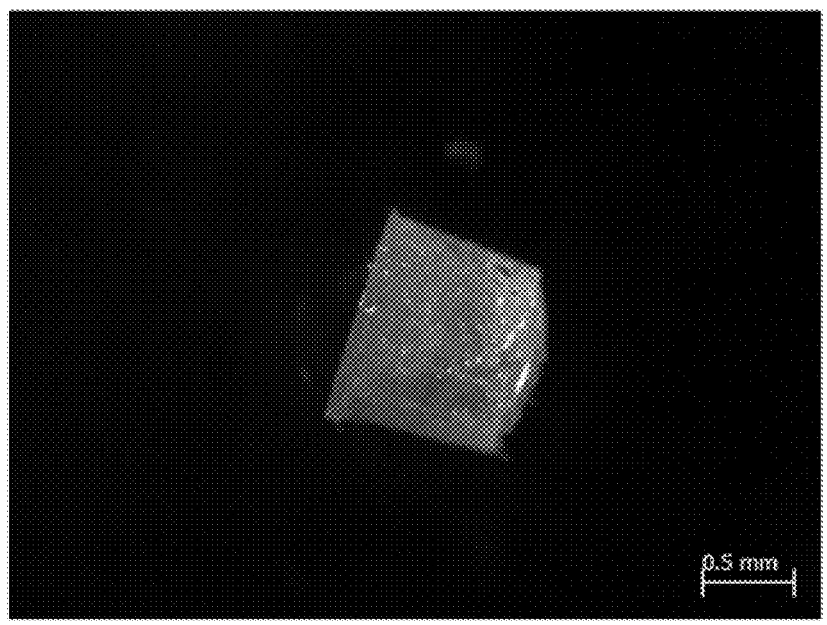

For example, FIG. 18 shows purity of compound 5 before (pre-sterilization) or post sterilization of Compound 5 in ethylene oxide, or by gamma-radiation or E-beam.

Example 6: In Vivo Evaluation

Biological Example 1: Implantation of Extruded Rod of Compound 5 in Rabbit Eye

Compound 5 was formed into rods by melt extrusion and were cut to 1, 1.5 or 2 mm length. The resulting implants were loaded in the lumen of needles, terminally sterilized, and injected into the anterior chamber of rabbits. Implants settled into the inferior iridocorneal angle and were visualized by anterior chamber optical coherence tomography.

Biological Example 2: Implantation of Extruded Rod of Compound 6 in Rabbit Eye

Compound 6 was formed into rods by melt extrusion and were cut to 1.5 mm length. The resulting implants were loaded in the lumen of needles, terminally sterilized, and injected into the anterior chamber of rabbits. Implants settled into the inferior iridocorneal angle and were visualized by anterior chamber optical coherence tomography.

Figure 14:
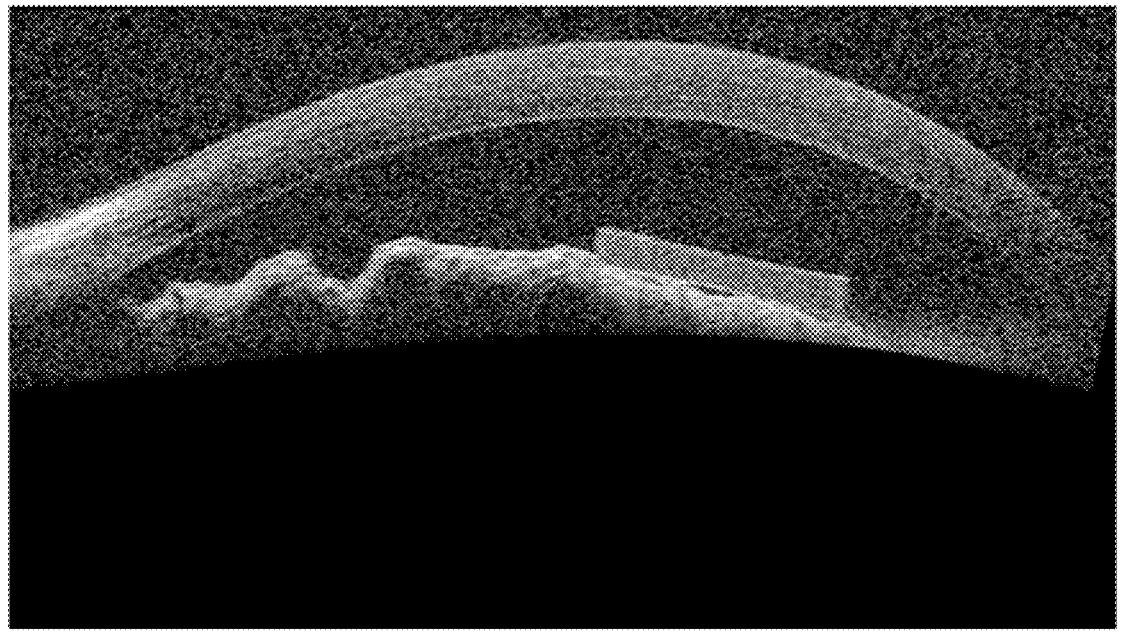
FIG. 14 shows an extruded rod of a steroid-prostaglandin heterodimer (bimatoprost-anecortave, Compound 5) exemplified herein in a rabbit eye.
Figure 15A:
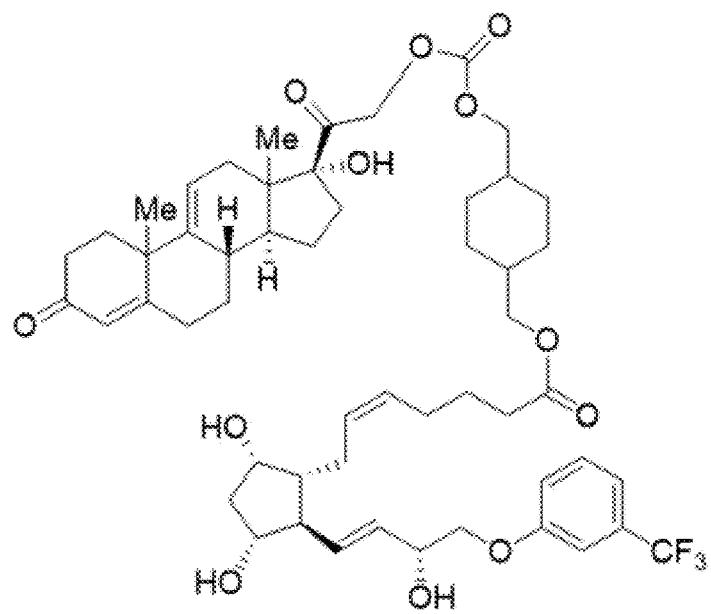
FIG. 15 shows the chemical structure (FIG. 15A) and the heat processed pellet (FIG. 15B) of a steroid-prostaglandin heterodimer (travoprost-cyclohexanedimethanol-anecortave, Compound 8) exemplified herein.
FIG. 15C shows the drug release profile for Compound 8 (pellet) in fetal bovine serum (FBS) over 8 days.
Figure 15B:
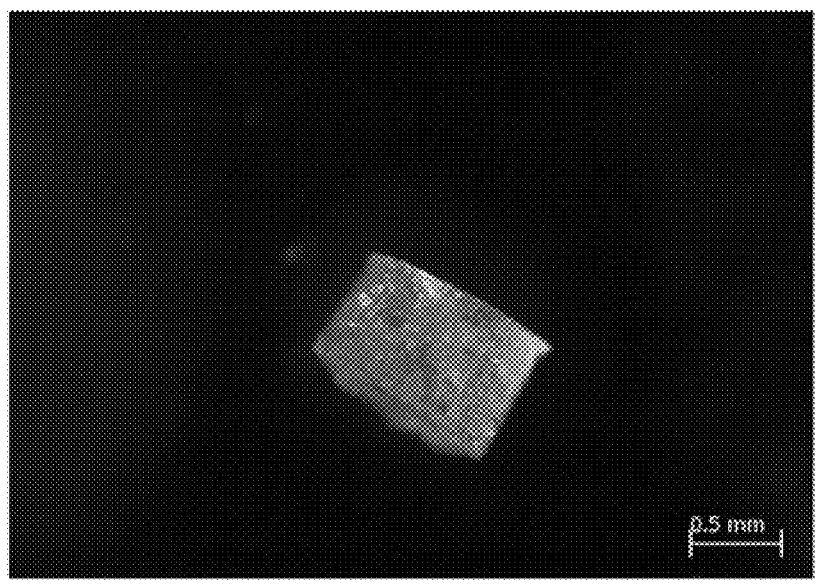
Figure 15C:
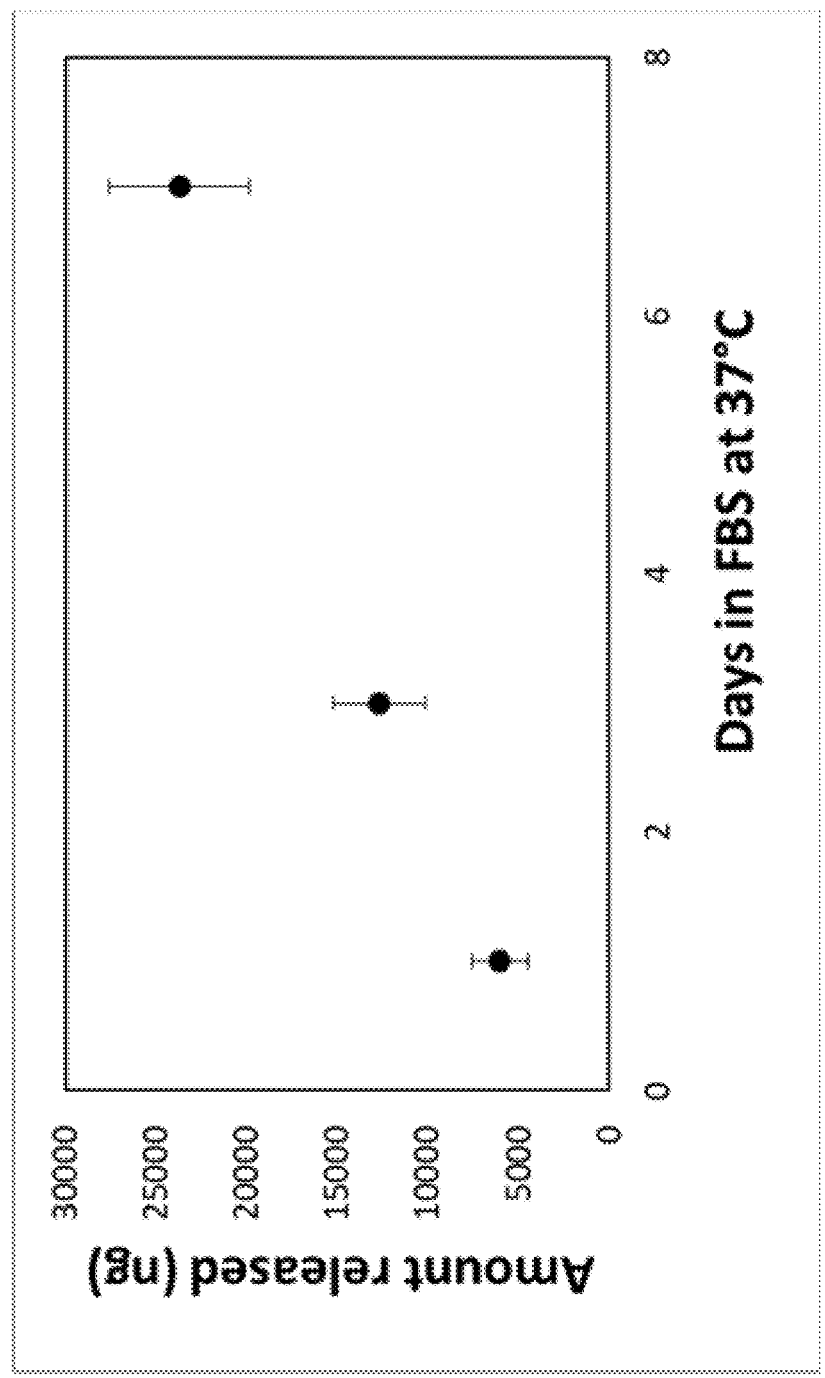
Figure 16:
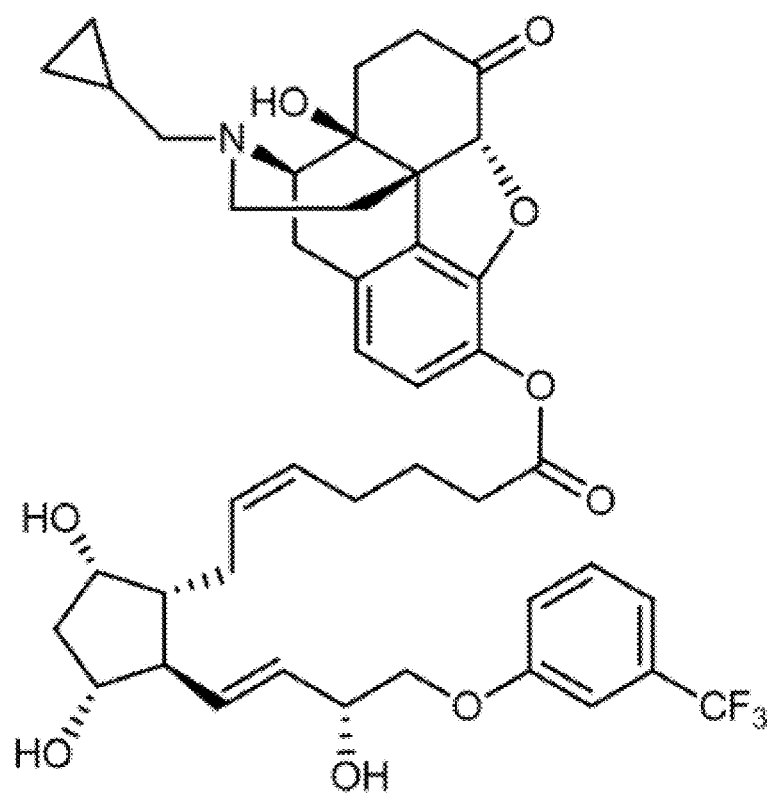
FIG. 16 shows the chemical structure of a steroid-prostaglandin heterodimer (travoprost-naltrexone, Compound 9) exemplified herein.
Figure 17:
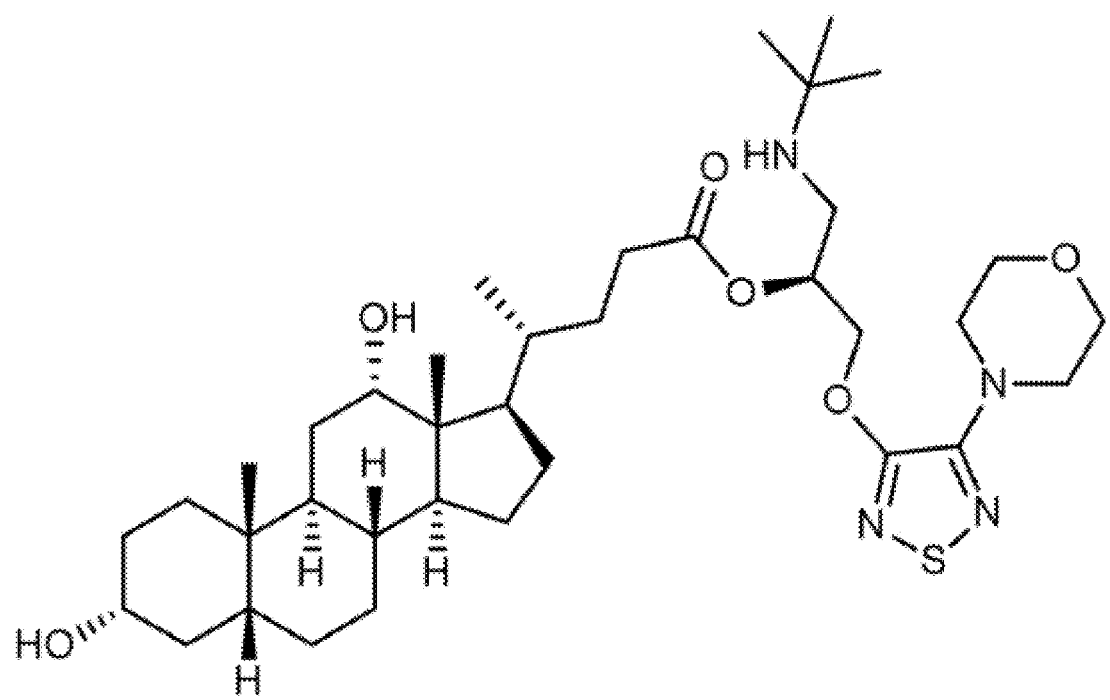
FIG. 17 shows the chemical structure of a steroid-prostaglandin heterodimer (timolol-deoxycholic acid, Compound 10) exemplified herein.

For example, FIG. 14 shows an extruded rod steroid-prostaglandin heterodimer (bimatoprost-anecortave, Compound 5) exemplified herein in a rabbit eye.

We claim:

1. A compound of a structure represented by Formula (VI-C):

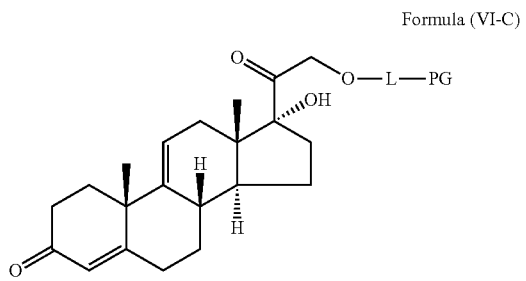

Formula (VI-C)

or a pharmaceutically acceptable salt thereof, wherein,
L is a linker; and
PG is a prostaglandin radical.

2. The compound of claim 1, wherein PG is represented by a structure of Formula (IIA):

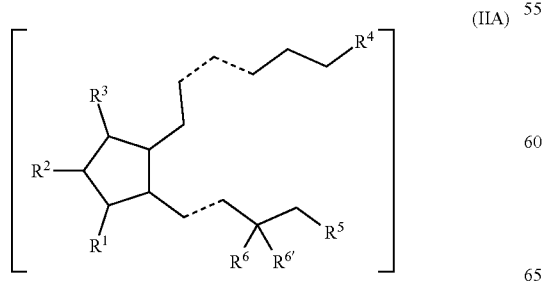

(IIA)

wherein:
⌇ is a single bond or a double bond;
$R^1$ and $R^3$ are OH;
$R^2$ is hydrogen;
$R^4$ is alkyl substituted with oxo, —C(=O)OC$_1$-C$_3$alkyl, —COOH, —CONH$_2$, or —CONHC$_1$-C$_3$alkyl;
$R^5$ is —O-aryl or arylalkyl; and
$R^6$ and $R^{6'}$ are each independently hydrogen, halogen, or OH.

3. The compound of claim 1, wherein L is a bond.

4. The compound of claim 1, wherein L comprises one or more linker group, each linker group being independently selected from the group consisting of alkyl, cycloalkyl, heteroalkyl, and alkoxy, wherein the alkyl, cycloalkyl, heteroalkyl, or alkoxy is optionally substituted.

5. The compound of claim 1, of the structure:

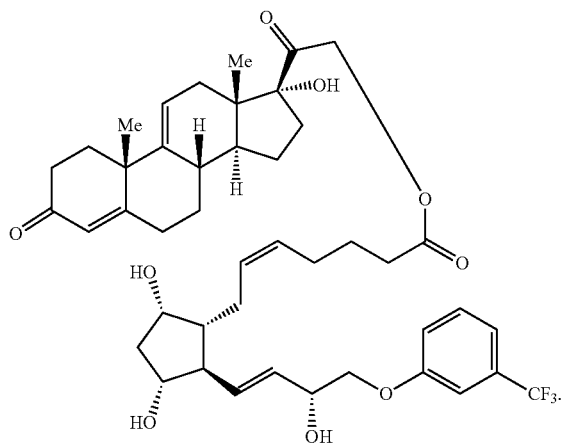

6. The compound of claim 1, of the structure:

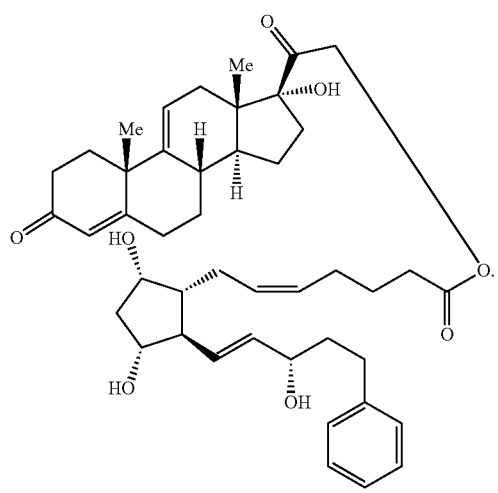

7. The compound of claim 1, of the structure:
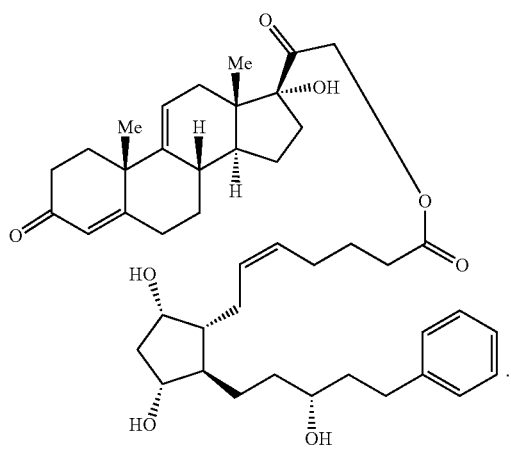
8. The compound of claim 1, of the structure:
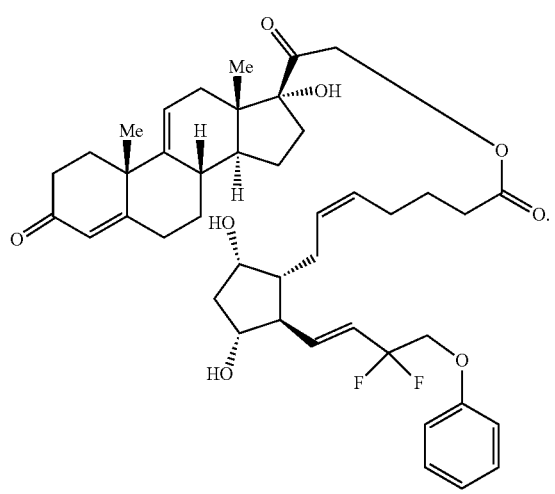
9. The compound of claim 1, of the structure:
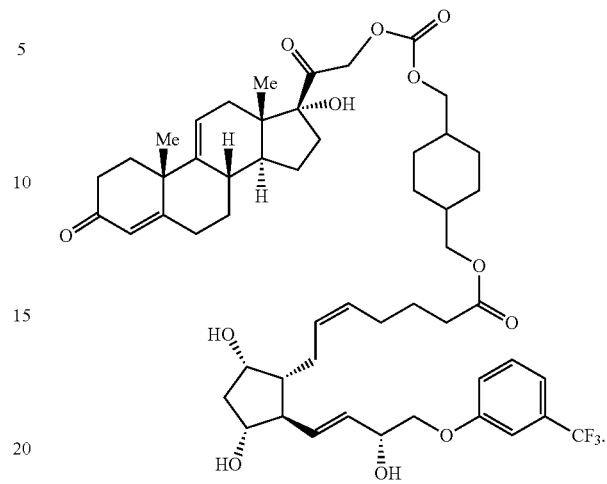
10. The compound of claim 1, having of the structure:
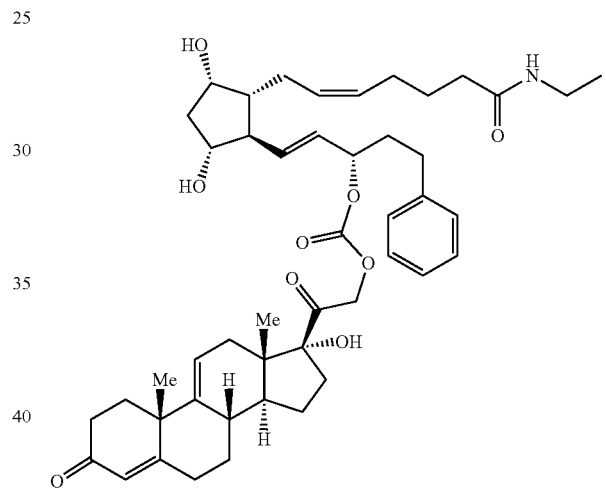
11. A pharmaceutical implant comprising at least 50 wt. % of the compound of claim 1.
* * * * *